(12) United States Patent
Andrianova et al.

(10) Patent No.: US 11,965,198 B2
(45) Date of Patent: Apr. 23, 2024

(54) METHOD FOR PRODUCING TARGET SUBSTANCE BY BACTERIAL FERMENTATION

(71) Applicant: AJINOMOTO CO., INC., Tokyo (JP)

(72) Inventors: Ekaterina Andrianova, Moscow (RU); Maria Kharchenko, Moscow (RU); Natalia Zakataeva, Moscow (RU); Elvira Voroshilova, Moscow (RU); Aleksander Krylov, Moscow (RU); Evgeniya Malykh, Moscow (RU); Sergei Mashko, Moscow (RU); Natalia Stoynova, Moscow (RU); Mikhail Baboshin, Moscow (RU); Lyubov Golubeva, Moscow (RU); Ekaterina Kovaleva, Moscow (RU); Mikhail Shupletsov, Moscow (RU)

(73) Assignee: AJINOMOTO CO., INC., Tokyo (JP)

( * ) Notice: Subject to any disclaimer, the term of this patent is extended or adjusted under 35 U.S.C. 154(b) by 342 days.

(21) Appl. No.: 17/221,308

(22) Filed: Apr. 2, 2021

(65) Prior Publication Data

US 2021/0269842 A1 Sep. 2, 2021

Related U.S. Application Data

(63) Continuation of application No. PCT/JP2019/039297, filed on Oct. 4, 2019.

(30) Foreign Application Priority Data

Oct. 5, 2018 (RU) .......................... RU2018135075

(51) Int. Cl.
| | | |
|---|---|---|
| C12P 21/02 | (2006.01) | |
| C12N 1/20 | (2006.01) | |
| C12N 9/14 | (2006.01) | |
| C12N 15/52 | (2006.01) | |
| C12P 5/00 | (2006.01) | |
| C12P 19/02 | (2006.01) | |
| C12R 1/15 | (2006.01) | |
| C12R 1/19 | (2006.01) | |

(52) U.S. Cl.
CPC ................ *C12P 21/02* (2013.01); *C12N 1/20* (2013.01); *C12N 9/14* (2013.01); *C12N 15/52* (2013.01); *C12P 5/007* (2013.01); *C12P 19/02* (2013.01); *C12R 2001/15* (2021.05); *C12R 2001/19* (2021.05); *C12Y 306/01009* (2013.01)

(58) Field of Classification Search
None
See application file for complete search history.

(56) References Cited

U.S. PATENT DOCUMENTS

| | | | |
|---|---|---|---|
| 1,069,697 A * | 8/1913 | Hills ...................... | B23K 9/282 439/729 |
| 3,736,228 A | 5/1973 | Nakayama et al. | |
| 3,912,587 A | 10/1975 | Enei et al. | |
| 3,960,660 A | 6/1976 | Enei et al. | |
| 3,960,661 A | 6/1976 | Enei et al. | |
| 4,278,765 A | 7/1981 | Debabov et al. | |
| 4,346,170 A | 8/1982 | Sano et al. | |
| 4,701,413 A | 10/1987 | Miyagawa et al. | |
| 5,661,012 A | 8/1997 | Sano et al. | |
| 5,965,391 A | 10/1999 | Reinscheid et al. | |
| 6,040,160 A | 3/2000 | Kojima et al. | |
| 7,435,560 B1 | 10/2008 | Matsui et al. | |
| 8,951,764 B2 * | 2/2015 | Bergsma .......... | C12Y 205/0101 435/254.2 |
| 9,540,657 B2 * | 1/2017 | Yu .......................... | C12N 15/85 |
| 10,167,482 B2 * | 1/2019 | Coffin .................. | C12N 15/8251 |
| 2006/0216796 A1 | 9/2006 | Hashiguchi et al. | |
| 2014/0234901 A1 | 8/2014 | Matsuda et al. | |
| 2018/0037918 A1 | 2/2018 | Matsuda et al. | |
| 2018/0265555 A1 | 9/2018 | Nakase et al. | |
| 2019/0241621 A1 | 8/2019 | Ito et al. | |

FOREIGN PATENT DOCUMENTS

| | | |
|---|---|---|
| EP | 0628636 A1 | 12/1994 |
| EP | 0685555 A1 | 12/1995 |
| EP | 2024504 B1 | 2/2016 |
| JP | 51-005075 A | 2/1976 |
| JP | 51-005075 B1 | 2/1976 |
| JP | 54-017033 B2 | 6/1979 |
| JP | 55-002956 B2 | 1/1980 |
| JP | 55-045199 B2 | 11/1980 |
| JP | 57-014160 B2 | 3/1982 |
| JP | 57-041915 B2 | 9/1982 |
| JP | 58-017592 B2 | 4/1983 |
| JP | 59-042895 A | 3/1984 |
| JP | 2011-505841 A | 3/2011 |
| JP | 2011-518564 A | 6/2011 |
| JP | 2014-057545 A | 4/2014 |
| WO | WO95/16042 A1 | 6/1995 |
| WO | WO96/15246 A1 | 5/1996 |
| WO | WO99/03988 A1 | 1/1999 |
| WO | WO2009/076676 A2 | 6/2009 |

(Continued)

OTHER PUBLICATIONS

Schocke et al. (Eur. J Biochem., 256, pp. 589-594, 1998).*
Schocke et al. (Arch. Microbiol., vol. 171, pp. 331-337, 1999).*
Kotani, Y., et al., "Inosine Accumulation by Mutants of Brevibacterium ammoniagenes Strain Improvement and Culture Conditions," Agric. Biol. Chem. 1978;42(2):399-405.
Zhou, J., et al., "Atypical Glycolysis in Clostridium thermocellum," Appl. Environmen. Microbiol. 2013;79 (9):3000-3008.

(Continued)

*Primary Examiner* — Hope A Robinson

(74) *Attorney, Agent, or Firm* — Cermak Nakajima & McGowan LLP; Shelly Guest Cermak

(57) ABSTRACT

The present invention provides a method for producing a target substance, the biosynthetic pathway of which is ATP-dependent, for example, amino acids, nucleosides, nucleotides, isoprenoids, and peptides, by fermentation of a bacterium which has been modified to overexpress a gene encoding a protein having $H^+$-translocating membrane-bound pyrophosphatase activity, for example, the hppA gene native to *R. rubrum* or a variant thereof.

14 Claims, 17 Drawing Sheets

Specification includes a Sequence Listing.

(56) References Cited

FOREIGN PATENT DOCUMENTS

| WO | WO2009/132220 A2 | 10/2009 |
| WO | WO2010/031076 A2 | 3/2010 |
| WO | WO2013/065772 A1 | 5/2013 |
| WO | WO2014/052054 A1 | 4/2014 |
| WO | WO2014/178446 A1 | 11/2014 |
| WO | WO2016/171224 A1 | 10/2016 |
| WO | WO2017/051930 A1 | 3/2017 |
| WO | WO2017/090665 A1 | 6/2017 |
| WO | WO2018/074578 A1 | 4/2018 |

OTHER PUBLICATIONS

Kaleta, C., et al., "Metabolic costs of amino acid and protein production in *Escherichia coli*," Biotechnol. J. 2013;8(9):1105-1114.
Baltscheffsky, M., et al., "A pyrophosphate synthase gene: molecular cloning and sequencing of the cDNA encoding the inorganic pyrophosphate synthase from Rhodospirillum rubrum," Biochimica Et Biophysica Acta 1998;1364(3):301-306.
Baltscheffsky, M., et al., "H+-proton-pumping inorganic pyrophosphatase: a tightly membrane-bound family," FEBS Lett. 1999;452(3):121-127.
International Search Report for PCT Patent App. No. PCT/JP2019/039297 (dated Jan. 15, 2020).
Written Opinion for PCT Patent App. No. PCT/JP2019/039297 (dated Jan. 15, 2020).

* cited by examiner

[FIG. 17]
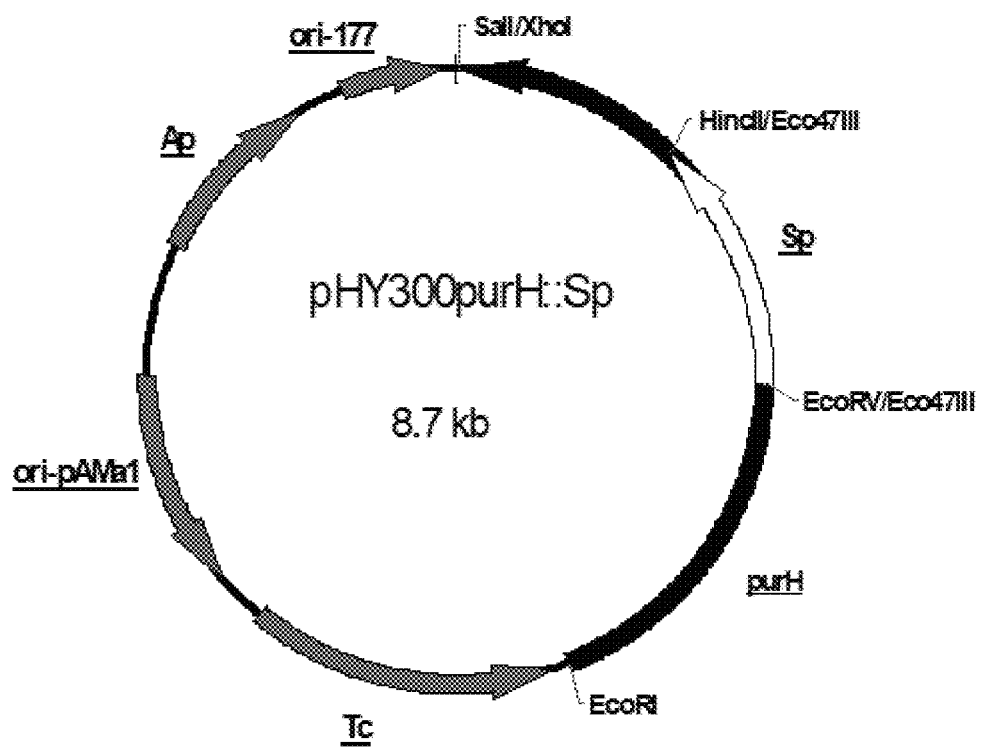

METHOD FOR PRODUCING TARGET SUBSTANCE BY BACTERIAL FERMENTATION

This application is a Continuation of, and claims priority under 35 U.S.C. § 120 to, International Application No. PCT/JP2019/039297, filed Oct. 4, 2019, and claims priority therethrough under 35 U.S.C. § 119 to Russian Patent Application No. 2018135075, filed Oct. 5, 2018, the entireties of which are incorporated by reference herein. Also, the Sequence Listing filed electronically herewith is hereby incorporated by reference (File name: 2021-04-02T US-629_Seq_List; File size: 60 KB; Date recorded: Apr. 2, 2021).

GENERAL FIELD

The present invention relates to the microbiological industry, and specifically to a method for producing a target substance from a carbon source by fermentation of a bacterium. The biosynthesis of the target substance requires adenosine triphosphate (ATP), and the bacterium has been modified to overexpress a gene encoding a protein having $H^+$-translocating membrane-bound pyrophosphatase activity. The target substance can be, for example, an amino acid, a nucleoside, a nucleotide, an isoprenoid, or a peptide.

DESCRIPTION OF THE RELATED ART

Conventionally, target substances such as amino acids, nucleosides, isoprenoids, peptides, their intermediates and derivatives such as, for example, nucleotides, and other chemicals of bacterial metabolism are produced by fermentation methods in which bacterial strains isolated from natural sources, or mutants of these, have been modified to enhance production yields of the target substances.

For example, many techniques to enhance L-amino acids production yields have been reported, including transformation of microorganisms with recombinant DNA (see, for example, U.S. Pat. No. 4,278,765 A) and alteration of expression regulatory regions such as promoters, leader sequences, and/or attenuators, or others known to the person skilled in the art (see, for example, US20060216796 A1 and WO9615246 A1). Other techniques for enhancing production yields include increasing activities of the enzymes involved in amino acid biosynthesis and/or desensitizing the target enzymes to the feedback inhibition by the resulting L-amino acid (see, for example, WO9516042 A1, EP0685555 A1 or U.S. Pat. Nos. 4,346,170 A, 5,661,012 A, and 6,040,160 A).

Another method for enhancing L-amino acids production yields is to attenuate expression of a gene or several genes which are involved in degradation of the target L-amino acid, genes which divert the precursors of the target L-amino acid from the L-amino acid biosynthetic pathway, genes involved in the redistribution of the carbon, nitrogen, sulfur, and phosphate fluxes, and genes encoding toxins, etc.

Methods for production of nucleosides by fermentation of bacterial strains are known. For example, fermentative production of purine nucleosides utilizing mutant microorganisms auxotrophic for adenine, or microorganisms resistant to various drugs such as purine analogues and sulfaguanidine, have been reported previously. Examples of the mutant microorganisms used in these methods include Bacillus strains (Japanese Patent, Publication Nos. 38-23039 (1963), 54-17033 (1979), 55-2956 (1980), and 55-45199 (1980); Japanese Patent Application, Publication No. 56-162998 (1981); Japanese Patent, Publication Nos. 57-14160 (1982) and 57-41915 (1982); and Japanese Patent Application, Publication No. 59-42895 (1984)), Brevibacterium strains (Japanese Patent, Publication Nos. 51-5075 (1976) and 58-17592 (1972); and Kotani Yu. et al., Agric. Biol. Chem., 1978, 42:399-405), and Escherichia strains (WO9903988 A1), and the like.

Examples of methods for production of isoprenoids by fermentation of genetically modified host cells are known (see, for example, WO2017051930 A1, EP2024504 B1, U.S. Pat. No. 8,951,764 B2, and so forth). In particular, methods for fermentative production of isoprene, which is the simplest isoprenoid, are known, and these include, but are not limited to, a method for producing an isoprene monomer using a bacterium that has been modified by integrating an isoprene synthase gene derived from kudzu or poplar (see, for example, Japanese Laid-Open Publication No. 2011-505841, Japanese Laid-Open Publication No. 2011-518564, International Publication WO2010/031076, and International Publication WO2014/052054).

Methods for producing peptides by fermentation of bacterial cells are known, and these include, for example, a method in which a peptide can be produced efficiently by culturing bacterial cells that have been transformed with the plm2 gene from Streptomyces plumbeus (JP2014057545 A). The method can be suitable for producing a dipeptide having an acidic amino acid at the N-terminus by culturing the transformed cells of Escherichia coli. In another example, a fibroin-like protein was produced by culturing in a medium a bacterium of the species Escherichia coli having a gene encoding a fibroin-like protein (WO2017090665 A1). Furthermore, methods for secretory production of heterologous proteins have been reported using a coryneform bacterium that has been modified to lower activity of RegX3 protein (WO2018074578 A1), to harbor a mutant phoS gene (WO2016171224 A1), to express a genetic construct encoding a heterologous fusion protein including an extein and an intein having an activity of acyl rearrangement (WO2014178446 A1), or to have improved expression of a gene encoding a metallopeptidase (WO2013065772 A1), and so forth.

However, a method for producing a target substance, the biosynthesis of which from a carbon source requires ATP, by fermentation of a bacterium that has been modified to overexpress a gene encoding a protein having $H^+$-translocating membrane-bound pyrophosphatase activity has not been previously reported.

SUMMARY

According to the presently disclosed subject matter, a novel method for production of a target substance, the biosynthesis of which from a carbon source requires one or more molecules of ATP, such as, for example, an amino acid, a nucleoside, a nucleotide, an isoprenoid, and a peptide, by fermentation of a bacterium that has been modified to overexpress a gene encoding a protein having $H^+$-translocating membrane-bound pyrophosphatase activity, such as, for example, the hppA gene native to R. rubrum or a variant thereof, is provided herein. A bacterium can can be engineered to produce a target substance by fermentation in a higher amount and more efficiently as compared with a non-modified bacterium, when the bacterium is modified to overexpress a gene encoding a protein having $H^+$-translocating membrane-bound pyrophosphatase activity. That is, the ability of a bacterium to produce a target substance by fermentation can be improved as compared with a non-modified bacterium, when the bacterium is modified to overexpress a gene encoding a protein having H$^+$-translocating membrane-bound pyrophosphatase activity. Moreover, the ability of a bacterium that has been modified to overexpress a gene encoding a protein having H$^+$-translocating membrane-bound pyrophosphatase activity to produce a target substance by fermentation can be improved by further modifying the bacterium such that the expression of a gene encoding a protein having an activity of inorganic pyrophosphatase is attenuated. Therefore, the cost of the process for production of a target substance by fermentation of a bacterium can be reduced when the method as described herein is used.

It was confirmed by and it was substantiated by the following detailed description of embodiments taken in conjunction with the accompanying drawings, that i) the number of molecules of adenosine triphosphate (ATP) that are synthesized in, for example, the tricarboxylic acid (TCA) cycle can be decreased in a bacterium that has been modified to overexpress a gene encoding a protein having H$^+$-translocating membrane-bound pyrophosphatase activity when the bacterium is cultured in a medium, and ii) the synthesis of molecules of ATP that are synthesized from adenosine 5'-diphosphate (ADP) and a phosphate by membrane-bound proton-mediated ATP synthase (EC: 3.6.3.14) using the proton-motive force can be enhanced in the bacterium as a result of an increase in the activity of a protein having H$^+$-translocating membrane-bound pyrophosphatase activity, such that the overall amount of molecules of ATP in the modified bacterium is not altered as compared with a non-modified bacterium. Moreover, the cellular energy in a bacterium can be redirected from the heat energy, which is generated as a result of the activity of a protein having inorganic pyrophosphatase activity and, hence, cannot be used in biosynthesis of cellular metabolites, toward the energy that can be used to generate a proton-motive force through the membrane of a cell of the bacterium, when the bacterium is modified to overexpress a gene encoding a protein having H$^+$-translocating membrane-bound pyrophosphatase activity. As a result, the modified bacterium i) is rendered able to utilize ATP that is synthesized in, for example, the TCA cycle more freely in cellular processes such as, for example, the biosynthesis of cellular metabolites, ii) becomes more efficient in saving energy and carbon and redirecting them between different cellular needs, and iii) has an increased ability to synthesize a target substance from an ATP-dependent biosynthetic pathway, as compared with a non-modified bacterium. Consequently, the fermentative production of a target substance, the biosynthesis of which from a carbon source requires one or more molecules of ATP, can be improved when a bacterium that has been modified to overexpress a gene encoding a protein having H$^+$-translocating membrane-bound pyrophosphatase activity is used. Moreover, the production of a target substance by fermentation of the bacterium can be further improved when the bacterium is further modified to attenuate expression of a gene encoding a protein having inorganic pyrophosphatase activity.

It is an aspect of the present invention to provide a method for producing a target substance comprising (i) cultivating in a culture medium a bacterium which has an ability to produce the target substance to produce and accumulate the target substance in the culture medium or cells of the bacterium, or both, and (ii) collecting the target substance from the culture medium or the cells, or both, wherein the target substance is a substance from an ATP-dependent biosynthetic pathway, and wherein the bacterium has been modified to overexpress a gene encoding a protein having H$^+$-translocating membrane-bound pyrophosphatase activity.

It is another aspect of the present invention to provide the method as described above, wherein said gene encoding a protein having H$^+$-translocating membrane-bound pyrophosphatase activity is selected from the group consisting of: (A) a DNA comprising the nucleotide sequence shown in SEQ ID NO: 1, (B) a DNA comprising a nucleotide sequence that is able to hybridize under stringent conditions with a nucleotide sequence complementary to the sequence shown in SEQ ID NO: 1, and wherein said DNA encodes a protein having the H$^+$-translocating membrane-bound pyrophosphatase activity, (C) a DNA encoding a protein comprising the amino acid sequence shown in SEQ ID NO: 2, (D) a DNA encoding a protein comprising the amino acid sequence shown in SEQ ID NO: 2, but wherein said amino acid sequence includes substitution, deletion, insertion, and/or addition of about 1 to 70 amino acid residues, and wherein said protein has an H$^+$-translocating membrane-bound pyrophosphatase activity, (E) a DNA encoding a protein comprising an amino acid sequence having an identity of not less than 70% with respect to the entire amino acid sequence shown in SEQ ID NO: 2, and wherein said protein has the H$^+$-translocating membrane-bound pyrophosphatase activity, and (F) a DNA comprising a variant nucleotide sequence of SEQ ID NO: 1 due to the degeneracy of the genetic code.

It is another aspect of the present invention to provide the method as described above, wherein said gene encoding a protein having H$^+$-translocating membrane-bound pyrophosphatase activity is overexpressed by increasing the copy number of said gene, by modifying an expression regulatory region of said gene, or by a combination thereof, so that the expression of said gene is enhanced as compared with a non-modified bacterium.

It is another aspect of the present invention to provide the method as described above, wherein said target substance is selected from the group consisting of an amino acid, a nucleoside, a nucleotide, an isoprenoid, and a peptide.

It is another aspect of the present invention to provide the method as described above, wherein said amino acid is selected from the group consisting of L-alanine, L-arginine, L-asparagine, L-aspartic acid, L-citrulline, L-cysteine, L-glutamic acid, glycine, L-glutamine, L-histidine, L-isoleucine, L-leucine, L-lysine, L-methionine, L-ornithine, L-phenylalanine, L-proline, L-serine, L-threonine, L-tryptophan, L-tyrosine, and L-valine.

It is another aspect of the present invention to provide the method as described above, wherein said nucleoside is selected from the group consisting of cytidine, thymidine, uridine, 5-aminoimidazole-4-carboxamide ribonucleoside (AICAr), adenosine, guanosine, xanthosine, and inosine.

It is another aspect of the present invention to provide the method as described above, wherein said nucleotide is selected from the group consisting of uridine 5'-monophosphate, 5-aminoimidazole-4-carboxamide ribonucleotide (AICAR), adenosine 5'-monophosphate, guanosine 5'-monophosphate, xanthosine 5'-monophosphate, and inosine 5'-monophosphate. It is another aspect of the present invention to provide the method as described above, wherein said isoprenoid is selected from the group consisting of an isoprene, a monoterpenoid, a sesquiterpenoid, a diterpenoid, a sesterpenoid, a triterpenoid, a tetraterpenoid, and a polyterpenoid.

It is another aspect of the present invention to provide the method as described above, wherein said peptide is selected from the group consisting of an oligopeptide, a polypeptide, and a protein.

It is another aspect of the present invention to provide the method as described above, wherein said bacterium is a Gram-positive bacterium or a Gram-negative bacterium.

It is another aspect of the present invention to provide a method as described above, wherein said bacterium is selected from the group consisting of a coryneform bacterium, a bacterium belonging to the family Enterobacteriaceae, and a bacterium belonging to the genus *Bacillus*.

It is another aspect of the present invention to provide the method as described above, wherein: said coryneform bacterium is a bacterium belonging to the genus *Corynebacterium* or *Brevibacterium*, said bacterium belonging to the family Enterobacteriaceae is a bacterium belonging to the genus *Escherichia* or *Pantoea*, and said bacterium belonging to the genus *Bacillus* is *Bacillus amyloliquefaciens* or *Bacillus subtilis*.

It is another aspect of the present invention to provide the method as described above, wherein said coryneform bacterium is *Corynebacterium glutamicum*, and wherein said bacterium belonging to the family Enterobacteriaceae is *Escherichia coli* or *Pantoea ananatis*.

It is another aspect of the present invention to provide the method as described above, wherein said bacterium has been further modified to attenuate expression of a gene encoding a protein having inorganic pyrophosphatase activity.

It is another aspect of the present invention to provide the method as described above, wherein said gene encoding a protein having inorganic pyrophosphatase activity is a ppa gene.

It is another aspect of the present invention to provide the method as described above, wherein said gene encoding a protein having inorganic pyrophosphatase activity is deleted.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF DRAWINGS

FIG. 17 shows the structure of the pHY300purH::Sp plasmid.

DETAILED DESCRIPTION

Figure 1:
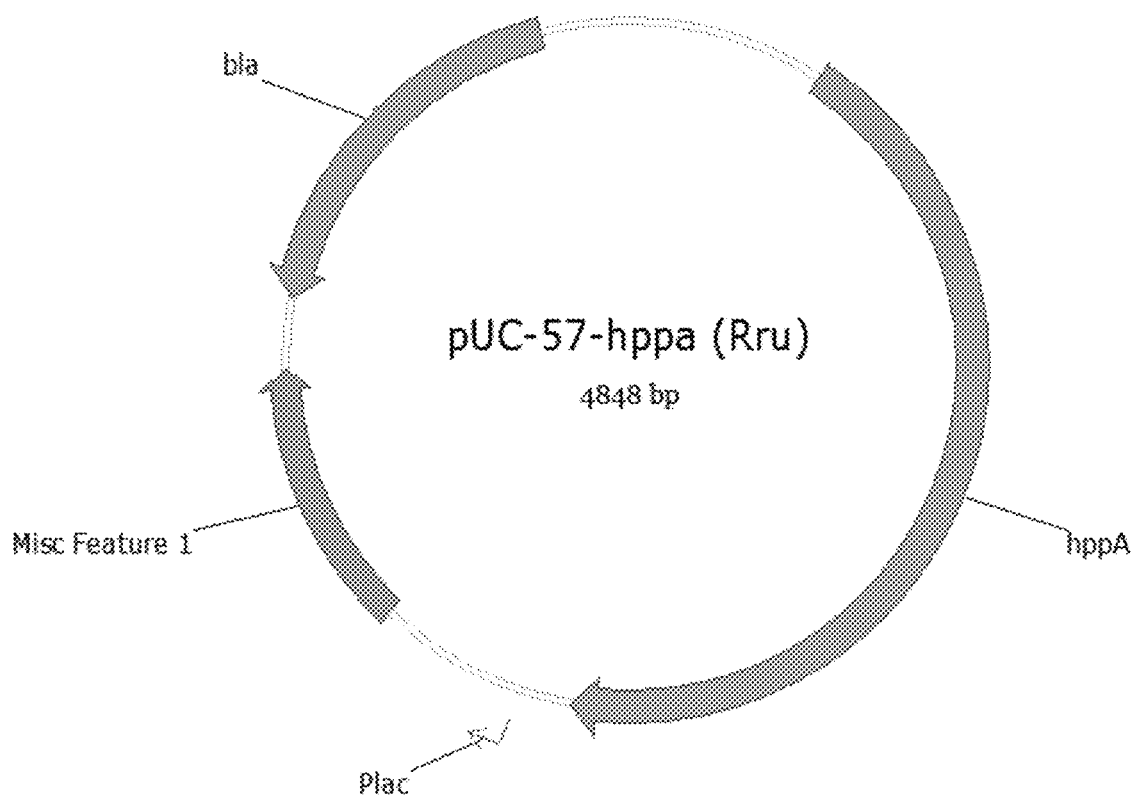
FIG. 1 shows the structure of the pUC-57-hppA(Rru) plasmid.

The invention of the present application will now be described in more detail with reference to the exemplary embodiments, given only by way of example, and with reference to the accompanying drawings.

1. Bacterium

The bacterium as described herein is a target substance-producing bacterium that has been modified to overexpress a gene encoding a protein having $H^+$-translocating membrane-bound pyrophosphatase activity. The bacterium as described herein can be used in the method as described herein. Hence, the explanations given hereinafter to the bacterium can be applied similarly to any bacterium that can be used interchangeably or equivalently in the method as described herein.

Any target substance-producing bacterium that has been modified to overexpress a gene encoding a protein having $H^+$-translocating membrane-bound pyrophosphatase activity can be used in the method as described herein. For example, a target substance-producing bacterium can be used in the method as described herein, provided that the bacterium has been modified to overexpress a gene encoding a protein having $H^+$-translocating membrane-bound pyrophosphatase activity, so that the production of a target substance by the bacterium has been enhanced as compared with a non-modified bacterium. The bacterium thus modified, for example, may be able to cause accumulation in a medium and/or cells of the bacterium of a higher amount of the target substance as compared with a non-modified bacterium.

The phrase "a target substance-producing bacterium" or the may be used interchangeably or equivalently to the phrase "a bacterium that is able to produce a target substance" or the phrase "a bacterium having an ability to produce a target substance".

The phrase "a target substance-producing bacterium" can mean a bacterium that is able to produce, excrete or secrete, and/or cause accumulation of a target substance in a culture medium and/or cells of the bacterium when the bacterium is cultured in the medium.

The phrase "a bacterium having an ability to produce a target substance" can also mean a bacterium that is able to produce, excrete or secrete, and/or cause accumulation of a target substance in a culture medium and/or cells of the bacterium in an amount larger than a non-modified bacterium. The phrase "a non-modified bacterium" may be used interchangeably or equivalently to the phrase "a non-modified strain". The phrase "a non-modified strain" can mean a control strain that has not been modified to overexpress a gene encoding a protein having $H^+$-translocating membrane-bound pyrophosphatase activity. Examples of the non-modified strain can include a wild-type or parental strain such as, for example, Corynebacterium glutamicum (C. glutamicum) ATCC13032, Escherichia coli (E. coli) K-12, Pantoea ananatis (P. ananatis) AJ13355, Bacillus subtilis (B. subtilis) 168, or Bacillus amyloliquefaciens (B. amyloliquefaciens) FZB42. The phrase "an L-methionine-producing bacterium" can also mean a bacterium that is able to cause accumulation in the medium and/or the cells of the bacterium of an amount, for example, not less than 0.001 g/L, not less than 0.01 g/L, not less than 0.1 g/L, not less than 0.5 g/L, or not less than 1.0 g/L of the target substance. The phrase "a bacterium having an ability to produce a target substance" can also mean a bacterium that is able to produce, excrete or secrete, and/or cause accumulation of a target substance in a culture medium and/or cells of the bacterium in an amount larger than a non-modified bacterium, and is able to cause accumulation in the medium and/or cells of the bacterium of an amount, for example, not less than 0.001 g/L, not less than 0.01 g/L, not less than 0.1 g/L, not less than 0.5 g/L, or not less than 1.0 g/L of the target substance.

The bacterium may inherently have an ability to produce a target substance or may be modified to have the ability to produce a target substance. Such modification can be attained by using, for example, a mutation method or DNA recombination techniques. The bacterium can be obtained by overexpressing a gene encoding a protein having $H^+$-translocating membrane-bound pyrophosphatase activity in a bacterium that inherently has the ability to produce a target substance, or in a bacterium that has already been imparted with the ability to produce a target substance. Alternatively, the bacterium can be obtained by imparting the ability to produce a target substance to a bacterium already modified to overexpress a gene encoding a protein having $H^+$-translocating membrane-bound pyrophosphatase activity. Alternatively, the bacterium may have been imparted with the ability to produce a target substance by being modified to overexpress a gene encoding a protein having $H^+$-translocating membrane-bound pyrophosphatase activity. The bacterium as described herein can be obtained, specifically, for example, by modifying a bacterial strain described hereinafter.

The phrase "an ability to produce a target substance" can mean the ability of a bacterium to produce, excrete or secrete, and/or cause accumulation of a target substance in a culture medium and/or cells of the bacterium when the bacterium is cultured in the medium. The phrase "an ability to produce a target substance" can specifically mean the ability of a bacterium to produce, excrete or secrete, and/or cause accumulation of a target substance in a culture medium and/or cells of the bacterium to such a level that a target substance can be collected from the culture medium and/or the cells when the bacterium is cultured in the medium. The phrase "cultured" with reference to a bacterium which is grown in a medium and used according to the method as described herein may be used interchangeably or equivalently to the phrase "cultivated", or the like, that are well-known to the persons skilled in the art.

The bacterium that can be used in the method as described herein, or can be modified to obtain the bacterium as described herein, can be, for example, a Gram-positive bacterium or a Gram-negative bacterium. Examples of Gram-positive bacteria include coryneform bacteria and bacteria belonging to the genera Bacillus, Listeria, Staphylococcus, Streptococcus, Enterococcus, Clostridium, and Streptomyces. Particular examples of Gram-positive bacteria include coryneform bacteria and bacteria of the genus Bacillus. Examples of Gram-negative bacteria include bacteria belonging to the family Enterobacteriaceae such as bacteria belonging to the genera Escherichia, Pantoea, Salmonella, Vibrio, Serratia, Enterobacter, and Pseudomonas. Particular examples of Gram-negative bacteria include bacteria belonging to the genera Escherichia, Pantoea, and Enterobacter.

The coryneform bacteria are aerobic Gram-positive bacilli. Examples of the coryneform bacteria include Corynebacterium bacteria, Brevibacterium bacteria, Microbacterium bacteria, and so forth. The coryneform bacteria include bacteria which were previously classified into the genus Brevibacterium, but have been united into the genus Corynebacterium (Liebl W. et al., Transfer of Brevibacterium divaricatum DSM 20297T, "Brevibacterium flavum" DSM 20411, "Brevibacterium lactofermentum" DSM 20412 and DSM 1412, and Corynebacterium glutamicum and their distinction by rRNA gene restriction patterns, Int. J. Syst. Bacteriol., 1991, 41:255-260). The coryneform bacteria also include bacteria which have previously been classified into Corynebacterium ammoniagenes, but are presently reclassified into Corynebacterium stationis by nucleotide sequence analysis of 16S rRNA and so forth (Bernard K. A. et al., Assignment of Brevibacterium stationis (ZoBell and Upham 1944) Breed 1953 to the genus Corynebacterium, as Corynebacterium stationis comb. nov., and emended description of the genus Corynebacterium to include isolates that can alkalinize citrate, Int. J. Syst. Evol. Microbiol., 2010, 60:874-879). One advantage of using the coryneform bacteria is that they are Gram-positive bacteria having a thick peptidoglycan layer in the bacterial cell wall which makes the bacteria resistant to various environmental conditions such as, for example, temperature and chemically active agents (e.g., oxidative and toxic chemicals). Another advantage of using the coryneform bacteria is that they can grow well in a simple medium containing a saccharide, ammonia, mineral salts, etc., and therefore they are excellent in view of cost of medium, culture method, and culture productivity, and so forth.

Specific examples of coryneform bacteria include the following species:
Corynebacterium acetoacidophilum,
Corynebacterium acetoglutamicum,
Corynebacterium alkanolyticum,
Corynebacterium callunae,
Corynebacterium crenatum
Corynebacterium glutamicum,
Corynebacterium lilium,
Corynebacterium melassecola,
Corynebacterium thermoaminogenes (Corynebacterium efficiens),
Corynebacterium herculis,
Brevibacterium divaricatum,
Brevibacterium flavum,

*Brevibacterium immariophilum,*
*Brevibacterium lactofermentum* (*Corynebacterium glutamicum*),
*Brevibacterium roseum,*
*Brevibacterium saccharolyticum,*
*Brevibacterium thiogenitalis,*
*Corynebacterium ammonia* genes (*Corynebacterium stationis*),
*Brevibacterium album,*
*Brevibacterium cerinum,*
*Microbacterium ammoniaphilum.*

Specific examples of coryneform bacteria include the following strains:
*Corynebacterium acetoacidophilum* ATCC 13870,
*Corynebacterium acetoglutamicum* ATCC 15806,
*Corynebacterium alkanolyticum* ATCC 21511,
*Corynebacterium callunae* ATCC 15991,
*Corynebacterium crenatum* AS1.542
*Corynebacterium glutamicum* ATCC 13020, ATCC 13032, ATCC 13060, ATCC 13869, FERM BP-734,
*Corynebacterium lilium* ATCC 15990,
*Corynebacterium melassecola* ATCC 17965,
*Corynebacterium thermoaminogenes* AJ12340 (FERM BP-1539),
*Corynebacterium herculis* ATCC 13868,
*Brevibacterium divaricatum* ATCC 14020,
*Brevibacterium flavum* ATCC 13826, ATCC 14067, AJ12418 (FERM BP-2205),
*Brevibacterium immariophilum* ATCC 14068,
*Brevibacterium lactofermentum* ATCC 13869,
*Brevibacterium roseum* ATCC 13825,
*Brevibacterium saccharolyticum* ATCC 14066,
*Brevibacterium thiogenitalis* ATCC 19240,
*Corynebacterium ammoniagenes* (*Corynebacterium stationis*) ATCC 6871, ATCC 6872,
*Brevibacterium album* ATCC 15111,
*Brevibacterium cerinum* ATCC 15112,
*Microbacterium ammoniaphilum* ATCC 15354.

Examples of the bacteria of the genus *Bacillus* include bacteria classified into the genus *Bacillus* according to the taxonomy of the NCBI (National Center for Biotechnology Information) database (ncbi.nlm.nih.gov/Taxonomy/Browser/wwwtax.cgi?mode=Undef&id=1386&lvl=3&lin=f&keep=1 &srchmode=1&unlock). Examples of the bacteria of the genus *Bacillus* can include *Bacillus subtilis* (*B. subtilis*), such as the strain *B. subtilis* 168, and *Bacillus amyloliquefaciens* (*B. amyloliquefaciens*). *B. amyloliquefaciens* is a heterogenic species, and specific examples thereof can include many known strains, such as SB, T, P, W, F, N, K, and H (Welker N. E. and Campbell L. L., *J. Bacteriol.*, 1967, 94:1124-1130). Recently, *Bacillus* strains were isolated from plants, however such isolates are usually considered as a distinct ecotype of *B. amyloliquefaciens* (Reva O. N. et al., *FEMS Microbiol. Ecol.*, 2004, 48:249-259). The entire nucleotide sequence of one of the strains isolated from a plant, *B. amyloliquefaciens* FZB42, has been reported (Chen X. H. et al., *Nat. Biotechnol.*, 2007, 25:1007-1014). In addition, the complete genome sequence of the *B. amyloliquefaciens* DSM7 strain was recently determined as well (Rueckert C. et al., *J. Biotechnol.*, 2011, 155:78-85). Examples of bacteria of the genus *Bacillus* can also include *Bacillus lichenformis, Bacillus pumilis, Bacillus megaterium, Bacillus brevis, Bacillus polymyxa* (now classified as *PaeniBacillus*), *Bacillus stearothermophilus*, and so forth.

Examples of parental *Bacillus* strains that can be used to derive or produce the bacterium that can be used in the method can be *B. subtilis* KMBS375 strain (Ppur*-ΔattΔpurAΔpurRΔpupGΔdeoD guaB24; Russian Patent No. 2422510 C2 and PCT Application, Publication No. WO2010038903 A1), *B. amyloliquefaciens* FZB42 strain (DSM 23117), *B. amyloliquefaciens* DSM7 strain (ATCC No. 23350, NRRL B-14393), *B. subtilis* strain AJ12707 (FERM P-12951; Japanese Patent Application, Publication No. 6-113876 (1994)), *B. subtilis* strain AJ3772 (FERM P-2555; Japanese Patent Application, Publication No. 62-014794 (1987)), *Bacillus pumilus* NA-1102 (FERM BP-289), *B. subtilis* NA-6011 (FERM BP-291), *B. subtilis* GI 136A (ATCC No. 19222; U.S. Pat. No. 3,575,809; also identified as *B. amyloliquefaciens* K (AJ1991), deposited at the Russian National Collection of Industrial Microorganisms (VKPM, FGUP GosNII Genetika, 1 Dorozhny proezd., 1 Moscow 117545, Russia) on Mar. 10, 2005 as *B. amyloliquefaciens* GI 136A (VKPM B-8994) and converted to an international deposit on Oct. 13, 2006), *B. subtilis* NA-6012 (FERM BP-292; U.S. Pat. No. 4,701,413), *B. pumilis* Gottheil No. 3218 (ATCC No. 21005; U.S. Pat. No. 3,616, 206), *B. amyloliquefaciens* strain AS115-7 (VKPM B-6134; Russian Patent No. 2003678 C1). A further example is *B. subtilis* strain KMBS16, which is a derivative of the known *B. subtilis* 168 trpC2 strain and contains mutations in the purR gene encoding a purine repressor (purR::spc), the purA gene encoding succinyl-AMP synthase (purA::erm), and the deoD gene encoding purine nucleoside phosphorylase (deoD::kan) (Russian Patent Application No. 2002103333 A, U.S. Pat. No. 7,326,546).

Examples of the bacteria belonging to the family Enterobacteriaceae include bacteria belonging to the genera *Enterobacter, Erwinia, Escherichia, Klebsiella, Morganella, Pantoea, Photorhabdus, Providencia, Salmonella, Yersinia,* and so forth. Specifically, bacteria classified into the family Enterobacteriaceae according to the taxonomy used in the NCBI (National Center for Biotechnology Information) database (www.ncbi.nlm.nih.gov/Taxonomy/Browser/wwwtax.cgi?id=543) can be used. Particular examples of the bacteria belonging to the family Enterobacteriaceae include bacteria belonging to the genera *Escherichia, Enterobacter,* and *Pantoea.*

*Escherichia* bacteria are not particularly limited, and examples thereof include those described in the work of Neidhardt et al. (Bachmann, B. J., Derivations and genotypes of some mutant derivatives of *Escherichia coli* K-12, p. 2460-2488. In F. C. Neidhardt et al. (ed.), *Escherichia coli* and *Salmonella*: cellular and molecular biology, 2$^{nd}$ ed., ASM Press, Washington, D.C., 1996). The species *Escherichia coli* (*E. coli*) is a particular example. Specific examples of *E. coli* include *E. coli* K-12 strain, which is a prototype wild-type strain, such as *E. coli* W3110 (ATCC 27325), *E. coli* MG1655 (ATCC 47076), and so forth.

Examples of the *Enterobacter* bacteria include *Enterobacter agglomerans, Enterobacter aerogenes,* and so forth. Examples of the *Pantoea* bacteria include *Pantoea ananatis* (*P. ananatis*), and so forth. Some strains of *Enterobacter agglomerans* were recently reclassified into *Pantoea agglomerans, Pantoea ananatis* or *Pantoea stewartii* on the basis of nucleotide sequence analysis of 16S rRNA, etc. A bacterium belonging to either genus *Enterobacter* or *Pantoea* may be used so long as it is a bacterium classified into the family Enterobacteriaceae. Specific examples of *P. ananatis* include *P. ananatis* AJ13355 strain (FERM BP-6614), AJ13356 strain (FERM BP-6615), AJ13601 strain (FERM BP-7207), and derivatives thereof. These strains were identified as *Enterobacter agglomerans* when they were isolated, and deposited as *Enterobacter agglomerans.* However, they were recently re-classified as *P. ananatis* on the basis of nucleotide sequencing of 16S rRNA and so forth as described above.

These strains are available from, for example, the American Type Culture Collection (ATCC; Address: 10801 University Boulevard, Manassas, Va. 20110 USA). That is, registration numbers are assigned to the respective strains, and the strains can be ordered by using these registration numbers (refer to atcc.org). The registration numbers of the strains are listed in the catalogue of the American Type Culture Collection. These strains can also be obtained from, for example, the depositories at which the respective strains were deposited.

The phrase "cultured" in reference to a bacterium that can be used in the method as described herein may be used interchangeably or equivalently to the phrase "cultivated", or the like, that are well-known to the person skilled in the art.

The bacterium can produce a target substance either alone or as a mixture of the target substance with one or more kinds of other substances. The phrase "other substance" can mean a substance that can be produced by a bacterium as described herein and that is different from the chosen target substance. It is acceptable that the "other substance" may be a target substance per se, which is produced by the bacterium in addition to another target substance. That is, the bacterium as described herein which can be used in the method as described herein may have an ability to produce, virtually, one or more kinds of target substances. The phrase "other substance" can also mean a substance that is not regarded as a target substance. Therefore, the "other substance" may be, for example, a by-product substance with respect to the target substance that is produced by the bacterium. That is, the bacterium as described herein which can be used in the method as described herein may have an ability to produce, virtually, one or more kinds of other substances that is/are not regarded as a target substance, in addition to a target substance. It is also acceptable that the bacterium has an ability to produce one or more kinds of target substances and one or more kinds of other substances that is/are not regarded as a target substance.

When a target substance is a compound that can form a derivative form, such as a salt, a hydrate, an adduct, or a combination of these, the target substance can be produced in a free form, a derivative form, or a mixture of these. An adduct can be a compound formed by the target substance in combination with another organic or inorganic compound. Hence, the phrase "a target substance" can mean, for example, a target substance in a free form, a derivative form, or a mixture of these. The phrase "a target substance" can particularly mean, for example, a target substance in a free form, a salt thereof, or a mixture of these. Unless otherwise stated, the phrase "a target substance" without referring to hydration, such as the phrases "a target substance in a free form" and "a salt of a target substance", can include both an anhydrate and a hydrate thereof. Such interpretation of the phrase "a target substance" can also be applied similarly to the phrase "other substance".

The target substance is not particularly limited, and it may be a substance that can be produced by the bacterium as described herein or that can be produced using the method as described herein. That is, the target substance may be any desired substance that is intended to be produced using the bacterium as described herein or the method as described herein. The terms "substance", "metabolite", "cellular compound", and the like may be used herein equivalently and/or interchangeably with each other. The target substance can be, for example, a substance from an ATP-dependent biosynthetic pathway. The abbreviation "ATP" can refer to adenosine 5'-triphosphate (CAS Registry Number: 56-65-5) or a salt thereof, and it is well-known to the person skilled in the art. The phrase "a substance from an ATP-dependent biosynthetic pathway" can mean a substance, the biosynthesis of which from a carbon source requires one or more molecules of ATP. That is, the phrase "a substance from an ATP-dependent biosynthetic pathway" can mean a substance, in the biosynthetic pathway of which, if starting from a carbon source, one or more molecules of ATP are utilized. The explanations of a phrase "a carbon source" are given hereinafter.

The ATP may serve in a biosynthetic pathway of a target substance as, for example, a co-factor and/or a reacting molecule. In this regard, a co-factor may also be considered as a reacting molecule. A biosynthetic pathway that requires one or more molecules of ATP for the biosynthesis of a chosen substance, if starting from a carbon source, can be referred to as "ATP-dependent biosynthetic pathway", which definition is well-known to the person skilled in the art. It is therefore acceptable that the phrase "ATP-dependent biosynthetic pathway" can also mean a pathway, in which one or more molecules of ATP can be utilized as a donor of phosphate and/or pyrophosphate group for a co-factor and/or a reacting molecule in the biosynthetic pathway of a chosen substance. For example, an ATP-dependent biosynthetic pathway can be a pathway for the biosynthesis of a chosen substance in which one or more molecules of guanosine 5'-triphosphate (GTP) is/are utilized as a co-factor and/or a reacting molecule, provided that one or more molecules of ATP is/are utilized for the biosynthesis of the GTP. Specifically, for example, an ATP-dependent biosynthetic pathway can be a pathway for the biosynthesis of a chosen substance in which one or more molecules of GTP is/are utilized as a co-factor and/or a reacting molecule, wherein the molecule(s) of GTP is/are a result of the de novo pathway for purine nucleotides and nucleosides biosynthesis, if starting from 5-phosphoribosyl-1-pyrophosphate (PRPP). The chosen substance referred to in the description of the ATP-dependent biosynthetic pathway can be regarded as a target substance.

The phrase "ATP-dependent biosynthetic pathway" can also refer to a biosynthetic pathway that requires one or more molecules of a substance that can be used interchangeably to one or more molecules of ATP for the biosynthesis of a chosen substance, if starting from a carbon source. Examples of "a substance that can be used interchangeably to one or more molecules of ATP" can include, but are not limited to, an aforementioned GTP, a reduced nicotinamide adenine dinucleotide (NADH), a reduced nicotinamide adenine dinucleotide phosphate (NADPH), a reduced flavin adenine dinucleotide (FADH, $FADH_2$), acetyl co-enzyme A (acetyl-CoA), phosphoenolpyruvate (PEP), and combinations of these. That is, the phrase "utilization of ATP" is not necessarily limited to direct utilization of ATP per se, but can include indirect utilization of ATP, such as utilization of "a substance that can be used interchangeably to one or more molecules of ATP".

Most biosynthetic pathways, also referred to as "anabolic pathways", in animal cells and non-animal cells such as, for example, plant, yeast, and bacterial cells involve the use of ATP for the synthesis of macromolecules and other cellular constituents (so-called metabolites) (see, for example, Geoffrey M. Cooper, The Cell: A Molecular Approach, The Biosynthesis of Cell Constituents, $2^{nd}$ ed., Boston University, Sunderland (Mass.): Sinauer Associates, 2000). For example, one of the most ATP-demanding cellular process in *E. coli* is the formation of biomass. The biomass includes mainly macromolecules such as deoxyribonucleic acid (DNA), ribonucleic acid (RNA), proteins, lipids, and carbohydrates which are synthesized and localized in a cell as a result of independent reactions such as i) assembly reactions in which the macromolecules are modified and transported to prespecified locations in the cell, and associate to form cellular structures such as the cell wall, membranes, nucleus, and so forth, ii) polymerization reactions in which cellular substances (so-called building blocks) react to form polymeric chains of the macromolecules, and iii) biosynthetic reactions in which the building blocks that are used in the polymerization reactions, coenzymes and various metabolic factors, including signal molecules are produced, and iv) fueling reactions in which 12 precursor metabolites (G6P, F6P, R5P, E4P, Gly3P, 3PGly, PEP, PYR, AcCoA, α-KG, SucCoA, and OAC) that are required for biosynthesis of the building blocks are produced (G. Stephanopoulos et al., In: Metabolic Engineering. Principles and Methodologies, A P 1998, pp. 22-24).

Therefore, an ATP-dependent biosynthetic pathway and a substance from this pathway are not limited in any way, so long as the substance can be produced as a target substance using the pathway as described herein. Moreover, the bacterium as described herein which can be used in the method as described herein is not limited in any way, so long as the bacterium harbors, at least, one ATP-dependent biosynthetic pathway of a target substance. Examples of ATP-dependent biosynthetic pathway can include, but are not limited to, the biosynthetic pathways for the biosynthesis of amino acids, nucleosides, nucleotides, isoprenoids, and peptides, in which pathways one or more molecules of ATP is/are utilized by a bacterium. Therefore, examples of a target substance can include, but are not limited to, an amino acid, a nucleoside, a nucleotide, an isoprenoid, a peptide, and so forth, and a combination of these, so long as the target substance can be a substance from an ATP-dependent biosynthetic pathway. An amino acid, a nucleoside, a nucleotide, an isoprenoid, and a peptide that can be a target substance can also be referred to as "a target amino acid", "a target nucleoside", "a target nucleotide", "a target isoprenoid", and "a target peptide", respectively.

It is known that the biosynthesis of amino acids from a carbon source requires one or more molecules of ATP. For example, the biosynthesis of L-glutamic acid from alpha-ketoglutarate (α-KG) requires 1 molecule of ATP, if the glutamine synthetase-glutamate synthase (GOGAT)-dependent pathway is utilized by a bacterium (Helling R. B., Pathway choice in glutamate synthesis in *Escherichia coli*, J. Bacteriol., 1998, 180(17): 4571-4575). Furthermore, for example, 6 molecules of ATP are required to synthesize one molecule of histidine from ribose-5-phosphate (Ru5P) in *E. coli* (G. Stephanopoulos et al., In: Metabolic Engineering. Principles and Methodologies, A P 1998, Table S1; for the requirement of ATP for the biosynthesis of histidine in a coryneform bacterium, see, for example, Kulis-Horn R. K. et al., Histidine biosynthesis, its regulation and biotechnological application in *Corynebacterium glutamicum*, Microb. Biotechnol., 2014, 7(1):5-25). Furthermore, for example, methionine is considered as the most expensive amino acid in terms of the number of ATP molecules (typically, 20) consumed per one molecule of produced methionine, if starting from oxaloacetic acid (OAA) (G. Stephanopoulos et al., In: Metabolic Engineering. Principles and Methodologies, A P 1998, Table S1; Kaleta C. et al., Metabolic costs of amino acid and protein production in *Escherichia coli*, Biotechnol. J., 2013, 8(9):1105-1114). Furthermore, for example, as for the biosynthesis of glutamine, 1 molecule of ATP is required, if starting from glutamate, or 3 molecules of ATP are required, if starting from α-KG (Krishnaswamy P. R. et al., Studies on the mechanism of glutamine synthesis: evidence for the formation of enzyme-bound activated glutamic acid, J. Biol. Chem., 1962, 237:2932-2940; G. Stephanopoulos et al., In: Metabolic Engineering. Principles and Methodologies, A P 1998, Table S1). Furthermore, for example, despite that ATP is not required for the biosynthesis of glycine from phosphoglycerate (PG), the biosynthesis of PG itself from glucose requires 1 molecule of NADH which is equivalent to 2 molecules of ATP (G. Stephanopoulos et al., In: Metabolic Engineering. Principles and Methodologies, A P 1998, Table S1 and Table 2.10).

The biosynthesis of purine and pyrimidine nucleosides and nucleotides in plant cells and microorganisms, including Gram-positive bacteria, Gram-negative bacteria, and yeast, is also known to depend on ATP (see, for example, G. Stephanopoulos et al., In: Metabolic Engineering. Principles and Methodologies, A P 1998, Table 2.6; Hove-Jensen B. et al., Phosphoribosyl diphosphate (PRPP): biosynthesis, enzymology, utilization, and metabolic significance, Microbiol. Mol. Biol. Rev., 2016, 81(1), pii: e00040-16, doi: 10.1128/MMBR.00040-16; Zhang Y. et al., Structural biology of the purine biosynthetic pathway, Cell Mol. Life Sci., 2008, 65(23): 3699-3724; Moffatta B. A. and Ashihara H., Purine and pyrimidine nucleotide synthesis and metabolism, *Arabidopsis* Book, 2002, 1: e0018, doi: 10.1199/tab.0018). For example, from 5 to 11 molecules of ATP are required for the biosynthesis of ribonucleotides and deoxyribonucleotides from OAA or phosphoglyceraldehyde (PGA) and pentosophosphate (G. Stephanopoulos et al., In: Metabolic Engineering. Principles and Methodologies, A P 1998, Table 2.6).

The mevalonate pathway for the biosynthesis of isopentyl pyrophosphate (IPP) and dimethylallyl pyrophosphate (DMAPP), which are the precursors for isoprenoid synthesis including an isoprene monomer, requires several molecules of ATP in order to activate intermediate compounds starting from acetyl-CoA (see, for example, Miziorko H. M., Enzymes of the mevalonate pathway of isoprenoid biosynthesis, Arch. Biochem. Biophys., 2011, 505(2):131-143).

As for the biosynthesis of peptides, incorporation of each L-amino acid residue into a peptide chain requires the hydrolysis of one molecule of ATP to adenosine 5'-monophosphate (AMP) (that is, the energy that is equivalent to the hydrolysis of two molecules of ATP to two molecules of ADP) and two molecules of guanosine 5'-triphosphate (GTP) (Dennis M. Bier, The Role of Protein and Amino Acids in Sustaining and Enhancing Performance: The Energy Costs of Protein Metabolism: Lean and Mean on Uncle Sam's Team; Institute of Medicine (US) Committee on Military Nutrition Research, Washington (D.C.), Nat. Acad. Press (US), 1999). Moreover, about 0.3 molecules of ATP per one L-amino acid residue incorporated are required for, in particular, the synthesis of mRNA and proofreading (Ingraham J. L. et al., Growth of the bacterial cell. Sunderland: Sinnauer Associated, 1983).

Examples of amino acids that can each be a target substance include amino acids in L-form. An amino acid in L-form can also be referred to as "an L-amino acid". An L-amino acid that can be a target substance can also be referred to as "a target L-amino acid".

The bacterium can produce a target L-amino acid either alone or as a mixture of the target L-amino acid and one or more kinds of amino acids that are different from the target L-amino acid. That is, examples of the "other substance" include amino acids that are different from the target L-amino acid. Examples of amino acids that are different from a target L-amino acid include L-amino acids other than the target L-amino acid. An L-amino acid other than a target L-amino acid can also be referred to as "a non-target L-amino acid".

Examples of L-amino acids, which can each be a target or non-target L-amino acid, can include, but are not limited to, L-alanine, L-arginine, L-asparagine, L-aspartic acid, L-citrulline, L-cysteine, L-glutamic acid, L-glutamine, glycine, L-histidine, L-isoleucine, L-leucine, L-lysine, L-methionine, L-ornithine, L-phenylalanine, L-proline, L-serine, L-threonine, L-tryptophan, L-tyrosine, and L-valine. In other words, a target L-amino acid and a non-target L-amino acid each can be selected, for example, from these L-amino acids.

An L-amino acid may be an aromatic L-amino acid or a non-aromatic L-amino acid.

The phrase "an aromatic L-amino acid" can include, for example, L-phenylalanine, L-tryptophan, and L-tyrosine. As L-histidine has an aromatic moiety such as imidazole ring, the phrase "aromatic L-amino acid" can also include, besides the aforementioned aromatic L-amino acids, L-histidine.

The phrase "a non-aromatic L-amino acid" can include, for example, L-alanine, L-arginine, L-asparagine, L-aspartic acid, L-citrulline, L-cysteine, L-glutamic acid, L-glutamine, glycine, L-isoleucine, L-leucine, L-lysine, L-methionine, L-ornithine, L-proline, L-serine, L-threonine, and L-valine. As the biosynthetic pathway of aromatic amino acids such as L-phenylalanine, L-tryptophan, and L-tyrosine is different from the biosynthetic pathway of L-histidine, the phrase "non-aromatic L-amino acid" can also include, besides the aforementioned non-aromatic L-amino acids, L-histidine.

An L-amino acid can belong to one or more L-amino acid families. As an example, an L-amino acid can belong to the glutamate family including L-arginine, L-glutamic acid, L-glutamine, and L-proline; the serine family including L-cysteine, glycine, and L-serine; the aspartate family including L-asparagine, L-aspartic acid, L-isoleucine, L-lysine, L-methionine, and L-threonine; the pyruvate family including L-alanine, L-isoleucine, L-valine, and L-leucine; and the aromatic family including L-phenylalanine, L-tryptophan, and L-tyrosine. As some L-amino acids can be intermediate amino acids in a biosynthetic pathway of a target L-amino acid, the aforementioned families of amino acids may also include other L-amino acids, for example, non-proteinogenic L-amino acids. For example, L-citrulline and L-ornithine are amino acids from the L-arginine biosynthetic pathway. Therefore, the glutamate family may include L-arginine, L-citrulline, L-glutamic acid, L-glutamine, L-ornithine, and L-proline.

Furthermore, the bacterium can produce a target L-amino acid either alone or as a mixture of the target L-amino acid and one or more kinds of other organic acids. That is, examples of the "other substance" include other organic acids. Examples of organic acids include, but are not limited to, carboxylic acids. Examples of carboxylic acids include, but are not limited to, formic acid, acetic acid, citric acid, butyric acid, lactic acid, and propionic acid, and derivatives of these.

The phrases "L-amino acid" and "carboxylic acid" can refer not only to an L-amino acid and a carboxylic acid in a free form, but may also include a derivative form thereof, such as a salt, a hydrate, an adduct, or a combination of these. An adduct can be a compound formed by the L-amino acid or the carboxylic acid in combination with another organic or inorganic compound. Hence, the phrases "an L-amino acid" and "a carboxylic acid" can mean, for example, an L-amino acid and a carboxylic acid in a free form, a derivative form, or a mixture of these. The phrases "an L-amino acid" and "a carboxylic acid" can particularly mean, for example, an L-amino acid and a carboxylic acid in a free form, a salt thereof, or a mixture of these. The phrases "an L-amino acid" and "a carboxylic acid" can include, for example, sodium, potassium, ammonium, mono-, di- and trihydrate, mono- and dichlorhydrate, and so forth salts of these. The descriptions concerning salts of these substances can also be applied similarly to other target substances. Unless otherwise stated, the phrases "an L-amino acid" and "a carboxylic acid" without referring to hydration, such as the phrases "an L-amino acid or a carboxylic acid in a free form" and "a salt of an L-amino acid or a carboxylic acid", each can include both an anhydrate and a hydrate thereof.

Examples of a nucleoside that can be a target substance include a pyrimidine nucleoside and a purine nucleoside. Examples of a pyrimidine nucleoside include a pyrimidine ribonucleoside. Examples of a purine nucleoside include a purine ribonucleoside. Specific examples of nucleosides include, but are not limited to, cytidine, thymidine, uridine, 5-aminoimidazole-4-carboxamide ribonucleoside (AICAr), adenosine, guanosine, xanthosine, and inosine. Cytidine, thymidine, and uridine can be examples of pyrimidine nucleosides. Adenosine, guanosine, xanthosine, and inosine can be examples of purine nucleosides.

Examples of a nucleotide that can be a target substance include, but are not limited to, a phosphate ester of a nucleoside as described herein, in which at least one phosphate group, such as a monophosphate group, a diphosphate group, or a triphosphate group, is coupled to a hydroxyl group of the sugar moiety of the nucleoside. Specific examples of nucleotides include a pyrimidine nucleotide and a purine nucleotide. Examples of a pyrimidine nucleotide include a pyrimidine ribonucleotide. Examples of a purine nucleotide include a purine ribonucleotide. More specific examples of nucleotides include, but are not limited to, a nucleoside 5'-monophosphate, a nucleoside 5'-diphosphate, and a nucleoside 5'-triphosphate. Examples of a nucleoside 5'-monophosphate include, for example, uridine 5'-monophosphate (also referred to as "5'-uridylic acid" or "UMP"), 5-aminoimidazole-4-carboxamide ribonucleotide (AICAR), adenosine 5'-monophosphate (also referred to as "5'-adenylic acid" or "AMP"), guanosine 5'-monophosphate (also referred to as "5'-guanylic acid" or "GMP"), xanthosine 5'-monophosphate (also referred to as "5'-xanthylic acid" or "XMP"), and inosine 5'-monophosphate (also referred to as "5'-inosinic acid" or "IMP"). Examples of a nucleoside 5'-diphosphate and a nucleoside 5'-triphosphate include derivatives of a nucleoside 5'-monophosphate as described herein, which derivatives have respectively a diphosphate group and a triphosphate group instead of a monophosphate group, such as, for example, adenosine 5'-diphosphate (ADP) and adenosine 5'-triphosphate (ATP). Phosphate esters of pyrimidine nucleosides, such as UMP, can be examples of pyrimidine nucleotides. Phosphate esters of purine nucleosides, such as AMP, GMP, XMP, IMP, ADP, and ATP, can be examples of purine nucleotides.

The term "a nucleotide" is not particularly limited to the nucleotides that are described herein, but may also include salts of the nucleotides. The salts may include, for example, as one or more counter-ions, i) inorganic ions such as metal-ions, for example, sodium, potassium, lithium, calcium, magnesium ions, and so forth, or ammonium ions; or ii) organic ions such as derivatives of the ammonium ion having one, two, three, or four hydrogen atoms substituted with alkyl, alkenyl, alkynyl and/or aryl group(s), and the like; or iii) a combination of i) and ii). The descriptions concerning salts of nucleotides can also be applied similarly to other target substances.

Examples of an isoprenoid that can be a target substance include, virtually, any compound that has one or more isoprene units and is described by the molecular formula $(C_5H_8)_n$, wherein "n" is natural number (for example, 1, 2, 3, 4, 5, 6, 7, 8, or larger). More than 30,000 kinds of isoprenoid compounds have been identified. Isoprenoids are also known as terpenoids. Terpenoids are structurally similar to terpenes. The difference between terpenes and terpenoids is that terpenes are hydrocarbons, whereas terpenoids may contain additional functional groups. That is, terpenes can be modified by substituting one or more hydrogen atoms for one or more functional groups or rearranging the carbon skeleton to obtain terpenoids. Terpenoids can be classified by the number of isoprene units (n) or carbon atoms (C) present in the molecule: isoprene (n=1, C=5), monoterpenoids (n=2, C=10), sesquiterpenoids (n=3, C=15), diterpenoids (n=4, C=20), sesterpenoids (n=5, C=25), triterpenoids (n=6, C=30), tetraterpenoids (n=8, C=40), and polyterpenoids (n>8, C>40). Examples of monoterpenoids include geraniol, limonene, linalool, menthol, bornane, norbornane, and α-pinene. Examples of sesquiterpenoids include nerolidol, farnesol, valencene, bisabolane, and cadinene. Examples of diterpenoids include phytol and vitamin A. Examples of sesterpenoids include β-cadinene and abscisic acid. Examples of triterpenoids include oleanolic acid and maslinic acid. Examples of tetraterpenoids include carotenoids. There are more than 1100 known carotenoids which can be classified into two classes such as carotenes and xanthophylls. Examples of carotenoids include α-carotene, β-carotene, γ-carotene, lycopene, lutein, meso-zeaxanthin, zeaxanthin, astaxanthin, alloxanthin, cryptomonaxanthin, phleixanthophyll, torularhodinaldehyde, echinenone, and so forth. A particular example of the isoprenoid is isoprene (2-methyl-1,3-butadiene).

Examples of a peptide that can be a target substance include, virtually, any peptide that can be synthesized in and/or produced by a bacterium. A particular example of the peptide can be a peptide that can be synthesized in and/or produced by the bacterium that can be used in the method as described herein. The phrase "peptide" as used herein can refer to a peptide of any length so long as the peptide can be synthesized in and/or produced by a bacterium. The peptide may be a dipeptide, a tripeptide, a tetrapeptide, or a peptide having a longer length such as a length of 10 or more amino acid residues, or 50 or more amino acid residues. Examples of a peptide include an oligopeptide, a polypeptide, and a protein. It is generally, but not obligatory, accepted in the art that a peptide composed of 10 or less amino acid residues is referred to as "oligopeptide", and a peptide composed of more than 10 amino acid residues is referred to as "polypeptide" (see, for example, D. Gonzalez de Llano and C. Polo Sanchez, Peptides. In Encyclopedia of Food Sciences and Nutrition, $2^{nd}$ ed., Elsevier Science Ltd., 2003, pp. 4468-4473). The phrase "peptide" including oligopeptides and polypeptides can be used interchangeably or equivalently to the phrase "protein". Meanwhile, proteins can be normally composed of, for example, more than 10 amino acid residues, or more than 50 amino acid residues. Therefore, in particular, proteins may be examples of polypeptides. The peptide may be a linear peptide, a branched peptide, a circular peptide, or a combination of these. The peptide may be a monomeric peptide or a multimeric peptide. The peptide may be a secretory peptide or a non-secretory peptide.

The peptide may be a peptide derived from the host bacterium or a heterogenous peptide. The term "heterologous peptide" can refer to a peptide exogenous to the host bacterium that produce the peptide, i.e. exogenous to the bacterium as described herein. The peptide may be, for example, a peptide having a naturally-occurring amino acid sequence, a peptide having a modified amino acid sequence thereof, or a peptide having an artificially-designed amino acid sequence. The peptide may be, for example, a peptide derived from a microorganism, a peptide derived from a plant, a peptide derived from an animal, or a peptide derived from a virus.

Specific examples of the peptide include, for example, enzymes, physiologically active peptides, receptor peptides, antigenic peptides, and any other peptides.

Examples of the enzymes include, for example, cellulase, transglutaminase, protein glutaminase, isomaltodextranase, protease, endopeptidase, exopeptidase, aminopeptidase, carboxypeptidase, collagenase, and chitinase.

Examples of the physiologically active peptides include, for example, growth factors, hormones, cytokines, and antibody-related molecules.

Examples of the growth factors include, for example, epidermal growth factor (EGF), insulin-like growth factor-1 (IGF-1), transforming growth factor (TGF), nerve growth factor (NGF), brain-derived neurotrophic factor (BDNF), vesicular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Examples of the hormones include, for example, insulin, glucagon, somatostatin, human growth hormone (hGH), parathyroid hormone (PTH), calcitonin, and exenatide.

Examples of the cytokines include, for example, interleukins, interferons, and tumor necrosis factors (TNFs).

Furthermore, the physiologically active peptide may be an intact peptide, or may be a fragment of a peptide. Examples of a fragment of a peptide include, for example, a fragment having physiological activity. Specific examples of a fragment having physiological activity include, for example, teriparatide, a physiologically active peptide having the N-terminal 34 amino acid residues of parathyroid hormone (PTH).

The term "antibody-related molecule" can refer to a peptide containing a molecular species having a single domain or a combination of two or more domains such as domains constituting a complete antibody. Examples of the domains constituting a complete antibody include heavy chain domains VH, CH1, CH2, and CH3, and light chain domains VL and CL. The antibody-related molecule may be a monomeric peptide, or may be a multimeric peptide, so long as it contains the above-mentioned molecular species. When the antibody-related molecule is a multimeric peptide, it may be a homo-multimer having a single kind of subunit, or may be a hetero-multimer having two or more kinds of subunits. Specific examples of the antibody-related molecules include, for example, complete antibody, Fab, F(ab'), F(ab')$_2$, Fc, dimer consisting of a heavy chain (H chain) and a light chain (L chain), Fc-fusion protein, heavy chain (H chain), light chain (L chain), light chain Fv (scFv), sc(Fv)$_2$, disulfide-bonded Fv (sdFv), diabody, and VHH fragment (Nanobody (registered trademark)). More specific examples of the antibody-related molecules include, for example, Trastuzumab.

Examples of the receptor peptides include, for example, receptor peptides for any of physiologically active peptides and other physiologically active substances. Examples of the other physiologically active substances include, for example, neurotransmitters such as dopamine. The receptor peptide may also be an orphan receptor of which the corresponding ligand is not known.

The antigen peptides are not particularly limited, so long as they can induce an immune response. The antigen peptides can be appropriately selected depending on the intended object of the immune response.

Examples of the other peptides include liver-type fatty acid-binding protein (LFABP), fluorescent protein, immunoglobulin-binding protein, albumin, fibroin-like protein, and extracellular protein. Examples of the fluorescent protein include Green Fluorescent Protein (GFP). Examples of the immunoglobulin-binding protein include Protein A, Protein G, and Protein L. Examples of albumin include human serum albumin. Examples of the fibroin-like protein include those disclosed in WO2017/090665 and WO2017/171001. Examples of the extracellular protein include fibronectin, vitronectin, collagen, osteopontin, laminin, and partial sequences thereof. Examples of the partial sequences include laminin E8, which is an E8 fragment of laminin.

The peptide can be a peptide having a known amino acid sequence of any of the peptides exemplified above. The peptide can also be a peptide having a variant sequence of a known amino acid sequence of any of the peptides exemplified above. As for such a variant sequence, the descriptions concerning variants of a protein having H$^+$-translocating membrane-bound pyrophosphatase activity described herein can be similarly applied.

Hereinafter, the target substance-producing bacteria, such as L-amino acid-producing bacteria, nucleoside-producing bacteria, nucleotide-producing bacteria, isoprenoid-producing bacteria, and peptide-producing bacteria, and methods for imparting or enhancing a target substance-producing ability, such as an L-amino acid-producing ability, nucleoside-producing ability, nucleotide-producing ability, isoprenoid-producing ability, and peptide-producing ability, will be specifically exemplified. All of the properties of target substance-producing bacteria and modifications for imparting or enhancing a target substance-producing ability may be used independently or in any appropriate combination.

Methods for imparting or enhancing a target substance-producing ability are not particularly limited. As methods for imparting or enhancing a target substance-producing ability, for example, known methods can be used. Methods for imparting or enhancing L-amino acid-producing ability are disclosed in, for example, WO2015/060391 and WO2018/030507. Methods for imparting or enhancing a nucleoside-producing ability or a nucleotide-producing ability are disclosed in, for example, WO2015/060391, JP2001-149068A, and JPH02-002349A. Methods for imparting or enhancing an isoprenoid-producing ability are disclosed in, for example, WO2012/149491, WO2016/084963, and WO2015/147341. Methods for imparting or enhancing an ability to produce a peptide are disclosed in, for example, WO2013/065869, WO2013/065772, WO2013/118544, WO2016/171224, WO2018/074578, WO2018/074579, WO2013/062029, and JP patent 4730302, in which peptides such as oligopeptides and polypeptides are collectively referred to as "proteins".

<L-Amino Acid-Producing Bacteria>

To impart or enhance an L-amino acid-producing ability, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. Also, in the breeding of L-amino acid-producing bacteria, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain having an L-amino acid-producing ability can be obtained by subjecting a parental strain or wild-type strain to a usual mutagenesis treatment, and then selecting a strain exhibiting autotrophy, analogue resistance, or a metabolic regulation mutation, and having an L-amino acid-producing ability from the obtained mutant strains. Examples of the usual mutagenesis treatment include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. Methods for overexpressing a gene encoding a protein having H$^+$-translocating membrane-bound pyrophosphatase activity described below can be applied similarly to enhancing the activity of an enzyme or enhancing the expression of a gene encoding the enzyme.

Furthermore, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" referred to herein includes an enzyme involved in decomposition of the objective amino acid. Methods for attenuating the expression of a gene encoding a protein having inorganic pyrophosphatase activity described below can be applied similarly to reducing the activity of an enzyme or reducing the expression of a gene encoding the enzyme.

Hereinafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-Producing Bacteria>

Examples of methods for imparting or enhancing L-glutamic acid-producing ability include, for example, a method of modifying a bacterium so that the bacterium has an increased activity or activities of one or more kinds of enzymes such as the L-glutamic acid biosynthesis enzymes. Examples of such enzymes include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgml), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are examples of genes encoding the enzymes (the same shall apply to the same occasions hereinafter). It is preferable to enhance the activity or activities of one or more kinds of enzymes such as, for example, glutamate dehydrogenase, citrate synthase, phosphoenol pyruvate carboxylase, and methylcitrate synthase, among these enzymes.

Examples of strains belonging to the family Enterobacteriaceae and modified so that the expression of the citrate synthase gene, phosphoenolpyruvate carboxylase gene, and/or glutamate dehydrogenase gene are increased include those disclosed in EP1078989A, EP955368A, and EP952221A. Furthermore, examples of strains belonging to the family Enterobacteriaceae and modified so that the expression of a gene of the Entner-Doudoroff pathway (edd, eda) is increased include those disclosed in EP1352966B. Examples of coryneform bacteria modified so that the expression of the glutamate synthetase gene (gltBD) is increased include those disclosed in WO99/07853.

Examples of methods for imparting or enhancing L-glutamic acid-producing ability also include, for example, a method of modifying a bacterium so that the bacterium has a reduced activity or activities of one or more kinds of enzymes such as the enzymes that catalyze a reaction branching away from the biosynthesis pathway of L-glutamic acid to generate a compound other than L-glutamic acid. Examples of such enzymes include, but are not particularly limited to, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). It is preferable to reduce or delete, for example, the α-ketoglutarate dehydrogenase activity, among these enzymes.

*Escherichia* bacteria having a reduced α-ketoglutarate dehydrogenase activity or are deficient in the α-ketoglutarate dehydrogenase activity, and methods for obtaining them are described in U.S. Pat. Nos. 5,378,616 and 5,573,945. Furthermore, methods for reducing or deleting the α-ketoglutarate dehydrogenase activity of Enterobacteriaceae bacteria such as *Pantoea* bacteria, *Enterobacter* bacteria, *Klebsiella* bacteria, and *Erwinia* bacteria are disclosed in U.S. Pat. Nos. 6,197,559, 6,682,912, 6,331,419, and 8,129,151, and WO2008/075483. Specific examples of *Escherichia* bacteria having a reduced α-ketoglutarate dehydrogenase activity or deficient in the α-ketoglutarate dehydrogenase activity include the following strains.

E. coli W3110sucA::Km$^r$
E. coli AJ12624 (FERM BP-3853)
E. coli AJ12628 (FERM BP-3854)
E. coli AJ12949 (FERM BP-4881)

E. coli W3110sucA::Km$^r$ is a strain obtained by disrupting the sucA gene encoding α-ketoglutarate dehydrogenase of E. coli W3110. This strain is completely deficient in the α-ketoglutarate dehydrogenase activity.

Coryneform bacteria in which the α-ketoglutarate dehydrogenase activity is reduced or eliminated, and methods for obtaining those are disclosed in WO2008/075483. Specific examples of coryneform bacteria in which the α-ketoglutarate dehydrogenase activity is reduced or eliminated include, for example, the following strains:

*Corynebacterium glutamicum* (*Brevibacterium lactofermentum*) L30-2 strain (Japanese Patent Laid-open (Kokai) No. 2006-340603)

*Corynebacterium glutamicum* (*Brevibacterium lactofermentum*) AS strain (WO95/34672)

*Corynebacterium glutamicum* (*Brevibacterium lactofermentum*) AJ12821 (FERM BP-4172, French Patent No. 9401748)

*Corynebacterium glutamicum* (*Brevibacterium flavum*) AJ12822 (FERM BP-4173, French Patent No. 9401748)

*Corynebacterium glutamicum* AJ12823 (FERM BP-4174, French Patent No. 9401748) Examples of L-glutamic acid-producing bacteria and parental strains for deriving them also include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain is a strain isolated from soil in Iwata-shi, Shizuoka-ken, Japan as a strain that can proliferate in a low pH medium containing L-glutamic acid and a carbon source. The SC17 strain is a strain selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depository (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Furthermore, examples of L-glutamic acid-producing bacteria and parental strains for deriving them also include *Pantoea* bacteria having a reduced α-ketoglutarate dehydrogenase activity or are deficient in the α-ketoglutarate dehydrogenase activity. Examples of such strains include the AJ13356 strain (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusaka-matari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusaka-matari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, they are referred to as *Pantoea ananatis* in this specification.

Examples of L-glutamic acid-producing bacteria and parental strains for deriving them also include auxotrophic mutant strains. Specific examples of auxotrophic mutant strains include, for example, *E. coli* VL334thrC$^+$ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is an L-isoleucine-auxotrophic L-glutamic acid-producing bacterium obtained by introducing a wild-type allele of the thrC gene into the VL334 strain. The wild-type allele of the thrC gene was introduced by the method of general transduction using a bacteriophage P1 grown on the wild-type *E. coli* K-12 strain (VKPM B-7) cells.

Examples of L-glutamic acid-producing bacteria and parental strains for deriving them also include strains having resistance to an aspartic acid analogue. Such strains can also be deficient in the α-ketoglutarate dehydrogenase activity. Specific examples of strains having resistance to an aspartic acid analogue and are deficient in the α-ketoglutarate dehydrogenase activity include, for example, *E. coli* AJ13199 (FERM BP-5807, U.S. Pat. No. 5,908,768), *E. coli* FFRM P-12379, which additionally has a reduced L-glutamic acid-decomposing ability (U.S. Pat. No. 5,393,671), and *E. coli* AJ13138 (FERM BP-5565, U.S. Pat. No. 6,110,714).

Examples of methods for imparting or enhancing L-glutamic acid-producing ability also include, for example, a method of enhancing the expression of an L-glutamic acid secretion gene, such as yhfK gene (WO2005/085419) or ybjL gene (WO2008/133161).

Furthermore, examples of methods for imparting or enhancing L-glutamic acid-producing ability to or in coryneform bacteria also include methods of imparting resistance to an organic acid analogue, respiratory inhibitor, or the like, and methods of imparting sensitivity to a cell wall synthesis inhibitor. Specific examples of such methods include, for example, the method of imparting monofluoroacetic acid resistance (Japanese Patent Laid-open (Kokai) No. 50-113209), the method of imparting adenine resistance or thymine resistance (Japanese Patent Laid-open (Kokai) No. 57-065198), the method of attenuating urease (Japanese Patent Laid-open (Kokai) No. 52-038088), the method of imparting malonic acid resistance (Japanese Patent Laid-open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-open (Kokai) No. 57-2689), the method of imparting guanidine resistance (Japanese Patent Laid-open (Kokai) No. 56-35981), the method of imparting sensitivity to penicillin (Japanese Patent Laid-open (Kokai) No. 4-88994), and so forth.

Specific examples of such resistant or sensitive bacteria include the following strains:

*Corynebacterium glutamicum* (*Brevibacterium flavum*) AJ3949 (FERM BP-2632, Japanese Patent Laid-open (Kokai) No. 50-113209)

*Corynebacterium glutamicum* AJ11628 (FERM P-5736, Japanese Patent Laid-open (Kokai) No. 57-065198)

*Corynebacterium glutamicum* (*Brevibacterium flavum*) AJ11355 (FERM P-5007, Japanese Patent Laid-open (Kokai) No. 56-1889)

*Corynebacterium glutamicum* AJ11368 (FERM P-5020, Japanese Patent Laid-open (Kokai) No. 56-1889)

*Corynebacterium glutamicum* (*Brevibacterium flavum*) AJ11217 (FERM P-4318, Japanese Patent Laid-open (Kokai) No. 57-2689)

*Corynebacterium glutamicum* AJ11218 (FERM P-4319, Japanese Patent Laid-open (Kokai) No. 57-2689)

*Corynebacterium glutamicum* (*Brevibacterium flavum*) AJ11564 (FERM BP-5472, Japanese Patent Laid-open (Kokai) No. 56-140895)

*Corynebacterium glutamicum* (*Brevibacterium flavum*) AJ11439 (FERM BP-5136, Japanese Patent Laid-open (Kokai) No. 56-35981)

*Corynebacterium glutamicum* H7684 (FERM BP-3004, Japanese Patent Laid-open (Kokai) No. 04-88994)

*Corynebacterium glutamicum* (*Brevibacterium lactofermentum*) AJ11426 (FERRM P-5123, Japanese Patent Laid-open (Kokai) No. 56-048890)

*Corynebacterium glutamicum* AJ11440 (FERM P-5137, Japanese Patent Laid-open (Kokai) No. 56-048890)

*Corynebacterium glutamicum* (*Brevibacterium lactofermentum*) AJ11796 (FERM P-6402, Japanese Patent Laid-open (Kokai) No. 58-158192)

Furthermore, examples of methods for imparting or enhancing L-glutamic acid-producing ability to or in coryneform bacteria also include a method of enhancing the expression of yggB gene and a method of introducing a mutant yggB gene having a mutation in the coding region (WO2006/070944). That is, the bacterium may have been modified so that the expression of yggB gene is increased, or may have been modified so as to harbor (have) a mutant yggB gene. Examples of the mutation contained in the mutant yggB gene include mutation on the C-terminus side and mutation in a transmembrane region (WO2006/070944).

The methods for imparting or enhancing L-glutamic acid-producing ability can also be effective for imparting or enhancing an ability to produce L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid may have, as required, such a property possessed by an L-glutamic acid-producing bacterium as mentioned above. For example, a bacterium having an ability to produce any of these L-amino acids that are biosynthesized via L-glutamic acid may have been modified so that the activity of α-ketoglutarate dehydrogenase and/or succinate dehydrogenase is reduced.

<L-Glutamine-Producing Bacteria>

Examples of the method for imparting or enhancing L-glutamine-producing ability include, for example, a method of modifying a bacterium so that the activity or activities of one or more kinds of enzymes such as the L-glutamine biosynthesis enzymes are enhanced. Examples of such enzymes include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP1229121).

Examples of the method for imparting or enhancing L-glutamine-producing ability also include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes include, but are not particularly limited to, glutaminase. Specific examples of L-glutamine-producing bacteria and parent strains for deriving them include, for example, coryneform bacteria in which the activity or activities of glutamate dehydrogenase (gdhA) and/or glutamine synthetase (glnA) (EP1229121, EP1424398) are enhanced, and coryneform bacteria in which the glutaminase activity (Japanese Patent Laid-open (Kokai) No. 2004-187684) is reduced. Examples of L-glutamine-producing bacteria and parental strains for deriving them include a strain belonging to the genus *Escherichia* and having a mutant glutamine synthetase in which the tyrosine residue of the position 397 of glutamine synthetase has been replaced with another amino acid residue (US2003-0148474A).

Examples of the methods for imparting or enhancing L-glutamine-producing ability to or in coryneform bacteria also include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria having L-glutamine-producing ability include, for example, the following strains:

Corynebacterium glutamicum (Brevibacterium flavum) AJ11573 (FERM P-5492, Japanese Patent Laid-open (Kokai) No. 56-151495)

Corynebacterium glutamicum (Brevibacterium flavum) AJ11576 (FERM BP-10381, Japanese Patent Laid-open (Kokai) No. 56-151495)

Corynebacterium glutamicum (Brevibacterium flavum) AJ12212 (FERM P-8123, Japanese Patent Laid-open (Kokai) No. 61-202694)

<L-Proline-Producing Bacteria>

Examples of methods for imparting or enhancing L-proline-producing ability include, for example, a method of modifying a bacterium so that the bacterium has an increased activity or activities of one or more kinds of enzymes such as the L-proline biosynthesis enzymes. Examples of such enzymes include glutamate-5-kinase (proB), γ-glutamylphosphate reductase, and pyroline-5-carboxylate reductase (putA). For enhancing the activity of such an enzyme, for example, the proB gene encoding a glutamate-5-kinase desensitized to feedback inhibition by L-proline (German Patent No. 3127361) can be used.

Examples of methods for imparting or enhancing L-proline-producing ability also include, for example, a method of modifying a bacterium so that the bacterium has a reduced activity of an enzyme involved in decomposition of L-proline. Examples of such an enzyme include proline dehydrogenase and ornithine aminotransferase.

Specific examples of L-proline-producing bacteria and parental strains for deriving them include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPM B-8011), which is a 3,4-dehydroxyproline and azetidine-2-carboxylate resistant strain, and *E. coli* 702ilvA strain (VKPM B-8012), which is an ilvA gene-deficient strain of the 702 strain (EP1172433).

<L-Threonine-Producing Bacteria>

Examples of methods for imparting or enhancing L-threonine-producing ability include, for example, a method of modifying a bacterium so that the bacterium has an increased activity or activities of one or more kinds of enzymes such as the L-threonine biosynthesis enzymes. Examples of such enzymes include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is preferable to enhance activity or activities of one or more kinds of enzymes such as aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed include, for example, the *E. coli* TDH6 strain, which is deficient in the threonine dehydrogenase activity (Japanese Patent Laid-open (Kokai) No. 2001-346578).

The activities of the L-threonine biosynthesis enzymes are inhibited by the end product, L-threonine. Therefore, for constructing L-threonine-producing strains, it is preferred that the genes of the L-threonine biosynthesis enzymes are modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under control of the repressor and promoter of λ-phage (EP0593792B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

It is preferred that the expression amount of the threonine operon that is modified so as to be desensitized to feedback inhibition by L-threonine as described above is increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting or enhancing L-threonine-producing ability also include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance include the rhtA gene (Res. Microbiol. 154:123-135 (2003)), rhtB gene (EP0994190A), rhtC gene (EP1013765A), yfiK gene, and yeaS gene (EP1016710A). Examples of methods for imparting L-threonine resistance to a host include those described in EP0994190A and WO90/04636.

Specific examples of L-threonine-producing bacteria and parental strains for deriving them include, for example, E. coli TDH-6/pVIC40 (VKPM B-3996, U.S. Pat. Nos. 5,175,107 and 5,705,371), E. coli 472T23/pYN7 (ATCC 98081, U.S. Pat. No. 5,631,157), E. coli NRRL-21593 (U.S. Pat. No. 5,939,307), E. coli FERM BP-3756 (U.S. Pat. No. 5,474,918), E. coli FERM BP-3519 and FERM BP-3520 (U.S. Pat. No. 5,376,538), E. coli MG442 (Gusyatiner et al., Genetika (in Russian), 14, 947-956 (1978)), E. coli VL643 and VL2055 (EP1149911A), and E. coli VKPM B-5318 (EP0593792B).

The VKPM B-3996 strain is a strain obtained by introducing the plasmid pVIC40 into the TDH-6 strain. The TDH-6 strain has sucrose-assimilating ability and is deficient in the thrC gene, and the ilvA gene thereof has a leaky mutation. The TDH-6 strain also has a mutation in the rhtA gene, which imparts resistance to high concentration of threonine or homoserine. The plasmid pVIC40 is a plasmid obtained by inserting the thrA*BC operon containing a mutant thrA gene encoding an aspartokinase-homoserine dehydrogenase I resistant to feedback inhibition by threonine and the wild-type thrBC genes into an RSF1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 of which the regulatory region of the threonine operon is replaced with the temperature-sensitive λ-phage Cl repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene which encodes aspartokinase-homoserine dehydrogenase I of E. coli has been elucidated (nucleotide numbers 337 to 2799, GenBank accession NC_000913.2, gi: 49175990). The thrA gene is located between the thrL and thrB genes on the chromosome of E. coli K-12. The thrB gene which encodes homoserine kinase of Escherichia coli has been elucidated (nucleotide numbers 2801 to 3733, GenBank accession NC_000913.2, gi: 49175990). The thrB gene is located between the thrA and thrC genes on the chromosome of E. coli K-12. The thrC gene which encodes threonine synthase of E. coli has been elucidated (nucleotide numbers 3734 to 5020, GenBank accession NC_000913.2, gi: 49175990). The thrC gene is located between the thrB gene and the yaaX open reading frame on the chromosome of E. coli K-12. The thrA*BC operon containing a mutant thrA gene which encodes an aspartokinase-homoserine dehydrogenase I resistant to feedback inhibition by threonine and the wild-type thrBC genes can be obtained from the well-known plasmid pVIC40, which is present in the threonine-producing E. coli strain VKPM B-3996 (U.S. Pat. No. 5,705,371).

The rhtA gene of E. coli is located at 18 min on the E. coli chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and is located between the pexB and ompX genes. The unit expressing a protein encoded by the ORF1 has been designated the rhtA gene (rht: resistance to homoserine and threonine). It has also been revealed that the rhtA23 mutation that imparts resistance to high concentration of threonine or homoserine is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, California Aug. 24-29, 1997, abstract No. 457; EP1013765A).

The asd gene of E. coli has already been elucidated (nucleotide numbers 3572511 to 3571408, GenBank accession NC_000913.1, gi:16131307), and can be obtained by PCR (White, T. J., et al., Trends Genet, 5:185-189, 1989) utilizing primers prepared on the basis of the nucleotide sequence of the gene. The asd genes of other microorganisms can also be obtained in a similar manner.

The aspC gene of E. coli has also already been elucidated (nucleotide numbers 983742 to 984932, GenBank accession NC_000913.1, gi:16128895), and can be obtained by PCR utilizing primers prepared on the basis of the nucleotide sequence of the gene. The aspC genes of other microorganisms can also be obtained in a similar manner.

Furthermore, examples of coryneform bacteria having L-threonine-producing ability include, for example, Corynebacterium acetoacidophilum AJ12318 (FERM BP-1172, U.S. Pat. No. 5,188,949).

<L-Lysine-Producing Bacteria>

Examples of methods for imparting or enhancing L-lysine-producing ability include, for example, a method of modifying a bacterium so that the bacterium has an increased activity or activities of one or more kinds of enzymes such as the L-lysine biosynthesis enzymes. Examples of such enzymes include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). It is preferable to enhance the activity or activities of one or more kinds of enzymes such as, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase, among these enzymes. Furthermore, L-lysine-producing bacteria and parental strains for deriving them can express an increased level of the gene involved in energy efficiency (cyo) (EP1170376A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III desensitized to feedback inhibition by L-lysine (U.S. Pat. No. 5,932,453) may be used for enhancing the activity of this enzyme. Examples of the aspartokinase III desensitized to feedback inhibition by L-lysine include aspartokinase III derived from *Escherichia coli* and having one or more mutations such as a mutation for replacing the methionine residue at position 318 with an isoleucine residue, a mutation for replacing the glycine residue at position 323 with an aspartic acid residue, and a mutation for replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase desensitized to feedback inhibition by L-lysine may be used for enhancing the activity of this enzyme. Examples of the dihydrodipicolinate synthase desensitized to feedback inhibition by L-lysine include dihydrodipicolinate synthase derived from *Escherichia coli* and having a mutation for replacing the histidine residue at position 118 with a tyrosine residue (U.S. Pat. No. 6,040,160).

Examples of methods for imparting or enhancing L-lysine-producing ability also include, for example, a method of modifying a bacterium so that the bacterium has a reduced activity or activities of one or more kinds of enzymes such as the enzymes that catalyze a reaction branching away from the biosynthetic pathway of L-lysine to generate a compound other than L-lysine. Examples of such enzymes include, but are not particularly limited to, homoserine dehydrogenase, lysine decarboxylase (U.S. Pat. No. 5,827,698), and malic enzyme (WO2005/010175).

Furthermore, examples of methods for imparting or enhancing L-lysine-producing ability to or in coryneform bacteria also include a method of modifying the bacteria so that the activity of a lysine excretion system (lysE) is increased (WO97/23597). The lysE gene of *Corynebacterium glutamicum* ATCC 13032 corresponds to the sequence complementary to the sequence of the nucleotide numbers 1,329,712 to 1,330,413 in the genome sequence registered as Genbank Accession No. NC_006958 (VERSION NC_006958.1 GI:62388892) in the NCBI database. The LysE protein of *Corynebacterium glutamicum* ATCC 13032 is registered as GenBank accession No. YP_225551 (YP_225551.1 GI:62390149).

Examples of L-lysine-producing bacteria and parental strains for deriving them also include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of L-lysine-producing bacteria and parental strains for deriving them include *E. coli* AJ11442 (FERM BP-1543, NRRL B-12185, U.S. Pat. No. 4,346,170) and *E. coli* VL611. In these strains, aspartokinase is desensitized to feedback inhibition by L-lysine.

Specific examples of L-lysine-producing bacteria and parental strains for deriving them also include the *E. coli* WC196 strain. The WC196 strain was bred by imparting AEC resistance to the W3110 strain, which was derived from *E. coli* K-12 (U.S. Pat. No. 5,827,698). The WC196 strain was designated *E. coli* AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of L-lysine-producing bacteria include *E. coli* WC196ΔcadAΔldc and *E. coli* WC196ΔcadAΔldc/pCABD2 (WO2010/061890). The *E. coli* WC196ΔcadAΔldc is a strain constructed from the WC196 strain by disrupting the cadA and ldcC genes encoding lysine decarboxylase. The WC196ΔcadAΔldc/pCABD2 strain was constructed by introducing the plasmid pCABD2 containing lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant dapA gene derived from *Escherichia coli* and encoding a dihydrodipicolinate synthase (DDPS) having a mutation for desensitization to feedback inhibition by L-lysine (H118Y), a mutant lysC gene derived from *Escherichia coli* and encoding aspartokinase III having a mutation for desensitization to feedback inhibition by L-lysine (T352I), the dapB gene derived from *Escherichia coli* and encoding dihydrodipicolinate reductase, and the ddh gene derived from *Brevibacterium lactofermentum* and encoding diaminopimelate dehydrogenase.

Examples of L-lysine-producing bacteria also include *E. coli* AJIK01 (NITE BP-01520). The AJIK01 strain was designated *E. coli* AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Examples of coryneform bacteria having L-lysine-producing ability include, for example, the AEC-resistant mutant strains (*Corynebacterium glutamicum* (*Brevibacterium lactofermentum* AJ11082) (NRRL B-11470) strain etc., Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437, and 7-112438); mutant strains requiring an amino acid such as L-homoserine for their growth (Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (U.S. Pat. Nos. 3,708, 395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411,997).

<L-Arginine-Producing Bacteria>

Examples of methods for imparting or enhancing L-arginine-producing ability include, for example, a method of modifying a bacterium so that the bacterium has an increased activity or activities of one or more kinds of enzymes such as the L-arginine biosynthesis enzymes. Examples of such enzymes include, but are not particularly limited to, N-acetylglutamate synthase (argA), N-acetylglutamate kinase (argB), N-acetylglutamyl phosphate reductase (argc), acetylornithine transaminase (argD), acetylornithine deacetylase (argE), ornithine carbamoyl transferase (argF, argI), argininosuccinate synthetase (argG), argininosuccinate lyase (argH), ornithine acetyl transferase (argJ), and carbamoyl phosphate synthetase (carAB). As the N-acetylglutamate synthase gene (argA), for example, a gene encoding a mutant N-acetylglutamate synthase desensitized to feedback inhibition by L-arginine by substitution for the amino acid residues corresponding to the positions 15 to 19 of the wild type enzyme (EP1170361A) can be used.

Specific examples of L-arginine-producing bacteria and parental strains for deriving them include, for example, the *E. coli* 237 strain (VKPM B-7925, US2002-058315A1), derivative strains thereof introduced with the argA gene encoding a mutant N-acetyl glutamate synthase (Russian Patent Application No. 2001112869, EP1170358A1), *E. coli* 382 strain derived from the 237 strain and having an improved acetic acid-assimilating ability (VKPM B-7926, EP1170358A1), and *E. coli* 382ilvA+ strain, which is a strain obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of the Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under the accession number of VKPM B-7926.

Examples of L-arginine-producing bacteria and parental strains for deriving them also include strains having resistance to amino acid analogues, and so forth. Examples of such strains include *E. coli* mutant strains having resistance to α-methylmethionine, β-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

Examples of L-arginine-producing bacteria and parent strains for deriving them also include such coryneform bacteria as a strain deficient in ArgR, which is an arginine repressor (US2002-0045223A), and a strain in which glutamine synthetase activity is increased (US2005-0014236A).

Examples of L-arginine-producing bacteria and parent strains for deriving them also include mutant strains of coryneform bacteria, the mutant strains having resistance to an amino acid analogue or the like. Examples of such strains include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability include the following strains:

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Citrulline-Producing Bacteria and L-Ornithine-Producing Bacteria>

L-citrulline and L-ornithine are intermediates in the biosynthetic pathway of L-arginine. Hence, examples of methods for imparting or enhancing an ability to produce L-citrulline and/or L-ornithine include, for example, a method of modifying a bacterium so that the bacterium has an increased activity or activities of one or more kinds of enzymes such as the L-arginine biosynthesis enzymes. Examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyl transferase (argJ), and carbamoyl phosphate synthetase (carAB), for L-citrulline. Furthermore, examples of such enzymes include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyl transferase (argJ), for L-ornithine.

An L-citrulline-producing bacterium can be easily obtained from, for example, an L-arginine bacterium such as the E. coli 382 strain (VKPM B-7926) by decreasing the activity of argininosuccinate synthetase encoded by argG gene. Also, an L-ornithine-producing bacterium can be easily obtained from, for example, an L-arginine bacterium such as the E. coli 382 strain (VKPM B-7926) by decreasing the activity of ornithine carbamoyl transferase encoded by argF and argI genes.

Specific examples of L-citrulline-producing bacteria and parental strains for deriving them include, for example, strains belonging to the genus Escherichia, such as the E. coli strains 237/pMADS11, 237/pMADS12, and 237/pMADS13, which have a mutant N-acetylglutamate synthase (Russian patent No. 2,215,783, U.S. Pat. No. 6,790,647, and EP1170361B1), E. coli strains 333 (VKPM B-8084) and 374 (VKPM B-8086), which have carbamoyl phosphate synthetase resistant to feedback inhibition (Russian patent No. 2,264,459), and E. coli strains having an increased activity of α-ketoglutarate synthase and having a modified activity of ferredoxin NADP$^+$ reductase, pyruvate synthase, and/or α-ketoglutarate dehydrogenase (EP2133417A).

<L-Histidine-Producing Bacteria>

Examples of methods for imparting or enhancing L-histidine-producing ability include, for example, a method of modifying a bacterium so that the bacterium has an increased activity or activities of one or more kinds of enzymes such as the L-histidine biosynthesis enzymes. Examples of such enzymes include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation for conferring resistance to feedback inhibition into the gene encoding ATP phosphoribosyltransferase (hisG) (Russian Patent Nos. 2,003,677 and 2,119,536).

Specific examples of L-histidine-producing bacteria and parental strains for deriving them include, for example, strains belonging to the genus Escherichia, such as the E. coli 24 strain (VKPM B-5945, RU2003677), E. coli NRRL B-12116 to B-12121 (U.S. Pat. No. 4,388,405), E. coli H-9342 (FERM BP-6675) and H-9343 (FERM BP-6676, U.S. Pat. No. 6,344,347), E. coli H-9341 (FERM BP-6674, EP1085087), E. coli AI80/pFM201 (U.S. Pat. No. 6,258,554), E. coli FERM P-5038 and FERM P-5048, which have been introduced with a vector carrying a DNA encoding an L-histidine-biosynthesis enzyme (Japanese Patent Laid-open (Kokai) No. 56-005099), E. coli strains introduced with a gene for amino acid transport (EP1016710A), and E. coli 80 strain, which has been imparted with resistance to sulfaguanidine, DL-1,2,4-triazole-3-alanine, and streptomycin (VKPM B-7270, Russian Patent No. 2119536).

<L-Cysteine-Producing Bacteria>

Examples of methods for imparting or enhancing L-cysteine-producing ability include, for example, a method of modifying a bacterium so that the bacterium has an increased activity or activities of one or more kinds of enzymes such as the L-cysteine biosynthesis enzymes. Examples of such enzymes include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting or enhancing L-cysteine-producing ability also include, for example, a method of modifying a bacterium so that the bacterium has a reduced activity or activities of one or more kinds of enzymes such as the enzymes that catalyze a reaction branching away from the biosynthesis pathway of L-cysteine to generate a compound other than L-cysteine. Examples of such enzymes include, for example, enzymes involved in decomposition of L-cysteine. Examples of the enzymes involved in decomposition of L-cysteine include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), O-acetylserine sulfhydrylase B (cysM, Japanese Patent Laid-open (Kokai) No. 2005-245311), the malY gene product (Japanese Patent Laid-open (Kokai) No. 2005-245311), the d0191 gene product of Pantoea ananatis (Japanese Patent Laid-open (Kokai) No. 2009-232844), and cysteine desulfhydrase (aecD, Japanese Patent Laid-open (Kokai) No. 2002-233384).

Furthermore, examples of methods for imparting or enhancing L-cysteine-producing ability also include, for example, a method of enhancing the L-cysteine excretory system, and a method of enhancing the sulfate/thiosulfate transport system. Examples of proteins of the L-cysteine excretory system include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system include the proteins encoded by the cysPTWAM gene cluster.

Specific examples of L-cysteine-producing bacteria and parental strains for deriving them include, for example, E. coli JM15 transformed with different cysE alleles encoding feedback-resistant serine acetyltransferases (U.S. Pat. No. 6,218,168, Russian patent application 2003121601), E. coli W3110 having an over-expressed gene encoding a protein suitable for secretion of a cytotoxic substance (U.S. Pat. No. 5,972,663), *E. coli* strains having a reduced cysteine desulfohydrase activity (Japanese Patent Laid-open (Kokai) No. 11-155571), and *E. coli* W3110 having an increased activity of a positive transcriptional regulator for cysteine regulon encoded by the cysB gene (WO01/27307A1).

Furthermore, examples of coryneform bacteria having L-cysteine-producing ability include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Serine-Producing Bacteria>

Examples of methods for imparting or enhancing L-serine-producing ability include, for example, a method of modifying a bacterium so that the bacterium has an increased activity or activities of one or more kinds of enzymes such as the L-serine biosynthesis enzymes. Examples of such enzymes include, but are not particularly limited to, 3-phosphoglycerate dehydrogenase (serA), phosphoserine transaminase (serC), and phosphoserine phosphatase (serB) (Japanese Patent Laid-open (Kokai) No. 11-253187). 3-phosphoglycerate dehydrogenase activity can be increased by, for example, introducing a mutant serA gene encoding a mutant 3-phosphoglycerate dehydrogenase resistant to feedback inhibition by L-serine into a bacterium. The mutant 3-phosphoglycerate dehydrogenase is disclosed in, for example, U.S. Pat. No. 6,180,373.

Examples of L-serine-producing bacteria and parental strains for deriving them include, for example, coryneform bacteria resistant to azaserine or β-(2-thienyl)-DL-alanine and deficient in L-serine decomposition ability (Japanese Patent Laid-open (Kokai) No. 10-248588). Specific examples of such coryneform bacteria include, for example, *Corynebacterium glutamicum* (*Brevibacterium flavum*) AJ13324 (FERM P-16128), which is resistant to azaserine and deficient in L-serine decomposition ability, and *Corynebacterium glutamicum* (*Brevibacterium flavum*) AJ13325 (FERM P-16129), which is resistant to β-(2-thienyl)-DL-alanine and deficient in L-serine decomposition ability (Japanese Patent Laid-open (Kokai) No. 10-248588).

<L-Methionine-Producing Bacteria>

Examples of L-methionine-producing bacteria and parental strains for deriving them include L-threonine auxotrophic strains and mutant strains resistant to norleucine (Japanese Patent Laid-open (Kokai) No. 2000-139471). Examples of L-methionine-producing bacteria and parental strains for deriving them also include a strain containing a mutant homoserine transsuccinylase resistant to feedback inhibition by L-methionine (Japanese Patent Laid-open (Kokai) No. 2000-139471, US2009-0029424A). Since L-methionine is biosynthesized via L-cysteine as an intermediate, L-methionine-producing ability can also be improved by improving L-cysteine-producing ability (Japanese Patent Laid-open (Kokai) No. 2000-139471, US2008-0311632A).

Examples of L-methionine-producing bacteria of the genus *Pantoea* and parent strains thereof that can be used to derive L-methionine-producing bacteria includes, but are not limited to, *P. ananatis* strain AJ13355 (FERM BP-6614) and *P. ananatis* SC17(0) strain (VKPM B-9246). The AJ13355 strain is also known as *P. ananatis* strain SC17 (FERM BP-11091), and it was isolated from soil in Iwatashi (Shizuoka, Japan) as a bacterium that is able to grow at acidic pH and showing resistance to high concentrations of glutamic acid (U.S. Pat. No. 7,319,025 B2; Katashkina J. I. et al., Use of the λ Red-recombineering method for genetic engineering of *Pantoea ananatis*, BMC Mol. Biol., 2009, 10:34). The SC17(0) strain was constructed as a strain resistant to the λRed gene products for performing gene disruption in *P. ananatis* (WO2008075483).

Examples of L-methionine-producing bacteria of the genus *Escherichia* and parent strains thereof that can be used to derive L-methionine-producing bacteria includes, but are not limited to, *E. coli* strain that is deficient in repressor of L-methionine biosynthesis system (MetJ) and has increased activity of intracellular homoserine transsuccinylase (MetA) (U.S. Pat. No. 7,611,873 B1), *E. coli* strain in which activity of cobalamin-independent methionine synthase (MetE) is suppressed and activity of cobalamin-dependent methionine synthase (MetH) is increased (EP2861726 B1), *E. coli* strain that has an ability to produce L-threonine and is transformed with vector(s) expressing threonine dehydratase (tdcB, ilvA) and, at least, O-succinylhomoserine lyase (metB), cystathionine beta-lyase (metC), 5,10-methylenetetrahydrofolate reductase (metF) and serine hydroxymethyltransferase (glyA) (U.S. Pat. No. 7,790,424 B2), *E. coli* strain in which activity of transhydrogenase (pntAB) is enhanced (EP2633037 B1), and so forth. Specific examples of L-methionine-producing bacteria of the genus *Escherichia* and parent strains thereof that can be used to derive L-methionine-producing bacteria include, for example, *E. coli* AJ11539 (NRRL B-12399), *E. coli* AJ11540 (NRRL B-12400), *E. coli* AJ11541 (NRRL B-12401), *E. coli* AJ11542 (NRRL B-12402, British Patent No. 2075055), the *E. coli* 218 strain (VKPM B-8125, Russian Patent No. 2209248) and the 73 strain (VKPM B-8126, Russian Patent No. 2215782), which are resistant to norleucine, which is an analogue of L-methionine, and *E. coli* AJ13425 (FERM P-16808, Japanese Patent Laid-open (Kokai) No. 2000-139471). The AJ13425 strain is an L-threonine auxotrophic strain derived from the *E. coli* W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting or enhancing L-leucine-producing ability include, for example, a method of modifying a bacterium so that the bacterium has an increased activity or activities of one or more kinds of enzymes such as the L-leucine biosynthesis enzymes. Examples of such enzymes include, but are not particularly limited to, the enzymes encoded by the genes of the leuABCD operon. Furthermore, for enhancing the activity of such an enzyme, for example, the mutant leuA gene encoding an isopropyl maleate synthase desensitized to feedback inhibition by L-leucine (U.S. Pat. No. 6,403,342) can be used.

Specific examples of L-leucine-producing bacteria and parental strains for deriving them include, for example, strains belonging to the genus *Escherichia*, such as *E. coli* strains resistant to leucine, for example, the 57 strain (VKPM B-7386, U.S. Pat. No. 6,124,121); *E. coli* strains resistant to a leucine analogue such as 0-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879); *E. coli* strains obtained by a gene engineering technique described in WO96/06926; and *E. coli* H-9068 (Japanese Patent Laid-open (Kokai) No. 8-70879).

Examples of coryneform bacteria having L-leucine-producing ability include, for example, *Corynebacterium glutamicum* (*Brevibacterium lactofermentum*) AJ3718 (FERM P-2516), which is resistant to 2-thiazole alanine and p-hydroxyleucine and is auxotrophic for isoleucine and methionine.

<L-Isoleucine-Producing Bacteria>

Examples of methods for imparting or enhancing L-isoleucine-producing ability include, for example, a method of modifying a bacterium so that the bacterium has increased activity or activities of one or more enzymes such as the L-isoleucine biosynthesis enzymes. Examples of such enzymes include, but are not particularly limited to, threonine deaminase and acetohydroxy acid synthase (Japanese Patent Laid-open (Kokai) No. 2-458, EP0356739A, U.S. Pat. No. 5,998,178).

Specific examples of L-isoleucine-producing bacteria and parental strains for deriving them include, for example, *Escherichia* bacteria such as mutant strains having resistance to 6-dimethylaminopurine (Japanese Patent Laid-open (Kokai) No. 5-304969), mutant strains having resistance to an isoleucine analogue such as thiaisoleucine and isoleucine hydroxamate, and mutant strains having resistance to such an isoleucine analogue and further having resistance to DL-ethionine and/or arginine hydroxamate (Japanese Patent Laid-open (Kokai) No. 5-130882).

Examples of coryneform bacteria having L-isoleucine-producing ability include, for example, the coryneform bacterium in which brnE gene encoding a branched chain amino acid excretion protein is amplified (Japanese Patent Laid-open (Kokai) No. 2001-169788), the coryneform bacterium to which L-isoleucine-producing ability is imparted by protoplast fusion with an L-lysine-producing bacterium (Japanese Patent Laid-open (Kokai) No. 62-74293), the coryneform bacterium in which homoserine dehydrogenase is enhanced (Japanese Patent Laid-open (Kokai) No. 62-91193), the threonine hydroxamate resistant strain (Japanese Patent Laid-open (Kokai) No 62-195293), the α-ketomalonic acid resistant strain (Japanese Patent Laid-open (Kokai) No. 61-15695), the methyllysine resistant strain (Japanese Patent Laid-open (Kokai) No. 61-15696), and *Corynebacterium glutamicum* (*Brevibacterium flavum*) AJ12149 (FERM BP-759, U.S. Pat. No. 4,656,135).

<L-Valine-Producing Bacteria>

Examples of methods for imparting or enhancing L-valine-producing ability include, for example, a method of modifying a bacterium so that the bacterium has an increased activity or activities of one or more kinds of enzymes such as the L-valine biosynthesis enzymes. Examples of such enzymes include, but are not particularly limited to, the enzymes encoded by the genes of the ilvGMEDA operon and the enzymes encoded by the genes of the ilvBNC operon. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, for enhancing the activity of such an enzyme, it is preferred that the suppression of expression by the produced L-valine is released by removing or modifying a region required for the attenuation. Furthermore, the threonine deaminase encoded by the ilvA gene is an enzyme that catalyzes the deamination reaction of L-threonine resulting in 2-ketobutyric acid, which is the rate-limiting step of the L-isoleucine biosynthesis system. Therefore, for L-valine production, it is preferred that the ilvA gene is, for example, disrupted, and thereby the threonine deaminase activity is decreased.

Examples of methods for imparting or enhancing L-valine-producing ability also include, for example, a method of modifying a bacterium so that the bacterium has a reduced activity or activities of one or more kinds of enzymes such as the enzymes that catalyze a reaction branching away from the biosynthesis pathway of L-valine to generate a compound other than L-valine. Examples of such enzymes include, but are not particularly limited to, threonine dehydratase involved in the L-leucine synthesis, and the enzymes involved in the D-pantothenic acid synthesis (WO00/50624).

Specific examples of L-valine-producing bacteria and parental strains for deriving them include, for example, *E. coli* strains modified so as to overexpress the ilvGMEDA operon (U.S. Pat. No. 5,998,178).

Examples of L-valine-producing bacteria and parental strains for deriving them also include mutant strains having a mutation in amino-acyl t-RNA synthetase (U.S. Pat. No. 5,658,766). Examples of such strains include, for example, *E. coli* VL1970, which has a mutation in the ileS gene encoding isoleucine t-RNA synthetase. *E. coli* VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains for deriving them also include mutant strains requiring lipoic acid for growth and/or lacking H$^+$-ATPase (WO96/06926).

Examples of L-valine-producing bacteria and parent strains for deriving them also include strains resistant to an amino acid analogue or the like. Examples of such strains include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM P-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-Producing Bacteria>

Examples of L-alanine-producing bacteria and parent strains for deriving them include the coryneform bacteria deficient in the H$^+$-ATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-Producing Bacteria, L-Phenylalanine-Producing Bacteria, and L-Tyrosine-Producing Bacteria>

Examples of methods for imparting or enhancing L-tryptophan-producing ability, L-phenylalanine-producing ability, and/or L-tyrosine-producing ability include, for example, a method of modifying a bacterium so that the bacterium has an increased activity or activities of one or more enzymes such as the L-tryptophan, L-phenylalanine, and/or L-tyrosine biosynthesis enzymes.

Examples of enzymes common to the biosynthesis systems of these aromatic amino acids include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP763127B). The expressions of the genes encoding these enzymes are controlled by the tyrosine repressor (tyrR), and the activities of these enzymes may be enhanced by deleting the tyrR gene (EP763127B).

Examples of the L-tryptophan biosynthesis enzymes include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase has α and β subunits encoded by the trpA and trpB genes, respectively. Since the anthranilate synthase is subject to feedback inhibition by L-tryptophan, a gene encoding this enzyme introduced with a mutation for desensitization to feedback inhibition may be used for enhancing the activity of that enzyme. Since the phosphoglycerate dehydrogenase is subject to feedback inhibition by L-serine, a gene encoding this enzyme introduced with a mutation for desensitization to feedback inhibition may be used for enhancing the activity of that enzyme. Furthermore, by increasing the expression of the operon (ace operon) having the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthesis enzymes include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, genes encoding these enzymes introduced with a mutation for desensitization to feedback inhibition may be used for enhancing the activities of these enzymes.

Examples of the L-tyrosine biosynthesis enzymes include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, genes encoding these enzymes introduced with a mutation for desensitization to feedback inhibition may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Furthermore, the L-tryptophan, L-phenylalanine, and/or L-tyrosine-producing bacteria may be modified so that a by-product uptake system is enhanced. Examples of the by-product include aromatic amino acids other than the objective aromatic amino acid. Examples of the gene encoding such a by-product uptake system include, for example, tnaB and mtr, which are genes encoding the L-tryptophan uptake system, pheP, which is a gene encoding the L-phenylalanine uptake system, and tyrP, which is a gene encoding the L-tyrosine uptake system (EP1484410).

Specific examples of L-tryptophan-producing bacteria and parental strains for deriving them include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient tryptophanase (U.S. Pat. No. 4,371,614), E. coli AGX17/pGX50, pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (US2003-0148473A1 and US2003-0157667A1).

Examples of coryneform bacteria having L-tryptophan-producing ability include, for example, Corynebacterium glutamicum AJ12118 (FERM BP-478, Japanese Patent No. 1681002), which is resistant to sulfaguanidine, the strain introduced with the tryptophan operon (Japanese Patent Laid-open (Kokai) No. 63-240794), and the strain introduced with a gene encoding shikimate kinase derived from a coryneform bacterium (Japanese Patent No. 1994749).

Specific examples of L-phenylalanine-producing bacteria and parental strains for deriving them include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutantpheA34 gene encoding a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of L-phenylalanine-producing bacteria and parental strains for deriving them also include, for example, E. coli K-12 <W3110(tyrA)/pPHAB> (FERM BP-3566), E. coli K-12<W3110(tyrA)/pPHAD> (FERM BP-12659), E. coli K-12<W3110(tyrA)/pPHATerm> (FERM BP-12662), and E. coli K-12 AJ12604 <W3110(tyrA)/pBR-aroG4, pAC-MAB> (FERM BP-3579), which contains a gene encoding a chorismate mutase-prephenate dehydratase desensitized to feedback inhibition (EP488424B1). Specific examples of L-phenylalanine-producing bacteria and parental strains for deriving them further include, for example, strains belonging to the genus Escherichia having an increased activity of the protein encoded by the yedA gene or the yddG gene (US2003-0148473A, US2003-0157667A, WO03/044192).

Examples of coryneform bacteria having L-phenylalanine-producing ability include, for example, the Corynebacterium glutamicum strains BPS-13 (FERM BP-1777), K77 (FERM BP-2062), and K78 (FERM BP-2063) (EP331145A, Japanese Patent Laid-open (Kokai) No. 02-303495), of which phosphoenolpyruvate carboxylase or pyruvate kinase activity is reduced, and the tyrosine-auxotrophic strain (Japanese Patent Laid-open (Kokai) No. 05-049489).

Examples of coryneform bacteria having L-tyrosine-producing ability include, for example, Corynebacterium glutamicum AJ11655 (FERM P-5836, Japanese Patent Publication No. 2-6517), and Corynebacterium glutamicum (Brevibacterium lactofermentum) AJ12081 (FERM P-7249, Japanese Patent Laid-open (Kokai) No. 60-70093).

Furthermore, examples of methods for imparting or enhancing an L-amino acid-producing ability include, for example, a method of modifying a bacterium so that the bacterium has an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids include, for example, b2682 gene (ygaZ), b2683 gene (ygaH), b1242 gene (ychE), and b3434 gene (yhgN) (Japanese Patent Laid-open (Kokai) No. 2002-300874).

Furthermore, examples of methods for imparting or enhancing an L-amino acid-producing ability also include, for example, a method of modifying a bacterium so that the bacterium has an increased activity or activities of one or more proteins involved in the glycometabolism and proteins involved in the energy metabolism.

Examples of the proteins involved in the glycometabolism include proteins involved in uptake of saccharides and the glycolysis system enzymes. Examples of genes encoding a protein involved in the glycometabolism include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism include the transhydrogenase gene (pntAB, U.S. Pat. No. 5,830,716) and cytochrome bo-type oxidase gene (cyoB, EP1070376A).

Furthermore, examples of methods for imparting or enhancing an L-amino acid-producing ability also include, for example, a method of modifying a bacterium so that the activity of phosphoketolase is increased (WO2006/016705). Hence, the bacterium may have been modified so that the activity of phosphoketolase is increased. This method may be effective particularly for imparting or enhancing an ability to produce an L-amino acid of glutamate family such as L-glutamic acid. Examples of phosphoketolase include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" refers to an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1966) or the method described by L. Meile (J. Bacteriol., 183:2929-2936, 2001). Examples of D-xylulose-5-phosphate phosphoketolase include those native to bacteria belonging to the genera *Acetobacter, Bifidobacterium, Lactobacillus, Thiobacillus, Streptococcus, Methylococcus, Butyrivibrio*, and *Fibrobacter*, and yeast belonging to the genera *Candida, Rhodotorula, Rhodosporidium, Pichia, Yarrowia, Hansenula, Kluyveromyces, Saccharomyces, Trichosporon*, and *Wingea*. Specific examples of D-xylulose-5-phosphate phosphoketolase and genes encoding them are disclosed in WO2006/016705.

The term "fructose-6-phosphate phosphoketolase activity" refers to an activity of converting fructose-6-phosphate into erythrose-4-phosphate and acetyl phosphate with consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase include those native to bacteria belonging to the genera *Acetobacter, Bifidobacterium, Chlorobium, Brucella, Methylococcus*, and *Gardnerella*, and yeast belonging to the genera *Rhodotorula, Candida*, and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme (i.e. D-xylulose-5-phosphate phosphoketolase/fructose-6-phosphate phosphoketolase).

<Nucleoside-Producing Bacteria and Nucleotide-Producing Bacteria>

As methods for imparting or enhancing a nucleoside or nucleotide-producing ability, those for purine substances and pyrimidine substances have been known (WO2015/060391, JP2001-149068A, and JPH02-002349A). The phrase "purine substances" can collectively refer to purine nucleosides and purine nucleotides. The phrase "pyrimidine substances" can collectively refer to pyrimidine nucleosides and pyrimidine nucleotides.

A purine substance-producing ability can be imparted or enhanced by the methods conventionally employed in the breeding of purine substance-producing bacteria such as those of *Bacillus* bacteria and *Escherichia* bacteria.

A purine substance-producing ability can be imparted or enhanced by, for example, imparting auxotrophy such as adenine auxotrophy, or further imparting resistance to purine analogues and a drug such as sulfaguanidine (refer to Japanese Patent Publication (Kokoku) Nos. 38-23099, 54-17033, 55-45199, 57-14160, 57-41915 and 59-42895, Published U.S. Patent Application No. 20040166575). A mutant strain having a purine substance-producing ability, such as an auxotrophic strain and a drug-resistant strain, can be obtained by subjecting a parent strain or wild-type strain to a mutagenesis treatment and selecting a mutant strain showing a desired phenotype using an appropriate selection medium. Examples of the mutagenesis treatment include, for example, X-ray irradiation, ultraviolet irradiation, and treatment with a mutagenesis agent such as N-methyl-N'-nitro-N-nitrosoguanidine (MNNG), ethyl methanesulfonate (EMS), and methyl methanesulfonate (MMS).

A purine substance-producing ability can also be imparted or enhanced by enhancing the intracellular activity of an enzyme involved in biosynthesis of a purine substance. Activity of one kind of enzyme may be enhanced, or activities of two or more kinds of enzymes may be enhanced. Methods for enhancing an enzyme activity will be explained later. An enzyme activity can be enhanced by, for example, modifying a bacterium so that expression of a gene encoding the enzyme is enhanced. Methods for enhancing gene expression are described in WO18935, EP 1010755 A, and so forth.

Purine nucleotides are biosynthesized via phosphoribosylpyrophosphate (PRPP) as an intermediate. Purine nucleosides are biosynthesized by dephosphorylation of purine nucleotides. Examples of enzymes involved in the biosynthesis of these purine substances include, for example, PRPP synthetase (prs) and the proteins encoded by the purine operon.

Examples of the purine operon include, for example, the purEKBCSQLFMNHD operon of *Bacillus subtilis* (*Bacillus subtilis* and Its Closest Relatives, Editor in Chief: A. L. Sonenshein, ASM Press, Washington D.C., 2002) and the pur regulon of *Escherichia coli* (*Escherichia* and *Salmonella*, Second Edition, Editor in Chief: F. C. Neidhardt, ASM Press, Washington D.C., 1996). For example, expression of the total purine operon may be enhanced, or expression of one or more genes contained in the purine operon may be enhanced.

Among these, for example, activity or activities of one or more kinds of enzymes such as PRPP synthetase (prs) and PRPP amidotransferase (purF) can be enhanced.

When an enzyme involved in biosynthesis of a purine substance is negatively regulated by feedback inhibition, expression inhibition, or the like, the enzymatic activity can be enhanced by, for example, reducing or eliminating such regulation, and the purine substance-producing ability can be thereby improved (WO99/003988).

Expression of the purine operon is suppressed by the purine repressor encoded by the purR gene. Therefore, expression of the purine operon can be enhanced by, for example, reducing the activity of the purine repressor (U.S. Pat. No. 6,284,495). The activity of the purine repressor can be reduced by, for example, disrupting the purR gene encoding the purine repressor (U.S. Pat. No. 6,284,495). Furthermore, expression of the purine operon is regulated by the terminator-antiterminator sequence (it is also called attenuator sequence) located downstream from the promoter (Ebbole, D. J. and Zalkin, H., J. Biol. Chem., 1987, 262, 8274-8287; Ebbole, D. J. and Zalkin, H., J. Biol. Chem., 1988, 263, 10894-10902; Ebbole, D. J. and Zalkin, H., J. Bacteriol., 1989, 171, 2136-2141). Therefore, expression of the purine operon can be enhanced by, for example, deleting the attenuator sequence. Deletion of the attenuator sequence can be attained by the same method as that used for disruption of a gene explained later.

The PRPP synthetase is subject to feedback inhibition by ADP. Therefore, for example, by making a bacterium harbor a mutant PRPP synthetase gene encoding a desensitized-type PRPP synthetase for which the feedback inhibition by ADP is reduced or eliminated, the PRPP synthetase activity can be enhanced, and the purine substance-producing ability can be thereby improved (WO99/003988). Examples of the desensitized-type PRPP synthetase include PRPP synthetase having a mutation that substitutes Ala (A) for Asp (D) of the position 128 of the wild-type PRPP synthetase (S. G. Bower et al., J. Biol. Chem., 264, 10287 (1989)).

The PRPP amidotransferase is subject to feedback inhibition by AMP and GMP. Therefore, for example, by making a bacterium harbor a mutant PRPP amidotransferase gene encoding a desensitized-type PRPP amidotransferase for which the feedback inhibition by AMP and/or GMP is reduced or eliminated, the PRPP amidotransferase activity can be enhanced, and the purine substance-producing ability can be thereby improved (WO99/003988). Examples of the desensitized-type PRPP amidotransferase include PRPP amidotransferase in which Gln (Q) substitutes for Lys (K) of the position 326 of the wild-type PRPP amidotransferase, and PRPP amidotransferase in which Gln (Q) substitutes for Lys (K) of the position 326, and Trp (W) substitutes for Pro (P) of the position 410 of the wild-type PRPP amidotransferase (G. Zhou et al., J. Biol. Chem., 269, 6784 (1994)).

A purine substance-producing ability can also be imparted or enhanced by reducing activity of an enzyme that catalyzes a reaction branching away from biosynthetic pathway of a purine substance to generate another compound (WO99/003988). Activity of one kind of enzyme may be reduced, or activities of two or more kinds of enzymes may be reduced. The "enzyme that catalyzes a reaction branching away from biosynthetic pathway of a purine substance to generate another compound" referred to here also includes an enzyme involved in decomposition of a purine substance. Methods for reducing enzymatic activity will be explained later.

Examples of the enzyme that catalyzes a reaction branching away from biosynthetic pathway of a purine substance to generate another compound include, for example, purine nucleoside phosphorylase (deoD, pupG), succinyl-AMP synthase (purA), adenosine deaminase (add), inosine-guanosine kinase (gsk), GMP reductase (guaC), 6-phosphogluconate dehydrase (edd), phophoglucose isomerase (pgi), adenine deaminase (yicP), xanthosine phosphorylase (xapA), and IMP dehydrogenase (guaB). The enzyme of which activity is to be reduced may be chosen according to kind of the target purine substance, and so forth.

A purine substance-producing ability can also be imparted or enhanced by reducing the activity of fructose bisphosphatase (fructose 1,6-bisphosphatase) (fbp) (WO2007/125782).

A purine substance-producing ability can also be imparted or enhanced by reducing the activity of a protein involved in uptake of a purine substance (WO99/003988). Examples of such a protein involved in uptake of a purine substance include, for example, nucleoside permease (nupG) (WO99/003988).

A purine substance-producing ability can also be imparted or enhanced by enhancing the activity of a protein involved in excretion of a purine substance. Examples of such a protein involved in excretion of a purine substance include, for example, proteins encoded by the rhtA (ybiF) gene (Russian Patent No. 2239656), yijE gene (Russian Patent No. 2244003), ydeD gene (Russian Patent No. 2244004), yicM gene (Russian Patent No. 2271391), ydhL gene (Japanese Patent Laid-open (Kohyo) No. 2007-530011), and nepI gene (FEMS Microbiology Letters, Volume 250, Issue 1, pages 39-47, September 2005).

Furthermore, IMP-producing ability can be imparted or enhanced by imparting resistance to an L-glutamine analogue and resistance to a proline analogue to a bacterium (Japanese Patent Laid-open (Kokai) No. 2004-516833). Examples of the L-glutamine analogue include azaserine and 6-diazo-5-oxo-L-norleucine (DON). Examples of the proline analogue include 3,4-dehydroproline, L-azetidine-2-carboxylic acid, L-thiazolidine-4-carboxylic acid, (S)-2,2-dimethyl-4-oxazolide-carboxylic acid, (S)-5,5-dimethyl-4-thiazolide-carboxylic acid, (4S,2RS)-2-ethyl-4-thiazolidine-carboxylic acid, (2S,4S)-4-hydroxy-2-pyrroline-carboxylic acid, 2-piperidine-carboxylic acid, and 2,5-pyrrolidin-edione. Examples of IMP-producing bacteria include, for example, *Corynebacterium ammoniagenes* CJIP009 (KCCM-10226, Japanese Patent Laid-open (Kokai) No. 2004-516833).

Furthermore, XMP-producing ability can be imparted or enhanced by the methods used for breeding of XMP-producing bacteria of coryneform bacteria, of which a typical example is *Corynebacterium ammoniagenes*. Examples of such methods include, for example, enhancing the PRPP amidotransferase activity (Japanese Patent Laid-open (Kokai) No. 8-168383), imparting resistance to an aliphatic amino acid (Japanese Patent Laid-open (Kokai) No. 4-262790), and imparting resistance to dehydroproline (South Korean Patent Laid-open No. 2003-56490).

Such methods for imparting or enhancing purine substance-producing ability as mentioned above may be used independently, or used as an arbitrary combination of them.

A pyrimidine substance-producing ability, such as a uridine or UMP-producing ability, can be imparted or enhanced by imparting resistance to a pyrimidine analogue to a bacterium (JP2001-149068A and JPH02-002349A). Examples of the pyrimidine analogue include 6-azauracil, 2-thiouracil, 5-hydroxyuracil, 5-fluorouracil, 2-thiocytocine, 5-hydroxycytocine, and 5-fluorocytocine, as well as ribosides and ribotides thereof. Examples of pyrimidine substance-producing bacteria, such as uridine or UMP-producing bacteria, include, for example, *Corynebacterium ammoniagenes* LK 75-15 (VKPM B-7812) and LK 75-66 (VKPM B-7813) (JP2001-149068A), and *Bacillus subtilis* AA47 (JPH02-002349A).

<Isoprenoid-Producing Bacteria>

Examples of methods for imparting or enhancing isoprenoid-producing ability include, for example, a method of modifying a bacterium so that the bacterium has an increased activity or activities of one or more kinds of enzymes such as the isoprenoid biosynthesis enzymes (WO2012/149491, WO2016/084963, and WO2015/147341). Examples of such enzymes include, but are not particularly limited to, mevalonate pathway enzymes such as acetoacetyl-CoA synthase (e.g., thiolase), 3-hydroxy-3-methylglutaryl-CoA synthase, 3-hydroxy-3-methylglutaryl-CoA reductase, mevalonate kinase, phosphomevalonate kinase, diphosphomevalonate decarboxylase, and isopentenyl diphosphate isomerase.

<Peptide-Producing Bacteria>

A target peptide can be expressed from a gene encoding the target peptide. Hence, a peptide-producing bacteria can have a gene encoding the target peptide. A gene encoding a target peptide can also be referred to as "a target peptide gene".

A target peptide may be produced so that it is secreted to the outside of cells, for example, in a culture medium or on a cell surface layer, by secretory production, or may be accumulated in cells. For example, a target peptide can be produced by secretory production by using a signal peptide. It is sufficient that a target peptide gene is harbored by a host bacterium so that the gene can be expressed. Specifically, for example, secretory production of a target peptide can be enabled by making a host bacterium harbor a genetic construct including, in the direction from 5' to 3', a promoter sequence that functions in the host bacterium, a nucleic acid sequence encoding a signal peptide that functions in nucleic acid bacterium, and a nucleic acid sequence encoding a target peptide. It is sufficient that the nucleic acid sequence encoding the target peptide is ligated downstream from the nucleic acid sequence encoding the signal peptide so that the target peptide is expressed as a fusion peptide with the signal peptide. In such a fusion protein, the signal peptide and the target peptide may be or may not be adjacent to each other. For secretory production of peptides, for example, coryneform bacteria can be used. Examples of coryneform bacteria to be used for secretory production of peptides include, for example, strains of which the activity of cell surface peptide is reduced. Examples of such strains include the *C. glutamicum* YDK010 strain (WO2004/029254), which is a cell surface protein PS2-deficient strain of the *C. glutamicum* AJ12036 strain (FERM BP-734). Furthermore, examples of methods for imparting or enhancing an ability of secretory production of a peptide for a coryneform bacterium as an expression host include, for example, modifying a host so that the activity of a cell surface protein is reduced (WO2013/065869, WO2013/065772, WO2013/118544, and WO2013/062029), modifying a host so that the activity of a penicillin-binding protein is reduced (WO2013/065869), modifying a host so that the expression of the gene encoding a metallopeptidase is increased (WO2013/065772), modifying a host so as to harbor a mutant ribosomal protein S1 gene (i.e. mutant rpsA gene) (WO2013/118544), modifying a host so as to harbor a mutant phoS gene (WO2016/171224), modifying a host so that the activity of a RegX3 protein is reduced (WO2018/074578), modifying a host so that the activity of a HrrSA system is reduced (WO2018/074579), expressing a target peptide that has an amino acid sequence containing Gln-Glu-Thr inserted between a signal peptide and the target peptide (WO2013/062029), and modifying a host so that a protein secretion system such as Tat secretion system is enhanced (JP patent 4730302). Such methods for imparting or enhancing a peptide-producing ability as mentioned above may be used independently, or may be used in an arbitrary combination.

The genes and proteins used for breeding target substance-producing bacteria may have, for example, known nucleotide sequences and amino acid sequences of the genes and proteins exemplified above, respectively. Also, the genes and proteins used for breeding target substance-producing bacteria may be variants of the genes and proteins exemplified above, such as genes and proteins having such known nucleotide sequences and amino acid sequences, respectively, so long as the original function thereof, such as respective enzymatic activities in cases of proteins, is maintained. As for variants of genes and proteins, the descriptions concerning variants of a gene encoding a protein having $H^+$-translocating membrane-bound pyrophosphatase activity and the encoded protein described herein can be similarly applied.

The bacterium as described herein has been modified to overexpress a gene encoding a protein having $H^+$-translocating membrane-bound pyrophosphatase activity.

The phrase "a protein having $H^+$-translocating membrane-bound pyrophosphatase activity" can be equivalent to the phrase "a protein having proton-translocating membrane-bound pyrophosphatase activity", and can mean a protein that i) is able to cause catalysis of the following reaction: diphosphate+$H_2O \leftrightarrow$ 2 phosphate+$H^+$ (Enzyme Commission (EC) number 3.6.1.1), and ii) is able to transport protons ($H^+$) across the membrane of a cell (Baltscheffsky M. et al., $H^+$-proton-pumping inorganic pyrophosphatase: a tightly membrane-bound family, *FEBS Lett.*, 1999, 452(3):121-127; Baykov A. A. et al., Kinetic characterization of the hydrolytic activity of the $H^+$-pyrophosphatase of *Rhodospirillum rubrum* in membrane-bound and isolated states, *Eur. J. Biochem.*, 1996, 236:121-127; Kajander T. et al., Inorganic pyrophosphatases: one substrate, three mechanisms, *FEBS Lett.*, 2013, 587(13):1863-1869). For example, a protein having $H^+$-translocating membrane-bound pyrophosphatase activity can mean a protein having the amino acid sequence shown in SEQ ID NO: 2 and homologue(s) thereof that i) is/are able to cause hydrolysis of diphosphate in the following reaction: diphosphate+$H_2O \rightarrow$ 2 phosphate+$H^+$, and export protons out of the cell; and/or ii) is able to cause synthesis of diphosphate in the following reaction: 2 phosphate+$H^+ \rightarrow$ diphosphate+$H_2O$, and import protons into the cell (see, for example, Belogurov G. A. et al., $H^+$-pyrophosphatase of *Rhodospirillum rubrum*, *J. Biol. Chem.*, 2002, 277(25):22209-22214).

The phrase "a protein is able to transport protons across the membrane of a cell" can mean that a protein is able to cause a gradient of the electrochemical proton potential ($\Delta\mu H^+$) through the membrane of a cell. That is, the phrase "a protein is able to transport protons across the membrane of a cell" can mean that a protein is able to generate a proton-motive force (so-called proton-pumping) as a result of activity of the protein.

The activity of a protein having $H^+$-translocating membrane-bound pyrophosphatase activity can be determined by i) evaluating the activity of the protein to cause hydrolysis of diphosphate or synthesis of diphosphate, and ii) measuring electrochemical proton potential of cellular membrane. The activity of a protein to cause hydrolysis of diphosphate or synthesis of diphosphate can be determined by evaluating the amount of orthophosphate using, for example, an automated phosphate analyzer (Baykov A. A. and Avaeva S. M., A simple and sensitive apparatus for continuous monitoring of orthophosphate in the presence of acid-labile compounds, Anal. Biochem., 1981, 116(1):1-4; Baykov A. A. et al., Kinetic characterization of the hydrolytic activity of the H+-pyrophosphatase of *Rhodospirillum rubrum* in membrane-bound and isolated states, Eur. J Biochem., 1996, 236:121-127).

The electrochemical proton potential (ΔµH+) of a cellular membrane can be determined by, for example, measuring membrane potential using intracellular microelectrodes or evaluating steady-state distribution of tetraphenylphosphonium (Felle H. et al., Quantitative measurements of membrane potential in *Escherichia coli*, Biochemistry, 1980, 19(15):3585-3590), or applying voltage-sensitive dyes to a medium containing cells and measuring fluorescence intensity (Suzuki H. et al., Probing the transmembrane potential of bacterial cells by voltage-sensitive dyes, Anal. Sci., 2003, 19(9):1239-1242).

In a particular example, the activity of a protein to cause hydrolysis of diphosphate or synthesis of diphosphate and the electrochemical proton potential of cellular membrane, that is, the activity of a protein having H+-translocating membrane-bound pyrophosphatase activity, can be determined using the inner membrane vesicles (IMV) as described in detail in Belogurov G. A. et al., 2002.

An example of the protein having H+-translocating membrane-bound pyrophosphatase activity can be a protein having the amino acid sequence shown in SEQ ID NO: 2. The amino acid sequence shown in SEQ ID NO: 2 can be encoded by the nucleotide sequence shown in SEQ ID NO: 1, which corresponds to the hppA gene native to a Gram-negative bacterium *Rhodospirillum rubrum* (*R. rubrum*) strain ATCC 11170 (also referred to as strain ATH 1.1.1/ DSM 467/LMG 4362/NCIB 8255/S1). That is, an example of the gene encoding a protein having H+-translocating membrane-bound pyrophosphatase activity can be a hppA gene. In addition, an example of the protein having H+-translocating membrane-bound pyrophosphatase activity can be a HppA protein, which is a protein encoded by a hppA gene. The hppA gene (synonyms: rrpP, vppA, hppA$^{Rru}$) of *R. rubrum* strain ATCC 11170 encodes the membrane-bound H+-translocating pyrophosphatase (synonyms: K(+)-insensitive pyrophosphate-energized proton pump, pyrophosphate-energized inorganic pyrophosphatase, H(+)-PPase, H+-PPase) HppA (KEGG, Kyoto Encyclopedia of Genes and Genomes, entry No. Rru_A1818; Protein Knowledgebase, UniProtKB/Swiss-Prot, accession No. O68460). The hppA gene (GenBank, accession No. NC_007643.1; nucleotide positions: 2116926 to 2119034, complement; Gene ID: 3835242) is located between the Rru_A1817 gene and the Rru_A1819 gene on the same strand of the chromosome of *R. rubrum* strain ATCC 11170.

That is, the gene encoding a protein having H+-translocating membrane-bound pyrophosphatase activity, such as a hppA gene, may be a gene, such as DNA, having the nucleotide sequence of SEQ ID NO: 1, and the protein having H+-translocating membrane-bound pyrophosphatase activity, such as a HppA protein, may be a protein having the amino acid sequence of SEQ ID NO: 2. The phrase "a gene or protein has a nucleotide or amino acid sequence" can mean that a gene or protein includes the nucleotide or amino acid sequence among other sequences unless otherwise stated, and can also include when the gene or protein contains only the nucleotide or amino acid sequence.

The nucleotide sequence of the hppA gene (SEQ ID NO: 1) and the amino acid sequence of the HppA protein (SEQ ID NO: 2) encoded by the hppA gene native to *R. rubrum* strain ATCC 11170 are known as described above. That is, the protein having H+-translocating membrane-bound pyrophosphatase activity native to *R. rubrum* strain ATCC 11170, and the gene encoding it are known. Moreover, proteins having H+-translocating membrane-bound pyrophosphatase activity and genes encoding these proteins from other organisms are also known, and examples thereof include, for example, homologues of the HppA protein native to *R. rubrum* strain ATCC 11170, such as those listed in Tables 1 and 2. Other examples of protein homologues of the HppA protein native to *R. rubrum* strain ATCC 11170 and genes encoding such protein homologues can be found in, for example, the NCBI (National Center for Biotechnology Information) database (www.ncbi.nlm.nih.gov/protein/). Therefore, examples of the protein having H+-translocating membrane-bound pyrophosphatase activity can also include the proteins that are homologues of the protein having the amino acid sequence shown in SEQ ID NO: 2.

TABLE 1

Examples of HppA proteins.

| Entry No.* | Bacterial species | Identity** |
|---|---|---|
| O68460 | *Rhodospirillum rubrum* (strain ATCC 11170/ATH 1.1.1/DSM 467/LMG 4362/ NCIB 8255/S1) | 100.0% |
| H6SRK6 | *Pararhodospirillum photometricum* DSM 122 | 79.5% |
| A0A1G6XAT1 | *Rhodospira trueperi* | 79.3% |
| A0A0A0DDM5 | *Inquilinus limosus* MP06 | 78.1% |
| B6IMS1 | *Rhodospirillum centenum* (strain ATCC 51521/SW) | 76.5% |
| A0A2N3EE02 | *Alphaproteobacteria bacterium* HGW-Alphaproteobacteria-11 | 76.4% |
| A7HX90 | *Parvibaculum lavamentivorans* (strain DS-1/ DSM 13023/NCIMB 13966) | 76.4% |
| A0A2E8XQT2 | *Alphaproteobacteria bacterium* | 76.2% |
| A0A255YRX1 | *Niveispirillum lacus* | 76.1% |
| A0A081B7U0 | *Tepidicaulis marinus* | 76.0% |
| A0A2D5FW68 | *Pelagibacterales bacterium* | 75.9% |
| A0A1Y5STS9 | *Oceanibacterium hippocampi* | 75.6% |
| A0A2M9G1F1 | *Rhizobiales bacterium* | 75.5% |
| D0RNV6 | *alpha proteobacterium* HIMB 114 | 74.7% |
| A0A239CFR4 | *Azospirillum* sp. RU38E | 74.7% |
| A0A2E7RA03 | *Rhodospirillaceae bacterium* | 74.7% |
| A0A2D5LW14 | *Pelagibacteraceae bacterium* | 74.5% |
| A0A2E5BM54 | *Rhodobiaceae bacterium* | 74.1% |
| A0A0D2ULY1 | *Skermanella aerolata* KACC 11604 | 73.2% |
| A0A1Y6C5N3 | *Tistlia consotensis* USBA 355 | 73.2% |
| B6JGI6 | *Oligotropha carboxidovorans* (strain ATCC 49405/DSM 1227/KCTC 32145/OM5) | 73.0% |
| A0A1W6ZW14 | *Pseudorhodoplanes sinuspersici* | 72.9% |
| A0A165WNS2 | *Pseudovibrio axinellae* | 72.8% |
| A0A1G5NJY3 | *Afifella marina* DSM 2698 | 72.7% |
| A0A1Q3VZ14 | *Afipia* sp. 64-13 | 72.7% |
| A0A0M6ZYL2 | *Labrenzia alexandrii* | 72.7% |
| A0A2M8UID8 | *Ferrovibrio* sp. | 72.6% |
| A0A0K6IB43 | *Pannonibacter indicus* | 72.5% |
| A0A1G6DAM9 | *Bauldia litoralis* | 72.4% |
| F7QNX6 | *Bradyrhizobiaceae bacterium* SG-6C | 72.4% |

*In the UniProtKB database (uniprot.org/uniprot).
**Identity was calculated with respect to the HppA protein native to *R. rubrum* (entry No. O68460) using blastp and default settings (Matrix: BLOSUM62, Threshold: 10, Filtered: false, Gapped: true) provided by the UniProtKB database.

TABLE 2

Examples HppA proteins.

| Entry No.* | Bacterial species | Identity** |
|---|---|---|
| K8PIX2 | *Afipia broomeae* ATCC 49717 | 72.3% |
| A0A127EXU3 | *Rhodoplanes* sp. Z2-YC6860 | 72.3% |
| A0A1G7Y673 | *Roseospirillum parvum* | 72.3% |
| A0A0N1LQS0 | *Rhodopseudomonas* sp. AAP120 | 72.2% |
| K8PDH5 | *Afipia clevelandensis* ATCC 49720 | 72.1% |
| A0A150U6L4 | *Bradyrhizobium* sp. AT1 | 72.1% |
| X5MPD4 | *Candidatus Phaeomarinobacter ectocarpi* | 72.1% |
| A0A1U7JFX4 | *Nesiotobacter exalbescens* | 72.1% |
| G1Y0L2 | *Nitrospirillum amazonense* Y2 | 72.1% |
| A0A2E3PRV0 | *Rhodobacteraceae bacterium* | 72.1% |
| B7KUJ9 | *Methylobacterium extorquens* (strain CM4/NCIMB 13688) (*Methylobacterium chloromethanicum*) | 71.9% |
| A0A1W6RP73 | *Methylobacterium zatmanii* | 71.9% |
| A0A0K6HGV4 | *Chelatococcus sambhunathii* | 71.8% |
| A0A2D7PCQ0 | *Candidatus Pelagibacter* sp. | 71.7% |
| A0A0F2RIA3 | *Rhodospirillaceae bacterium* BRH_c57 | 71.7% |
| A0A285S8N7 | *Stappia indica* | 71.7% |
| A0A1X3HEP3 | *Bradyrhizobium canariense* | 71.5% |
| A0A161RMC1 | *Tardiphaga robiniae* | 71.5% |
| A0A0R3BXX2 | *Bradyrhizobium yuanmingense* | 71.4% |
| A0A2E2QGT6 | *Sneathiella* sp. | 71.3% |
| V4RD02 | *Lutibaculum baratangense* AMV1 | 71.2% |
| A0A0D1NT21 | *Bradyrhizobium elkanii* | 71.0% |
| A0A0Q7TZG1 | *Pseudolabrys* sp. Root1462 | 70.9% |
| A0A1F2XSY3 | *Alphaproteobacteria bacterium* RBG_16_64_48 | 70.8% |
| A0A1Z9ALL8 | *Gammaproteobacteria bacterium* TMED95 | 70.8% |
| A0A1V4HZ43 | *Nitrobacter vulgaris* | 70.8% |
| A0A0R3D8Q4 | *Bradyrhizobium manausense* | 70.7% |
| A0A176YQP1 | *Bradyrhizobium neotropicale* | 70.6% |
| A0A0D7F5A1 | *Rhodopseudomonas palustris* | 70.6% |
| J5PDP9 | *Rhodovulum* sp. PH10 | 70.3% |

*In the UniProtKB database (uniprot.org/uniprot).
**Identity was calculated with respect to the HppA protein native to *R. rubrum* (entry No. O68460) using blastp and default settings (Matrix: BLOSUM62, Threshold: 10, Filtered: false, Gapped: true) provided by the UniProtKB database.

The phrase "a bacterium has been modified to overexpress a gene encoding a protein having H⁺-translocating membrane-bound pyrophosphatase activity" can mean that the bacterium has been modified in such a way that in the modified bacterium the total amount and/or the total activity of the corresponding gene product, specifically the total amount and/or the total activity of a protein that i) is able to cause hydrolysis of diphosphate and/or synthesis of diphosphate, and ii) is able to transport protons across the membrane of a cell, is increased (i.e. higher than), or the expression level (i.e. expression amount) of said gene is increased as compared with that observed for a non-modified strain. The phrase "a non-modified strain" can refer to a bacterial strain that can serve as a reference for the above comparison. The phrase "a non-modified strain" can be used interchangeably or equivalently to the phrases "a non-modified bacterium" and "a non-modified bacterial strain". Examples of a non-modified strain can include, for example, a wild-type or parental strain. Specific examples of a non-modified strain can include a wild-type strain of a coryneform bacterium such as the strains *C. glutamicum* ATCC 13032 and ATCC 13869, a wild-type strain of a bacterium belonging to the family Enterobacteriaceae such as the strains *E. coli* MG1655 (ATCC 47076) and W3110 (ATCC 27325) and the strain *P. ananatis* AJ13355 (FERM BP-6614), a wild-type strain of a bacterium of the genus *Bacillus* such as the strains *B. subtilis* 168 and *B. amyloliquefaciens* FZB42, and so forth.

The total amount and/or the total activity of the corresponding gene product of a gene encoding a protein having H⁺-translocating membrane-bound pyrophosphatase activity, specifically the total amount and/or the total activity of a protein that i) is able to cause hydrolysis of diphosphate and/or synthesis of diphosphate, and ii) is able to transport protons across the membrane of a cell, can be increased by, for example, increasing (i.e. enhancing) the expression level of said gene, or increasing the activity per molecule (may be referred to as "specific activity") of the protein encoded by said gene, as compared with a non-modified strain, for example, a wild-type or parental strain. An increase in the total amount or the total activity of a protein can be measured as, for example, an increase in the amount or activity of the protein per cell, which may be an average amount or activity of the protein per cell. The bacterium may be modified so that the amount and/or the activity of a protein having H⁺-translocating membrane-bound pyrophosphatase activity per cell is increased to, for example, 150% or more, 200% or more, or 300% or more, of the activity of that protein in a non-modified strain. The bacterium may also be modified so that the activity of a protein having H⁺-translocating membrane-bound pyrophosphatase activity is conferred on the non-modified strain that does not have said activity prior to the modification, so that the modified bacterium is rendered having the activity of a protein having H⁺-translocating membrane-bound pyrophosphatase activity.

The phrase "a bacterium has been modified to overexpress a gene encoding a protein having H⁺-translocating membrane-bound pyrophosphatase activity" can also mean that the bacterium has been modified in such a way that in the modified bacterium the expression level (i.e. expression amount) of a gene encoding a protein having H⁺-translocating membrane-bound pyrophosphatase activity is enhanced or increased as compared with a non-modified strain, for example, a wild-type or parental strain. Therefore, the phrase "a gene is overexpressed" can be used interchangeably or equivalently to the phrase "the expression of a gene is enhanced or increased" or the phrase "the expression level of a gene is enhanced or increased". Furthermore, the phrase "a bacterium has been modified to overexpress a gene encoding a protein having H⁺-translocating membrane-bound pyrophosphatase activity" can also mean that the expression level of a gene encoding a protein having H⁺-translocating membrane-bound pyrophosphatase activity in the modified bacterium is higher than that observed for a non-modified strain. An increase in the expression level of a gene can be measured as, for example, an increase in the expression level of the gene per cell, which may be an average expression level of the gene per cell. The phrase "the expression level of a gene" or "the expression amount of a gene" can mean, for example, the amount of an expression product of a gene, such as the amount of mRNA of the gene or the amount of the protein encoded by the gene. The bacterium may be modified so that the expression level of the gene encoding a protein having H⁺-translocating membrane-bound pyrophosphatase activity per cell is increased to, for example, 150% or more, 200% or more, or 300% or more, of the expression level of that gene in a non-modified strain.

The protein concentration can be determined by the Bradford protein assay, the method of Lowry using bovine serum albumin (BSA) as a standard and a Coomassie dye, or a Western blot analysis (Bradford M. M., *Anal. Biochem.*, 1976, 72:248-254; Lowry O. H. et al., *J Biol. Chem.*, 1951, 193:265-275; Belogurov G. A. et al., 2002).

The aforementioned descriptions concerning overexpression of the gene encoding a protein having H⁺-translocating membrane-bound pyrophosphatase activity can also be applied similarly to overexpression of any genes.

Methods for modifying a bacterium to overexpress a gene encoding a protein having H$^+$-translocating membrane-bound pyrophosphatase activity and methods which can be used to overexpress the gene encoding a protein having H$^+$-translocating membrane-bound pyrophosphatase activity in the bacterium as described herein may depend on the bacterium that is chosen for the modification. Any method for gene overexpression may be used so long as the overexpression of the gene can be attained using that method.

Examples of methods which can be used to overexpress a gene can include, but are not limited to, increasing the copy number of the gene, such as the copy number of the gene in the chromosome of a bacterium and/or in the autonomously replicating vector, such as a plasmid, harbored by the bacterium. The copy number of a gene can be increased by, for example, introducing the gene into the chromosome of the bacterium and/or introducing an autonomously replicating vector containing the gene into the bacterium. Such increasing of the copy number of a gene can be carried out according to genetic engineering methods known to one of ordinary skill in the art.

The bacterium as described herein can be modified to overexpress a gene encoding a protein having H$^+$-translocating membrane-bound pyrophosphatase activity so that the bacterium can harbor said gene after introduction of said gene. Also, the bacterium can be modified in such a way that the activity of the protein having H$^+$-translocating membrane-bound pyrophosphatase activity can be determined in the modified bacterium. That is, any bacterium natively or naturally not having a gene encoding a protein having H$^+$-translocating membrane-bound pyrophosphatase activity can be used so long as the bacterium can be modified to overexpress the gene encoding a protein having W-translocating membrane-bound pyrophosphatase activity so that the activity of the protein having W-translocating membrane-bound pyrophosphatase activity can be determined in the modified bacterium and the modified bacterium is able to produce a target substance.

The copy number of a gene can be increased in a bacterium which does not have said gene before modification or in a bacterium which has said gene even before modification. That is, the bacterium as described herein can be obtained by, for example, introducing a gene encoding a protein having H$^+$-translocating membrane-bound pyrophosphatase activity into a bacterium, which may or may not have said gene before the introduction of said gene, so that the bacterium harbors an increased copy number of said gene. In an embodiment, the bacterium as described herein can be obtained by, for example, introducing a gene encoding a protein having H$^+$-translocating membrane-bound pyrophosphatase activity into the bacterium which does not have said gene before the introduction of said gene so that the bacterium harbors said gene. A bacterium to be introduced with a gene, which may or may not have said gene before the introduction of said gene, can also be referred to as a "recipient bacterium". In an embodiment, the phrase "a bacterium is modified to harbor a gene encoding a protein having H$^+$-translocating membrane-bound pyrophosphatase activity" can mean, for example, that a recipient bacterium naturally or natively not having a gene encoding a protein having H$^+$-translocating membrane-bound pyrophosphatase activity is modified to harbor said gene, such as a gene encoding a protein having H$^+$-translocating membrane-bound pyrophosphatase activity native to another organism which is different from the recipient bacterium (so-called a donor organism). The donor organism may be, for example, a bacterium other than the recipient bacterium. Therefore, a gene encoding a protein having H$^+$-translocating membrane-bound pyrophosphatase activity may be native to a bacterial species. Examples of the recipient bacterium include the bacterium as described herein, such as a coryneform bacterium including a bacterium belonging to the genus *Corynebacterium* or *Brevibacterium*, a bacterium belonging to the family Enterobacteriaceae, and a bacterium of the genus *Bacillus*. Examples of the donor organism include bacteria of the genera *Rhodospirillum*, *Bradyrhizobium*, *Rhodospirillum*, *Methylobacterium*, and so forth, such as the bacteria listed in Tables 1 and 2. For example, a gene encoding a protein having H$^+$-translocating membrane-bound pyrophosphatase activity can be the hppA gene native to *R. rubrum* strain ATCC 11170, and the recipient bacterium may be a coryneform bacterium such as, for example, *C. glutamicum*, a bacterium belonging to the family Enterobacteriaceae such as, for example, *E. coli* or *P. ananatis*, or a bacterium of the genus *Bacillus* such as, for example, *B. subtilis* or *B. amyloliquefaciens*.

Examples of methods which can be used to overexpress a gene can also include, but are not limited to, modifying an expression regulatory region of the gene.

Modification of an expression regulatory region of a gene can be employed in combination with an increase in the copy number of the gene.

When two or more genes, such as the gene encoding a protein having H$^+$-translocating membrane-bound pyrophosphatase activity and other genes, are overexpressed, those two or more genes can be overexpressed using one method for gene overexpression, or those genes can be overexpressed using different methods for gene overexpression. Furthermore, those two or more genes can be overexpressed, for example, one by one or simultaneously.

Methods as described herein for overexpression of a gene, such as the gene encoding a protein having H$^+$-translocating membrane-bound pyrophosphatase activity, can be applied similarly to overexpression of any genes.

As a coryneform bacterium, a bacterium belonging to the family Enterobacteriaceae, or a bacterium of the genus *Bacillus* can be an example of the bacterium as described herein; methods for overexpression of a gene encoding a protein having H$^+$-translocating membrane-bound pyrophosphatase activity are described hereinafter by referring to such a bacterium. The below description of such methods can be generalized similarly to modification of any bacterium and for overexpression of any genes. For example, methods for overexpression of a gene encoding a protein having H$^+$-translocating membrane-bound pyrophosphatase activity described hereinafter can be applied similarly and interchangeably for any coryneform bacterium, a bacterium belonging to the family Enterobacteriaceae, and a bacterium of the genus *Bacillus*.

A method for the overexpression of a gene encoding a protein having H$^+$-translocating membrane-bound pyrophosphatase activity in a coryneform bacterium can be a method of introducing a nucleic acid (DNA) having the gene into the bacterium, so that the copy number of the gene is increased. Examples of methods which can be used to introduce a nucleic acid such as, for example, a gene, a vector, and the like into a coryneform bacterium can include, but are not limited to, genetic engineering methods known to the person of ordinary skill in the art. In the bacterium as described herein, the gene encoding a protein having H$^+$-translocating membrane-bound pyrophosphatase activity can be present on a vector that autonomously replicates outside of the chromosome such as a plasmid, or may be incorporated into the chromosome, or a combination of these, if the bacterium is modified to harbor two or more copies of the gene encoding a protein having $H^+$-translocating membrane-bound pyrophosphatase activity. In addition, as described above, for constructing the bacterium as described herein, introduction of the gene encoding a protein having $H^+$-translocating membrane-bound pyrophosphatase activity and impartation to or enhancement in the bacterium of the ability to produce a target substance can be performed in any order.

A nucleic acid can be introduced into a coryneform bacterium by using, for example, a vector. The vector is not particularly limited so long as it is able to be autonomously replicable in the chosen coryneform bacterium, and may be, for example, a vector native to a bacterial plasmid, a vector native to a yeast plasmid, a vector native to a bacteriophage, cosmid, phagemid, or the like. As the vector, for example, a plasmid native to a coryneform bacterium can be used. Also, as the vector, a vector autonomously replicable in a cell of the coryneform bacterium can be used. The vector can be a multi-copy vector. Furthermore, the vector can include a marker such as an antibiotic resistance gene for selection of transformants. The vector may be, for example, a vector native to a bacterial plasmid, a vector native to a yeast plasmid, a vector native to a bacteriophage, cosmid, phagemid, or the like. Specific examples of vector autonomously replicable in coryneform bacteria can include pHM1519 (Miwa K. et al., *Agric. Biol. Chem.,* 1984, 48:2901-2903); pAM330 (Miwa K. et al., 1984); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAM330 described in Japanese Patent Laid-open (Kokai) No. 58-67679; pHM1519 described in Japanese Patent Laid-open (Kokai) No. 58-77895; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVC7 described in Japanese Patent Laid-open (Kokai) No. 9-070291; and so forth.

Furthermore, an artificial transposon and so forth can also be used to introduce a nucleic acid into a coryneform bacterium. When a transposon is used, a protein-encoding gene can be introduced into a chromosome by homologous recombination or translocation ability of the transposon itself. Other examples of the introduction method utilizing homologous recombination can include, for example, the methods utilizing a linear DNA, a plasmid having a temperature sensitive replication origin, a plasmid capable of conjugative transfer, a suicide vector not having a replication origin that does not function in the chosen host, and so forth. A gene to be introduced into a coryneform bacterium may be used as it is, or it may be modified so that it has the optimal codons according to codon frequencies in the coryneform bacterium. Specifically, the expression of a gene, which is native to a donor bacterium, in a recipient bacterium can be achieved by substituting rare (low-usage in the host organism) codons in the gene for synonymous middle- or high-usage codons, where codon usage can be defined as the number of times (frequency) a codon is translated per unit time in the cell of an organism or an average codon frequency of the sequenced protein-coding reading frames of an organism (Zhang S. P. et al., *Gene,* 1991, 105(1):61-72). The codon usage per organism can be found in the Codon Usage Database, which is an extended web-version of the CUTG (Codon Usage Tabulated from GenBank) (www.kazusa.or.jp/codon/; Nakamura Y. et al., Codon usage tabulated from the international DNA sequence databases: status for the year 2000, *Nucleic Acids Res.,* 2000, 28(1):292). The substitution of low-usage codons for synonymous high-usage codons can be preferable. The substituting rare and/or low-usage codons for synonymous middle- or high-usage codons may be combined with co-expression of the genes which encode tRNAs recognizing rare codons.

A gene to be introduced into the bacterium as described herein can be ligated downstream from a promoter. The promoter is not particularly limited so long as it can function in the chosen coryneform bacterium, and it may be a promoter native to a coryneform bacterium, or it may be a heterologous promoter. The phrase "a promoter that can function in a coryneform bacterium" can refer to a promoter that possesses promoter activity in a coryneform bacterium. Specific examples of the heterologous promoter include, for example, promoters native to *E. coli* such as lac promoter, trp promoter, and araBAD promoter, and tac promoter which is a hybrid promoter of the lac and trp promoters. Specific examples of the heterologous promoter include, for example, F1 promoter (WO2018/179834). Among these, potent promoters such as the tac promoter are particular examples, and inducible promoters such as the araBAD promoter are also particular examples.

The potent promoter, such as a highly active variant of an existing promoter, may also be obtained by using various reporter genes. For example, by making the −35 and −10 regions in a promoter region closer to a consensus sequence, the activity of the promoter can be enhanced (WO0018935 A1). The strength of a promoter can be defined by the frequency of initiation acts of RNA synthesis. Examples of the method for evaluating the strength of a promoter and strong promoters are described in the paper of Goldstein M. A. et al. (Prokaryotic promoters in biotechnology, *Biotechnol. Annu. Rev.,* 1995, 1:105-128) and so forth.

The method for introducing a gene into a coryneform bacterium is not particularly limited, and a generally used method, for example, the protoplast method (Miwa K. et al., *Gene,* 1985, 39:281-286), the electroporation method (Dunican L. K. and Shivnan E., *Nat. Biotechnol.,* 1989, 7:1067-1070), the electric pulse method (JP H2-207791 A), and so forth can be used.

Another method for the overexpression of a gene encoding a protein having $H^+$-translocating membrane-bound pyrophosphatase activity in a coryneform bacterium can be a method of increasing the expression level of the gene by modification of an expression regulatory region of the gene. An expression regulatory region of a gene can be modified by, for example, replacing the native expression regulatory region of the gene with a native and/or modified foreign expression regulatory region. The phrase "an expression regulatory region" can be used interchangeably or equivalently to the phrase "an expression regulatory sequence". As the gene encoding a protein having $H^+$-translocating membrane-bound pyrophosphatase activity may be organized in operon structure in combination with one or more other gene(s), the method which can be used to enhance expression of the gene also includes increasing the expression level of the operon having these genes by modification of an expression regulatory region of the operon, wherein the modification can be carried out by, for example, replacing the native expression regulatory region of the operon with a native and/or modified foreign expression regulatory region. In this method, the expression of two or more genes, including the gene encoding a protein having H$^+$-translocating membrane-bound pyrophosphatase activity, can be enhanced at the same time.

Expression regulatory regions can be exemplified by promoters, enhancers, operators, attenuators and termination signals, anti-termination signals, ribosome-binding sites (RBS) and other expression control elements (e.g., regions to which repressors or activators bind and/or binding sites for transcriptional and translational regulatory proteins, for example, in the transcribed mRNA). Such regulatory regions are described, for example, in known documents (Sambrook J., Fritsch E. F. and Maniatis T., "Molecular Cloning: A Laboratory Manual", 2$^{nd}$ ed., Cold Spring Harbor Laboratory Press (1989); Pfleger B. F. et al., Combinatorial engineering of intergenic regions in operons tunes expression of multiple genes, *Nat. Biotechnol.*, 2006, 24:1027-1032; Mutalik V. K. et al., Precise and reliable gene expression via standard transcription and translation initiation elements, Nat. Methods, 2013, 10:354-360). Modification of an expression regulatory region of a gene can be combined with increasing the copy number of the gene (see, for example, Akhverdyan V. Z. et al., *Appl. Microbiol. Biotechnol.*, 2011, 91:857-871; Tyo K. E. J. et al., *Nature Biotechnol.*, 2009, 27:760-765).

The exemplary promoters suitable for enhancing expression of a gene encoding a protein having H$^+$-translocating membrane-bound pyrophosphatase activity can be potent promoters that are stronger than the native promoters of that gene. Examples of potent promoters that can function in a coryneform bacterium can include, but are not limited to, those exemplified above. Alternatively, the effect of a promoter can be enhanced by, for example, introducing a mutation into the promoter region of a gene to obtain a stronger promoter function, thus resulting in the increased transcription level of the gene located downstream from the promoter. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA. Hence, these portions can be examples of expression regulatory regions of a gene. For example, a 20-fold range in the expression levels was found, depending on the nature of the three nucleotides preceding the start codon (Gold L. et al., *Annu. Rev. Microbiol.*, 1981, 35:365-403; Hui A. et al., *EMBO J.*, 1984, 3:623-629).

Examples of the vectors that can be used for a bacterium belonging to the family Enterobacteriaceae can include, but are not limited to, conditionally-replicated vectors such as, for example, the vectors having R6K (oriRγ) origin replication such as, for example, the pAH162 vector and the like, narrow-host-range plasmids such as pMW118/119, pBR322, pUC19 and the like, or broad-host-range plasmids such as RSF1010, RP4 and the like. The gene encoding a protein having H$^+$-translocating membrane-bound pyrophosphatase activity can also be introduced into the chromosomal DNA of a bacterium by, for example, homologous recombination, Mu-driven integration, or the like. Only one copy, or two or more copies of the gene encoding a protein having H$^+$-translocating membrane-bound pyrophosphatase activity may be introduced. For example, homologous recombination can be carried out using a nucleotide sequence multiple copies of which exist in the chromosomal DNA as a target to introduce multiple copies of the gene encoding a protein having H$^+$-translocating membrane-bound pyrophosphatase activity into the chromosomal DNA. Examples of a nucleotide sequence in which multiple copies exist in the chromosomal DNA can include, but are not limited to, repetitive DNA, and inverted repeats present at the end of a transposable element. In addition, it is possible to incorporate a gene into a transposon and allow it to be transferred to introduce multiple copies of the gene into the chromosomal DNA. A method for intrachromosomal amplification can be used to introduce multiple copies of a gene into the chromosomal DNA. By using Mu-driven transposition, more than 3 copies of the gene can be introduced into the chromosomal DNA of a recipient strain in one step (Akhverdyan V. Z. et al., *Biotechnol.* (*Russian*), 2007, 3:3-20).

Examples of potent promoters that can function in a bacterium belonging to the family Enterobacteriaceae can include, but are not limited to, lac promoter, trp promoter, trc promoter, tac promoter, tet promoter, araBAD promoter, rpoH promoter, msrA promoter, Pm1 promoter (derived from the genus *Bifidobacterium*), and P$_R$ and P$_L$ promoters of lambda (λ) phage.

Examples of the vectors that can be used for a bacterium of the genus *Bacillus* can include, but are not limited to, *E. coli-B. subtilis* shuttle vectors such as pHY300PLK, pMWMX1, pMWAL1, pLF22, pKS1, pGK12, pLF14, or the like, phage vectors such as 11059, IBF101, M13mp9, Mu phage (Japanese Patent Application, Publication No. 2-109985), or the like, plasmid-based expression vectors (Nguyen et al., Plasmid, 2005, 54(3):241-248, and the like.

Examples of potent promoters that can function in a bacterium of the genus *Bacillus* can include, but are not limited to, Pspac, Pgrac, PrplU, and PrepAB from pLF22, PgsiB, and Ppur.

Site-specific mutation(s) can be introduced into the chromosomes of exemplary *Bacillus* strains. First, the delivery plasmid carrying a site-directed mutation is constructed and then transformed into the desired *Bacillus* strain. Then, a two-step replacement recombination procedure is performed in the resulting transformants to incorporate a site-specific mutation into the chromosome by gene substitution. To transfer the delivery plasmid into a naturally non-transformable *Bacillus* strain, an intermediate host, such as, for example, *B. subtilis* 168 harboring the delivery plasmid, can be obtained by transformation. Finally, a bacterial phage propagated on the resulting transformants is used for transduction of the delivery plasmid into the targeted bacterium. This method is suitable for introducing marker-free deletions, insertions, point mutations, and so forth into the chromosomes of *Bacillus* strains (Zakataeva et al., A simple method to introduce marker-free genetic modifications into the chromosome of naturally nontransformable *Bacillus amyloliquefaciens* strains, *Appl. Microbiol. Biotechnol.*, 2010, 85(4):1201-1209). Furthermore, the incorporation of a site-specific mutation by gene substitution using homologous recombination such as set forth above can also be conducted with a plasmid that is unable to replicate in the host.

The copy number of a gene or the presence or absence of a gene can be measured, for example, by restricting the chromosomal DNA followed by Southern blotting using a probe based on the gene sequence, fluorescence in situ hybridization (FISH), and the like. The level of gene expression can be determined by measuring the amount of mRNA transcribed from the gene using various well-known methods, including Northern blotting, quantitative RT-PCR, and the like. The amount of the protein encoded by the gene can be measured by known methods including SDS-PAGE followed by immunoblotting assay (Western blotting analysis), or mass spectrometry analysis of the protein samples, and the like.

Methods for manipulation with recombinant molecules of DNA and molecular cloning such as preparation of plasmid DNA, digestion, ligation and transformation of DNA, selection of an oligonucleotide as a primer, incorporation of mutations, and the like may be ordinary methods well-known to the persons of ordinary skill in the art. These methods are described, for example, in Sambrook J., Fritsch E. F. and Maniatis T., "Molecular Cloning: A Laboratory Manual", $2^{nd}$ ed., Cold Spring Harbor Laboratory Press (1989) or Green M. R. and Sambrook J. R., "Molecular Cloning: A Laboratory Manual", $4^{th}$ ed., Cold Spring Harbor Laboratory Press (2012); Bernard R. Glick, Jack J. Pasternak and Cheryl L. Patten, "Molecular Biotechnology: principles and applications of recombinant DNA", $4^{th}$ ed., Washington, D.C., ASM Press (2009).

Any method for manipulation with recombinant DNA can be used including conventional methods such as, for example, transformation, transfection, infection, conjugation, and mobilization. Transformation, transfection, infection, conjugation or mobilization of a bacterium with the DNA encoding a protein can impart to the bacterium the ability to synthesize the protein encoded by the DNA. Methods of transformation, transfection, infection, conjugation, and mobilization include any known methods. For example, a method of treating recipient cells with calcium chloride so as to increase permeability of the cells of E. coli K-12 to DNA has been reported for efficient DNA transformation and transfection (Mandel M. and Higa A., Calcium-dependent bacteriophage DNA infection, J. Mol. Biol., 1970, 53:159-162). Methods of specialized and/or generalized transduction were described (Morse M. L. et al., Transduction in Escherichia coli K-12, Genetics, 1956, 41(1):142-156; Miller J. H., Experiments in Molecular Genetics. Cold Spring Harbor, N.Y.: Cold Spring Harbor La. Press, 1972). Other methods for random and/or targeted integration of DNA into the host microorganism can be applied, for example, "Mu-driven integration/amplification" (Akhverdyan et al., Appl. Microbiol. Biotechnol., 2011, 91:857-871), "Red/ET-driven integration" or "λRed/ET-mediated integration" (Datsenko K. A. and Wanner B. L., Proc. Natl. Acad. Sci. USA 2000, 97(12):6640-45; Zhang Y., et al., Nature Genet., 1998, 20:123-128). Moreover, for multiple insertions of desired genes in addition to Mu-driven replicative transposition (Akhverdyan et al., Appl. Microbiol. Biotechnol., 2011, 91:857-871) and chemically inducible chromosomal evolution based on recA-dependent homologous recombination resulting in amplification of desired genes (Tyo K. E. J. et al., Nature Biotechnol., 2009, 27:760-765), other methods can be used, which utilize different combinations of transposition, site-specific and/or homologous Red/ET-mediated recombinations, and/or P1-mediated generalized transduction (see, for example, Minaeva N. et al., BMC Biotechnology, 2008, 8:63; Koma D. et al., Appl. Microbiol. Biotechnol., 2012, 93(2):815-829).

Methods for overexpression of a gene encoding a protein having $H^+$-translocating membrane-bound pyrophosphatase activity in bacterial species other than a coryneform bacterium, a bacterium belonging to the family Enterobacteriaceae, and a bacterium of the genus Bacillus can be applied similarly by referring to the methods described herein for the coryneform bacterium, the bacterium belonging to the family Enterobacteriaceae, and the bacterium of the genus Bacillus, or those methods can be used that are known to the persons of ordinary skill in the art. Furthermore, it is within the ordinary skill that common methods can be used that are suitable for the gene overexpression in a coryneform bacterium, a bacterium belonging to the family Enterobacteriaceae, and a bacterium of the genus Bacillus. Moreover, the methods suitable for the gene overexpression in a coryneform bacterium can be appropriately modified and used to overexpress a gene in a bacterium belonging to the family Enterobacteriaceae and/or a bacterium of the genus Bacillus, and contrariwise. Therefore, the methods for gene overexpression as described herein may be applied to any bacterium as described herein.

Hereinafter, variants of the gene encoding a protein having $H^+$-translocating membrane-bound pyrophosphatase activity and variants of the protein having $H^+$-translocating membrane-bound pyrophosphatase activity, specifically variants of those native to R. rubrum strain ATCC 11170, will be described. The below descriptions of such variants of the gene and protein can also be applied similarly to any gene and protein, including a gene native to the bacterial species other than R. rubrum strain ATCC 11170 and encoding a protein having $H^+$-translocating membrane-bound pyrophosphatase activity and the encoded protein, as well as a gene encoding a protein having inorganic pyrophosphatase activity and the encoded protein described below.

There may be differences in DNA sequences between Gram-positive and Gram-negative bacteria, the bacterial families, genera, species, or strains. Therefore, the gene encoding a protein having $H^+$-translocating membrane-bound pyrophosphatase activity, such as a hppA gene, is not limited to the gene having the nucleotide sequence shown in SEQ ID NO: 1, but may include genes having a variant nucleotide sequence of SEQ ID NO: 1 and encoding a protein having $H^+$-translocating membrane-bound pyrophosphatase activity. Similarly, the protein having $H^+$-translocating membrane-bound pyrophosphatase activity, such as a HppA protein, is not limited to the protein having the amino acid sequence shown in SEQ ID NO: 2, but may include proteins having a variant amino acid sequence of SEQ ID NO: 2 and having $H^+$-translocating membrane-bound pyrophosphatase activity. Examples of such variant nucleotide sequences or variant amino acid sequences may include homologues and artificially modified sequences of the gene encoding a protein having $H^+$-translocating membrane-bound pyrophosphatase activity exemplified above or of the protein having $H^+$-translocating membrane-bound pyrophosphatase activity exemplified above.

The phrase "a variant protein" can mean a protein which has a variant amino acid sequence of SEQ ID NO: 2.

The phrase "a variant protein" can specifically mean a protein which has one or more mutations in the sequence as compared with the amino acid sequence shown in SEQ ID NO: 2, whether they are substitutions, deletions, insertions, and/or additions of one or several amino acid residues, but which still maintains the $H^+$-translocating membrane-bound pyrophosphatase activity as described herein, or of which the three-dimensional structure is not significantly changed relative to the non-modified protein such as, for example, the protein having the amino acid sequence shown in SEQ ID NO: 2. The number of changes in the variant protein depends on the position of amino acid residue(s) in the three-dimensional structure of the protein or the type of amino acid residue(s). It can be, but is not strictly limited to, 1 to 70, in another example 1 to 50, in another example 1 to 30, in another example 1 to 15, in another example 1 to 10, and in another example 1 to 5, in SEQ ID NO: 2. This is possible because amino acids can have high homology to one another, so that the activity of a protein is not affected by a change between such amino acids, or the three-dimensional structure of a protein is not significantly changed relative to the corresponding non-modified protein by a change between such amino acids. Therefore, the variant protein may be a protein having an amino acid sequence having a homology, defined as the parameter "identity" when using the computer program blastp, of not less than 70%, not less than 75%, not less than 80%, not less than 85%, not less than 90%, not less than 95%, not less than 98%, or not less than 99% with respect to the entire amino acid sequence shown in SEQ ID NO: 2, as long as the $H^+$-translocating membrane-bound pyrophosphatase activity of the protein is maintained, or the three-dimensional structure of the protein is not significantly changed relative to the non-modified protein such as, for example, the protein having the amino acid sequence shown in SEQ ID NO: 2. In this specification, "homology" may mean "identity", which is the identity of amino acid residues. The sequence identity between two sequences is calculated as the ratio of residues matching in the two sequences when aligning the two sequences so as to achieve a maximum alignment with each other.

The exemplary substitution, deletion, insertion, and/or addition of one or several amino acid residues can be a conservative mutation(s). The representative conservative mutation can be a conservative substitution. The conservative substitution can be, but is not limited to, a substitution, wherein substitution takes place mutually among Phe, Trp and Tyr, if the substitution site is an aromatic amino acid; among Ala, Leu, Ile and Val, if the substitution site is a hydrophobic amino acid; between Glu, Asp, Gln, Asn, Ser, His and Thr, if the substitution site is a hydrophilic amino acid; between Gln and Asn, if the substitution site is a polar amino acid; among Lys, Arg and His, if the substitution site is a basic amino acid; between Asp and Glu, if the substitution site is an acidic amino acid; and between Ser and Thr, if the substitution site is an amino acid having hydroxyl group. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

The exemplary substitution, deletion, insertion, and/or addition of one or several amino acid residues can also be a non-conservative mutation(s) provided that the mutation(s) is/are compensated by one or more secondary mutation(s) in the different position(s) of amino acids sequence so that the $H^+$-translocating membrane-bound pyrophosphatase activity of the variant protein is maintained, or the three-dimensional structure of the protein is not significantly changed relative to the non-modified protein such as, for example, the protein having the amino acid sequence shown in SEQ ID NO: 2.

The calculation of a percent identity of a polypeptide can be carried out using the algorithm blastp. More specifically, the calculation of a percent identity of a polypeptide can be carried out using the algorithm blastp in the default settings of Scoring Parameters (Matrix: BLOSUM62; Gap Costs: Existence=11 Extension=1; Compositional Adjustments: Conditional compositional score matrix adjustment) provided by National Center for Biotechnology Information (NCBI). The calculation of a percent identity of a polynucleotide can be carried out using the algorithm blastn. More specifically, the calculation of a percent identity of a polynucleotide can be carried out using the algorithm blastn in the default settings of Scoring Parameters (Match/Mismatch Scores=1,−2; Gap Costs=Linear) provided by NCBI.

The phrase "a variant nucleotide sequence" can mean a nucleotide sequence which encodes a protein having $H^+$-translocating membrane-bound pyrophosphatase activity, such as the protein having the amino acid sequence shown in SEQ ID NO: 2, using any synonymous amino acid codons according to the standard genetic code table (see, e.g., Lewin B., "Genes VIII", 2004, Pearson Education, Inc., Upper Saddle River, N.J. 07458). Therefore, the gene encoding a protein having $H^+$-translocating membrane-bound pyrophosphatase activity can be a gene having a variant nucleotide sequence due to the degeneracy of the genetic code.

The phrase "a variant nucleotide sequence" can also mean a nucleotide sequence that is able to hybridize under stringent conditions with the nucleotide sequence complementary to the sequence shown in SEQ ID NO: 1 or a probe that can be prepared from the nucleotide sequence provided that it encodes a protein having $H^+$-translocating membrane-bound pyrophosphatase activity. The phrase "stringent conditions" can include those conditions under which a specific hybrid, for example, a hybrid having homology, defined as the parameter "identity" when using the computer program blastn, of not less than 70%, not less than 75%, not less than 80%, not less than 85%, not less than 90%, not less than 95%, not less than 96%, not less than 97%, not less than 98%, or not less than 99% is formed, and a non-specific hybrid, for example, a hybrid having homology lower than the above is not formed. For example, stringent conditions can be exemplified by washing one time or more, or in another example, two or three times, at a salt concentration of 1×SSC (standard sodium citrate or standard sodium chloride), 0.1% SDS (sodium dodecyl sulphate) at 60° C., 0.1×SSC, 0.1% SDS at 60° C., or 0.1×SSC, 0.1% SDS at 65° C. Duration of washing can depend on the type of membrane used for the blotting and, as a rule, should be what is recommended by the manufacturer. For example, the recommended duration of washing for the Amersham Hybond™-N+ positively charged nylon membrane (GE Healthcare) under stringent conditions is 15 minutes. The washing step can be performed 2 to 3 times. As the probe, a part of the sequence complementary to the sequence shown in SEQ ID NO: 1 may also be used. Such a probe can be produced by PCR (polymerase chain reaction; refer to White T. J. et al., The polymerase chain reaction, *Trends Genet.*, 1989, 5:185-189) using oligonucleotides as primers prepared on the basis of the sequence shown in SEQ ID NO: 1 and a DNA fragment containing the nucleotide sequence to be used as the probe as a template. The length of the probe is recommended to be >50 bp; it can be suitably selected depending on the hybridization conditions, and is usually 100 bp to 1 kbp. For example, when a DNA fragment having a length of about 300 bp is used as the probe, the washing conditions after the hybridization can be, for example, 2×SSC, 0.1% SDS at 50° C., 60° C. or 65° C.

The phrase "a variant nucleotide sequence" can also mean a nucleotide sequence that encodes a variant protein.

Since the nucleotide sequence of the gene encoding a protein having $H^+$-translocating membrane-bound pyrophosphatase activity native to bacterial species such as *R. rubrum* and other ones listed in Tables 1 and 2 and the amino acid sequence of the protein encoded by that gene have already been elucidated (see above), the gene native to such a bacterial species or a variant nucleotide sequence thereof can be obtained by cloning from the bacterial species by PCR utilizing DNA of the bacterial species and oligonucleotide primers prepared based on the nucleotide sequence of the hppA gene native to the bacterial species; or a mutagenesis method of treating a DNA containing the hppA gene, in vitro, for example, with hydroxylamine, or a mutagenesis method of treating the bacterial species harboring the hppA gene with ultraviolet (UV) irradiation or a mutating agent such as N-methyl-N'-nitro-N-nitrosoguanidine (NTG) and nitrous acid usually used for the such treatment; or chemical synthesis as a full-length gene structure. Genes encoding a protein having $H^+$-translocating membrane-bound pyrophosphatase activity native to any other organisms, including other bacterial species, or a variant nucleotide sequence thereof can be obtained in a similar manner.

The phrase "non-modified", which can be used interchangeably or equivalently to the phrases "native", "natural", and "wild-type", in reference to a gene (for example, "a non-modified gene") and a protein (for example, "a non-modified protein"), can mean, respectively, a native gene and a native protein that exist naturally in, are expressed naturally in, and/or are produced naturally by an organism, specifically a non-modified strain of a bacterium. Examples of such an organism can include any organism having the corresponding gene or protein, and specific examples thereof can include, for example, a coryneform bacterium such as, for example, the *C. glutamicum* ATCC13032 strain, a bacterium belonging to the family Enterobacteriaceae such as, for example, the *E. coli* MG1655 strain (ATCC 47076), the *E. coli* W3110 strain (ATCC 27325), the *P. ananatis* AJ13355 strain (FERM BP-6614), a bacterium of the genus *Bacillus* such as, for example, the *B. subtilis* 168 strain, the *B. amyloliquefaciens* FZB42 strain, bacterial species listed in Tables 1 and 2, and so forth. A non-modified gene can encode a non-modified protein.

The phrase "native to" in reference to a protein or a nucleic acid can mean that the protein or the nucleic acid is native to a particular organism such as, for example, mammals, plants, insects, bacteria, and viruses. That is, a protein or a nucleic acid native to a particular organism can mean the protein or the nucleic acid, respectively, that exists naturally in that organism. A protein or a nucleic acid native to a particular organism can be isolated from that organism and sequenced using means known to one of ordinary skill in the art. Moreover, as the amino acid sequence or the nucleotide sequence of a protein or nucleic acid, respectively, isolated from an organism in which the protein or nucleic acid exists, can easy be determined, the phrase "native to" in reference to a protein or a nucleic acid can also refer to a protein or a nucleic acid that can be obtained using any means, for example, a genetic engineering technique, including recombinant DNA technology, or a chemical synthesis method, or the like, so long as the amino acid sequence of the protein or the nucleotide sequence of the nucleic acid thus obtained is identical to the amino acid sequence of the protein or the nucleotide sequence of the nucleic acid that exists naturally in, is expressed naturally in, and/or is produced naturally by the organism. The phrase "a protein" can include, but is not limited to, peptides, oligopeptides, polypeptides, proteins, enzymes, and so forth. The phrase "a nucleic acid" can include deoxyribonucleic acid (DNA) and ribonucleic acid (RNA), and can specifically include, but is not limited to, expression regulatory sequences, including promoters, attenuators, terminators, and the like, genes, intergenic sequences, nucleotide sequences encoding signal peptides, pro-moieties of proteins, or artificial amino acid sequences, and so forth. For example, a gene can particularly be DNA. Specific examples of a protein and a nucleic acid native to a particular organism are described herein, and include the protein having the amino acid sequences shown in SEQ ID NO: 2 and the gene having the nucleotide sequence shown in SEQ ID NO: 1, which are native to *R. rubrum* strain ATCC 11170.

The bacterium as described herein may be further modified to attenuate expression of a gene encoding a protein having inorganic pyrophosphatase activity. Modifications for constructing the bacterium as described herein can be performed in any order.

The phrase "a protein having inorganic pyrophosphatase activity" can mean a protein that causes catalysis of the following reaction: i) diphosphate+$H_2O \leftrightarrow$ 2 phosphate+$H^+$, and/or ii) triphosphate+$H_2O \leftrightarrow$ phosphate+diphosphate (EC: 3.6.1.1; Baykov A. A. et al., Catalysis by *Escherichia coli* inorganic pyrophosphatase: pH and $Mg^{2+}$ dependence, *Biochemistry*, 1996, 35(15):4655-4661).

The activity of a protein having inorganic pyrophosphatase activity can be determined by evaluating, for example, the amount of orthophosphate as described above (Baykov A. A. and Avaeva S. M., 1981; Baykov A. A. et al., Kinetic characterization of the hydrolytic activity of the $H^+$-pyrophosphatase of *Rhodospirillum rubrum* in membrane-bound and isolated states, *Eur. J. Biochem.*, 1996, 236:121-127) or by measuring spectrophotometrically at 360 nm accumulation of diphosphate in a medium supplemented with acetyl-CoA synthetase and luciferase (Upson R. H. et al., A spectrophotometric method to measure enzymatic activity in reactions that generate inorganic pyrophosphate, *Anal. Biochem.*, 1996, 243(1):41-45).

The expression of any gene encoding a protein having inorganic pyrophosphatase activity can be attenuated so long as the gene encodes the protein having inorganic pyrophosphatase activity as described herein. Examples of the gene encoding a protein having inorganic pyrophosphatase activity include a ppa gene. The ppa gene encoding a protein having inorganic pyrophosphatase activity that is native to various organisms is known, and the specific examples of the gene include, but are not limited to, the ppa gene native to bacterial species such as, for example, *C. glutamicum* strain ATCC 13032 (UniProtKB, accession No.: Q8NM79), *E. coli* strain K-12 (accession No.: P0A7A9), *P. ananatis* strain AJ13355 (accession No.: A0A0H3L6E9), *B. subtilis* strain BEST7613 (accession No.: L8ATJ2), and so forth.

The phrase "a bacterium has been modified to attenuate expression of a gene encoding a protein having inorganic pyrophosphatase activity" can mean that the bacterium has been modified in such a way that in the modified bacterium expression of a gene encoding a protein having inorganic pyrophosphatase activity is attenuated. The expression of a gene encoding a protein having inorganic pyrophosphatase activity can be attenuated due to, for example, inactivation of the gene.

The phrase "a gene encoding a protein having inorganic pyrophosphatase activity is inactivated" can mean that the modified gene encodes a completely inactive or non-functional protein as compared with the gene encoding a protein that has inorganic pyrophosphatase activity. It is also acceptable that the modified DNA region is unable to naturally express the gene due to deletion of a part of the gene or deletion of the entire gene, replacement of one base or more to cause an amino acid substitution in the protein encoded by the gene (missense mutation), introduction of a stop codon (nonsense mutation), deletion of one or two bases to cause a reading frame shift of the gene, insertion of a drug-resistance gene and/or transcription termination signal, or modification of an expression regulatory region such as promoters, enhancers, operators, attenuators and termination signals, anti-termination signals, ribosome-binding sites (RBS) and other expression control elements. Inactivation of the gene can also be performed, for example, by conventional methods such as a mutagenesis treatment using UV irradiation or nitrosoguanidine (N-methyl-N'-nitro-N-nitrosoguanidine), site-directed mutagenesis, gene disruption using homologous recombination, and/or insertion-deletion mutagenesis (Yu D. et al., *Proc. Natl. Acad. Sci. USA*, 2000, 97(11):5978-5983; Datsenko K. A. and Wanner B. L., *Proc. Natl. Acad. Sci. USA*, 2000, 97(12):6640-6645; Zhang Y. et al., *Nature Genet.*, 1998, 20:123-128) based on "Red/ET-driven integration" or "λRed/ET-mediated integration".

The phrase "a bacterium has been modified to attenuate expression of a gene encoding a protein having inorganic pyrophosphatase activity" can also mean that the modified bacterium contains a region operably linked to the gene, including sequences controlling gene expression such as promoters, enhancers, attenuators and transcription termination signals, ribosome-binding sites (RBSs), and other expression control elements, which is modified so that the expression level of the gene encoding a protein having inorganic pyrophosphatase activity is decreased as compared with a non-modified strain; and other examples (see, for example, WO95/34672; Carrier T. A. and Keasling J. D., *Biotechnol. Prog.*, 1999, 15:58-64). The phrase "operably linked" in reference to a gene can mean that the regulatory region(s) is/are linked to the nucleotide sequence of the gene in such a manner so that the expression of the gene can be attained (for example, enhanced, increased, constitutive, basal, antiterminated, attenuated, deregulated, decreased, or repressed expression), and/or mRNA of the gene and/or an amino acid sequence encoded by the gene (so-called expression product) can be produced as a result of expression of the gene.

The phrase "a bacterium has been modified to attenuate expression of a gene encoding a protein having inorganic pyrophosphatase activity" can also mean that the bacterium has been modified in such a way that in the modified bacterium, the expression level (i.e. expression amount) of a gene encoding a protein having inorganic pyrophosphatase activity is attenuated as compared with a non-modified strain, for example, a wild-type or parental strain. A decrease in the expression level of a gene can be measured as, for example, a decrease in the expression level of the gene per cell, which may be an average expression level of the gene per cell. The phrase "the expression level of a gene" or "the expression amount of a gene" can mean, for example, the amount of an expression product of a gene, such as the amount of mRNA of the gene or the amount of the protein encoded by the gene. The bacterium may be modified so that the expression level of the gene encoding a protein having inorganic pyrophosphatase activity per cell is reduced to, for example, 50% or less, 20% or less, 10% or less, 5% or less, or 0% of that in a non-modified strain.

The phrase "a bacterium has been modified to attenuate expression of a gene encoding a protein having inorganic pyrophosphatase activity" can also mean that the bacterium has been modified in such a way that in the modified bacterium the total amount and/or the total activity of the corresponding gene product, i.e. a protein having inorganic pyrophosphatase activity, is decreased as compared with a non-modified strain. A decrease in the total amount and/or the total activity of a protein can be measured as, for example, a decrease in the amount or activity of the protein per cell, which may be an average amount or activity of the protein per cell. The bacterium can be modified so that the amount or activity of the protein having inorganic pyrophosphatase activity per cell is decreased to, for example, 50% or less, 20% or less, 10% or less, 5% or less, or 0% of that in a non-modified strain.

Examples of a non-modified strain serving as a reference for the above comparisons can include a wild-type strain of a coryneform bacterium such as the strains *C. glutamicum* ATCC 13032 and ATCC 13869, a wild-type strain of a bacterium belonging to the family Enterobacteriaceae such as the strains *E. coli* MG1655 (ATCC 47076) and W3110 (ATCC 27325) and the strain *P. ananatis* AJ13355 (FERM BP-6614), a wild-type strain of a bacterium of the genus *Bacillus* such as the strains *B. subtilis* 168 and *B. amyloliquefaciens* FZB42, and so forth. Examples of a non-modified strain serving as a reference for the above comparisons can also include a parental strain which has not been modified to attenuate expression of a gene encoding a protein having inorganic pyrophosphatase activity or a bacterium in which expression of a gene encoding a protein having inorganic pyrophosphatase activity is not attenuated.

Expression of a gene encoding a protein having inorganic pyrophosphatase activity can also be attenuated by, for example, modifying an expression regulatory region of the gene. Examples of modification of an expression regulatory region of a gene include, for example, replacing the expression regulatory region, such as a promoter on the chromosomal DNA, with a weaker one. The strength of a promoter can be defined by the frequency of initiation acts of RNA synthesis. Examples of methods for evaluating the strength of promoters are described in Goldstein M. A. et al. (Goldstein M. A. and Doi R. H., Prokaryotic promoters in biotechnology, *Biotechnol. Annu. Rev.*, 1995, 1:105-128), and so forth. Furthermore, it is also possible to introduce one or more nucleotide substitutions in a promoter region of the gene and thereby modify the promoter to be weakened as disclosed in WO0018935 A1. Furthermore, it is known that substitution of several nucleotides in the Shine-Dalgarno (SD) sequence, and/or in the spacer between the SD sequence and the start codon, and/or a sequence immediately upstream and/or downstream from the start codon in the ribosome-binding site greatly affects the translation efficiency of mRNA.

Expression of a gene encoding a protein having inorganic pyrophosphatase activity can also be attenuated by, for example, inserting a transposon or an insertion sequence (IS) into the coding region of the gene (U.S. Pat. No. 5,175,107) or in the region controlling gene expression, or by conventional methods such as mutagenesis with ultraviolet (UV) irradiation or nitrosoguanidine (N-methyl-N'-nitro-N-nitrosoguanidine, NTG). Furthermore, the incorporation of a site-specific mutation can be conducted by known chromosomal editing methods based, for example, on λRed/ET-mediated recombination (Datsenko K. A. and Wanner B. L., *Proc. Natl. Acad. Sci. USA*, 2000, 97(12):6640-6645).

The bacterium can have, in addition to the properties already described, other specific properties such as various nutrient requirements, drug resistance, drug sensitivity, and drug dependence, without departing from the scope of the present invention.

2. Method

The method of producing a target substance using a bacterium as described herein includes the steps of cultivating (also called culturing) the bacterium in a culture medium to allow the target substance to be produced, excreted or secreted, and/or accumulated in the culture medium or in cells of the bacterium, or both, and collecting the target substance from the culture medium and/or the cells. The target substance can be produced in such a form as described above. In the method as described herein, a target substance can be accumulated in and collected from cells of the bacterium that is used in the method. It is, therefore, apparent to the person of ordinary skill in the art that, in an embodiment, a target substance can be accumulated in and collected from cells of the bacterium that is used in the method as described herein. The method may further include, optionally, the step of purifying a target substance from the culture medium and/or the cells.

The cultivation of the bacterium, and collection, and, optionally, purification of a target substance from the medium and the like may be performed in a manner similar to conventional fermentation methods wherein a target substance is produced using a microorganism. That is, the cultivation of the bacterium, and collection and purification of a target substance from the medium and the like may be performed by applying the conditions that are suitable for the cultivation of the bacterium, and appropriate for the collection and purification of the target substance, which conditions are well-known to the persons of ordinary skill in the art.

The culture medium can be either a synthetic or natural medium such as a typical medium that contains a carbon source, a nitrogen source, a sulphur source, a phosphorus source, inorganic ions, and other organic and inorganic components as required. As the carbon source, saccharides such as glucose, sucrose, lactose, galactose, fructose, arabinose, maltose, xylose, trehalose, ribose, and hydrolysates of starches; alcohols such as ethanol, glycerol, mannitol, and sorbitol; organic acids such as gluconic acid, fumaric acid, citric acid, malic acid, and succinic acid; fatty acids, and the like can be used. As the nitrogen source, inorganic ammonium salts such as ammonium sulfate, ammonium chloride, and ammonium phosphate; organic nitrogen such as of soy bean hydrolysate; ammonia gas; aqueous ammonia; and the like can be used. Furthermore, peptone, yeast extract, meat extract, malt extract, corn steep liquor, and so forth can also be utilized. The medium may contain one or more types of these nitrogen sources. The sulphur source can include ammonium sulphate, magnesium sulphate, ferrous sulphate, manganese sulphate, thiosulfate, sulfide, and the like. The medium can contain a phosphorus source in addition to the carbon source, the nitrogen source and the sulphur source. As the phosphorus source, potassium dihydrogen phosphate, dipotassium hydrogen phosphate, phosphate polymers such as pyrophosphoric acid and so forth can be utilized. Vitamins such as vitamin B1, vitamin B2, vitamin B6, nicotinic acid, nicotinamide, vitamin B12, required substances, for example, organic nutrients such as nucleic acids such as adenine and RNA, amino acids, peptone, casamino acid, yeast extract, and the like may be present in appropriate, even if trace, amounts. Other than these, small amounts of calcium phosphate, iron ions, manganese ions, and so forth may be added, if necessary.

Cultivation can be performed under conditions suitable for cultivating a bacterium chosen for use in the method for producing a target substance. For example, when a coryneform bacterium is cultivated, the cultivation can be performed under aerobic conditions for from 24 to 96 hours, the temperature can be maintained at from 24° C. to 42° C., and the pH can be maintained at from 5 to 9. When a bacterium belonging to the family Enterobacteriaceae such as, for example, a bacterium belonging to the genus *Escherichia* is cultivated, the cultivation can be performed under aerobic conditions for from 7 to 106 hours, for from 16 to 72 hours, or for from 32 to 48 hours, the culture temperature during cultivation can be controlled within from 30 to 45° C. or within from 30 to 37° C., and the pH can be adjusted between 5 and 8 or between 6 and 7.5. When a bacterium of the genus *Bacillus* is cultivated, the cultivation can be performed under aerobic conditions for 16 to 96 hours, the culture temperature during cultivation can be controlled within 28 to 45° C., or within 30 to 37° C., and the pH can be adjusted between 5 and 8, or between 5.5 and 6.5. The pH can be adjusted using an inorganic or organic acidic or alkaline substance such as urea, calcium carbonate, or ammonia gas.

After cultivation, the target substance can be collected from the culture medium. Specifically, the target substance present outside of cells can be collected from the culture medium. Also, after cultivation, the target substance can be collected from cells of the bacterium. Specifically, the cells can be disrupted, a supernatant can be obtained by removing solids such as the cells and the cell-disrupted suspension (so-called cell debris), and then the target substance can be collected from the supernatant. Disruption of the cells can be performed using, for example, methods that are well-known in the art, such as ultrasonic lysis using high frequency sound waves, or the like. Removal of solids can be performed by, for example, centrifugation or membrane filtration. Collection of the target substance from the culture medium or the supernatant etc. can be performed using, for example, conventional techniques such as salting out, ethanol precipitation, concentration, crystallization, ultrafiltration, gel filtration chromatography, ion exchange column chromatography, affinity chromatography, medium or high pressure liquid chromatography, reverse phase chromatography, and hydrophobic chromatography, or a combination of these.

EXAMPLES

The present invention is more precisely explained below with reference to the following non-limiting Examples.

Example 1. Production of Amino Acids 1.1. Chemical Synthesis of hppA Gene

The hppA gene native to *R. rubrum* having the nucleotide sequence shown in SEQ ID NO: 1 was codon-optimized for expression in *E. coli*, and then chemically synthesized on the pUC-57-hppA(Rru) plasmid, which is a derivative of the commercially available plasmid pUC57 (GenScript®), USA). Codon optimization was based on Codon-usage databases for *E. coli* and *R. rubrum* (refer to: www.kazusa.or.jp/codon/); codons were altered to keep the frequency of their usage in *E. coli* similar to that in *R. rubrum*. The structure of the pUC-57-hppA(Rru) plasmid is shown in FIG. 1, and the nucleotide sequence of the plasmid is shown in SEQ ID NO: 3. The PstI restriction site having at the 5'-end the nucleotide sequence ccaaatt and the SacI having at the 3'-end the nucleotide sequence atcccaaatt were used for cloning the hppA gene having optimized codons (SEQ ID NO: 4).

1.2. Verification of the Chemically Synthesized hppA Gene.

The nucleotide sequence of the chemically synthesized hppA gene that encodes H⁺-PPase native to *R. rubrum* was verified by sequence analysis using primers P1 (SEQ ID NO: 5) and P2 (SEQ ID NO: 6), and a DNA from the pUC-57-hppA(Rru) plasmid (SEQ ID NO: 3) as a template. Conditions for PCR were as follows: denaturation for 3 min at 95° C.; profile for the 30 cycles: 30 sec at 95° C., 30 sec at 55° C., 2.5 min at 72° C.; final elongation: 7 min at 72° C. The PCR product 1, obtained in the reaction using the DNA from the pUC-57-hppA(Rru) plasmid as a template, was 2265 bp in length (SEQ ID NO: 7).

1.3. Construction of pAH162-TetATetR-2Ter-hppA(Rru) Integrative Plasmid Having Promoter-Less hppA Gene.

Figure 2:
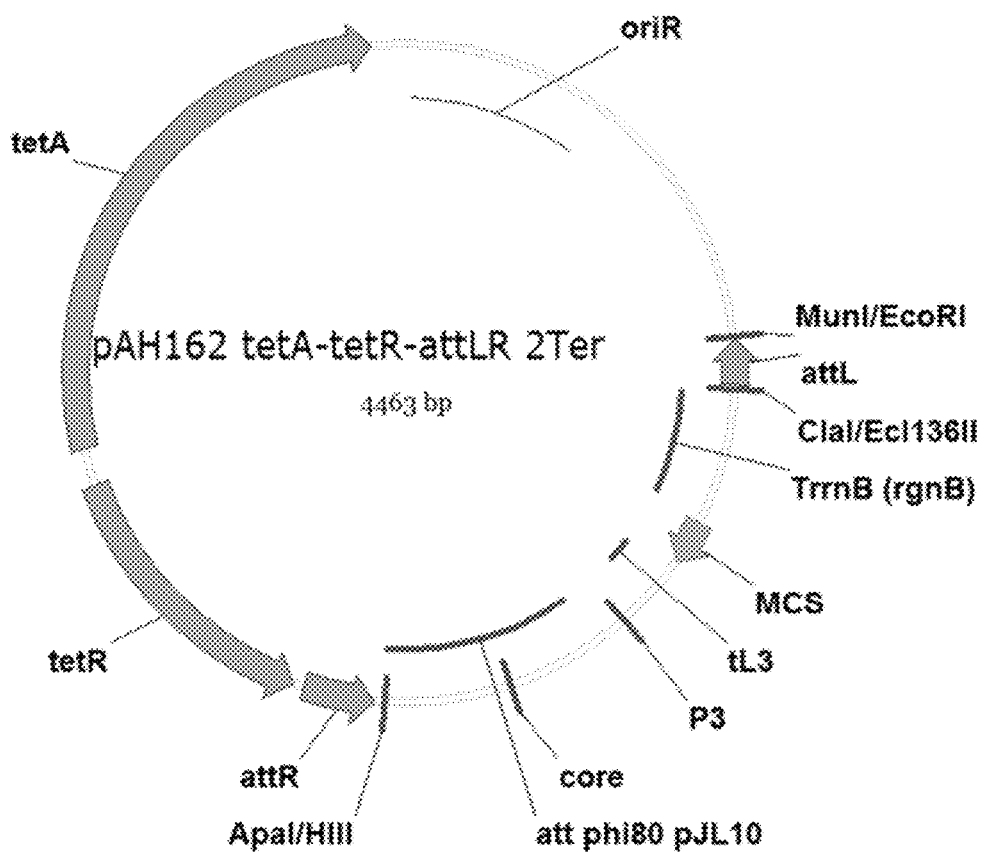
FIG. 2 shows the structure of the pAH162-TetATetR-2Ter vector.
Figure 3:
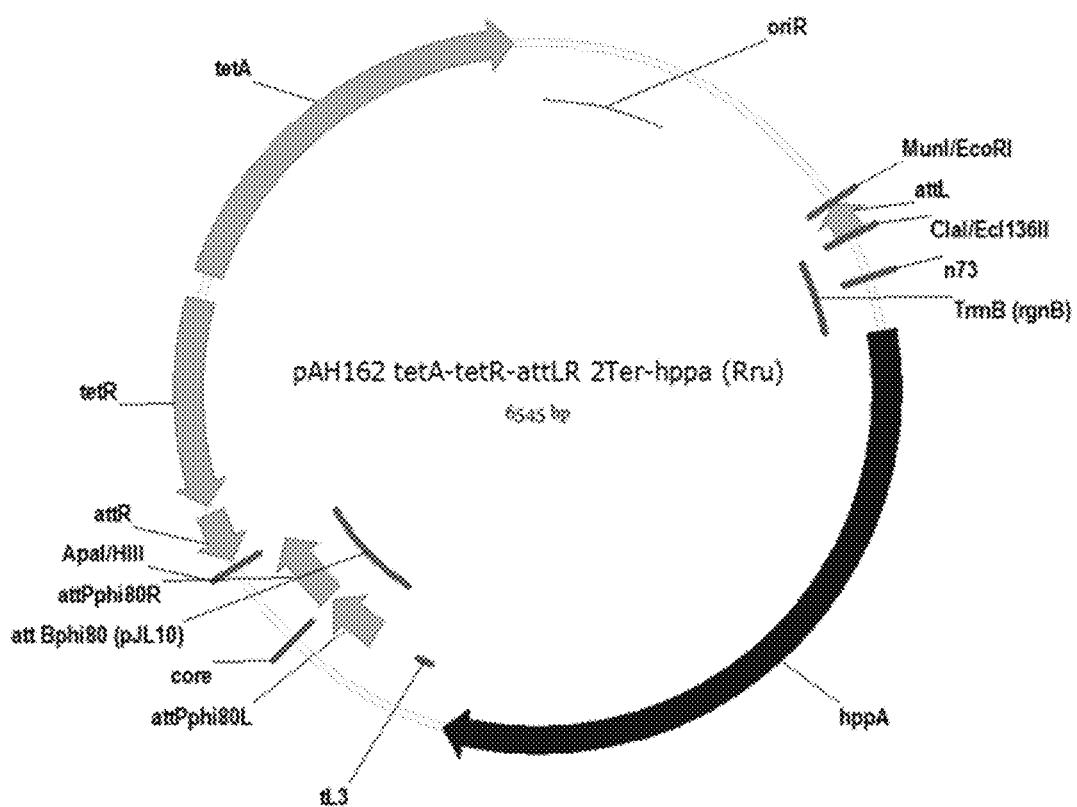
FIG. 3 shows the structure of the pAH162-TetATetR-2Ter-hppA(Rru) plasmid.

The chemically synthesized hppA gene (Example 1.1) was treated with PstI and SacI restriction enzymes and re-cloned from pUC-57-hppA(Rru) into the integrative vector pAH162-TetATetR-2Ter (SEQ ID NO: 8, FIG. 2) treated with the same restriction enzymes. The resulting plasmid pAH162-TetATetR-2Ter-hppA(Rru) (SEQ ID NO: 9, FIG. 3) was obtained after transformation of the CC118λpir⁺ *E. coli* strain (ATCC BAA-2426; Herrero M. et al., Transposon vectors containing non-antibiotic resistance selection markers for cloning and stable chromosomal insertion of foreign genes in gram-negative bacteria, J. Bacteriol., 1990, 172: 6557-6567) and purification from one of the independently grown clones on the plate with tetracycline (Tc) as the selectable marker. After verification of the desired recombinant structure (Example 1.4), the plasmid was used for φ80-Int-mediated integration into the artificial φ80-attB site on the chromosome of *E. coli* according to the Dual In/Out strategy (Minaeva N. I. et al., 2008).

1.4. Verification of the Presence of hppA Gene on pAH162-TetATetR-2Ter-hppA(Rru) Integrative Plasmid.

The presence of chemically synthesized hppA gene (Example 1.1) on pAH162-TetATetR-2Ter-hppA(Rru) integrative plasmid was verified using PCR and sequence analysis. The primers P3 (SEQ ID NO: 10) and P4 (SEQ ID NO: 11) were used for PCR verification from 5'-end. The primers P5 (SEQ ID NO: 12) and P6 (SEQ ID NO: 13) were used for PCR verification from 3'-end. A DNA from the pAH162-TetATetR-2Ter-hppA(Rru) plasmid (SEQ ID NO: 9) was used as a template. Conditions for the both PCRs were as follows: denaturation for 3 min at 95° C.; profile for the 30 cycles: 30 sec at 95° C., 30 sec at 55° C., 1.5 min at 72° C.; final elongation: 7 min at 72° C. The PCR products 2 and 3, obtained in the reaction using the DNA from the pAH162-TetATetR-2Ter-hppA(Rru) plasmid as a template, were 937 bp (SEQ ID NO: 14) and 1534 bp (SEQ ID NO: 15) in length, accordingly, as desired.

Primers P3 (SEQ ID NO: 10), P7 (SEQ ID NO: 16), P8 (SEQ ID NO: 17) and P9 (SEQ ID NO: 18), and a DNA from the pAH162-TetATetR-2Ter-hppA(Rru) plasmid (SEQ ID NO: 9) as a template were used for the sequence analysis. Conditions for PCR were as follows: denaturation for 8 min at 95° C.; profile for 25 cycles: 30 sec at 95° C., 30 sec at 57° C., 2.5 min at 68° C. (AccuTaq® LA DNA Polymerase High fidelity Taq enzyme); final elongation: 7 min at 68° C. The PCR product 4, obtained in the reaction using the DNA from the pAH162-TetATetR-2Ter-hppA(Rru) plasmid as a template and the primers P3 (SEQ ID NO: 10) and P6 (SEQ ID NO: 13), was 2383 bp in length (SEQ ID NO: 19).

1.5. Construction of *E. coli* MG1655 IS5.8::$P_L$-hppA Strain Having Overexpressed hppA Gene.

The pAH162-TetATetR-2Ter-hppA(Rru) plasmid (Example 1.3) was used for φ80-Int-mediated integration of the promoter-less hppA gene into the artificial φ80-attB site of the chromosome of *E. coli* MG1655 Δ(φ80-attB) IS5.8:: φ80-attB strain (Haldimann A. and Wanner B. L., J. Bacteriol., 2001, 183(21):6384-6393; Minaeva N. I et al., BMC Biotechnol., 2008, 8:63). The pAH123 plasmid (Haldimann A. and Wanner B. L., 2001; GenBank, accession No.: AY048726), which contains the thermoinducible φ80-int gene, was used to provide φ80-Int-mediated integration. A vector fragment of the integrated recombinant plasmid that includes oriRγ and the tetracycline resistance marker gene bracketed by attL/R sites of phage λ (Sanger F. et al., Nucleotide sequence of bacteriophage λ DNA, J. Mol. Biol., 1982, 162:729-773) was eliminated from the *E. coli* chromosome using Xis/Int site-specific recombination system using the pMWts-λInt/Xis helper plasmid (Minaeva N. I. et al., 2008). Expression of the hppA gene was activated by λRed-mediated insertion of the DNA fragment containing the chloramphenicol resistance marker (Cm$^R$) and λ$P_L$ promoter region in combination with the consensus SD-sequence using primers P10 (SEQ ID NO: 20) and P11 (SEQ ID NO: 21) and the chromosomal DNA of *E. coli* BW25113 cat-$P_L$-yddG as a template (Russian patent No. RU2222596 C1), yielding *E. coli* MG1655 IS5.8::cat-$P_L$-hppA strain.

The CmR$^{ex}$ marker was eliminated from the *E. coli* MG1655 IS5.8::cat-$P_L$-hppA chromosome using a Xis/Int site-specific recombination system using the pMWts-λInt/Xis helper plasmid (Minaeva N. I. et al., 2008). Thus, the *E. coli* MG1655 IS5.8::$P_L$-hppA strain was constructed.

1.6. Verification of the Modifications of Example 1.5.

The modifications, that were introduced into *E. coli* such as insertion of integrative plasmid harboring the hppA gene, elimination of TcR$^{ex}$ marker, and introduction of λ$P_L$ promoter upstream the hppA gene, were verified.

The presence of the integrated pAH162-TetATetR-2Ter-hppA(Rru) plasmid harboring the hppA gene in the artificial φ80-attB site of the *E. coli* MG1655 Δ(φ80-attB) IS5.8:: φ80-attB chromosome was verified by PCR using primers P12 (SEQ ID NO: 22) and P13 (SEQ ID NO: 23) and the chromosomal DNA from the *E. coli* MG1655 IS5.8::cat-$P_L$-hppA strain as a template. Conditions for PCR were as follows: denaturation for 3 min at 95° C.; profile for the 30 cycles: 30 sec at 95° C., 30 sec at 51° C., 1 min at 72° C.; final elongation: 7 min at 72° C. The PCR product 5, obtained in the reaction using the chromosomal DNA from the *E. coli* MG1655 IS5.8::cat-$P_L$-hppA strain as a template, having the promoter-less hppA gene, was 975 bp in length (SEQ ID NO: 24).

The elimination of the TcR$^{ex}$ marker-containing part of the insertion IS5.8::TetA-TetR-2Ter-hppA(Rru) from the *E. coli* chromosome was verified by PCR. The primers P14 (SEQ ID NO: 25) and P15 (SEQ ID NO: 26), and the chromosomal DNA from the *E. coli* MG1655 IS5.8::$P_L$-hppA strain as a template were used for the verification. Conditions for PCR were as follows: denaturation for 3 min at 95° C.; profile for the 30 cycles: 30 sec at 95° C., 30 sec at 51° C., 1 min at 72° C.; final elongation: 7 min at 72° C. The PCR product 6, obtained in the reaction using the chromosomal DNA from the *E. coli* MG1655 IS5.8::$P_L$-hppA strain as a template, was 1272 bp in length (SEQ ID NO: 27).

Introduction of λP$_L$ promoter into E. coli chromosome was verified by PCR. The primers P3 (SEQ ID NO: 10) and P15 (SEQ ID NO: 26), and the chromosomal DNA from the E. coli MG1655 IS5.8::cat-P$_L$-hppA strain having hppA gene under control of the λP$_L$ promoter as a template were used for the verification. Conditions for PCR were as follows: denaturation for 3 min at 95° C.; profile for the 30 cycles: 30 sec at 95° C., 30 sec at 51° C., 1.5 min at 72° C.; final elongation: 7 min at 72° C. The PCR product 7, obtained in the reaction using the chromosomal DNA from the E. coli MG1655 IS5.8::cat-P$_L$-hppA strain as the template, was 2132 bp in length (SEQ ID NO: 28).

1.7. Construction of E. coli MG1655 IS5.8::P$_L$-hppA ΔPpa::Cat Strain.

An E. coli strain having the overexpressed hppA gene and inactivated ppa gene was constructed using the recombineering-based method developed by Datsenko K. A. and Wanner B. L. (Datsenko K. A. and Wanner B. L., Proc. Natl. Acad. Sci. USA, 2000, 97(12):6640-6645). A DNA fragment containing the Cm$^R$ marker was obtained by PCR using primers P16 (SEQ ID NO: 29) and P17 (SEQ ID NO: 30), and the pMW118-λattL-Cm$^R$-λattR plasmid as a template. The primers P16 and P17 are homologous to both regions adjacent to the ppa gene and the gene cat conferring chloramphenicol resistance in the template chromosome. Conditions for PCR were as follows: denaturation for 5 min at 95° C.; profile for the 30 cycles: 30 sec at 95° C., 30 sec at 56° C., 1.5 min at 72° C.; final elongation: 5 min at 72° C.

The obtained PCR product 8 (SEQ ID NO: 31; 1708 bp) was purified by electrophoresis in agarose gel and used for electroporation of the E. coli MG1655 IS5.8::P$_L$-hppA strain containing the pKD46 plasmid having a temperature-sensitive replication origin. The pKD46 plasmid (Datsenko K. A. and Wanner B. L., One-step inactivation of chromosomal genes in Escherichia coli K-12 using PCR products, Proc. Natl. Acad. Sci. USA, 2000, 97(12):6640-6645) includes a 2,154 nucleotides DNA fragment of phage λ (nucleotide positions from 31088 to 33241; GenBank, accession No.: J02459), and contains genes of the λRed homologous recombination system (gamma, beta, and exo genes) under the control of the arabinose-inducible P$_{araB}$ promoter. The pKD46 plasmid is necessary for integration of the PCR product into the chromosome of the E. coli MG1655 IS5.8:: P$_L$-hppA strain (Example 1.5). The E. coli MG1655 IS5.8:: P$_L$-hppA strain harboring the hppA gene and the recombinant plasmid pKD46 was obtained according to a standard method for electroporation (Datsenko K. A. and Wanner B. L., 2000).

Electrocompetent cells were prepared as follows: the cells of E. coli MG1655 IS5.8::P$_L$-hppA/pKD46 strain were grown overnight at 30° C. in LB-medium (Luria-Bertani broth, also referred to as lysogenic broth; Sambrook J. and Russell D. W., Molecular Cloning: A Laboratory Manual (3$^{rd}$ ed.), Cold Spring Harbor Laboratory Press, 2001) containing ampicillin (100 mg/L); then the culture was diluted 100 times with 5 mL of SOB-medium (Sambrook J. et al., Molecular Cloning: A Laboratory Manual (2$^{nd}$ ed.), Cold Spring Harbor Laboratory Press, 1989) containing ampicillin (100 mg/L) and L-arabinose (1 mM). The obtained culture was grown with aeration (250 rpm) at 30° C. to OD$_{600}$ of approximately 0.6 and then made electrocompetent by concentrating 100-fold and washing three times with ice-cold deionized H$_2$O. Electroporation was performed using 70 L of cells and approximately 100 ng of the PCR product 8. Electroporated cells were incubated with 1 mL of SOC-medium (Sambrook J. et al., Molecular Cloning: A Laboratory Manual (2$^{nd}$ ed.), Cold Spring Harbor Laboratory Press, 1989) at 37° C. for 2.5 h, placed onto the plates containing the LB-medium, agar (1.5%) and chloramphenicol (20 mg/L), and grown at 37° C. to select Cm$^R$-recombinants. To eliminate the pKD46 plasmid, two passages on L-agar supplemented with chloramphenicol (20 mg/L) at 30° C. were performed, and the obtained colonies were tested for sensitivity to ampicillin. Thus, the E. coli MG1655 IS5.8::P$_L$-hppA Δppa::cat strain having the Cm$^R$ marker was obtained.

1.8. Verification of Inactivation of the Ppa Gene.

1.8.1. Verification Using PCR.

Mutants containing the inactivated ppa gene marked with chloramphenicol resistance gene (cat) were verified by PCR. The primers P18 (SEQ ID NO: 32) and P19 (SEQ ID NO: 33), and the chromosomal DNA from the E. coli MG1655 IS5.8::P$_L$-hppA Δppa::cat strain having the Cm$^R$ marker as a template, were used for the verification. Conditions for PCR were as follows: denaturation for 3 min at 94° C.; profile for the 30 cycles: 30 sec at 94° C., 30 sec at 51° C., 2 min at 72° C.; final elongation: 6 min at 72° C. The PCR product 9, obtained in the reaction using the chromosomal DNA from the E. coli MG1655 IS5.8::P$_L$-hppA Δppa::cat strain as a template, was 1754 bp in length (SEQ ID NO: 34) as desired.

1.8.2. Verification Using Southern-Blot Hybridization.

Figure 4:
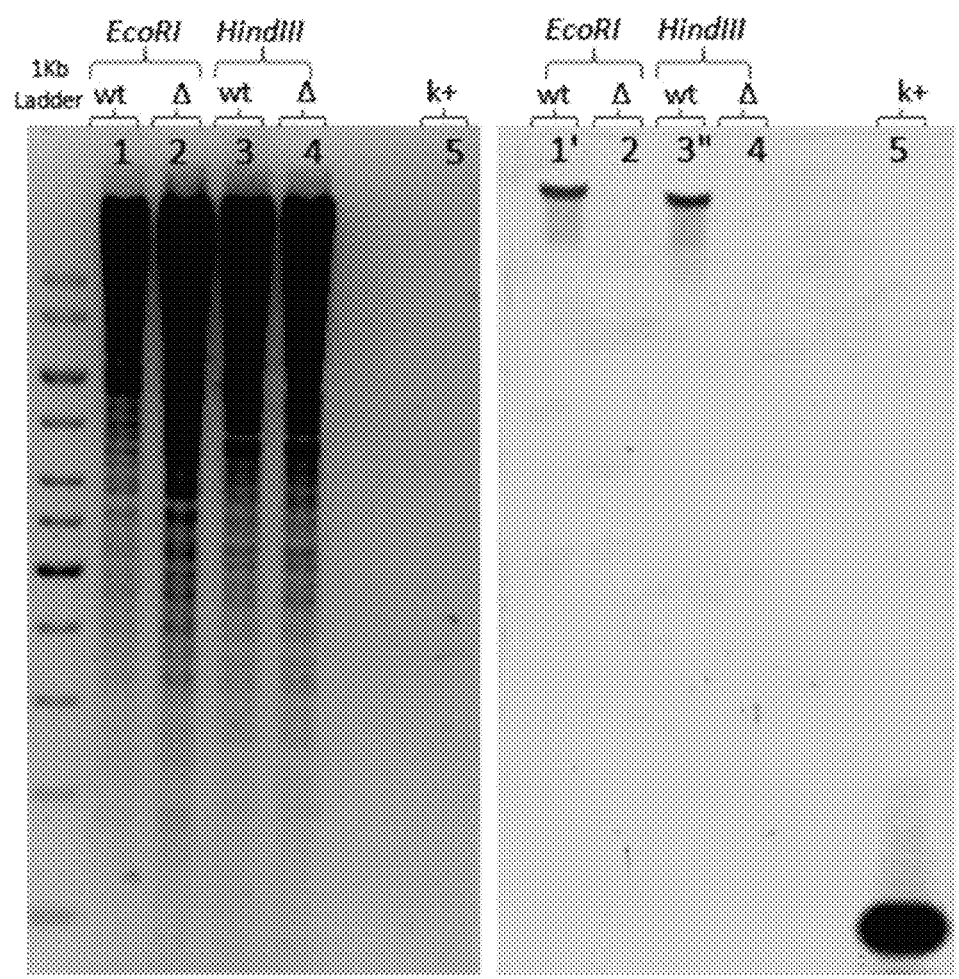
FIG. 4 (photograph) shows the results of the Southern-blot hybridization. Lanes: wt—*E. coli* MG1655 chromosome restrict, Δ—*E. coli* MG1655::IS5.8-$P_L$-hppA Δppa::cat chromosome restrict, k+—biotin-labeled PCR fragment of ppa gene, EcoRI and HindIII—chromosome restriction using the corresponding restrictases, 1'—a 18.447 kbp DNA fragment, 3"—a 16.618 kbp DNA fragment.

The deletion of ppa gene in E. coli was also confirmed using Southern-blot hybridization of biotin-labeled probes containing a fragment of the ppa gene (FIG. 4). A standard method for Southern-blot hybridization was used (Sambrook J. and Russell D. W., Molecular Cloning: A Laboratory Manual (3$^{rd}$ ed.), Cold Spring Harbor Laboratory Press, 2001). The obtained results confirmed deletion of ppa gene in the chromosome.

1.9. Construction of E. coli L-Histidine-Producing Strains Having Overexpressed hppA Gene.

1.9.1. Construction of E. coli EA92 IS5.8::P$_L$-hppA Strain.

The IS5.8::cat-P$_L$-hppA expression cassette was transferred from E. coli MG1655 IS5.8::cat-P$_L$-hppA strain (Example 1.5) to the L-histidine-producing E. coli strain EA92 (Auxiliary example 1) using P1-transduction (Miller, J. H. (1972)<Experiments in Molecular Genetics>, Cold Spring Harbor Lab. Press, Plainview, N.Y.). Thus, the E. coli EA92 IS5.8::cat-P$_L$-hppA strain having the CmR$^{ex}$ marker was obtained. Integration of the IS5.8::cat-P$_L$-hppA expression cassette was verified by PCR as described in Example 1.6. The CmR$^{ex}$ maker was eliminated from the E. coli EA92 IS5.8::cat-P$_L$-hppA chromosome using Xis/Int site-specific recombination system with the pMWts-λInt/Xis helper plasmid yielding the strain E. coli EA92 IS5.8::P$_L$-hppA. The elimination of the CmR$^{ex}$ marker was verified by PCR using the primers P15 (SEQ ID NO: 26) and P3 (SEQ ID NO: 10), and the chromosomal DNA from the E. coli EA92 IS5.8:: P$_L$-hppA strain as a template. Conditions for PCR were as follows: denaturation for 3 min at 95° C.; profile for the 30 cycles: 30 sec at 95° C., 30 sec at 55° C., 2 min at 72° C.; final elongation: 7 min at 72° C. The PCR product 10, obtained in the reaction with the chromosomal DNA from the E. coli EA92 IS5.8::P$_L$-hppA strain, was 535 bp in length (SEQ ID NO: 35).

1.9.2. Construction of E. coli EA92 IS5.8::P$_L$-hppA ΔPpa::Cat Strain.

The DNA fragment harboring the ppa gene deletion marked with cat gene was transferred from the chromosome of the E. coli MG1655 IS5.8::P$_L$-hppA Δppa::cat strain (Example 1.7) to the L-histidine-producing E. coli strain EA92 IS5.8::P$_L$-hppA (Example 1.9.1) using P1-transduction. Thus, the E. coli EA92 IS5.8::P$_L$-hppA Δppa::cat strain having the Cm$^R$ marker was obtained. The inactivation of ppa gene was verified by PCR as described (Example 1.8.1).

1.10. Production of L-Histidine Using *E. coli* Strains.

The *E. coli* strains EA92, EA92 IS5.8::P$_L$-hppA, and EA92 IS5.8::P$_L$-hppA Δppa::cat were each cultivated in 2 mL of LB-medium for 3 h at 30° C. Then, 0.1 mL of the obtained cultures were each inoculated into 2 mL of fermentation medium in 20×200-mm test tubes and cultivated for 72 h at 30° C. with shaking on a rotary shaker (250 rpm) until glucose consumption. The composition of the fermentation medium is shown in Table 3.

TABLE 3

Composition of fermentation medium

| Component | Final concentration (g/L) |
| --- | --- |
| Glucose | 50.0 |
| Mameno* | 0.2 (as the amount of nitrogen) |
| L-Aspartate | 1.0 |
| (NH$_4$)$_2$SO$_4$ | 18.0 |
| KCl | 1.0 |
| KH$_2$PO$_4$ | 0.5 |
| MgSO$_4$ × 7H$_2$O | 0.4 |
| FeSO$_4$ × 7H$_2$O | 0.02 |
| MnSO$_4$ × 5H$_2$O | 0.02 |
| ZnSO$_4$ × 7H$_2$O | 0.02 |
| Adenosine | 0.2 |
| Thiamine-HCl | 0.001 |
| Betaine | 2.0 |
| CaCO$_3$ | 60.0 |

*Mameno is the soybean meal hydrolysate (Ajinomoto Co., Inc.).

Glucose, magnesium sulfate, betaine, and CaCO$_3$ were sterilized separately. The pH was adjusted to 6.0 using 6 M KOH before sterilization.

After cultivation, the amount of L-histidine, which accumulated in the medium, was determined using thin layer chromatography (TLC). The 10×20-cm TLC plates coated with 0.11-mm layers of Sorbfil silica gel containing non-fluorescent indicator (Stock Company Sorbpolymer, Krasnodar, Russian Federation) were used. Samples were applied onto the plates using the Camag Linomat 5 sample applicator. The Sorbfil plates were developed with a mobile phase consisting of propan-2-ol:acetone:25% aqueous ammonia:water=6:6:1.5:1 (v/v). A solution of ninhydrin (1%, w/v) in acetone was used as a visualizing reagent. After development, plates were dried and scanned with the Camag TLC Scanner 3 in absorbance mode with detection at 520 nm using winCATS software (version 1.4.2).

The results of six independent test tube fermentations (as average values) are shown in Table 4. As one can see from the Table 4, the modified *E. coli* EA92 IS5.8::P$_L$-hppA strain was able to accumulate a higher amount of L-histidine as compared with the control *E. coli* EA92 strain. Also, the modified *E. coli* EA92 IS5.8::P$_L$-hppA Δppa::cat strain having inactivated ppa gene was able to accumulate a higher amount of L-histidine as compared with the parental *E. coli* EA92 IS5.8::P$_L$-hppA strain and the control *E. coli* EA92 strain.

TABLE 4

Production of L-histidine.

| *E. coli* strain | OD$_{600}$ | His, g/L |
| --- | --- | --- |
| EA92 (control) | 19.2 ± 0.2 | 5.7 ± 0.1 |
| EA92 IS5.8::P$_L$-hppA | 18.7 ± 0.8 | 6.1 ± 0.2 |
| EA92 IS5.8::P$_L$-hppA Δppa::cat | 17.4 ± 0.8 | 7.4 ± 0.7 |

1.11. Construction of *E. coli* L-Threonine-Producing Strains Having an Overexpressed hppA Gene.

DNA fragments harboring the overexpressed hppA gene marked with the cat gene was transferred from the chromosome of the *E. coli* MG1655 IS5.8::cat-P$_L$-hppA strain (Example 1.5) to the L-threonine-producing *E. coli* B-3996 strain using P1-transduction yielding the strain *E. coli* B-3996 IS5.8::cat-P$_L$-hppA. The CmR$^{ex}$ marker was eliminated from the *E. coli* B-3996 IS5.8::cat-P$_L$-hppA chromosome using a Xis/Int site-specific recombination system using the pMWts-λInt/Xis helper plasmid (Minaeva N. I. et al., 2008). Thus, the *E. coli* B-3996 IS5.8::P$_L$-hppA strain was constructed. Then, DNA fragments harboring the ppa gene deletion marked with cat gene was transferred from the chromosome of the *E. coli* MG1655 IS5.8::P$_L$-hppA Δppa::cat strain (Example 1.7) to the L-threonine-producing *E. coli* B-3996 IS5.8::P$_L$-hppA strain using P1-transduction. Thus, the *E. coli* B-3996 IS5.8::P$_L$-hppA Δppa::cat strain having the Cm$^R$ marker was obtained. The introduction of hppA gene and inactivation of ppa gene were verified by PCR as described (Examples 1.6 and 1.8.1), and the obtained results were as desired. The *E. coli* strain B-3996 was deposited on Nov. 19, 1987 in the All-Union Scientific Center of Antibiotics (Russian Federation, 117105 Moscow, Nagatinskaya Street, 3-A) under the accession number RIA 1867. The strain was also deposited in the Russian National Collection of Industrial Microorganisms (VKPM) (Russian Federation, 117545 Moscow, 1$^{st}$ Dorozhny proezd, 1) under the accession number B-3996.

The *E. coli* B-3996 IS5.8::P$_L$-hppA strain was constructed using the described procedure (Example 1.9.1 and 1.9.2) and the parental *E. coli* B-3996 strain.

1.12. Production of L-Threonine Using *E. coli* Strains.

The *E. coli* strains B-3996, B-3996 IS5.8::P$_L$-hppA, and B-3996 IS5.8::P$_L$-hppA Δppa::cat were each cultivated for 18 h at 37° C. on L-agar plates. To obtain a seed culture, the strains were grown on a rotary shaker (250 rpm) at 32° C. for 18 h in 20×200-mm test tubes containing 2 mL of L-broth (Sambrook, J. and Russell, D. W. (2001) "Molecular Cloning: A Laboratory Manual", 3$^{rd}$ ed., Cold Spring Harbor Laboratory Press) supplemented with glucose (4%, w/v). Then, the fermentation medium was inoculated with 0.2 mL (10%) of seed material. The fermentation was performed in 2 mL of minimal medium in 20×200-mm test tubes. Cells were grown for 72 h at 32° C. with shaking at 250 rpm.

After cultivation, the amount of L-threonine, which accumulated in the medium, was determined by paper chromatography using a mobile phase consisting of butan-1-ol:acetic acid:water=4:1:1 (v/v). A solution of ninhydrin (2%, w/v) in acetone was used as a visualizing reagent. A spot containing L-threonine was cut out, L-threonine was eluted with 0.5% water solution of CdCl$_2$, and the amount of L-threonine was evaluated spectrophotometrically at 540 nm. The composition of the fermentation medium is shown in Table 5.

TABLE 5

Composition of fermentation medium

| Component | Final concentration (g/L) |
| --- | --- |
| Glucose | 80.0 |
| (NH$_4$)$_2$SO$_4$ | 22.0 |
| NaCl | 0.8 |
| KH$_2$PO$_4$ | 2.0 |
| MgSO$_4$ × 7H$_2$O | 0.8 |
| FeSO$_4$ × 7H$_2$O | 0.02 |
| MnSO$_4$ × 5H$_2$O | 0.02 |
| Thiamine-HCl | 0.0002 |
| Yeast extract | 1.0 |
| CaCO$_3$ | 30.0 |

Glucose and magnesium sulfate were sterilized separately. CaCO$_3$ was sterilized by dry-heat at 180° C. for 2 h. The pH was adjusted to 7.0. The antibiotic was introduced into the medium after sterilization.

The results of six independent test tube fermentations (as average values) are shown in Table 6. As one can see from the Table 6, the modified E. coli B-3996 IS5.8::P$_L$-hppA Δppa::cat strain was able to accumulate a higher amount of L-threonine as compared with the control E. coli B-3996 strain.

TABLE 6

Production of L-threonine.

| E. coli strain | OD$_{600}$ | Thr, g/L |
| --- | --- | --- |
| B-3996 (control) | 16.0 ± 0.7 | 23.0 ± 0.7 |
| B-3996 IS5.8::P$_L$-hppA | 22.9 ± 0.6 | 23.3 ± 0.3 |
| B-3996 IS5.8::P$_L$-hppA Δppa::cat | 18.0 ± 0.8 | 25.3 ± 1.2 |

Example 2. Production of Nucleosides 2.1. Construction of B. amyloliquefaciens 5-Aminoimidazole-4-Carboxamide Ribonucleoside (AICAr)-Producing Strains Having Overexpressed hppA Gene.

The hppA gene native to R. rubrum was cloned into low-copy number expression plasmids pMWAL1T-Ppur and pMWAL1T-Prep (Auxiliary example 2) under control of the B. amyloliquefaciens pur operon promoter (Ppur) and a strong constitutive promoter (PrepAB) originated from the pLF22 plasmid (Tarakanov B. V., et al., Expression vector pLF22 for the lactic acid bacteria, Microbiology (Moscow, Russian Federation) (Translation of Mikrobiologiya), 2004, 73(2):170-175), respectively. Thus, the expression plasmids pMWAL1T-Ppur-hppA and pMWAL1T-Prep-hppA were obtained. The procedure was as follows.

An hppA-TargF DNA fragment containing the coding region of the hppA gene flanked at the 5'-end with a SD sequence suitable for the translation in Bacillus bacteria and the 3'-end with the B. amyloliquefaciens rho-independent transcription terminator argF was obtained using the overlap extension PCR (OE-PCR) method (Higuchi R. et al., A general method of in vitro preparation and specific mutagenesis of DNA fragments: study of protein and DNA interactions, Nucleic Acids Res, 1988, 16(15):7351-7367; Ho S. N. et al., Site-directed mutagenesis by overlap extension using the polymerase chain reaction, Gene, 1989, 77(1):51-59).

First, an hppA DNA fragment containing the coding region of the hppA gene flanked at the 5'-end with a SD sequence suitable for translation in Bacillus bacteria was amplified by PCR using primers P20 (SEQ ID NO: 36) and P21 (SEQ ID NO: 37), and pUC-57-hppA(Rru) plasmid (Example 1.1) as a template. The plasmid pUC-57-hppA (Rru) contains the coding region of the chemically synthesized hppA gene native to R. rubrum, the nucleotide sequence of which was codon-optimized for the expression in E. coli (Example 1.1). Analysis of the sequence of the hppA gene having optimized codons showed that this gene is suitable also for the expression in B. amyloliquefaciens.

Second, a TargF DNA fragment containing the argF gene terminator was amplified by PCR using primers P22 (SEQ ID NO: 38) and P23 (SEQ ID NO: 39), and genomic DNA of B. amyloliquefaciens IAM1523 (Zakataeva N. P. et al, 2010) as a template.

Third, the hppA and TargF DNA fragments having overlapping ends were fused using PCR. Then, PCR was performed using the resulting DNA fragment as a template, and primers P20 (SEQ ID NO: 36) and P23 (SEQ ID NO: 39).

Figure 5:
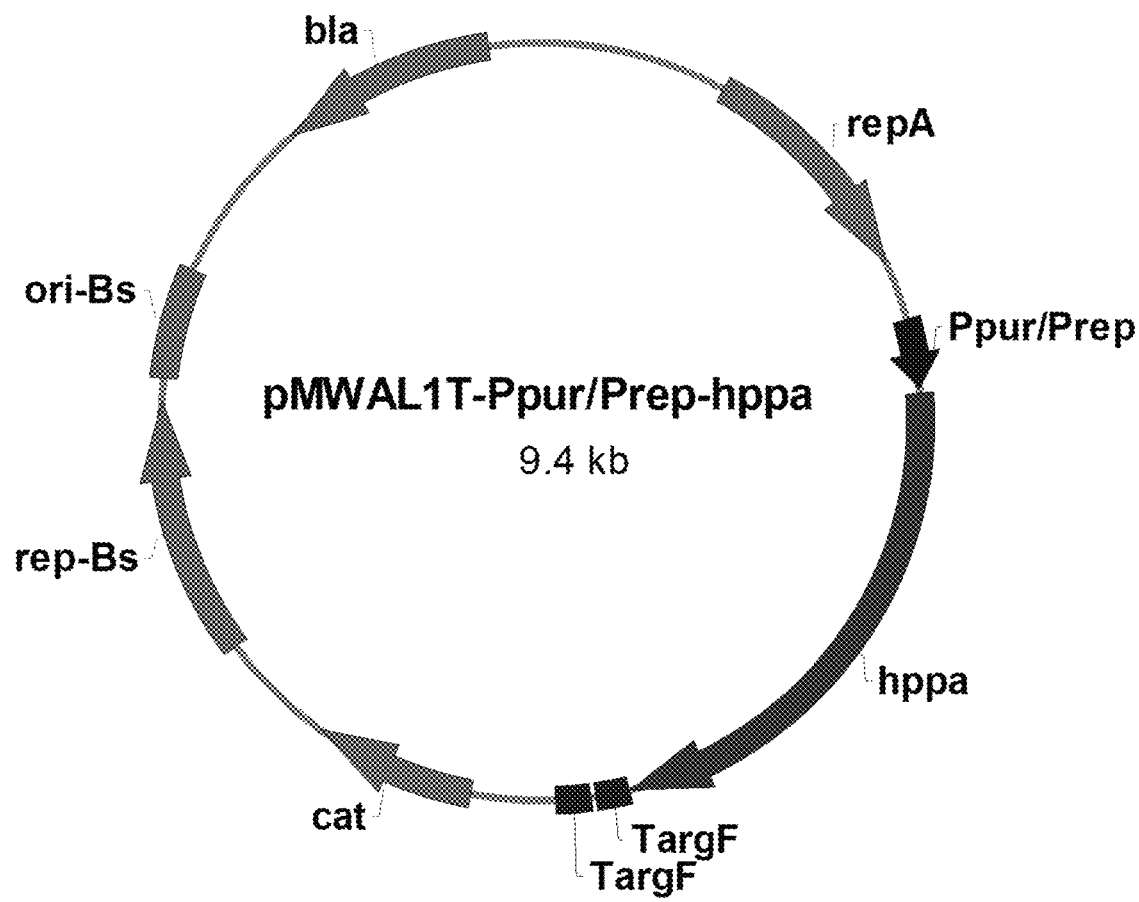
FIG. 5 shows the structure of the pMWAL1T-Ppur-hppA and pMWAL1T-Prep-hppA plasmids.

The resulting hppA-TargF DNA fragment was digested with XbaI and BstI 1071 restrictases, and cloned into pMWAL1T-Ppur and pMWAL1T-Prep plasmids (Auxiliary example 2) digested with XbaI and SmaI restrictases. Thus, the pMWAL1T-Ppur-hppA and pMWAL1T-Prep-hppA plasmids were constructed (FIG. 5). The accuracy of constructs was confirmed by sequence analysis.

2.2. Production of AICAr Using B. amyloliquefaciens Strains.

The control vector pMWAL1 (Auxiliary example 2) and the plasmids pMWAL1T-Ppur-hppA and pMWAL1T-Prep-hppA were each introduced into the B. amyloliquefaciens AICAr-producing strain AJ1991purH::Sp (Auxiliary example 2 (2.3)) by E40 bacteriophage transduction using B. subtilis 168 strain as an intermediate host (Zakataeva N. P. et al, 2010). Clones that harbored plasmids were selected on LB agar plates supplemented with chloramphenicol (7 mg/L). Presence of the plasmid was confirmed by PCR analysis using primers P20 (SEQ ID NO: 36) and P23 (SEQ ID NO: 39). The resulting strains were evaluated in test tube fermentation.

First, four separate colonies of each strain were grown overnight at 34° C. on LB agar plate supplemented with chloramphenicol (tryptone 10.0 g/L, yeast extract 5.0 g/L, NaCl 5.0 g/L, chloramphenicol 7 mg/L, and agar 20.0 g/L). The resulting cell biomasses were each inoculated into liquid LB media (5 mL per each test tube) supplemented with chloramphenicol (7 mg/L), and then cultured overnight at 34° C. with shaking (200 rpm).

Then, 0.3 mL of overnight cultures were each inoculated into 3 mL of fermentation media containing chloramphenicol (7 mg/L). The composition of the fermentation medium is shown in Table 7.

TABLE 7

Composition of fermentation medium

| Component | Final concentration (g/L) |
| --- | --- |
| Glucose | 60.0 |
| NH$_4$Cl | 15.0 |
| KH$_2$PO$_4$ | 1.0 |
| MgSO$_4$ × 7H$_2$O | 0.4 |
| FeSO$_4$ × 7H$_2$O | 0.01 |
| MnSO$_4$ × 4H$_2$O | 0.01 |
| Mameno (soybean hydrolysate) | 0.8 (as total nitrogen) |
| Adenine | 0.3 |
| CaCO$_3$ | 25 |

Glucose and CaCO$_3$ were sterilized separately. The pH of fermentation media was adjusted to 6.5 before sterilization.

Cultures were cultivated at 30° C. with shaking (200 rpm) for 72 h until glucose consumption completed. After cultivation, the amount of AICAr, which accumulated in the medium, was determined using high-performance liquid chromatography (HPLC). HPLC was carried out using a Shimadzu analytical system (Shimadzu) including a dual absorbance ultraviolet (UV) detector. The wavelength was set at 250 nm (and 280 nm for the comparison). Separation was performed at 37° C. using Inertsil ODS-3 (3×150 mm, 3 m) (GL Sciences) column. Samples (10 µL) of the appropriately diluted supernatants were injected into the chromatograph. The mobile phase contained 2% (v/v) CH$_3$CN, 0.8% (v/v) triethylamine, and 0.5% (v/v) CH$_3$COOH. Flow-rate of the mobile phase was 0.3 mL/min.

The results of three independent test tube fermentations (as average values) are shown in Table 8. As one can see from the Table 8, the modified *B. amyloliquefaciens* strains AJ1991purH::Sp (pMWAL1T-Ppur-hppA) and AJ1991purH:: Sp (pMWAL1T-Prep-hppA) were able to accumulate a higher amount of AICAr as compared with the control *B. amyloliquefaciens* AJ1991purH::Sp (pMWAL1) strain.

TABLE 8

Production of AICAr.

| *B. amyloliquefaciens* strain | AICAr, g/L |
|---|---|
| AJ1991purH::Sp (pMWAL1) (control) | 3.29 ± 0.02 |
| AJ1991purH::Sp (pMWAL1T-Ppur-hppA) | 3.74 ± 0.04 |
| AJ1991purH::Sp (pMWAL1T-Prep-hppA) | 3.62 ± 0.15 |

2.3. Production of Inosine and Guanosine Using *B. amyloliquefaciens* Strains.

The control vector pMWAL1 (Auxiliary example 2) and the expression plasmids pMWAL1T-Ppur-hppA and pMWAL1T-Prep-hppA (Example 2) were each introduced into the *B. amyloliquefaciens* inosine- and guanosine-producing strain AJ1991 (Zakataeva N. P. et al., A new function for the Bacillus PbuE purine base efflux pump: efflux of purine nucleosides. *Res. Microbiol.*, 2007, 158(8-9):659-665) by E40 bacteriophage transduction using *B. subtilis* 168 as an intermediate host (Example 2.2). Clones that harbored plasmids were selected on LB agar plates supplemented with chloramphenicol (7 mg/L). The resulting strains were evaluated in test tube fermentation as described in Example 2.2. The amount of inosine and guanosine, which accumulated in the medium, was determined using HPLC.

The results of four independent test tube fermentations (as average values) are shown in Table 9. As one can see from Table 9, the modified *B. amyloliquefaciens* strains AJ1991 (pMWAL1T-Ppur-hppA) and AJ1991 (pMWAL1T-Prep-hppA) were able to accumulate a higher amount of inosine and guanosine as compared with the control *B. amyloliquefaciens* AJ1991 (pMWAL1) strain.

TABLE 9

Production of inosine and guanosine.

| *B. amyloliquefaciens* strain | Inosine, g/L | Guanosine, g/L |
|---|---|---|
| AJ1991 (pMWAL1) (control) | 1.90 ± 0.01 | 1.77 ± 0.01 |
| AJ1991 (pMWAL1T-Ppur-hppA) | 1.92 ± 0.04 | 1.80 ± 0.03 |
| AJ1991 (pMWAL1T-Prep-hppA) | 1.96 ± 0.02 | 1.85 ± 0.02 |

Example 3. Production of Protein

The effect from overexpression of the hppA gene native to *R. rubrum* on production of a protein using a bacterium was confirmed. A yellow fluorescent protein (YFP) was used as the model protein to show the effect.

3.1. Construction of *E. coli* BL21(DE3) IS5.8::$P_L$-hppA/ pPK-T7lac-yfp Strain.

A pPK-T7lac-yfp plasmid (Auxiliary example 3, FIG. 6) harboring the kan gene encoding the kanamycin-resistance ($Km^R$) marker and the yfp gene encoding the YFP (Sheff M. A. and Thorn K. S., Optimized cassettes for fluorescent protein tagging in *Saccharomyces cerevisiae*, Yeast, 2004, 21(8):661-670) was used. In the pPK-T7lac-yfp plasmid, the yfp structural gene was linked with artificially constructed bacterial SD-sequence (Auxiliary example 3, FIG. 6) and placed under the transcriptional control of the hybrid T7lac-φ10/$O_{lac}$ promoter/operator (Studier F. W. et al., Use of T7 RNA polymerase to direct expression of cloned genes, *Methods Enzymol.*, 1990, 185:60-89), wherein the promoter is the T7 late promoter governed by phage T7 RNA polymerase (Y10), and the operator is the operator of *E. coli* lactose operon ($O_{lac}$) that can be repressed by LacI-repressor encoded by the lac gene located in the same plasmid pPK-T7lac-yfp. An *E. coli* strain BL21(DE3) (*E. coli* B F$^-$ompT gal dcm lon hsdS$_B$ ($r_B^- m_B^-$) λ(DE3$^{imm21}$)$_{K-12}$ (λ$^S$)) was used as a host strain for the T7 polymerase-mediated IPTG-induced gene expression (Studier F. W. and Moffatt B. A., Use of bacteriophage T7 RNA polymerase to direct selective high-level expression of cloned genes, 1986, 189 (1):113-130). The IS5.8::cat-$P_L$-hppA expression cassette (Example 1.5) was introduced into *E. coli* BL21(DE3) strain using P1 transduction. The strain BL21(DE3) is available from, for example, Life Technologies (product No. C6000-03). Then, pPK-T7lac-yfp plasmid was introduced into the *E. coli* control BL21(DE3) and test BL21(DE3) IS5.8::cat-$P_L$-hppA strains. Thus, the *E. coli* strains BL21(DE3)/pPK-T7lac-yfp and BL21(DE3) IS5.8::cat-$P_L$-hppA/pPK-T7lac-yfp were constructed.

3.2. Production of YFP Using *E. coli* Strains.

The cells of *E. coli* strains BL21(DE3)/pPK-T7lac-yfp and BL21(DE3) IS5.8::cat-$P_L$-hppA/pPK-T7lac-yfp were each grown in test tubes at 34° C. and aeration (250 rpm) in 5 mL of LB medium supplemented with kanamycin (50 mg/L) to an OD$_{600}$ of approximately 0.6. T7 RNA polymerase-governed expression of yfp gene was induced by the addition of isopropyl β-D-1-thiogalactopyranoside (IPTG) to the final concentration of 1 mM. The *E. coli* strains BL21(DE3)/pPK-T7lac-yfp and BL21(DE3) IS5.8::cat-$P_L$-hppA/pPK-T7lac-yfp that were not supplemented with IPTG were used as the control strains. Cells were incubated at 34° C. for 15 min. Then, a fresh solution of rifampicin (final concentration 200 mg/L) was added, and OD$_{600}$ was measured and set to zero at the time point of 0 hours. Cultivation of the cells was continued at 34° C. with aeration for 5 hours.

The kinetics of accumulation of the YFP was monitored for 5 hours. Samples (200 μL) of culture medium were centrifuged for 30 sec at 13200 rpm at 4° C., and cells were washed twice in NaCl solution. The fluorescence of YFP was immediately measured at excitation wavelength of 490 nm and emission wavelength of 540 nm in a UV (black) 96-well plate using TECAN$^{(R)}$ Reader. An OD$_{600}$ was also measured. A solution of NaCl was used as a control. The fluorescence (F)/optical density (OD) ratio (F/OD ratio) was calculated using the formula I:

$$F/OD=)/(OD_{ind}-OD)]-)/(OD_{non-ind}-OD)]I,$$

wherein, respectively, $F_{ind}$ and $OD_{ind}$ indicate the fluorescence and optical density of the IPTG-induced strains, $F_{non-ind}$ and $OD_{non-ind}$ indicate the fluorescence and optical density of the IPTG-non-induced strains, and F and OD indicate the fluorescence and optical density of NaCl solution.

Figure 7:
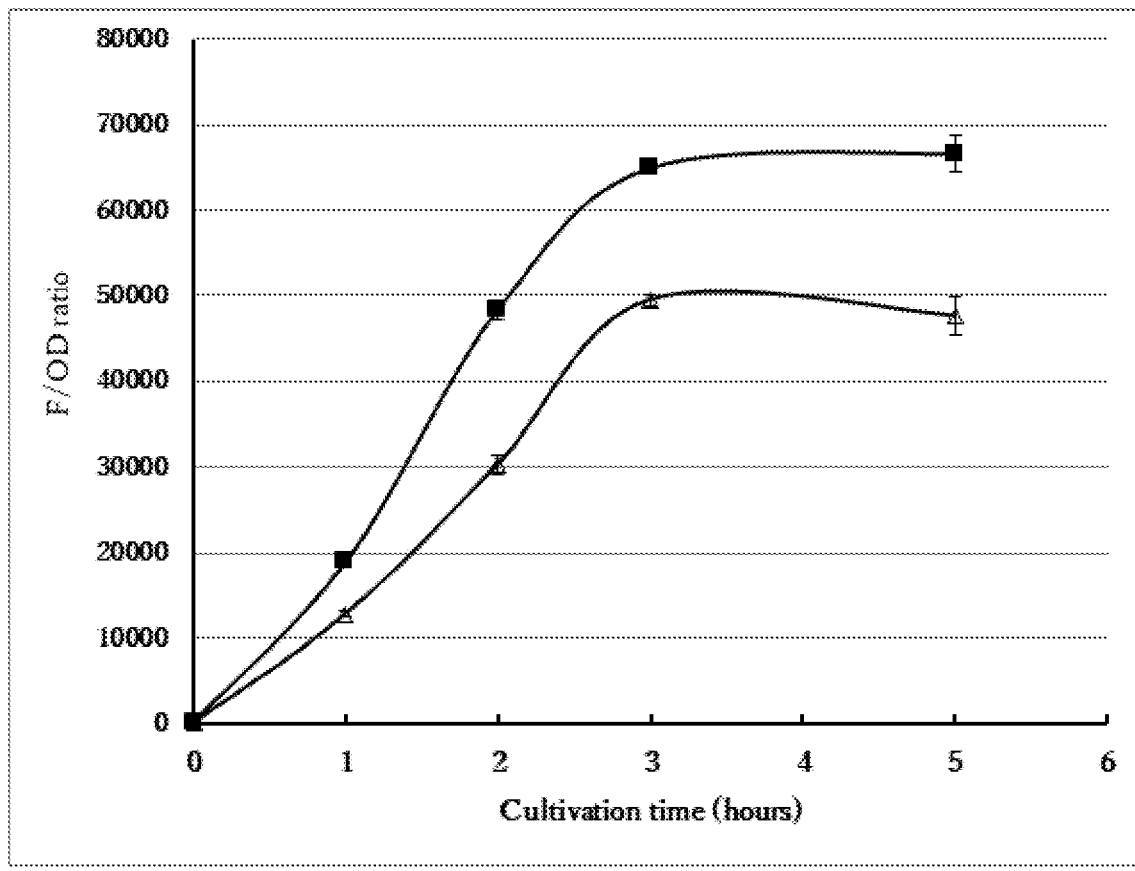
FIG. 7 shows the results of production of YFP protein using the modified *E. coli* strain BL21(DE3) IS5.8::cat-$P_L$-hppA/pPK-T7lac-yfp (solid squares) and the control *E. coli* strain BL21(DE3)/pPK-T7lac-yfp (open triangles).

The results of production of yellow fluorescent protein (YFP) are shown in FIG. 7. As one can see from FIG. 7, the modified *E. coli* strain BL21(DE3) IS5.8::cat-$P_L$-hppA/ pPK-T7lac-yfp was able to accumulate a higher amount of the YFP as compared with the control *E. coli* BL21(DE3)/ pPK-T7lac-yfp strain.

Example 4. $^{13}$C-Based Metabolic Flux Analysis ($^{13}$C-MFA) of E. coli Strains Having Overexpressed hppA Gene 4.1. Cultivation of E. coli Parental Strains.

Figure 8:
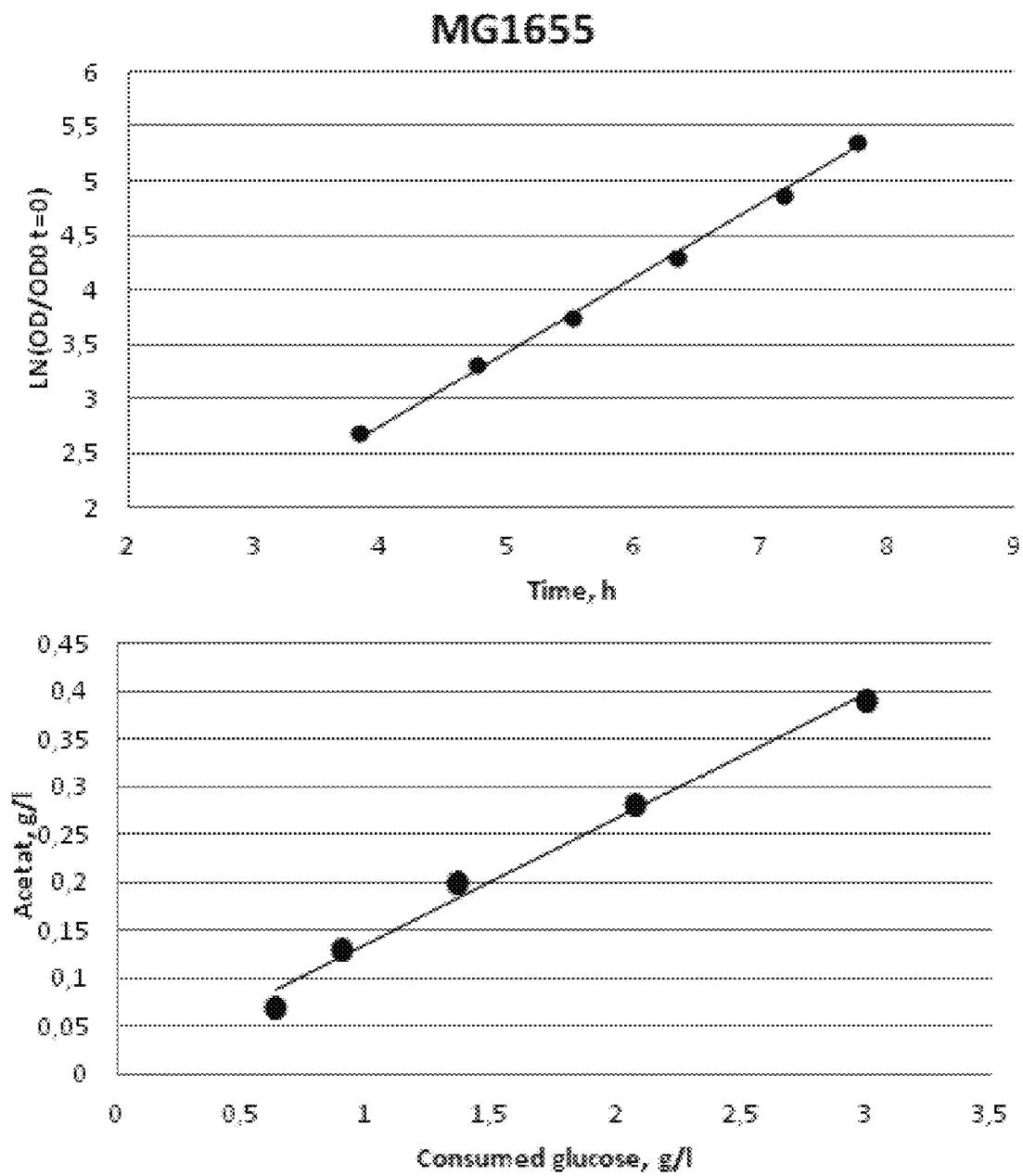
FIG. 8 shows the plot for the metabolic steady-state testing of *E. coli* MG1655 strain during batch cultivation on glucose.
Figure 9:
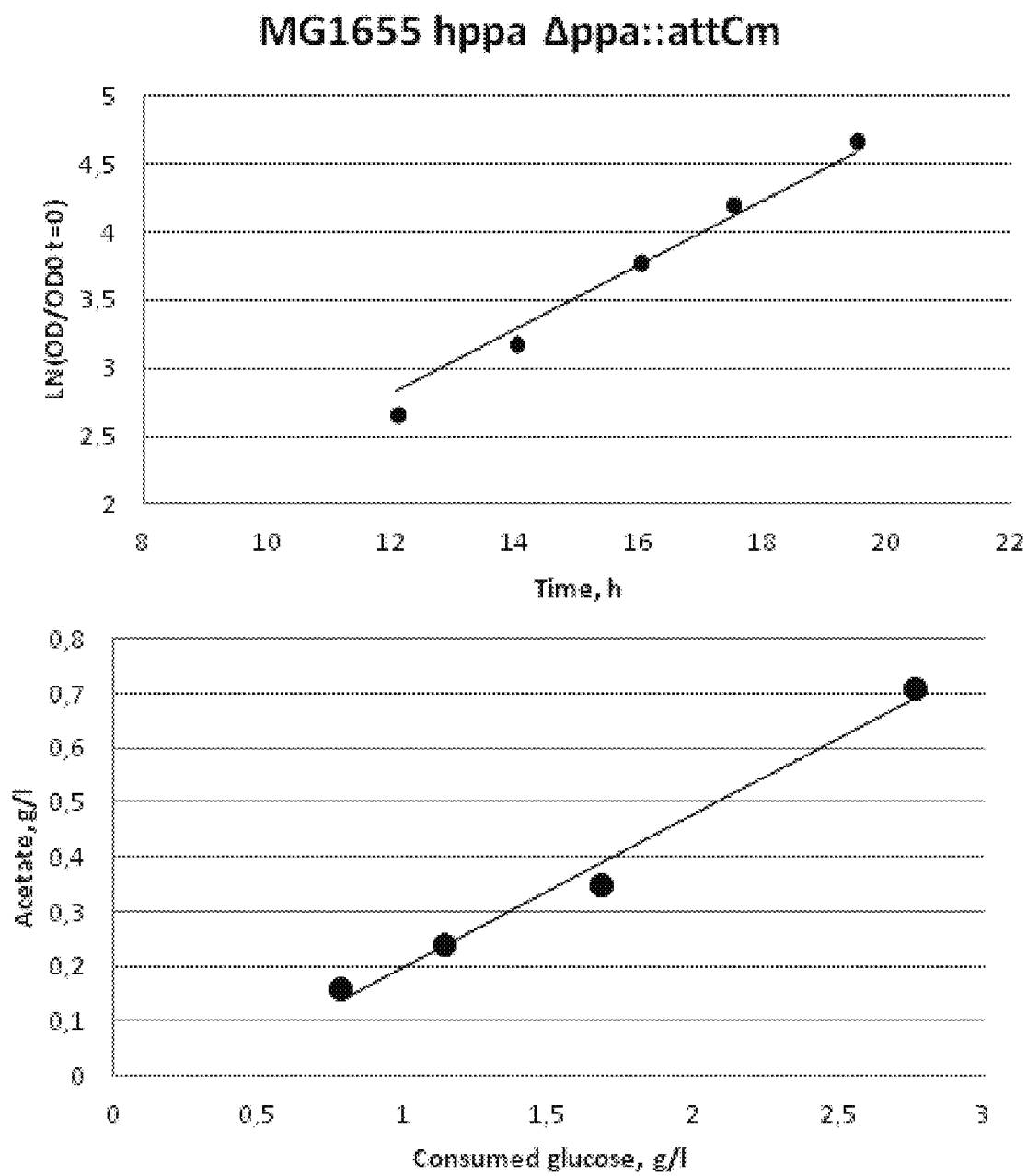
FIG. 9 shows the plot for the metabolic steady-state testing of *E. coli* MG1655 IS5.8::$P_L$-hppA Δppa::cat strain during batch cultivation on glucose.

E. coli parental strains MG1655 (a wild-type strain) and MG1655 IS5.8::P$_L$-hppA Δppa::cat were cultivated in three steps. First, cells of the E. coli MG1655 and MG1655 IS5.8::P$_L$-hppA Δppa::cat strains (Example 1.7) were each plated onto LB (Luria-Bertani broth, also referred to as lysogenic broth) agar plates from glycerol stock (40% (v/v) glycerol) and cultivated overnight (approximately 16 hours for MG1655 and approximately 22 hours for MG1655 IS5.8::P$_L$-hppA Δppa::cat) at 37° C. Then, cells from about 0.3 cm$^2$ of the plate surface were inoculated into 30 mL of fresh minimal medium (Table 10) and cultivated with aeration (250 rpm) in 750-mL flasks overnight (approximately 16 hours) at 37° C. Cells from the overnight cultures were inoculated into 30 mL of fresh minimal medium with the same composition (Table 10) with an initial biomass concentration of 0.2 at OD$_{595}$ and cultivated with aeration in 750-mL flasks until middle of logarithmic growth phase (OD$_{595}$ of 0.5-0.6) at 37° C. Finally, these cultures were inoculated into 150-mL microjars (ABLE Biot) containing 55 mL of the same medium with an initial biomass concentration of 0.01 at OD$_{595}$. Cells were cultivated at 37° C. The pH 7 was controlled by NH$_3$ gas. Aeration was provided by simultaneous atmospheric air flow (55 mL/min) and mixing at 700 rpm. The air was forwarded to the bioreactor through the system of two 0.2 μm sterile filters (Millipore, cat. No. MTGR05000). Optical density, glucose, and acetate concentrations in the medium were monitored during the cultivation. The strains possessed steady-state growth until full glucose consumption (FIGS. 8 and 9). The main growth parameters of the tested strains are shown in Table 11.

TABLE 10

Composition of minimal fermentation medium.

| Component | Final concentration |
|---|---|
| M9 salts | 1× |
| Glucose | 3 g/L |
|  | in mmol/L: |
| MgSO$_4$ | 2 |
| CaCl$_2$ | 0.8 |
| B1 (thiamine) | 4.9 |
| FeSO$_4$ × 7H$_2$O | 0.06400 |
| CuSO$_4$ × 5H$_2$O | 0.00613 |
| ZnSO$_4$ × 7H$_2$O | 0.00626 |
| MnSO$_4$ × 5H$_2$O | 0.00834 |
| CoCl$_2$ × 6H$_2$O | 0.00869 |

TABLE 11

Growth characteristics of E. coli MG1655 and MG1655 IS5.8::P$_L$-hppA Δppa::cat strains under batch cultivation conditions.

| Parameter | MG1655 | MG1655 IS5.8::P$_L$-hppA Δppa::cat |
|---|---|---|
| μ, 1/hour | 0.64 ± 0.07 | 0.23 ± 0.02 |
| Biomass yield, g/g | 0.40 ± 0.01 | 0.30 ± 0.01 |
| q glucose, mmol/gDW*hour | 9 ± 1 | 4.3 ± 0.2 |
| q CO$_2$, mmol/gDW*hour | 17 ± 4 | 12 ± 3 |
| q Acetate, mmol/gDW*hour | 3.3 ± 0.1 | 3.2 ± 0.7 |
| K$_{595}$, mg DW in 1 mL at OD$_{595}$ of 1 | 0.51 ± 0.03 | 0.68 ± 0.02 |
| C-mole yield biomass, % | 48 ± 2 | 37 ± 3 |
| C-mole yield CO$_2$, % | 33 ± 2 | 46 ± 11 |
| C-mole yield acetate, % | 13 ± 2 | 24 ± 5 |
| C-mol balance, % | 93 ± 2 | 108 ± 14 |

μ-growth rate,
q-specific rate of consumption or production of a substance,
K-a correlation coefficient between OD$_{595}$ and dry weigh of cells,
OD$_{595}$-optical density at 595 nm,
C-mol-mole of the carbon atom, and
DW-cell dry weight.

The carbon labeling experiment was carried out using 100% glucose (Cambridge Isotope Laboratories, Inc.; cat. No. CLM-504-1) as a labeled substrate and a carbon source. Biomass samples obtained at the end of the logarithmic phase (between 0.2-0.5 g/L of residual glucose concentration) was used for GC-MS analysis (Example 4.7).

4.2. Cultivation of E. coli L-Histidine-Producing Strains.

E. coli L-histidine-producing strains EA92 and EA92 IS5.8::P$_L$-hppA Δppa::cat were cultivated in two steps. First, cells of the EA92 and EA92 IS5.8::P$_L$-hppA Δppa::cat strains (Example 1.9) were each plated onto LB agar plates from glycerol stock (40% (v/v) glycerol) and cultivated overnight (approximately 16 hours for EA92 and approximately 22 hours for EA92 IS5.8::P$_L$-hppA Δppa::cat). Then, cells from about 0.3 cm$^2$ of the plate surface were inoculated into 5 mL of fresh liquid LB medium and cultivated in test tubes (20 mm×200 mm) at 30° C. with aeration on a rotary shaker (250 rpm) until OD$_{540}$ of 0.5-0.6. Cells from the LB-growing cultures were washed with 0.9% NaCl and inoculated into 2 mL of synthetic medium with glucose as a main carbon source (Table 12) with initial biomass concentration of 0.025 at OD$_{540}$. Cells were cultivated under the same conditions as in the previous step. Optical density, glucose, histidine, and acetate concentrations in the medium were monitored during the cultivation.

TABLE 12

Composition of synthetic fermentation medium.

| Component | Concentration, g/L |
|---|---|
| Glucose | 50 |
| (NH$_4$)$_2$SO$_4$ | 18 |
| KCl | 3.35 |
| KH$_2$PO$_4$ | 0.53 |
| FeSO$_4$ × 7H$_2$O | 0.02 |
| MgSO$_4$ × 5H$_2$O | 0.48 |
| ZnSO$_4$ × 7H$_2$O | 0.02 |
| MnSO$_4$ × 5H$_2$O | 0.02 |
| Aspartic acid | 1.15 |
| Betaine | 2 |
| Adenosine | 0.2 |
| Thiamine | 0.001 |
| CaCO$_3$ | 25 |

Figure 10:
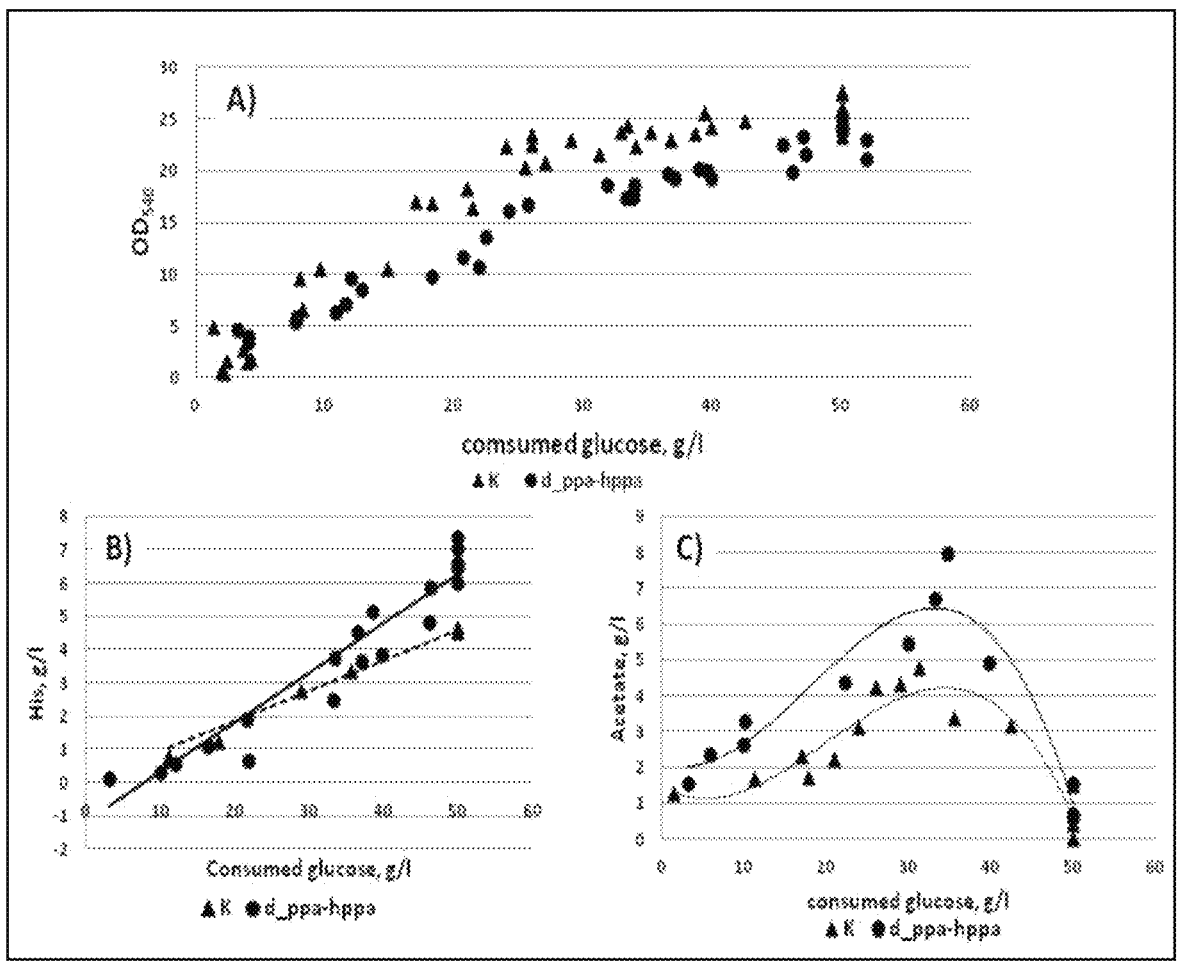
FIG. 10 shows the main growth characteristics of *E. coli* strains EA92 (K) and EA92 IS5.8::$P_L$-hppA Δppa::cat during test tube fermentation in a medium containing glucose (5%, w/v): A) synthesis of biomass, B) synthesis of L-histidine, C) accumulation of acetate. Data from at least three independent fermentations are represented.

Examination of the biomass, threonine, and acetate accumulation from glucose (FIG. 10) showed that three phases of fermentation can be distinguished such as:

Phase I: The lag phase. Lag phase is a well-known effect which appears because of a shift from nutritional-rich LB medium used for the seed culture to the synthetic medium used for the fermentation (Kuroda A. et al., Inorganic polyphosphate kinase is required to stimulate protein degradation and for adaptation to amino acid starvation in *Escherichia coli, Proc. Natl. Acad. Sci. USA,* 1999, 96(25): 14264-14269). This phase is characterized by the lack of both cell growth and glucose utilization (not shown);

Phase II: The phase from the start of growth up to consumption of half of the glucose initially added. This phase is characterized by cell growth and production of L-histidine and acetate; and Phase III: The phase from the end of Phase II up to the complete consumption of glucose. This phase is characterized by decreased biomass yield, consumption of synthesized acetate, and continuous histidine synthesis.

Well-established steady-state $^{13}$C-MFA method is based on the measurement of isotope distributions of proteinogenic amino acids, and the method allows for estimation of fluxes in the period of intensive growth and protein synthesis (Becker J. and Wittmann C., GC-MS-Based 13C metabolic flux analysis. 2014. In: *Metabolic Flux Analysis: Methods and Protocols*, Methods in Molecular Biology edited by Jens O. Kroemer et al. (eds), vol. 1191). Thus, internal flux distribution at Phase II of fermentation can be evaluated by using steady-state $^{13}$C-MFA only. The experimental yields as the main growth parameters of the tested strains in Phase II are shown in Table 13.

TABLE 13

Experimental yields of *E. coli* EA92 and EA92 IS5.8::P$_L$-hppA Δppa::cat strains during the Phase II of cultivation.

| Parameter | EA92 | EA92 IS5.8::P$_L$-hppA Δppa::cat |
|---|---|---|
| Cell yield, OD$_{540}$/mM$_{glucose}$ | 0.15 ± 0.01 | 0.09 ± 0.01 |
| Acetate yield, mol/mol$_{glucose}$ | 0.35 ± 0.07 | 0.5 ± 0.1 |
| L-Histidine yield, mol/mol$_{glucose}$ | 0.11 ± 0.01 | 0.11 ± 0.01 |

The carbon labeling experiment was carried out using a parallel labeling approach in order to improve flux estimation precision (Leighty R. W. and Antoniewicz M. R., Parallel labeling experiments with glucose validate *E. coli* metabolic network model for 13C metabolic flux analysis, *Metab. Eng.*, 2012, 14(5):533-541; Crown S. B. and Antoniewicz M. R., Parallel labeling experiments and metabolic flux analysis: Past, present and future methodologies, *Metab. Eng.*, 2013, 16:21-32) using three differently labeled substrates such as glucose, glucose (Cambridge Isotope Laboratories, Inc.; cat. No. CLM-420-1), and a mixture of glucose (Cambridge Isotope Laboratories, Inc.; cat. No. CLM-1396-1) and natural glucose as 20:80. Biomass samples obtained at the end of Phase II (between 30-25 g/L of residual glucose) were used for the GC-MS analysis.

4.3. Analysis of Substrate and Product.

Concentrations of cells, glucose, and acetate were monitored during cultivation of the *E. coli* MG1655, MG1655 IS5.8::P$_L$-hppA Δppa::cat, EA92, and EA92 IS5.8::P$_L$-hppA Δppa::cat strains. Cells concentration was determined by measuring optical density (OD) at 595 nm (OD$_{595}$) using Biotek Synergy2 for MG1655 and MG1655 IS5.8::P$_L$-hppA Δppa::cat strains, and OD$_{540}$ using TECAN Infinite M200 for L-histidine-producing strains EA92, and EA92 IS5.8:: P$_L$-hppA Δppa::cat. In order to determine optical density during cultivation on a medium containing CaCO$_3$, an aliquot of the culture (0.02 mL) was added to 0.980 mL of 0.1 N HCl to dissolve the CaCO$_3$.

Glucose concentration was measured using Biosen Glucose/Lactose hemolyzing solution (EKF diagnostic, cat. No. 0209-0100-012) and Biosen C-Line clinic Glucose/Lactose analyzer. An aliquot of supernatant obtained by centrifugation at 13,000 rpm for 1 min was used for the measurements. The supernatant was dissolved in SupQ water to attain the concentration range of 0.5-2 g/L, if necessary.

Acetate concentration was measured using ion-exchange chromatography combined with pH-buffered electroconductivity method (Shimadzu HPLC Application Report No. 25, C190-E105: "Principles and Applications of the Prominence Organic Acid Analysis System"). An aliquot of supernatant obtained by centrifugation at 13,000 rpm for 1 min was used for the measurements. The supernatant was dissolved in SupQ water to attain the concentration range of 10-150 mg/L, if necessary.

Concentration of L-histidine in culture medium was determined using thin layer chromatography (TLC) as described (Example 1.10) or the ion-pair reversed-phase liquid chromatography.

4.4. Metabolic Map.

The "consensus" *E. coli* core metabolic model (Long C. P. et al., Fast growth phenotype of *E. coli* K-12 from adaptive laboratory evolution does not require intracellular flux rewiring, *Metab. Eng.*, 2017, 44:100-107) was used with minor changes. The model includes, in particular, the modeling of the transketolase (EC 2.2.1.1, TK) and transaldolase (EC 2.2.1.2, TA) catalyzed reactions of the non-oxidative branch of the pentose-phosphate (PP) pathway as metabolite-specific, reversible, C2 and C3 fragments producing, and consuming half-reactions TK-C2 and TA-C3 (Kleijn R. J. et al., Revisiting the $^{13}$C-label distribution of the non-oxidative branch of the pentose phosphate pathway based upon kinetic and genetic evidence, *FEBS J*, 2005, 272:4970-4982). The model includes glycolytic reactions such as the Embden-Meyerhof-Parnas (EMP), pentose-phosphate (PP), and Entner-Doudoroff (ED) pathways, the tricarboxylic acid (TCA) cycle, the glyoxylate bypass, anaplerotic carboxylation, and the decarboxylation reaction of oxaloacetate and malate.

In addition, reactions catalyzed by fructose-1,6-bisphosphatase and phosphoenolpyruvate synthetase were included. These enzymes can be detected in cells grown on glucose minimal medium (Sedivy J. M. et al., AMP-insensitive fructose bisphosphatase in *Escherichia coli* and its consequences. *Proc. Natl. Acad. Sci.,* 1986, 83(6):1656-1659; Oh M. K. et al., Global expression profiling of acetate-grown *Escherichia coli, J. Biol. Chem.,* 2002, 277(15):13175-13183; Trauchessec M. et al., Mass spectrometry-based workflow for accurate quantification of *Escherichia coli* enzymes: how proteomics can play a key role in metabolic engineering, *Mol. Cell Proteomics.*, 2014, 13(4):954-968). Reactions catalyzed by these two enzymes can form energy consuming futile cycles with corresponding partners such as 6-phosphofructokinase or pyruvate kinase reactions (Patnaik R. et al., Stimulation of glucose catabolism in *Escherichia coli* by a potential futile cycle, *J. Bacteriol.,* 1992, 174(23): 7527-7532; Chambost J. P. and Fraenkel D. G., The use of 6-labeled glucose to assess futile cycling in *Escherichia coli. J. Biol. Chem.,* 1980, 255(7):2867-2869; Daldal F. and Fraenkel D. G., Assessment of a futile cycle involving reconversion of fructose 6-phosphate to fructose 1,6-during gluconeogenic growth of *Escherichia coli, J. Bacteriol.,* 1983, 153(1):390-394; Torres J. C. and Babul J., An in vitro model showing different rates of substrate cycle for phosphofructokinases of *Escherichia coli* with different kinetic properties, Eur. J. Biochem., 1991, 200(2):471-476). It was shown that such cycles can alter the central metabolism of wild-type and producing strains (Haedicke O. et al., Enforced ATP futile cycling increases specific productivity and yield of anaerobic lactate production in *Escherichia coli*, *Biotechnol. Bioeng.*, 2015, 112(10):2195-2199).

Reaction for synthesis of secreted product (acetate and L-histidine) was expressed explicitly. Acetate synthesis was represented by two alternative pathways which are known to be active in *E. coli*: from acetyl-CoA catalyzed by reversible reactions of the phosphate acetyltransferase and acetate kinase, and irreversible synthesis from pyruvate catalyzed by pyruvate oxidase (Abdel-Hamid A. M. et al., Pyruvate oxidase contributes to the aerobic growth efficiency of *Escherichia coli*, Microbiology, 2001, 174:1483-1498; Dittrich C. R. et al., Characterization of the acetate-producing pathways in *Escherichia coli*, *Biotechnol. Prog.*, 2005, 21(4):1062-1067; De Mey M. et al., Comparison of different strategies to reduce acetate formation in *Escherichia coli*, *Biotechnol. Prog.*, 2007, 23:1053-1063). The accounting of these two alternative acetate synthesis fluxes can result in decrease of accuracy of the pyruvate dehydrogenase (PDH) flux estimation. Thus, PDH flux was characterized by values at the lower and upper bounds: the low bound of this flux was restricted by acetyl-CoA requirements for biomass synthesis, and the upper bound was calculated under the assumption that all secreted acetate is synthesized from acetyl-CoA.

In order to attain accurate accounting of $CO_2$-associated carbon transfer, the reactions that are accompanied by $CO_2$ production or consumption were expressed in an explicit manner, including an anabolic reaction and a reaction involving $CO_2$ exchange with an environment modeled as described in Leighty R. W. and Antoniewicz M. R., Parallel labeling experiments with glucose validate *E. coli* metabolic network model for 13C metabolic flux analysis, *Metab. Eng.*, 2012, 14(5):533-541.

Two known pathways for glycine synthesis in *E. coli* (Marcus J. P. and Dekker E. E., Threonine formation via the coupled activity of 2-amino-3-ketobutyrate coenzyme A lyase and threonine dehydrogenase, *J. Bacteriol.*, 1993, 175(20):6505-6511) were included such as the syntheses from serine and threonine.

Glycine cleavage was set to be irreversible according to previously performed estimation based on nuclear magnetic resonance (NMR) analysis of proteinogenic amino acids isotopomers isolated from cells grown aerobically on $^{13}C$-labeled glucose (Szyperski T., Biosynthetically directed fractional $^{13}C$-labeling of proteinogenic amino acids an efficient analytical tool to investigate intermediary metabolism, *FEBS*, 1995, 232:433-448).

The reversible reactions were modeled as forward (F) and reverse (R) fluxes (Quek L. E. et al., OpenFLUX: efficient modelling software for 13C-based metabolic flux analysis, *Microb. Cell Fact.*, 2009, 8:25), the difference between which gave a net flux value through the reversible reaction.

In the model used herein, the biosynthetic pathways for the amino acids, NTPs (nucleotide triphosphates), and dNTPs (deoxyribonucleotide triphosphates) were expressed explicitly as the experimental data concerning their mass isotopomer distribution (MID), and were used directly for flux estimation. A single biomass equation was designed by presenting the biomass composition of *E. coli* as the sum of the essential quantities of the amino acids, NTPs, dNTPs and the amounts of the precursors drained to produce residual biomass components (Example 4.5).

Atom transition schemes were extracted as described in Quek L. E. and Nielsen L. K., Steady-state $^{13}C$ fluxomics using OpenFLUX, *Methods Mol. Biol.*, 2014, 1191:209-224.

Measured external carbon fluxes (effluxes) were biomass synthesis, effluxes of secreted products, and the glucose uptake rate.

In the case of L-histidine producing strains, the aspartate and adenosine consumption reactions were included in the metabolic model. Adenosine was assumed to be directly utilized for biomass (RNA, DNA and histidine) synthesis after phosphorylation. Aspartate is known to be utilized by *E. coli* cells as a carbon and nitrogen source (McFall E. and Newman E. B., Amino acids as carbon sources. In *Escherichia coli* and *Salmonella*: cellular and molecular biology edited by Neidhardt F. C. ($2^{nd}$ ed.), 1996, ASM Press). According to recent genome-scale reconstruction of *E. coli* metabolism (Orth J. D. et al., A comprehensive genome-scale reconstruction of *Escherichia coli* metabolism-2011, *Molecular Systems Biology*, 2011, 7:535), external aspartate after its transport into the cell can be utilized directly for biomass synthesis (for example, synthesis of protein and nucleic acids), or used as an amino group donor in a biosynthetic reaction (for example, synthesis of arginine and histidine) including reversible transamination reaction between aspartate and glutamate catalyzed by aspartate transaminase (encoded by aspC gene). Finally, aspartate can donate carbon directly into the central metabolism via conversion to fumarate catalyzed by aspartase (encoded by aspA gene). All these pathways for external aspartate utilization were accounted for in the metabolic model used for L-histidine-producing strains flux estimation using $^{13}C$-MFA. The aspartase-catalyzed reaction generates a cycle "aspartate→fumarate→malate→oxaloacetate→aspartate" in which TCA cycle enzymes such as fumarase and malate dehydrogenase are involved. As a result, the flux estimation precision for fumarase and malate dehydrogenase is decreased. The final core metabolic model is described in Tables 14 to 20. In the column "Type of reaction" in these Tables, "F" refers to an irreversible reaction, "FR" refers to the forward direction of a reversible reaction, "R" refers to the backward direction of a reversible reaction, and "B" refers to a reaction that is excluded from isotopomer balance.

TABLE 14

The core metabolic model for *E. coli* parental (including a wild-type) and L-histidine producing strains.

| | No. | Reaction | Rearrangement of carbon atoms | Type of reaction |
|---|---|---|---|---|
| Input PTS transport | 1 | glc_D_e = glc_D_c | abcdef = abcdef | |
| | 2 | glc_D_c + pep_c = g6p_c + pyr_c | abcdef + ghi = abcdef + ghi | F |
| EMP | 3 | g6p_c = f6p_c | abcdef = abcdef | FR |
| | 4 | f6p_c = g6p_c | abcdef = abcdef | R |
| | 5 | f6p_c + ATP = fdp_c | abcdef + X = abcdef | F |
| | 6 | fdp_c = f6p_c | abcdef = abcdef | F |
| | 7 | fdp_c = dhap_c + g3p_c | abcdef = abc + def | FR |
| | 8 | dhap_c + g3p_c = fdp_c | abc + def = abcdef | R |
| | 9 | dhap_c = g3p_c | abc = cba | FR |
| | 10 | g3p_c = dhap_c | cba = abc | R |
| | 11 | g3p_c = 13dpg_c + NADH | abc = abc + X | FR |
| | 12 | 13dpg_c + NADH = g3p_c | abc + X = abc | R |
| | 13 | 13dpg_c = 3pg_c + ATP | abc = abc + X | FR |
| | 14 | 3pg_c + ATP = 13dpg_c | abc + X = abc | R |
| | 15 | 3pg_c = pep_c | abc = abc | FR |
| | 16 | pep_c = 3pg_c | abc = abc | R |
| | 17 | pep_c = pyr_c + ATP | abc = abc + X | F |
| | 18 | pyr_c + ATP + ATP = pep_c | abc + X + X = abc | F |
| PP | 19 | g6p_c = 6pgc_c + NADPH | abcdef = abcdef + X | F |
| | 20 | 6pgc_c = co2_c + ru5p_D_c + NADPH | abcdef = a + bcdef + X | F |

TABLE 14-continued

The core metabolic model for *E. coli* parental (including a wild-type) and L-histidine producing strains.

| No. | Reaction | Rearrangement of carbon atoms | Type of reaction |
|---|---|---|---|
| 21 | ru5p_D_c = xu5p_D_c | abcde = abcde | FR |
| 22 | xu5p_D_c = ru5p_D_c | abcde = abcde | R |
| 23 | ru5p_D_c = r5p_c | abcde = abcde | FR |
| 24 | r5p_c = ru5p_D_c | abcde = abcde | R |
| 25 | xu5p_D_c = c2 + g3p_c | abcde = ab + cde | FR |
| 26 | c2 + g3p_c = xu5p_D_c | ab + cde = abcde | R |
| 27 | f6p_c = c2 + e4p_c | abcdef = ab + cdef | FR |
| 28 | c2 + e4p_c = f6p_c | ab + cdef = abcdef | R |
| 29 | s7p_c = c2 + r5p_c | abcdefg = ab + cdefg | FR |
| 30 | c2 + r5p_c = s7p_c | ab + cdefg = abcdefg | R |
| 31 | f6p_c = c3 + g3p_c | abcdef = abc + def | FR |
| 32 | c3 + g3p_c = f6p_c | abc + def = abcdef | R |
| 33 | s7p_c = c3 + e4p_c | abcdefg = abc + defg | FR |
| 34 | c3 + e4p_c = s7p_c | abc + defg = abcdefg | R |

TABLE 15

The core metabolic model for *E. coli* parental (including a wild-type) and L-histidine producing strains.

| | No. | Reaction | Rearrangement of carbon atoms | Type of reaction |
|---|---|---|---|---|
| ED | 35 | 6pgc_c = 2ddg6p_c | abcdef = abcdef | F |
| | 36 | 2ddg6p_c = g3p_c + pyr_c | abcdef = def + abc | F |
| PRPP synthesis | 37 | r5p_c + ATP + ATP = prpp_c | abcde + X + X = abcde | F |
| PDH | 38 | pyr_c = accoa_c + co2_c + NADH | abc = bc + a + X | F |
| TCA | 39 | accoa_c + oaa_c = cit_c | ab + cdef = fedbac | F |
| | 40 | cit_c = icit_c | abcdef = abcdef | FR |
| | 41 | icit_c = cit_c | abcdef = abcdef | R |
| | 42 | icit_c = akg_c + co2_c + NADPH | abcdef = abcde + f + X | FR |
| | 43 | akg_c + co2_c + NADPH = icit_c | abcde + f + X = abcdef | R |
| | 44 | akg_c = co2_c + succoa_c + NADH | abcde = a + bcde + X | F |
| | 45 | succoa_c = succ_c + ATP | abcd = abcd + X | FR |
| | 46 | succ_c + ATP = succoa_c | abcd + X = abcd | R |
| | 47 | succ_c = 0.5fum + 0.5fum + FADH | abcd = 0.5abcd + 0.5dcba + X | FR |
| | 48 | fum + FADH = 0.5succ_c + 0.5succ_c | abcd + X = 0.5abcd + 0.5dcba | R |
| | 49 | fum = mal_L_c | abcd = abcd | FR |
| | 50 | mal_L_c = 0.5fum + 0.5fum | abcd = 0.5abcd + 0.5dcba | R |
| | 51 | mal_L_c = oaa_c + NADH | abcd = abcd + X | FR |
| | 52 | oaa_c + NADH = mal_L_c | abcd + X = abcd | R |
| GLX shunt | 53 | icit_c = glx_c + 0.5succ_c + 0.5succ_c | abcdef = ab + 0.5cdef + 0.5fedc | F |
| | 54 | accoa_c + glx_c = mal_L_c | ab + cd = cdba | F |
| malic enzyme | 55 | mal_L_c = co2_c + pyr_c + NADH | abcd = d + abc + X | F |
| | 56 | mal_L_c = co2_c + pyr_c + NADPH | abcd = d + abc + X | F |
| PCK | 57 | oaa_c + ATP = co2_c + pep_c | abcd + X = d + abc | F |
| PPC | 58 | co2_c + pep_c = oaa_c | d + abc = abcd | F |
| Acetate synthesis and excretion | 59 | accoa_c = ac_c + ATP | ab = ab + X | FR |
| | 60 | ac_c + ATP = accoa_c | ab + X = ab | R |
| | 61 | pyr_c + q8 = ac_c + co2_c + q8h2 | abc + X = bc + a + X | F |
| | 62 | ac_c = ac_ex | ab = ab | F |

TABLE 16

The core metabolic model for *E. coli* parental (including a wild-type) and L-histidine producing strains.

| | No | Reaction | Rearrangement of carbon atoms | Type of reaction |
|---|---|---|---|---|
| CO2 excretion | 63 | co2_c = co2_ex | a = a | F |
| CO2 exchange | 64 | co2_nat + co2_c = co2_c + co2_nat | a + b = a + b | F |
| C1 metabolism | 65 | mLthf_c = 10fthf_c + NADPH | a = a + X | F |
| | 66 | mLthf_c + NADH = 5mthf_c | a + X = a | F |
| Glu synthesis | 67 | akg_c + NADPH + NH3 = glu_L_c | abcde + X + X = abcde | F |
| Asp synthesis | 68 | glu_L_c + oaa_c = akg_c + asp_L_c | abcde + fghi = abcde + fghi | FR |
| | 69 | akg_c + asp_L_c = glu_L_c + oaa_c | abcde + fghi = abcde + fghi | R |
| Ala synthesis | 70 | glu_L_c + pyr_c = akg_c + ala_L_c | abcde + fgh = abcde + fgh | F |
| Gln synthesis | 71 | glu_L_c + ATP + NH3 = gln_L_c | abcde + X + X = abcde | F |
| Ser synthesis | 72 | 3pg_c + glu_L_c = akg_c + pser_L_c + NADH | abc + defgh = defgh + abc + X | F |
| | 73 | pser_L_c = ser_L_c | abc = abc | F |
| Ser degradation | 74 | ser_L_c = pyr_c + NH3 | abc = abc + X | F |
| Gly synthesis | 75 | ser_L_c = gly_c + mLthf_c | abc = ab + c | FR |
| | 76 | gly_c + mLthf_c = ser_L_c | ab + c = abc | R |
| | 77 | thr_L_c = accoa_c + gly_c + NADH | abcd = cd + ab + X | F |
| Gly cleavage | 78 | gly_c = co2_c + mLthf_c + NADH + NH3 | ab = a + b + X + X | F |
| Val synthesis | 79 | pyr_c + pyr_c = alac_S_c + co2_c | abc + def = abcef + d | F |
| | 80 | alac_S_c + NADPH = 3mob_c | abcde + X = abdce | F |
| | 81 | 3mob_c + glu_L_c = akg_c + val_L_c | abcde + fghij = fghij + abcde | F |

TABLE 17

The core metabolic model for *E. coli* parental (including a wild-type) and L-histidine producing strains.

| | No. | Reaction | Rearrangement of carbon atoms | Type of reaction |
|---|---|---|---|---|
| Leu synthesis | 82 | 3mob_c + accoa_c = 3c3hmp_c | abcde + fg = abfgcde | F |
| | 83 | 3c3hmp_c = 2ippc | abcdefg = abcdefg | F |
| | 84 | 2ippc = 3c2hmp_c | abcdefg = abcdefg | F |
| | 85 | 3c2hmp_c = 3c4mop_c + NADH | abcdefg = abcdefg + X | F |
| | 86 | 3c4mop_c = 4mop_c + co2_c | abcdefg = bcdefg + a | F |
| | 87 | 4mop_c + glu_L_c = akg_c + leu_L_c | abcdef + ghijk = ghijk + abcdef | F |
| Ile synthesis | 88 | thr_L_c = 2obut_c + NH3 | abcd = abcd + X | F |
| | 89 | 2obut_c + pyr_c = 2ahbut_c + co2_c | abcd + efg = abcdfg + e | F |
| | 90 | 2ahbut_c + NADPH = 23dhmp_c | abcdef + X = abecdf | F |
| | 91 | 23dhmp_c = 3mop_c | abcdef = abcdef | F |
| | 92 | 3mop_c + glu_L_c = akg_c + ile_L_c | fghijk + abcde = abcde + fghijk | F |
| Phe, Tyr, Trp synthesis | 93 | e4p_c + pep_c = 2dda7p_c | abcd + efg = efgabcd | F |
| | 94 | 2dda7p_c + NADPH = skm_c | abcdefg + X = bcdefga | F |
| | 95 | skm_c + ATP = skm5p_c | abcdefg + X = abcdefg | F |
| | 96 | pep_c + skm5p_c = 3psme_c | hij + abcdefg = abcdefhij | F |

TABLE 17-continued

The core metabolic model for *E. coli* parental (including a wild-type) and L-histidine producing strains.

| No. Reaction | Rearrangement of carbon atoms | Type of reaction |
|---|---|---|
| 97 3psme_c = chor_c | abcdefghij = abcdefghij | F |
| 98 chor_c = pphn_c | abcdefghij = abcdefghij | F |
| 99 pphn_c = co2_c + phpyr_c | abcdefghij = j + ghiabcdef | F |
| 100 glu_L_c + phpyr_c = akg_c + phe_L_c | abcde + fghijklmn = abcde + fghijklmn | F |
| 101 pphn_c = 34hpp_c + co2_c + NADH | abcdefghij = ghiabcdef + j + X | F |
| 102 34hpp_c + glu_L_c = akg_c + tyr_L_c | fghijklmn + abcde = abcde + fghijklmn | F |
| 103 chor_c + gln_L_c = anth_c + glu_L_c + pyr_c | abcdefghij + klmno = abcdefj + klmno + ghi | F |
| 104 anth_c + prpp_c = pran_c | abcdefg + hijkl = abcdefghijkl | F |
| 105 pran_c = 2cpr5p_c | abcdefghijkl = hijklbafedcg | F |
| 106 2cpr5p_c = 3ig3p_c + co2_c | abcdefghijkl = edcabghijkf + l | F |
| 107 3ig3p_c = g3p_c + indole_c | abcdefghijk = cba + defghijk | F |
| 108 indole_c + ser_L_c = trp_L_c | defghijk + abc = abcdefghijk | F |

TABLE 18

The core metabolic model for *E. coli* parental (including a wild-type) and L-histidine producing strains.

| | No. Reaction | Rearrangement of carbon atoms | Type of reaction |
|---|---|---|---|
| Cys synthesis | 109 accoa_c + ser_L_c = acser_c | ab + cde = cdeab | F |
| | 110 acser_c + h2s = ac_c + cys_L_c | abcde + X = de + abc | F |
| Met synthesis | 111 hoL_c + succoa_c = suchms_c | abcd + efgh = abcdefgh | F |
| | 112 cys_L_c + suchms_c = cyst_L_c + 0.5succ_c + 0.5succ_c | ijk + abcdefgh = abcdkji + 0.5efgh + 0.5hgfe | F |
| | 113 cyst_L_c = hcys_L_c + pyr_c + NH3 | abcdefg = abcd + gfe + X | F |
| | 114 5mthf_c + hcys_L_c = met_L_c | e + abcd = abcde | F |
| Lys synthesis | 115 asp_L_c + ATP + NADPH = aspsa_c | abcd + X + X = abcd | F |
| | 116 aspsa_c + pyr_c = 23dhdp_c | abcd + efg = abcdgfe | F |
| | 117 23dhdp_c + NADPH = thdp_c | abcdefg + X = abcdefg | F |
| | 118 succoa_c + thdp_c = sl2a60_c | hijk + abcdefg = abcdefghijk | F |
| | 119 glu_L_c + sl2a60_c = akg_c + sl26da_c | lmnop + abcdefghijk = lmnop + abcdefghijk | F |
| | 120 sl26da_c = 26dap_LL_c + 0.5succ_c + 0.5succ_c | abcdefghijk = abcdefg + 0.5hijk + 0.5kjih | F |
| | 121 26dap_LL_c = 0.526dap_c + 0.526dap_c | abcdefg = 0.5abcdefg + 0.5gfedcba | F |
| | 122 26dap_c = co2_c + lys_L_c | abcdefg = g + abcdef | F |
| Pro synthesis | 123 glu_L_c + ATP + NADPH + NADPH = pro_L_c | abcde + X + X + X = abcde | F |
| Arg synthesis | 124 accoa_c + glu_L_c = acglu_c | ab + cdefg = cdefgab | F |
| | 125 acglu_c + ATP = acg5p_c | abcdefg + X = abcdefg | F |

TABLE 18-continued

The core metabolic model for *E. coli* parental (including a wild-type) and L-histidine producing strains.

| No. Reaction | Rearrangement of carbon atoms | Type of reaction |
|---|---|---|
| 126 acg5p_c + NADPH = acg5sa_c | abcdefg + X = abcdefg | F |
| 127 acg5sa_c + glu_L_c = acorn_c + akg_c | abcdefg + hijkl = abcdefg + hijkl | F |
| 128 acorn_c = ac_c + orn_c | abcdefg = fg + abcde | F |
| 129 co2_c + gln_L_c + ATP + ATP = cbp_c + glu_L_c | a + bcdef + X + X = a + bcdef | F |
| 130 cbp_c + orn_c = citr_L_c | f + abcde = abcdef | F |
| 131 asp_L_c + citr_L_c + ATP + ATP = argsuc_c | abcd + efghij + X + X = efghijabcd | F |
| 132 argsuc_c = arg_L_c + 0.5fum + 0.5fum | abcdefghij = abcdef + 0.5ghij + 0.5jihg | F |

TABLE 19

The core metabolic model for *E. coli* parental (including a wild-type) and L-histidine producing strains.

| | No Reaction | Rearrangement of carbon atoms | Type of reaction |
|---|---|---|---|
| Thr synthesis | 133 aspsa_c + NADPH = hoL_c | abcd + X = abcd | F |
| | 134 hoL_c + ATP = thr_L_c | abcd + X = abcd | F |
| Asn synthesis | 135 asp_L_c + ATP + ATP + NH3 = asn_L_c | abcd + X + X + X = abcd | F |
| His synthesis | 136 atp_c + prpp_c = prbatp_c + aicar_c | f + abcde = abcdef + X | F |
| | 137 prbatp_c = prlp_c | abcdef = abcdef | F |
| | 138 gln_L_c + prlp_c = eig3p_c + glu_L_c | abcde + fghijk = fghijk + abcde | F |
| | 139 eig3p_c = imacp_c | abcdef = abcdef | F |
| | 140 glu_L_c + imacp_c = akg_c + hisp_c | abcde + fghijk = abcde + fghijk | F |
| | 141 hisp_c = his_L_c + 2NADH | abcdef = abcdef + X | F |
| UTP, CTP | 142 asp_L_c + cbp_c + q8 = orot_c + q8h2 | abcd + e + X = abcde + X | F |
| | 143 orot_c + prpp_c + ATP = udp_c + co2_c | abcde + X + X = bcde + a | F |
| | 144 udp_c + ATP = utp_c | | B |
| | 145 utp_c + gln_L_c + ATP = ctp_c + glu_L_c | X + abcde + X = X + abcde | F |
| IMP | 146 gln_L_c + prpp_c = glu_L_c + pram_c | abcde + X = abcde + X | F |
| | 147 pram_c + gly_c + ATP = gar_c | | B |
| | 148 gar_c + 10fthf_c + ATP = fgam_c | | B |
| | 149 fgam_c + gln_L_c + ATP = fpram_c + glu_L_c | X + abcde + X = X + abcde | F |
| | 150 fpram_c + co2_c + 2ATP = 5caiz_c | | B |
| | 151 5caiz_c + asp_L_c + ATP = 25aics_c | X + abcd + X = abcd | F |
| | 152 25aics_c = aicar_c + 0.5fum + 0.5fum | abcd = X + 0.5abcd + 0.5dcba | F |
| | 153 aicar_c + 10fthf_c = imp | X + a = a | F |
| ATP | 154 asp_L_c + imp + ATP = dcamp_c | abcd + e + X = abcde | F |
| | 155 dcamp_c + ATP = adp_c + 0.5fum + 0.5fum | abcde + X = e + 0.5abcd + 0.5dcba | F |
| | 156 adp_c + 0.5NADH + 0.25O2 = atp_c | a + X + X = a | F |
| GTP | 157 gln_L_c + imp + 4ATP = glu_L_c + gtp_c + NADH | abcde + X + X = abcde + X + X | F |

TABLE 20

The core metabolic model for E. coli parental (including a wild-type) and L-histidine producing strains.

| | No | Reaction | Rearrangement of carbon atoms | Type of reaction |
|---|---|---|---|---|
| dNTP (via thiore- doxine) | 158 | ctp_c + NADPH = dctp_c | | B |
| | 159 | atp_c + NADPH = datp_c | | B |
| | 160 | gtp_c + NADPH = dgtp_c | | B |
| | 161 | udp_c + NADPH = dump_c | | B |
| | 162 | utp_c + NADPH = dump_c | | B |
| dTTP | 163 | dump_c + mLthf_c + 2ATP = dttp_c | | B |
| Biomass | 164 | biomass | | B |
| Not carbon exchange reactions | 169 | so4_e + ATP = so4 | | ** |
| | 170 | so4 + 3ATP + 4NADPH = h2s | | |
| | 171 | NH3_ex = NH3 | | |
| | 172 | O2_ex = O2 | | |
| | 173 | ATP = ATP_ex | | |
| | 174 | NADH = NADPH | | |
| | 175 | 2NADH + O2 = 4ATP | | |
| | 176 | 2FADH + O2 = 2ATP | | |
| Reactions specific to L-histidine-producing strains | | | | |
| His transport | | his_L_c = his_L_ex | abcdef = abcdef | F |
| Asp utilization | | asp_L_e = asp_L_c | abcd = abcd | F |
| | aspA | asp_L_c = 0.5fum + 0.5fum + NH3 | abcd = 0.5abcd + 0.5dcba + X | F |
| | aspC | glu_L_c + oaa_c = akg_c + asp_L_c | abcde + fghi = abcde + fghi | FR |
| | | akg_c + asp_L_c = glu_L_c + oaa_c | abcde + fghi = abcde + fghi | R |
| Adenosine utilization | | ade + 3ATP = atp_c | a = a | F |

**The reaction Nos. 169-176 were excluded from the model used for flux calculation as they do not relate to carbon or isotopomer balancing.

4.5. Drain to Biomass Synthesis.

Accounting for the withdrawal of precursor fluxes from the central metabolism for biomass synthesis is crucial for stoichiometric carbon balancing during internal carbon flux estimation (Pramanik J. and Keasling J. D., Stoichiometric model of *Escherichia coli* metabolism: incorporation of growth-rate dependent biomass composition and mechanistic energy requirements, *Biotechnol. Bioeng.*, 1997, 56(4): 398-421; Pramanik J. and Keasling J. D., Effect of *Escherichia coli* biomass composition on central metabolic fluxes predicted by a stoichiometric model, *Biotechnol. Bioeng.*, 1998, 60(2):230-238; Dauner M. and Sauer U., Stoichiometric growth model for riboflavin-producing *Bacillus subtilis*, *Biotechnol Bioeng.*, 2001, 76(2):132-143). The drain of precursor and energy for biomass synthesis is accounted for by a biomass equation which is formulated based on biomass composition and precursor demands for the synthesis of each biomass component (Zamboni N. et al., $^{13}$C-based metabolic flux analysis, *Nat. Protoc.*, 2009, 4(6):878-892). The flux to the biomass synthesis is equal to the specific growth rate (1/h). After normalization to the specific rate of glucose consumption (mmol glucose/(gDW*h)), this value can be transferred to biomass yield from glucose (($g_{DW}$/$mmol_{GLC}$)*100).

Protein (Prot), RNA, DNA, phospholipids (PLP), lipopolysaccharides (LPS), peptidoglycan (PGL), and glycogen (GL) constitute 96% of *E. coli* cell dry weight (Neidhardt F. C. and Umbarger H. E., Chemical composition of *Escherichia coli*. In *Escherichia coli* and *Salmonella*: cellular and molecular biology edited by Neidhardt F. C. (2$^{nd}$ ed.), 1996, ASM Press). The protein and RNA content, as the most abundant and variable biomass components (Pramanik J. and Keasling J. D., 1997), were measured for each strain using the methods described in Example 4.6. The contents of other biomass components were taken from the literature (Neidhardt F. C. and Umbarger H. E., Chemical composition of *Escherichia coli*. In *Escherichia coli* and *Salmonella*: cellular and molecular biology edited by Neidhardt F. C. (2$^{nd}$ ed.), 1996, ASM Press) as described below. Drain for protein, RNA, and DNA synthesis accounted for in biomass equation as drain of the corresponding constituents (amino acids, NTP, and dNTP) which biosynthetic pathways expressed explicitly in the model (Example 4.4). The central metabolism precursor demands for other cellular component synthesis were reconstructed from biosynthetic pathways described in detail in EcoCyc database (www.ecocyc.org). The composition of biomass components (for example, an amino acid composition of a protein in *E. coli*) was taken from literature (Neidhardt F. C. and Umbarger H. E., Chemical composition of *Escherichia coli*. In *Escherichia coli* and *Salmonella*: cellular and molecular biology edited by Neidhardt F. C. (2$^{nd}$ ed.), 1996, ASM Press).

Stoichiometric coefficients in the biomass equation denote an amount of a constituent drained to synthesis of one gram of biomass (mmol/$g_{DW}$) (Marx A. et al., Determination of the fluxes in the central metabolism of *Corynebacterium glutamicum* by nuclear magnetic resonance spectroscopy combined with metabolite balancing, *Biotechnol. Bioeng.*, 1996, 49(2):111-129; Fischer E. et al., High-throughput metabolic flux analysis based on gas chromatography-mass spectrometry derived $^{13}$C constraints, *Anal. Biochem.*, 2004, 325(2):308-316).

The direct measurement of biomass dry weight (DW) was difficult for the producing strain due to the presence of insoluble $CaCO_3$ in the culture medium. Therefore, biomass composition was re-normalized to protein content rather than DW value using protein content values measured for MG1655 and MG1655 IS5.8::$P_L$-hppA Δppa::cat strains. Thus, total drain to biomass synthesis was accounted for by value of the protein yield from glucose ($g_{protein}$/$mmol_{GLC}$*100) measured experimentally for each strain. The stoichiometric coefficient in the biomass equation became the drain of a biomass precursor (i) per gram of protein (mmol$_i$/$g_{protein}$).

The protein content value ($g_{prot}$/$g_{DW}$) was set to be 55% for *E. coli* MG1655 and EA92 strains (as measured for MG1655 strain, Example 4.6) and 44.6% for *E. coli* MG1655 IS5.8::$P_L$-hppA Δppa::cat and EA92 IS5.8::$P_L$-hppA Δppa::cat strains (as measured for MG1655 IS5.8::$P_L$-hppA Δppa::cat strain, Example 4.6). In order to determine protein content of MG1655 and MG1655 IS5.8::$P_L$-hppA Δppa::cat strains experimentally, a correlation coefficient between $OD_{595}$ and dry weight of the cells (mg of the cells in 1 mL of a culture medium at $OD_{595}$ of 1) was determined by placing cells from 3-5 mL of exponentially-growing culture onto preliminary weighted 0.45 m filter (Millipore, cat. No. HAWP02500) followed by drying at 60° C. until a constant weight is achieved. Correlation coefficient was calculated as the difference of filter weight without cells and with cells divided by culture cell volume and $OD_{595}$. Filters were dried at 60° C. before the determination of the initial weight.

The coefficient for constituents of RNA was calculated from a correlation coefficient between RNA content and protein content ($g_{RNA}$/$g_{protein}$) measured experimentally for each strain.

DNA is a slightly variable compartment (J Pramanik J. and Keasling J. D., 1997). Therefore, the DNA content was assumed to be the same in all tested strains, and it was set to 3.1% ($g_{DNA}$/$g_{DW}$) (Neidhardt F. C. and Umbarger H. E., Chemical composition of *Escherichia coli*. In *Escherichia coli* and *Salmonella*: cellular and molecular biology edited by Neidhardt F. C. ($2^{nd}$ ed.), 1996, ASM Press). The content of other biomass components was approximated using the values known from literature (Neidhardt F. C. and Umbarger H. E., Chemical composition of *Escherichia coli*. In *Escherichia coli* and *Salmonella*: cellular and molecular biology edited by Neidhardt F. C. ($2^{nd}$ ed.), 1996, ASM Press) to fill up to 100% of dry weight (formula II) and using their mass ratios (formula III):

PLP+LPS+PGL+GL=DW−(Prot+RNA+DNA)   II, and

PLP:LPS:PGL:GL=9.1:3.4:2.5:2.5   III.

The biomass composition of the used *E. coli* strains is shown in Table 21.

TABLE 21

Biomass composition of *E. coli* strains.

| Biomass component | MG1655 | MG1655 IS5.8:: $P_L$-hppA Δppa::cat | EA92 | EA92 IS5.8:: $P_L$-hppA Δppa::cat |
|---|---|---|---|---|
| Protein, $g_{prot}$/mmol$_{glucose}$ | 0.038* | 0.023* | 0.030* | 0.030* |
| RNA, g/$g_{prot}$ | 0.21* | 0.17* | 0.17* | 0.17* |
| DNA, g/$g_{prot}$ | 0.06 | 0.07 | 0.06 | 0.07 |
| Phospholipids, g/$g_{prot}$ | 0.29 | 0.52 | 0.31 | 0.52 |
| Lipopolysaccharides, g/$g_{prot}$ | 0.11 | 0.19 | 0.11 | 0.19 |
| Peptydoglycan, g/$g_{prot}$ | 0.08 | 0.14 | 0.08 | 0.14 |
| Glycogen, g/$g_{prot}$ | 0.08 | 0.14 | 0.08 | 0.14 |

*The values were determined experimentally.

4.6. Determination of Protein and RNA Content.

Samples of biomass for the estimation of protein and RNA concentrations were collected by centrifugation at 8,000 rpm for 3 min, washed with 0.900 NaCl, and stored at −70° C. before used. The pellets of L-histidine-producing strains contained the cells and the undissolved $CaCO_3$.

Protein content in biomass was estimated by the Lowry method using Bio-Rad DC Protein Assay kit (Bio-Rad, cat. No. 500-0114) according to the manufacturer's instruction.

RNA content in biomass was estimated using the Schmidt-Tannhauser method (Herbert D. et al., Chemical analysis of microbial cells. In *Methods in Microbiology*, 1971, Edited by J. R. Norris and D. W. Ribbons, vol. 5, Part B: 209-344) in order to distinguish between RNA and DNA. The amount of nucleotide was determined spectrophotometrically (Spirin A. S., Spectrometric determination of a total quantity of nucleic acids (in Russian), *Biohimiya*, 1958, 23:656-662; Karklinya V. A. et al., Quantitative determination of nucleic acids in salmonidae milt by various methods, *Chem. Nat. Compd.*, 1989, 25:109-112). Briefly, for the removal of low-weight cytoplasmic metabolites, ice-cold 0.25 N $HClO_4$ (1 mL) was added to the samples followed by incubation at 0° C. for 30 min. The test tubes were gently inverted from time to time. Then, the biomass was precipitated at 8,000 g for 3 min, and the supernatant was removed. RNA was hydrolyzed by applying 0.5 mL of 1 N KOH at 37° C. for 1 hour. The test tubes were shaken using Vortex from time to time. Then, the test tubes were cooled on ice, and ice-cold 3 N $HClO_4$ (0.5 mL) was added to remove DNA and protein from the solution. After centrifugation at 13,000 g for 5 min at 0° C., supernatants were transferred to new test tubes, and UV-spectrum of the solutions was recorded using NanoDrop 2000 spectrophotometer (Thermo Scientific). RNA concentration (g/L) in the solution was calculated using the formula IV (Spirin A. S., *Biohimiya*, 1958; Karklinya V. A. et al., *Nat. Compd.*, 1989):

$$C = (OD_{270} - OD_{290}) \times \frac{10.3}{0.19} c = 0.05421 * (D_{270} - D_{290}),\quad \text{IV}$$

wherein 0.19 is the value of the ($OD_{270}$–$OD_{290}$) and corresponds to the nucleic acis hydrolyzate with 1 mg/L concentration of nucleic acid phosphate, and 10.3 is the average coefficient to transfer the phosphate amount to the ribonucleotide amount.

Finally, the RNA amount in the culture sample taken into the analysis was calculated using the formula V:

RNA=$V_1$×C   V, wherein $V_1$ is the volume of final RNA solution, and C is RNA concentration (g/L) in the solution determined using the formula IV.

$CaCO_3$ did not interfere with the methods that were used for determination of protein and RNA.

4.7. Preparation of Samples for GC-MS Analysis.

Amino acids of protein and ribose of RNA of biomass were used as a source of mass-isotopomer abundance data. Biomass was separated from the cultivation medium by centrifugation at 8,000 rpm for 3 min. Cells of L-histidine-producing strains were separated from $CaCO_3$ sediment using spatula. Cells were washed with 0.9% NaCl for MG1655 and MG1655 IS5.8::$P_L$-hppA Δppa::cat strains and with 0.9% NaCl in 0.1 N HCl for L-histidine-producing strains to remove the rest of $CaCO_3$.

Before the analysis, biomass protein and RNA were hydrolyzed down to monomers, and the obtained amino acids and ribose were derivatized to allow separation using gas chromatography. The acid protein hydrolysis was carried out as follows. A sample of biomass was suspended in 6 N HCl and incubated in a sealed test tube (Vacuum Hydrolysis test tube, Thermo Scientific, cat. No. 29570) for 20 hours at 105° C. Hydrolyzates were dried under vacuum (Concentrator Plus, Eppendorf, cat. No. 5305000304). Released proteinogenic amino acids were then derivatized according to a previously developed method (Antoniewicz M. R. et al., Accurate assessment of amino acid mass isotopomer distributions for metabolic flux analysis, Anal. Chem., 2007, 79:7554-7559). Briefly, dried amino acid residues were incubated for 5 min at 105° C. to remove residual moisture. Then, pyridine and a derivatization agent (N-tert-butyldimethylsilyl-N-methyltrifluoroacetamide (TBDMSTFA) with 1% tertbutyldimethylchlorosilane (TBDMST); Sigma, cat. No. 375934) were added, and the solutions were incubated for 30 min at 60° C. followed by GC-MS analysis.

For the preparation of ribose derivatives, a previously established method was used (Long C. P. et al., $^{13}$C metabolic flux analysis of microbal and mammalian systems is enhanced with GC-MS measurements of glycogen and RNA labeling, *Metab. Eng.*, 2016, 38:65-72). Briefly, biomass samples were dried under vacuum (Concentrator Plus, Eppendorf, cat. No. 5305000304). 6 N HCl was added to biomass pellets, and the samples were incubated for 30 min at 30° C. Then, the samples were diluted with $H_2O$ to bring the concentration of acid to 1 N, sonicated using an ultrasonic bath, and incubated for 1 hour at 110° C. After cooling, the hydrolizates were neutralized with 5 N NaOH solution and dried under vacuum. To obtain an aldonitrile derivatives of ribose, 50 μL of 2% (w/w) hydroxylamine hydrochloride in pyridine was added to dried samples followed by sonication and incubation for 1 hour at 90° C. For the propionylation of hydroxyl groups, 100 μL of propionic anhydride was added. The samples were sonicated, incubated for 30 min at 60° C., and analyzed using GC-MS.

4.8. GC-MS Analysis.

Gas chromatography-mass spectrometry (GC-MS) analysis was performed using Agilent 7890B gas chromatograph equipped with a DB-5MS capillary column (30 m, 0.25 mm i.d., 0.25 μm-phase thickness) connected to an Agilent 5977A mass spectrometer operating under electron ionization (EI) of 70 eV. For GC-MS analysis of amino acids derivatives, 1 μL was injected at 1:10 split ratio. Helium flow was maintained at 0.7 mL/min. The inlet temperature was maintained at 270° C., the source temperature—at 230° C., the quadrupole temperature—at 150° C., the interface temperature—at 300° C. The oven temperature program for amino acids derivatives was as follows: the column was started at 100° C. for 1.5 min, then increased to 130° C. at 20° C./min, increased to 220° C. at 10° C./min, held for 3 min, increased to 280° C. at 5° C./min, and held for 3 min (Antoniewicz M. R. et al., Anal. Chem., 2007). Amino acid derivatives were detected in scan mode from 140 to 550 m/z.

For GC-MS analysis of sugar derivatives, 1 μL was injected at 1:2 to 1:10 split ratios. Helium flow was maintained at 1 mL/min. The inlet temperature was maintained at 250° C., the source temperature—at 230° C., the quadrupole temperature—at 150° C., the interface temperature—at 280° C. The oven temperature program for the analysis of sugar derivatives was as follows: the column was started at 80° C. for 2 min, increased to 280° C. at 10° C./min, and held for 5 min. The m/z 173 and m/z 284 fragments of ribose derivative were measured in single ion monitoring (SIM) mode.

Chromatograms were analyzed using MassHunter Workstation Software. Calculation of Mass Isotopomer Distributions (MIDs) of amino acid and ribose derivatives was carried out based on the peak areas of the molecular ion fragments (Fernandez C. A. et al., Correction of 13C Mass isotopomer distributions for natural stable isotope abundance, J. Mass Spectrom., 1996, 31:255-262).

MIDs of 2 fragments of derivatized ribose (Rib173 and Rib284) in addition to MIDs of 31 fragments of amino acid TBDMS-derivatives (Ala232, Ala260, Asp302, Asp376, Asp390, Asp418, Glu330, Glu404, Glu432, Gly218, Gly246, Ile200, Ile274, Leu274, Met218, Met292, Met320, Ser288, Ser390, Phe302, Phe308, Phe336, Thr376, Thr404, Tyr302, Tyr438, Tyr466, Tyr508, Val260, and Val288) were used as the experimental data for flux calculation.

4.9. Flux Calculation and Statistics Analysis.

Flux calculation and statistics analysis were carried out using the previously developed OpenFLUX2 software (Shupletsov M. S. et al., OpenFLUX2: $^{13}$C-MFA modeling software package adjusted for the comprehensive analysis of single and parallel labeling experiments, Microb. Cell Fact., 2014, 13:152) modified for the high-throughput flux estimation for a middle-size metabolic model based on parallel labeling experiments. Modifications included a special optimization engine, which allowed for application of different algorithms for optimization of elementary metabolite unit based metabolic model. The optimization engine utilizes decomposition algorithms on the basis of strongly connected components, detection of isomorphic subgraphs, and optimization of the EMU equations with the use of sparse matrices and memory allocation techniques. The intracellular fluxes were calculated by minimizing the variance-weighted sum of squared residuals (SSR) between the experimentally measured values (extracellular fluxes and GC-MS-detected mass-isotopomer distributions) and that generated from the model using non-linear least-squares regression. To ensure global minimum detection, 300 independent iterative trials, starting from randomly selected points from a feasible free flux space, were applied. The flux parameters value that passed the $chi^2$-test and possessed minimal SSR were chosen as an optimal flux distribution for the corresponding metabolic model.

To characterize the uncertainty of the estimated flux parameters, the parametric bootstrap confidence intervals (PB-CIs) (Theorell A. et al., To be certain about the uncertainty: Bayesian statistics for $^{13}$C metabolic flux analysis, Biotechnol. Bioeng., 2017, 114(11):2668-2684) were calculated using a percentile method (Diciccio T. J. and Romano J. P., A review of bootstrap confidence intervals, J. Royal Stat. Soc. B, 1988, 50:338-354; Joshi M. et al., Exploiting the bootstrap method for quantifying parameter confidence intervals in dynamical systems, Metab. Eng., 2006, 8:447-455). The percentile method was realized in OpenFLUX2 and mentioned as a "discarding" method of Monte Carlo simulation (Shupletsov M. S. et al., 2014). The confidence intervals borders of the interested net fluxes were convergent under the selected settings of the Monte Carlo simulation method.

4.10. Carbon Flux Distribution in E. coli MG1655 and MG1655 IS5.8::$P_L$-hppA ΔPpa::Cat Strains.

Figure 11:
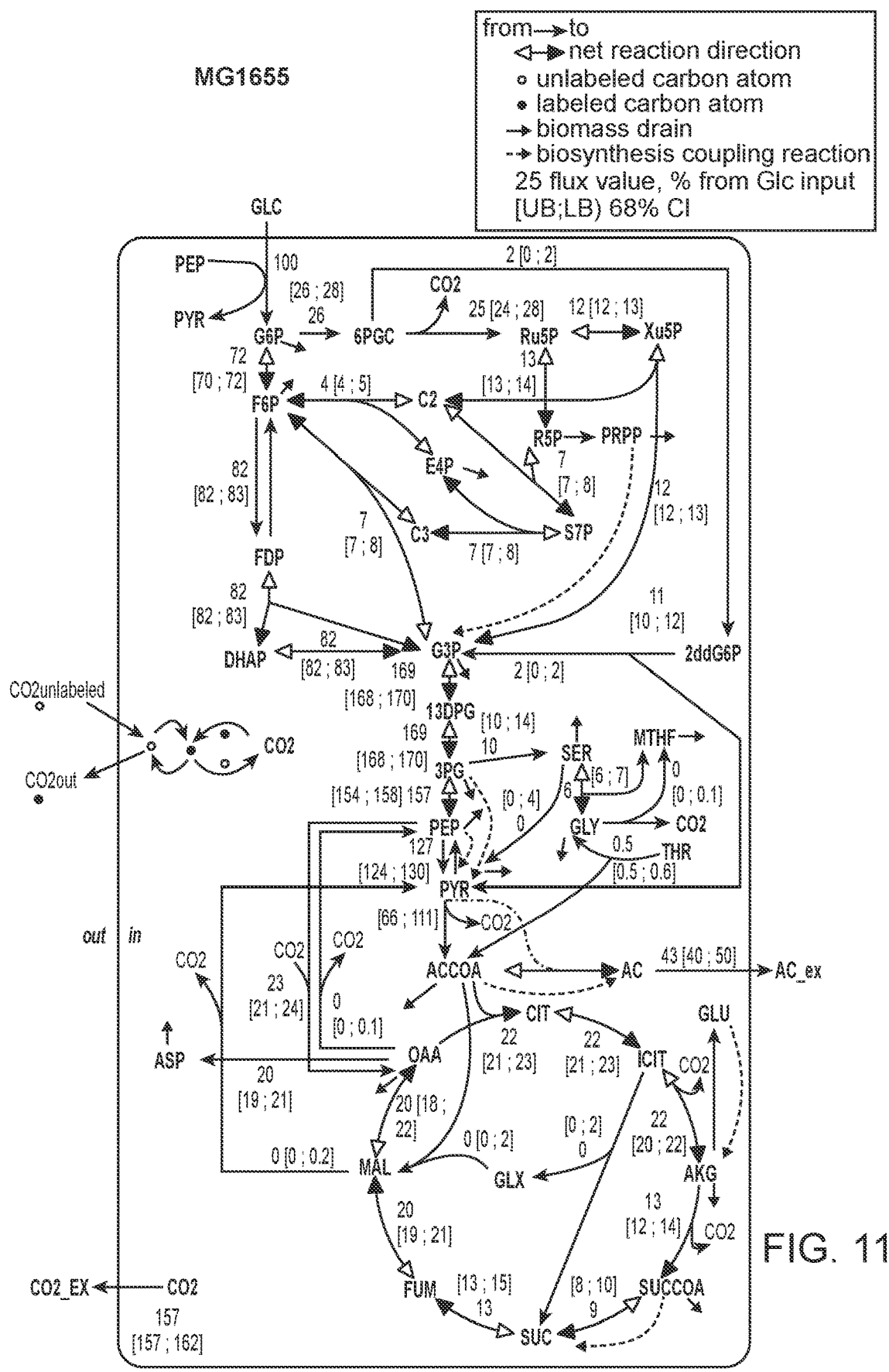
FIG. 11 shows the carbon flux distribution in *E. coli* MG1655 strain grown on 100%-glucose as a carbon source.

Optimal flux parameters and their confidence intervals were estimated as described in Example 4.9. As for the E. coli MG1655 strain, a good correlation with previously published data (Leighty R. W. and Antoniewicz M. R., COMPLETE-MFA: complementary parallel labeling experiments technique for metabolic flux analysis. Metab. Eng., 2013, 20:49-55) was observed, especially in the upper part of the metabolic map (FIG. 11). Little differences that were observed in the lower part of the metabolic map (FIG. 11) represented significantly more sensitivity of the corresponding fluxes to the even slightly different cultivation conditions (for example, aeration). In FIGS. 11 to 14, flux through the PEP→PYR reaction was a sum of PTS-dependent glucose transport reaction and pyruvate kinase reaction; and flux through pyruvate dehydrogenase reaction cannot be calculated precisely because of the presence of two possible acetate synthesis pathways: Pta-Ack and Pox (Example 4.4), and, therefore, it was expressed as a range.

Figure 12:
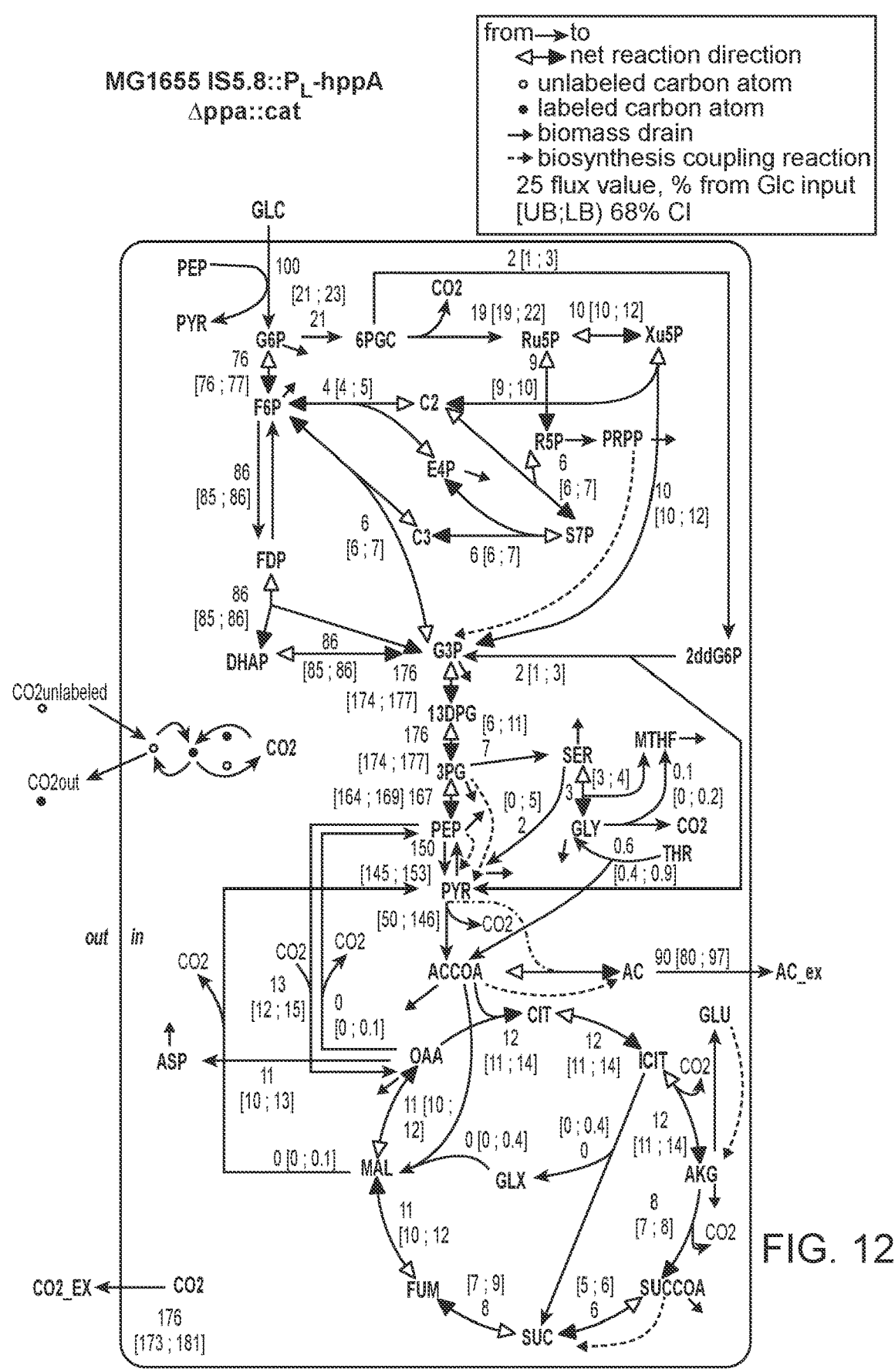
FIG. 12 shows the carbon flux distribution in *E. coli* MG1655 IS5.8::$P_L$-hppA Δppa::cat strain grown on 100%-glucose as a carbon source.
Figure 13:
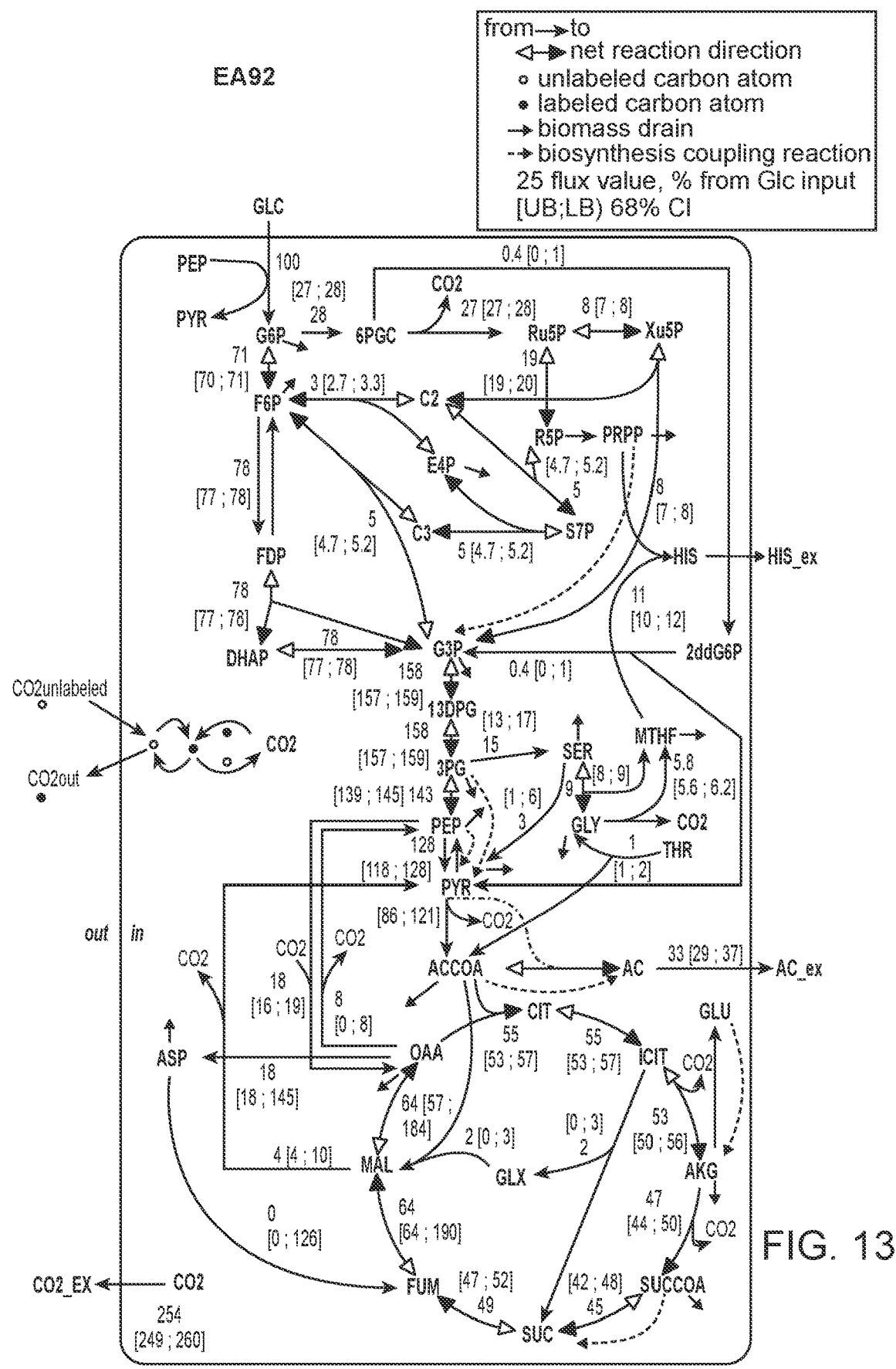
FIG. 13 shows the carbon flux distribution in *E. coli* L-histidine-producing strain EA92.
Figure 14:
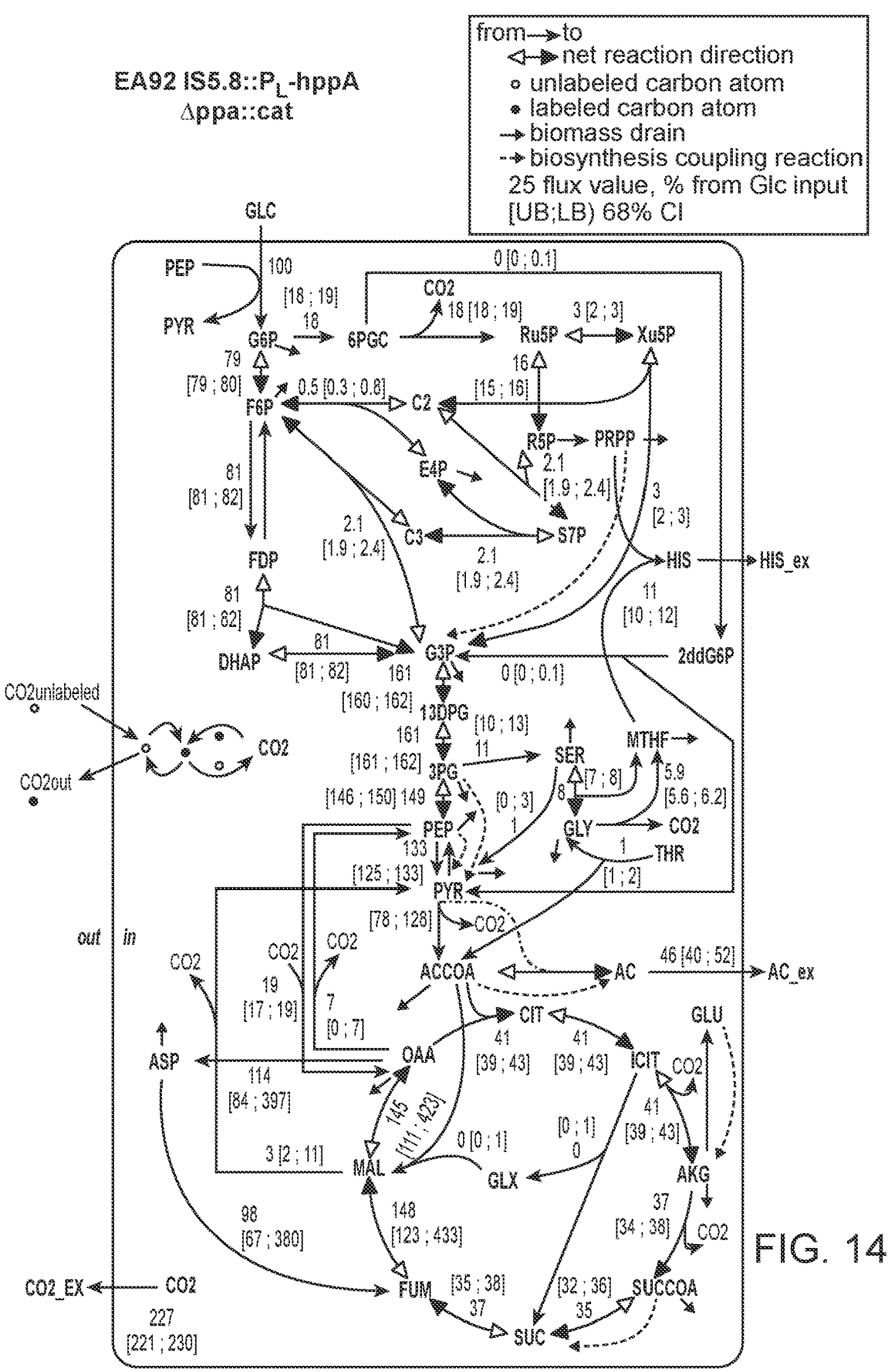
FIG. 14 shows the carbon flux distribution in *E. coli* L-histidine-producing strain EA92 IS5.8::$P_L$-hppA Δppa::cat.

Introduction of the overexpressed hppA gene into an E. coli strain that has been modified to inactivate ppa gene resulted in the statistically significant decrease of TCA fluxes as compared with the wild-type E. coli strain MG1655 (FIGS. 11 and 12).

The TCA cycle is the main source of energy in cells during aerobic growth (Cronan J. E. and Laporter D., Tricarboxylic acid cycle and glyoxylate bypass. In Escherichia coli and Salmonella: cellular and molecular biology, edited by Neidhardt F. C. ($2^{nd}$ ed.), 1996, ASM Press). One molecule of ATP and two molecules of NADH can be generated in the cycle. The NADH can then be oxidized in electron-transport chain to generate ATP, in particular. Also, succinate dehydrogenase directly connects the TCA cycle to the electron-transport chain. Hence, the significant (more than 45%) decrease of the carbon flux through TCA cycle in an E. coli MG1655 strain having overexpressed hppA gene as compared with a non-modified strain such as the wild-type E. coli strain MG1655 unambiguously confirmed the considerable increase of production of energy such as, for example, ATP by an alternative way in the E. coli strain having overexpressed the hppA gene. At the same time, the slight decrease in oxidative PP pathway flux was detected in the strain having overexpressed hppA gene as compared with the control strain (Sauer U. et al., The soluble and membrane-bound transhydrogenases UdhA and PntAB have divergent functions in NADPH metabolism of *Escherichia coli*, *J. Biol. Chem.*, 2004, 279(8):6613-6619). The observed flux re-distribution confirmed that cells of a bacterial strain that have been modified to overexpress a gene encoding a protein having H$^+$-translocating membrane-bound pyrophosphatase activity had another metabolic state as compared with the cells of a wild-type control strain.

4.11. Carbon Flux Distribution in *E. coli* L-Histidine-Producing Strains.

Steady-state $^{13}$C-MFA was performed for *E. coli* L-histidine-producing strains EA92 and EA92 IS5.8::P$_L$-hppA Δppa::cat during Phase II of the test tube fermentation (Example 4.2).

L-histidine-producing strains were characterized by flux distribution maps (FIGS. 13 and 14) that were different from the flux distribution map of the wild-type *E. coli* MG1655 strain (FIG. 11).

As for the comparison of fluxes distribution in the *E. coli* strains MG1655 and EA92 (FIGS. 11 and 13), one can see the following differences:
1) the decreased carbon flux through transaldolase and tranketolase reactions and increased flux through the ribulose-phosphate 3-epimerase reaction of non-oxidative PP pathway in EA92 strain as compared with MG1655 strain retained a considerable amount of carbon toward R5P, which is a precursor for L-histidine;
2) the increased carbon fluxes associated with 5,10-methylene tetrahydrofolate synthesis in *E. coli* EA92 strain;
3) the activation of the glycine cleavage system in EA92 strain as compared with MG1655 strain; and
4) the considerable increase (2.5 times) of the carbon flux through the TCA cycle in the EA92 strain as compared with the MG1655 strain.

The redistributions of flux in *E. coli* L-histidine producing strain EA92 described above correlated with the necessity of 1 molecule of R5P, 1 C1-unit, 1 NADPH, and 6 ATP molecules for the synthesis of 1 molecule of L-histidine.

As for the comparison of flux distribution in *E. coli* strains EA92 and EA92 IS5.8::P$_L$-hppA Δppa::cat (FIGS. 13 and 14), one can see that the global changes in flux distributions were qualitatively the same as between *E. coli* strains MG1655 and MG1655 IS5.8::P$_L$-hppA Δppa::cat. In particular:
1) the TCA fluxes were decreased by 25% in the EA92 IS5.8::P$_L$-hppA Δppa::cat strain as compared with the EA92 strain; and
2) oxidative PP pathway fluxes were decreased by 35% in the EA92 IS5.8::P$_L$-hppA Δppa::cat strain as compared with the EA92 strain.

The observed flux distribution in a bacterium that has been modified to overexpress a gene encoding a protein having H$^+$-translocating membrane-bound pyrophosphatase activity unambiguously confirmed that in the modified bacterium the native pathways for energy generation such as, for example, the TCA cycle are less active as compared with these pathways in a non-modified bacterium. The reason for this is that the modified bacterium can generate energy by using a proton-motive force that is produced as a result of the activity of a protein having H$^+$-translocating membrane-bound pyrophosphatase activity. Moreover, the proton-motive force generated as a result of activity of a protein having H$^+$-translocating membrane-bound pyrophosphatase activity in a bacterium that has been modified to overexpress a gene encoding that protein results in generation of the energy that is not related directly to carbon source catabolism. As a consequence, the modified bacterium becomes more fluent and efficient, as compared with a non-modified bacterium, in redistribution carbon, ATP, and molecules that can be used interchangeably to one or more molecules of ATP such as, for example, GTP, NADH, PEP, and the like, for the biosynthesis of cellular metabolites, and the energy that can be generated as a result of catabolism of the carbon source.

Auxiliary Example 1. Construction of *E. coli* EA92 Strain

An *E. coli* EA92 strain was constructed on the basis of the *E. coli* EA83 L-histidine-producing strain (MG1655rph$^+$ ilvG15---) (Malykh E. A. et al., Specific features of L-histidine production by *Escherichia coli* concerned with feedback control of AICAR formation and inorganic phosphate/metal transport, *Microb. Cell Fact.*, 2018, 17(1):42). The EA83 strain was modified to overexpress the aspC gene, to thereby construct the EA92 strain.

In detail, the upstream region of the aspC gene was modified by the replacement of a native regulatory region with λ-phage P$_L$ promoter using the λRed recombination system (Datsenko and Wanner, 2000). The primers P39 (SEQ ID NO: 55) and P40 (SEQ ID NO: 56) were used to construct a PCR fragment for λRed recombination that harbors an excisable cat marker and the nucleotide sequences homologous to a regulatory region of aspC gene. The presence of the P$_L$ promoter introduced into the chromosome was confirmed by PCR using the primers P41 (SEQ ID NO: 57) and P42 (SEQ ID NO: 58). Thus, the *E. coli* strain MG1655 cat-P$_L$-aspC was constructed. This strain was used as a donor to transfer the cat-P$_L$-aspC expression cassette into the chromosome of EA83 using the standard P1 transduction method (Moore S. D., Assembling new *Escherichia coli* strains by P1-duction, *Methods Mol. Biol.*, 2011, 765:155-169). The excisable chloramphenicol resistance marker (CmR$^{ex}$) was eliminated from the *E. coli* chromosome using Xis/Int site-specific recombination system with the use of pMWts-λInt/Xis helper plasmid (Minaeva N. I. et al., 2008). Thus, the *E. coli* EA92 strain was constructed.

Auxiliary Example 2. Construction of pMWAL1T-Ppur and pMWAL1T-Prep Plasmids, and *B. amyloliquefaciens* Strain AJ1991 purH::Sp (2.1) The pMWAL1T-Ppur Plasmid was Constructed as Follows.

First, pMWAL1-Ppur plasmid was constructed. The promoter of the *B. amyloliquefaciens* pur operon was amplified by PCR using primers P26 (SEQ ID NO: 42) and P27 (SEQ ID NO: 43), and the genomic DNA of *B. amyloliquefaciens* IAM1523 (Zakataeva et al., 2010) as a template. The obtained DNA fragment was digested using PaeI-XbaI restrictases and cloned into the PaeI-XbaI-digested pMWAL1 plasmid (see Auxiliary example 1 in the PCT Application Publication No. WO2015056813 A1). Thus, the pMWAL1-Ppur plasmid was constructed.

Second, in order to prevent read-through transcription, the *B. amyloliquefaciens* rho-independent transcription terminators eno and argF were successively cloned into the pMWAL1-Ppur plasmid. Specifically, the DNA fragment containing a terminator of the eno gene was amplified by PCR using the primers P28 (SEQ ID NO: 44) and P29 (SEQ ID NO: 45), and the genomic DNA of *B. amyloliquefaciens* IAM1523 as a template. The obtained DNA fragment was digested using the PaeI-XceI restrictases and cloned into the PaeI-digested pMWAL1-Ppur plasmid. Thus, the pMWAL1-Teno-Ppur plasmid was constructed.

Then, a DNA fragment containing the *B. amyloliquefaciens* transcription terminator argF was amplified by PCR using primers P23 (SEQ ID NO: 39) and P30 (SEQ ID NO: 46), and genomic DNA of *B. amyloliquefaciens* IAM1523 as a template. The obtained DNA fragment was digested using EcoRI-MunI restrictases and cloned into the EcoRI-digested pMWAL1-Teno-Ppur plasmid. Thus, the pMWAL1T-Ppur plasmid was constructed.

(2.2) The pMWAL1T-Prep Plasmid was Constructed as Follows.

A DNA fragment containing repAB promoter (PrepAB) was amplified by PCR using primers P31 (SEQ ID NO: 47) and P32 (SEQ ID NO: 48), and plasmid DNA of pLF22 as the template (Tarakanov B. V. et al, 2004). The obtained DNA fragment was digested using PaeI-XbaI restrictases and cloned into PaeI-XbaI-digested pMWAL1T-Ppur plasmid (Auxiliary example 2 (2.1)). Thus, the pMWAL1T-Prep plasmid was constructed.

(2.3) Construction of *B. amyloliquefaciens* AICAr-Producing Strain AJ1991purH::Sp.

A *B. amyloliquefaciens* strain AJ1991purH::Sp was constructed from the AJ1991 strain (Zakataeva N. P. et al., 2007) by inactivating the purH gene, that encodes the bifunctional purine biosynthesis protein PurH, through the insertion of a gene encoding spectinomycin resistance ($Sp^R$) marker.

First, the delivery plasmid pHY300-purH::Sp was constructed. A DNA fragment containing the purH gene was amplified by PCR using primers P24 (SEQ ID NO: 40) and P25 (SEQ ID NO: 41), and genomic DNA of *B. amyloliquefaciens* IAM1523 (Zakataeva N. P. et al., 2010) as a template. The obtained DNA fragment (2.7 kbp) was digested using XhoI-EcoRI restrictases and cloned into the XhoI-EcoRI-digested pHY300PLK shuttle vector (Ishiwa H. and Shibahara-Sone H., New shuttle vectors for *Escherichia coli* and *Bacillus subtilis*. IV. The nucleotide sequence of pHY300PLK and some properties in relation to transformation, *Jpn. J. Genet.*, 1986, 61:515-528). Thus, the plasmid pHY300-purH was obtained.

Second, the cassette containing a gene that confers resistance to spectinomycin (Sp) was cut out of the plasmid pDG1726 (Guerout-Fleury A.-M. et al., Antibiotic-resistance cassettes for *Bacillus subtilis*, Gene, 1995, 167:335-336) using restrictases EcoRV and HincII and cloned into the pHY300-purH plasmid digested with the Eco47III restrictase. Thus, the pHY300-purH::Sp plasmid was constructed (FIG. 17).

Finally, the plasmid pHY300-purH::Sp was introduced into the *B. amyloliquefaciens* inosine and guanosine producing strain AJ1991 (Zakataeva N. P. et al., 2007) by E40 bacteriophage transduction using *B. subtilis* 168 strain as an intermediate host (Zakataeva N. P. et al., 2010). Thus, the strain AJ1991 harboring the pHY300-purH::Sp plasmid was constructed. This strain was cultured in LB-broth for 60 generations without antibiotics (Sp). The clones that lost the plasmid and contained the purH::Sp mutation in the chromosome were selected. The inactivation of purH gene due to insertion of $Sp^R$ marker was verified by PCR using primers P24 and P25.

Auxiliary Example 3. Construction of pPK-T7lac-yfp Plasmid

Figure 16:
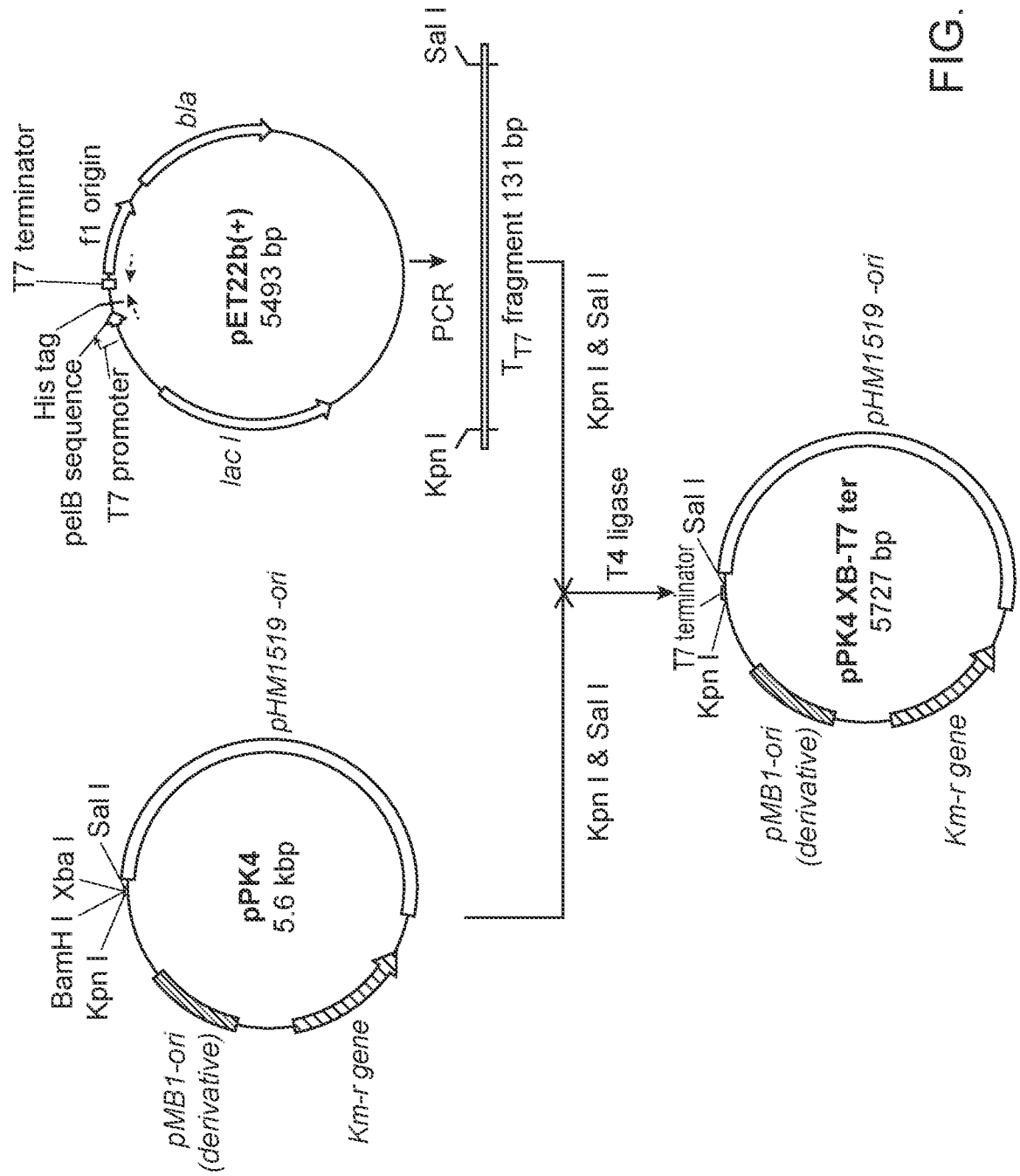
FIG. 16 shows the scheme for construction of the pPK4 XB-T7 ter plasmid.

A DNA fragment (131 bp) containing the terminator T7 ($T_{T7}$) was amplified from pET22b(+) (Novagen) by PCR using the primers P33 (SEQ ID NO: 49) and P34 (SEQ ID NO: 50). Then, the DNA fragment was digested using KpnI and SalI restrictases, cloned into pPK4 vector (U.S. Pat. No. 6,090,597A), and linearized using the same restrictases. The constructed plasmid was named pPK4 XB⁻T7 ter (FIG. 16).

Figure 15:
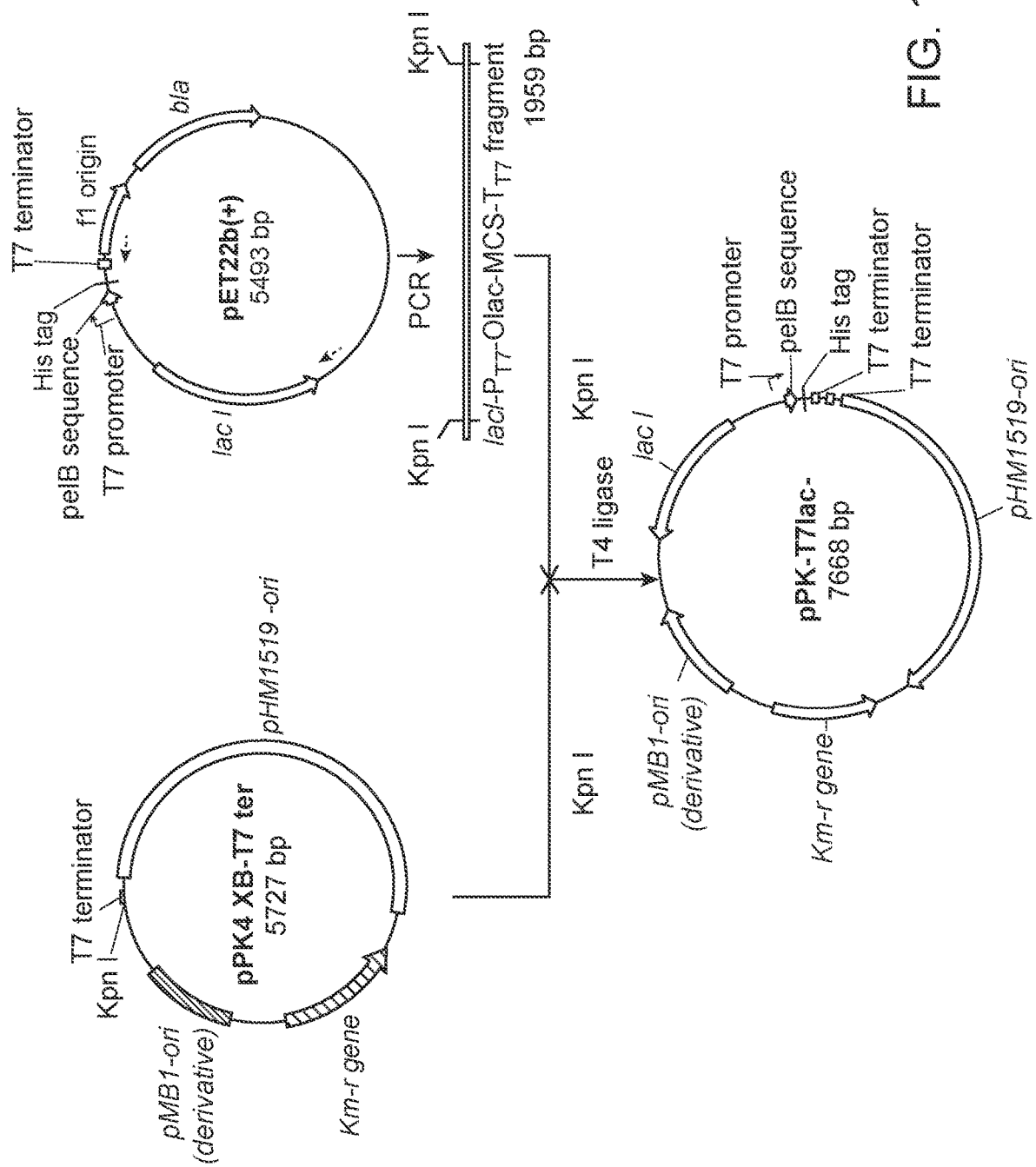
FIG. 15 shows the scheme for construction of the pPK-T7lac plasmid.

Then, a DNA fragment (1959 bp) containing a DNA region of lacI-$P_{T7}$-Olac-MCS-$T_{T7}$ was amplified from pET22b(+) by PCR using the primers P35 (SEQ ID NO: 51) and P36 (SEQ ID NO: 52). The obtained DNA fragment was digested using KpnI and cloned into pPK4 XB-T7 ter linearized by KpnI. The constructed plasmid was named pPK-T7lac (FIG. 15).

Figure 6:
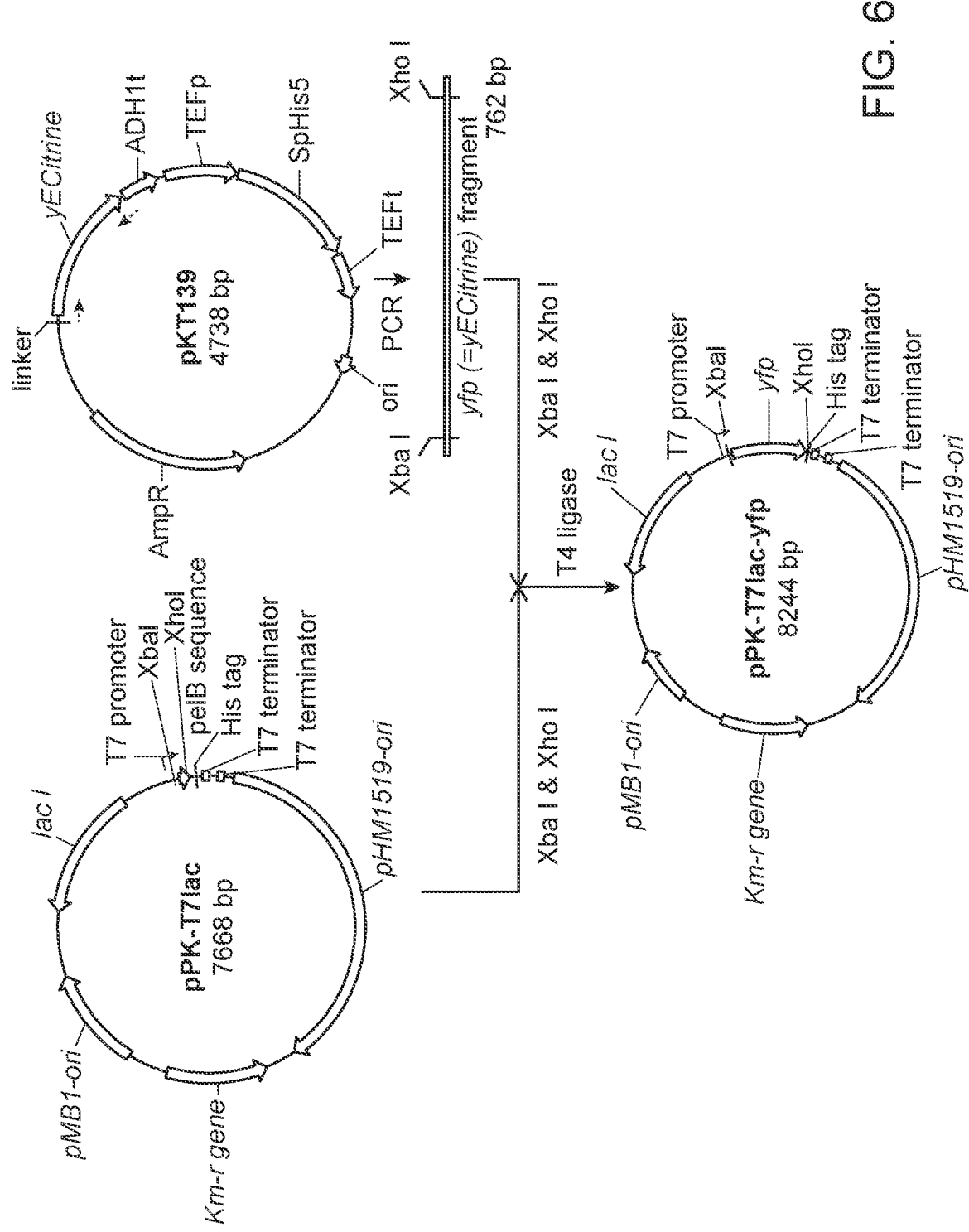
FIG. 6 shows the scheme for construction of the pPK-T7lac-yfp plasmid.

Finally, a DNA fragment (762 bp) containing the yfp gene (also shown as yECitrine in FIG. 6) was amplified by PCR using the primers P37 (SEQ ID NO: 53) and P38 (SEQ ID NO: 54), and the pKT139 plasmid (EUROSCARF P30186) as a template. The obtained DNA fragment was digested using the XbaI and XhoI restrictases and cloned into pPK-T7lac linearized by the same restrictases. The constructed plasmid was named pPK-T7lac-yfp (FIG. 6).

While the invention has been described in detail with reference to exemplary embodiments thereof, it will be apparent to the one of ordinary skill in the art that various changes can be made, and equivalents employed, without departing from the scope of the invention.

The method of the present invention is useful for the production by fermentation of a bacterium of various substances, the biosynthetic pathway of which is ATP-dependent.

The invention claimed is:

1. A method for producing a target substance selected from the group consisting of an amino acid, a nucleoside, a nucleotide, an isoprenoid, and a peptide, comprising:
   (i) cultivating in a culture medium a bacterium which has an ability to produce the target substance, wherein said bacterium is able to produce and accumulate the target substance in the culture medium or cells of the bacterium, or both, and
   (ii) collecting the target substance from the culture medium or the cells, or both,
   wherein the target substance is a substance from an ATP-dependent biosynthetic pathway, and
   wherein the bacterium has been modified to overexpress a gene encoding a protein having $H^+$-translocating membrane-bound pyrophosphatase activity; and
   wherein the gene encoding the protein having $H^+$-translocating membrane-bound pyrophosphatase activity is selected from the group consisting of:
   (A) a DNA comprising the nucleotide sequence set forth in SEQ ID NO: 1,
   (B) a DNA comprising a nucleotide sequence that hybridizes under stringent conditions to a nucleotide sequence complementary to the sequence set forth in SEQ ID NO: 1, and wherein the stringent conditions comprise washing at a salt concentration of 1×SSC, 0.1% SDS at 60° C., 0.1×SSC, 0.1% SDS at 60° C., or 0.1×SSC, 0.1% SDS at 65°,
   (C) a DNA encoding a protein comprising the amino acid sequence set forth in SEQ ID NO: 2,
   (D) a DNA encoding a protein comprising the amino acid sequence set forth in SEQ ID NO: 2, wherein the amino acid sequence comprises substitution, deletion, insertion, and/or addition of 1 to 70 amino acid residues and has $H^+$-translocating membrane-bound pyrophosphatase activity,
   (E) a DNA encoding a protein comprising an amino acid sequence at least 90% identical to the amino acid sequence set forth in SEQ ID NO: 2 and has $H^+$-translocatinq membrane-bound pyrophosphatase activity, and
   (F) a DNA comprising a variant nucleotide sequence set forth in SEQ ID NO: 1 due to the degeneracy of the genetic code.

2. The method of claim 1, wherein the gene encoding the protein having $H^+$-translocating membrane-bound pyrophosphatase activity is overexpressed by increasing the copy number of the gene, by modifying an expression regulatory region of the gene, or by a combination thereof, so that the expression of the gene is enhanced as compared with a non-modified bacterium.

3. The method of claim 1, wherein the amino acid is an L-amino acid selected from the group consisting of L-alanine, L-arginine, L-asparagine, L-aspartic acid, L-citrulline, L-cysteine, L-glutamic acid, glycine, L-glutamine, L-histidine, L-isoleucine, L-leucine, L-lysine, L-methionine, L-ornithine, L-phenylalanine, L-proline, L-serine, L-threonine, L-tryptophan, L-tyrosine, and L-valine.

4. The method of claim 1, wherein the nucleoside is selected from the group consisting of cytidine, thymidine, uridine, 5-aminoimidazole-4-carboxamide ribonucleoside, adenosine, guanosine, xanthosine, and inosine.

5. The method of claim 1, wherein the nucleotide is selected from the group consisting of uridine 5'-monophosphate, 5-aminoimidazole-4-carboxamide ribonucleotide, adenosine 5'-monophosphate, guanosine 5'-monophosphate, xanthosine 5'-monophosphate, and inosine 5'-monophosphate.

6. The method of claim 1, wherein the isoprenoid is selected from the group consisting of an isoprene, a monoterpenoid, a sesquiterpenoid, a diterpenoid, a sesterpenoid, a triterpenoid, a tetraterpenoid, and a polyterpenoid.

7. The method of claim 1, wherein the peptide is an oligopeptide, a polypeptide, or a protein.

8. The method of claim 1, wherein the bacterium is a Gram-positive bacterium or a Gram-negative bacterium.

9. The method of claim 1, wherein the bacterium is selected from the group consisting of a coryneform bacterium, a bacterium belonging to the family Enterobacteriaceae, and a bacterium belonging to the genus *Bacillus*.

10. The method of claim 9, wherein:
the coryneform bacterium is a bacterium belonging to the genus *Corynebacterium* or *Brevibacterium*,
the bacterium belonging to the family Enterobacteriaceae is a bacterium belonging to the genus *Escherichia* or *Pantoea*, and
the bacterium belonging to the genus *Bacillus* is *Bacillus amyloliquefaciens* or *Bacillus subtilis*.

11. The method of claim 8, wherein the coryneform bacterium is *Corynebacterium glutamicum*, and wherein the bacterium belonging to the family Enterobacteriaceae is *Escherichia coli* or *Pantoea ananatis*.

12. The method of claim 1, wherein the bacterium has been further modified to attenuate expression of a second gene encoding a second protein, wherein the second protein has inorganic pyrophosphatase activity.

13. The method of claim 12, wherein the second gene is a ppa gene.

14. The method of claim 12, wherein the second gene is deleted.

* * * * *

SEQUENCE LISTING

<160> NUMBER OF SEQ ID NOS: 58

<210> SEQ ID NO 1
<211> LENGTH: 2109
<212> TYPE: DNA
<213> ORGANISM: Rhodospirillum rubrum

<400> SEQUENCE: 1

```
atggctggca tctatctttt cgtcgtagcc gccgcactcg cggcccttgg ttatggcgct      60
ctcaccatca aaacaatcat ggcggctgat gccggcaccg cgcggatgca ggagatttcc     120
ggcgccgtgc aggaaggcgc cagcgcgttt ctcaatcgtc agtacaagac catcgccgtc     180
```

```
gtcggcgcgg ttgttttcgt tattctgacg gcgcttcttg gcatctcggt cggcttcggc    240
tttctgatcg gcgccgtgtg ctcgggcatc gccggttatg tcggcatgta catctcggtg    300
cgcgccaatg tgcgcgtcgc cgccggggcc cagcagggac tggcccgggg tctggaactc    360
gccttccagt cgggcgcggt gaccggcatg ctggtggccg tctggccct gctgtcggtg     420 gccttctatt acatcctgct cgtcggcatc ggcgcgaccg gccgcgcgct gatcgatccg    480
ctggtggctc tgggctttgg cgcctcgctg atctcgatct tcgcccgtct gggtggcggc    540
atcttcacca agggcgccga cgtgggcgcc gatctggtgg gcaaggtcga agcggggatc    600
cccgaggatg acccgcgcaa tcccgccgtc atcgccgaca cgtgggcga taacgtgggc     660 gattgcgccg gcatggcggc cgacctgttc gagacctatg ccgtgaccgt cgtcgccacc    720
atggtcctgg cctcgatctt cttcgccggc gttccggcga tgacctcgat gatggcctat    780
ccgctggcga tcggcggggt ctgcatcctg gcctcgatcc tcggcaccaa gttcgtgaag    840
cttggcccca agaacaacat catgggggcg ctctatcgcg gcttcctggt gtcggcggga    900
gcgtccttcg tcgggatcat cctggccacg gcgatcgtcc cgggctttgg cgacatccag    960
ggcgccaacg gggtgctcta ttcgggcttc gacctgttct tgtgcgccgt catcggcctg    1020
ctggtcaccg gtttgctgat ctgggtcacc gaatattaca ccggcaccaa tttccggccg    1080
gtccgttcgg tcgccaaggc ctcgaccacc ggccacggca ccaacgtgat ccagggtctg    1140
gcgatttcga tggaggcgac ggccctgccg gcgctgatca tctgcgcggc catcatcacc    1200
acctatcagc tgtcgggtct gtttggcatc gccatcaccg tgaccagcat gctggctttg    1260
gccgggatgg tcgtggcgct cgacgccgat ggtccggtga ccgataacgc cggcggcatc    1320
gccgaaatgg ccaatctgcc cgaggacgtg cgcaagacca ccgatgcgct cgacgccgtt    1380
ggcaacacca ccaaggcggt gaccaagggc tatgctatcg gttcggccgg ccttggcgcc    1440
ctggtgctgt cgccgcccta ccgaggat ctggccttct tcaaggccaa tgtcgacgcc     1500
tatccggcct tcgccggggt ggatgtcaac ttctcgctgt cgagcccta tgtggtggtc     1560 ggcctgttca tcggcggcct gctgccctat ctgttcggct cgatgggcat gaccgccgtc    1620
ggccgcgccg ctggcagcgt cgtcgaggag gttcgccgtc agttccgcga aatcccgggc    1680
atcatggaag gcaccgccaa gccggaatac ggccgctgcg tcgacatgct gaccaaggcg    1740
gcgatcaagg agatgatcat cccctcgctg ctgccggttc tggcgccgat cgtgctgtac    1800
ttcgttatcc tcggcatcgc cgataaatcg gccgccttct cggccctggg cgccatgctg    1860
ctcggcgtga tcgtcaccgg tctttttcgtg gcgatctcga tgaccgccgg tggcggcgcc    1920
tgggacaacg ccaagaagta catcgaagac ggccactacg gtggcaaggg gtcggaagcc    1980
cataaggccg ccgtcaccgg cgacaccgtt ggcgatccgt acaaggacac cgccggtccg    2040
gcggtcaatc cgatgatcaa gatcaccaac atcgtcgccc tgctgctgct ggcggtgctg    2100
gcccactaa                                                            2109

<210> SEQ ID NO 2
<211> LENGTH: 702
<212> TYPE: PRT
<213> ORGANISM: Rhodospirillum rubrum

<400> SEQUENCE: 2

Met Ala Gly Ile Tyr Leu Phe Val Val Ala Ala Ala Leu Ala Ala Leu
1               5                   10                  15

Gly Tyr Gly Ala Leu Thr Ile Lys Thr Ile Met Ala Ala Asp Ala Gly
            20                  25                  30
```

```
Thr Ala Arg Met Gln Glu Ile Ser Gly Ala Val Gln Glu Gly Ala Ser
         35                  40                  45

Ala Phe Leu Asn Arg Gln Tyr Lys Thr Ile Ala Val Val Gly Ala Val
 50                  55                  60

Val Phe Val Ile Leu Thr Ala Leu Leu Gly Ile Ser Val Gly Phe Gly
 65                  70                  75                  80

Phe Leu Ile Gly Ala Val Cys Ser Gly Ile Ala Gly Tyr Val Gly Met
                 85                  90                  95

Tyr Ile Ser Val Arg Ala Asn Val Arg Val Ala Ala Gly Ala Gln Gln
             100                 105                 110

Gly Leu Ala Arg Gly Leu Glu Leu Ala Phe Gln Ser Gly Ala Val Thr
             115                 120                 125

Gly Met Leu Val Ala Gly Leu Ala Leu Leu Ser Val Ala Phe Tyr Tyr
         130                 135                 140

Ile Leu Leu Val Gly Ile Gly Ala Thr Gly Arg Ala Leu Ile Asp Pro
145                 150                 155                 160

Leu Val Ala Leu Gly Phe Gly Ala Ser Leu Ile Ser Ile Phe Ala Arg
                 165                 170                 175

Leu Gly Gly Gly Ile Phe Thr Lys Gly Ala Asp Val Gly Ala Asp Leu
             180                 185                 190

Val Gly Lys Val Glu Ala Gly Ile Pro Glu Asp Asp Pro Arg Asn Pro
             195                 200                 205

Ala Val Ile Ala Asp Asn Val Gly Asp Asn Val Gly Asp Cys Ala Gly
         210                 215                 220

Met Ala Ala Asp Leu Phe Glu Thr Tyr Ala Val Thr Val Val Ala Thr
225                 230                 235                 240

Met Val Leu Ala Ser Ile Phe Phe Ala Gly Val Pro Ala Met Thr Ser
                 245                 250                 255

Met Met Ala Tyr Pro Leu Ala Ile Gly Gly Val Cys Ile Leu Ala Ser
             260                 265                 270

Ile Leu Gly Thr Lys Phe Val Lys Leu Gly Pro Lys Asn Asn Ile Met
             275                 280                 285

Gly Ala Leu Tyr Arg Gly Phe Leu Val Ser Ala Gly Ala Ser Phe Val
         290                 295                 300

Gly Ile Ile Leu Ala Thr Ala Ile Val Pro Gly Phe Gly Asp Ile Gln
305                 310                 315                 320

Gly Ala Asn Gly Val Leu Tyr Ser Gly Phe Asp Leu Phe Leu Cys Ala
             325                 330                 335

Val Ile Gly Leu Leu Val Thr Gly Leu Leu Ile Trp Val Thr Glu Tyr
             340                 345                 350

Tyr Thr Gly Thr Asn Phe Arg Pro Val Arg Ser Val Ala Lys Ala Ser
         355                 360                 365

Thr Thr Gly His Gly Thr Asn Val Ile Gln Gly Leu Ala Ile Ser Met
         370                 375                 380

Glu Ala Thr Ala Leu Pro Ala Leu Ile Cys Ala Ala Ile Ile Thr
385                 390                 395                 400

Thr Tyr Gln Leu Ser Gly Leu Phe Gly Ile Ala Ile Thr Val Thr Ser
                 405                 410                 415

Met Leu Ala Leu Ala Gly Met Val Val Ala Leu Asp Ala Tyr Gly Pro
             420                 425                 430

Val Thr Asp Asn Ala Gly Gly Ile Ala Glu Met Ala Asn Leu Pro Glu
             435                 440                 445
```

Asp Val Arg Lys Thr Thr Asp Ala Leu Asp Ala Val Gly Asn Thr Thr
    450                 455                 460

Lys Ala Val Thr Lys Gly Tyr Ala Ile Gly Ser Ala Gly Leu Gly Ala
465                 470                 475                 480

Leu Val Leu Phe Ala Ala Tyr Thr Glu Asp Leu Ala Phe Phe Lys Ala
            485                 490                 495

Asn Val Asp Ala Tyr Pro Ala Phe Ala Gly Val Asp Val Asn Phe Ser
        500                 505                 510

Leu Ser Ser Pro Tyr Val Val Gly Leu Phe Ile Gly Gly Leu Leu
    515                 520                 525

Pro Tyr Leu Phe Gly Ser Met Gly Met Thr Ala Val Gly Arg Ala Ala
    530                 535                 540

Gly Ser Val Val Glu Glu Val Arg Arg Gln Phe Arg Glu Ile Pro Gly
545                 550                 555                 560

Ile Met Glu Gly Thr Ala Lys Pro Glu Tyr Gly Arg Cys Val Asp Met
                565                 570                 575

Leu Thr Lys Ala Ala Ile Lys Glu Met Ile Pro Ser Leu Leu Pro
            580                 585                 590

Val Leu Ala Pro Ile Val Leu Tyr Phe Val Ile Leu Gly Ile Ala Asp
        595                 600                 605

Lys Ser Ala Ala Phe Ser Ala Leu Gly Ala Met Leu Leu Gly Val Ile
    610                 615                 620

Val Thr Gly Leu Phe Val Ala Ile Ser Met Thr Ala Gly Gly Gly Ala
625                 630                 635                 640

Trp Asp Asn Ala Lys Lys Tyr Ile Glu Asp Gly His Tyr Gly Gly Lys
                645                 650                 655

Gly Ser Glu Ala His Lys Ala Ala Val Thr Gly Asp Thr Val Gly Asp
            660                 665                 670

Pro Tyr Lys Asp Thr Ala Gly Pro Ala Val Asn Pro Met Ile Lys Ile
        675                 680                 685

Thr Asn Ile Val Ala Leu Leu Leu Leu Ala Val Leu Ala His
    690                 695                 700

<210> SEQ ID NO 3
<211> LENGTH: 4848
<212> TYPE: DNA
<213> ORGANISM: Artificial Sequence
<220> FEATURE:
<223> OTHER INFORMATION: Plasmid pUC-57-hppA(Rru)

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180

-continued

| | | | | |
|---|---|---|---|---|
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cgagctcggt | acctcgcgaa | 420 |
| tgcatctaga | tccaaattct | gcagatggct | ggcatctatc | ttttcgtcgt | agccgccgct | 480 |
| ctcgcggccc | ttggttatgg | cgctctcacc | atcaaaacaa | tcatggcggc | tgatgccggc | 540 |
| accgcgcgca | tgcaggagat | tccggcgcc | gtgcaggaag | gcgccagcgc | gtttctcaat | 600 |
| cgtcagtaca | agaccatcgc | cgtcgtcggc | gcggttgttt | tcgttattct | gacggcgctt | 660 |
| cttggcatct | cggtcggctt | cggctttctg | atcggcgccg | tgtgctcggg | catcgccggt | 720 |
| tatgtcggca | tgtacatctc | ggtgcgcgcc | aatgtgcgcg | tcgccgccgg | ggcccagcag | 780 |
| ggactggccc | gcggtctgga | actcgccttc | cagtcgggcg | cggtgaccgg | catgctggtg | 840 |
| gccggtctgg | ccctgctgtc | ggtggccttc | tattacatcc | tgctcgtcgg | catcggcgcg | 900 |
| accgccgcg | cgctgatcga | tccgctggtg | gctctgggct | ttggcgcctc | gctgatctcg | 960 |
| atcttcgccc | gtctgggtgg | cggcatcttc | accaagggcg | ccgacgtggg | cgccgatctg | 1020 |
| gtgggcaagg | tcgaagcggg | gatccccgag | gatgacccgc | gcaatcccgc | cgtcatcgcc | 1080 |
| gacaacgtgg | gcgataacgt | gggcgattgc | gccggcatgg | cggccgacct | gttcgagacc | 1140 |
| tatgccgtga | ccgtcgtcgc | caccatggtc | ctggcctcga | tcttcttcgc | cggcgttccg | 1200 |
| gcgatgacct | cgatgatggc | ctatccgctg | gcgatcggcg | gggtctgcat | cctggcctcg | 1260 |
| atcctcggca | ccaagttcgt | gaagcttggc | cccaagaaca | acatcatggg | ggcgctctat | 1320 |
| cgcggcttcc | tggtgtcggc | gggagcgtcc | ttcgtcggga | tcatcctggc | cacggcgatc | 1380 |
| gtcccgggct | ttggcgacat | ccagggcgcc | aacggggtgc | tctattcggg | cttcgacctg | 1440 |
| ttcttgtgcg | ccgtcatcgg | cctgctgtc | accggtttgc | tgatctgggt | caccgaatat | 1500 |
| tacaccggca | ccaatttccg | cccggtccgt | tcggtcgcca | aggcctcgac | caccggccac | 1560 |
| ggcaccaacg | tgatccaggg | tctggcgatt | tcgatggagg | cgacggccct | gccggcgctg | 1620 |
| atcatctgcg | cggccatcat | caccacctat | cagctgtcgg | gtctgtttgg | catcgccatc | 1680 |
| accgtgacca | gcatgctggc | tttggccggg | atggtcgtgg | cgctcgacgc | ctatggtccg | 1740 |
| gtgaccgata | acgccggcgg | catcgccgaa | atggccaatc | tgcccgagga | cgtgcgcaag | 1800 |
| accaccgatg | cgctcgacgc | cgttggcaac | accaccaagg | cggtgaccaa | gggctatgct | 1860 |
| atcggttcgg | ccggccttgg | cgccctggtg | ctgttcgccg | cctataccga | ggatctggcc | 1920 |
| ttcttcaagg | ccaatgtcga | cgcctatccg | gccttcgccg | gggtggatgt | caacttctcg | 1980 |
| ctgtcgagcc | cctatgtggt | ggtcggcctg | ttcatcggcg | gcctgctgcc | ctatctgttc | 2040 |
| ggctcgatgg | gcatgaccgc | cgtcggccgc | gccgctggca | gcgtcgtcga | ggaggttcgc | 2100 |
| cgtcagttcc | gcgaaatccc | gggcatcatg | gaaggcaccg | ccaagccgga | atacggccgc | 2160 |
| tgcgtcgaca | tgctgaccaa | ggcggcgatc | aaagagatga | tcatcccctc | gctgctgccg | 2220 |
| gttctggcgc | cgatcgtgct | gtacttcgtt | atcctcggca | tcgccgataa | atcggccgcc | 2280 |
| ttctcggccc | tgggcgccat | gctgctcggc | gtgatcgtca | ccggtctttt | cgtggcgatc | 2340 |
| tcgatgaccg | ccggtggcgg | cgcctgggac | aacgccaaga | agtacatcga | agacggccac | 2400 |
| tacggtggca | aggggtcgga | agcccataag | gccgccgtca | ccggcgacac | cgttggcgat | 2460 |
| ccgtacaaag | acaccgccgg | tccggcggtc | aatccgatga | tcaagatcac | caacatcgtc | 2520 |

```
gccctgctgc tgctggcggt gctggcccac taagagctca tcccaaatta tcggatcccg    2580
ggcccgtcga ctgcagaggc ctgcatgcaa gcttggcgta atcatggtca tagctgtttc    2640
ctgtgtgaaa ttgttatccg ctcacaattc cacacaacat acgagccgga agcataaagt    2700
gtaaagcctg gggtgcctaa tgagtgagct aactcacatt aattgcgttg cgctcactgc    2760
ccgctttcca gtcgggaaac ctgtcgtgcc agctgcatta tgaatcggc caacgcgcgg     2820 ggagaggcgg tttgcgtatt gggcgctctt ccgcttcctc gctcactgac tcgctgcgct    2880
cggtcgttcg gctgcggcga gcggtatcag ctcactcaaa ggcggtaata cggttatcca    2940
cagaatcagg ggataacgca ggaaagaaca tgtgagcaaa aggccagcaa aaggccagga    3000
accgtaaaaa ggccgcgttg ctggcgtttt tccataggct ccgcccccct gacgagcatc    3060
acaaaaatcg acgctcaagt cagaggtggc gaaacccgac aggactataa agataccagg    3120
cgtttccccc tggaagctcc ctcgtgcgct ctcctgttcc gaccctgccg cttaccggat    3180
acctgtccgc ctttctccct tcgggaagcg tggcgctttc tcatagctca cgctgtaggt    3240
atctcagttc ggtgtaggtc gttcgctcca agctgggctg tgtgcacgaa ccccccgttc    3300
agcccgaccg ctgcgcctta tccggtaact atcgtcttga gtccaacccg gtaagacacg    3360
acttatcgcc actggcagca gccactggta acaggattag cagagcgagg tatgtaggcg    3420
gtgctacaga gttcttgaag tggtggccta actacggcta cactagaaga acagtatttg    3480
gtatctgcgc tctgctgaag ccagttacct tcggaaaaag agttggtagc tcttgatccg    3540
gcaaacaaac caccgctggt agcggtggtt tttttgtttg caagcagcag attacgcgca    3600
gaaaaaaagg atctcaagaa gatcctttga tcttttctac ggggtctgac gctcagtgga    3660
acgaaaactc acgttaaggg attttggtca tgagattatc aaaaaggatc ttcacctaga    3720
tccttttaaa ttaaaaatga agttttaaat caatctaaag tatatatgag taaacttggt    3780
ctgacagtta ccaatgctta atcagtgagg cacctatctc agcgatctgt ctatttcgtt    3840
catccatagt tgcctgactc cccgtcgtgt agataactac gatacgggag ggcttaccat    3900
ctggccccag tgctgcaatg ataccgcgag acccacgctc accggctcca gatttatcag    3960
caataaacca gccagccgga agggccgagc gcagaagtgg tcctgcaact ttatccgcct    4020
ccatccagtc tattaattgt tgccgggaag ctagagtaag tagttcgcca gttaatagtt    4080
tgcgcaacgt tgttgccatt gctacaggca tcgtggtgtc acgctcgtcg tttggtatgg    4140
cttcattcag ctccggttcc caacgatcaa ggcgagttac atgatccccc atgttgtgca    4200
aaaaagcggt tagctccttc ggtcctccga tcgttgtcag aagtaagttg gccgcagtgt    4260
tatcactcat ggttatggca gcactgcata attctcttac tgtcatgcca tccgtaagat    4320
gcttttctgt gactggtgag tactcaacca agtcattctg agaatagtgt atgcggcgac    4380
cgagttgctc ttgcccggcg tcaatacggg ataataccgc gccacatagc agaactttaa    4440
aagtgctcat cattggaaaa cgttcttcgg ggcgaaaact ctcaaggatc ttaccgctgt    4500
tgagatccag ttcgatgtaa cccactcgtg cacccaactg atcttcagca tcttttactt    4560
tcaccagcgt ttctgggtga gcaaaaacag gaaggcaaaa tgccgcaaaa aagggaataa    4620
gggcgacacg gaaatgttga atactcatac tcttcctttt tcaatattat tgaagcattt    4680
atcagggtta ttgtctcatg agcggataca tatttgaatg tatttagaaa aataaacaaa    4740
taggggttcc gcgcacattt ccccgaaaag tgccacctga cgtctaagaa accattatta    4800
tcatgacatt aacctataaa aataggcgta tcacgaggcc ctttcgtc                 4848
```

```
<210> SEQ ID NO 4
<211> LENGTH: 2138
<212> TYPE: DNA
<213> ORGANISM: Artificial Sequence
<220> FEATURE:
<223> OTHER INFORMATION: Codon-optimized hppA gene

<400> SEQUENCE: 4
ccaaattctg cagatggctg gcatctatct tttcgtcgta gccgccgctc tcgcggccct      60
tggttatggc gctctcacca tcaaaacaat catggcggct gatgccggca ccgcgcgcat     120
gcaggagatt tccggcgccg tgcaggaagg cgccagcgcg tttctcaatc gtcagtacaa     180
gaccatcgcc gtcgtcggcg cggttgtttt cgttattctg acggcgcttc ttggcatctc     240
ggtcggcttc ggctttctga tcggcgccgt gtgctcgggc atcgccggtt atgtcggcat     300
gtacatctcg gtgcgcgcca atgtgcgcgt cgccgccggg gcccagcagg gactggcccg     360
cggtctggaa ctcgccttcc agtcgggcgc ggtgaccggc atgctggtgg ccggtctggc     420
cctgctgtcg gtggccttct attacatcct gctcgtcggc atcggcgcga ccggccgcgc     480
gctgatcgat ccgctggtgg ctctgggctt tggcgcctcg ctgatctcga tcttcgcccg     540
tctgggtggc ggcatcttca ccaagggcgc cgacgtgggc gccgatctgg tgggcaaggt     600
cgaagcgggg atccccgagg atgacccgcg caatcccgcc gtcatcgccg acaacgtggg     660
cgataacgtg ggcgattgcg ccggcatggc ggccgacctg ttcgagacct atgccgtgac     720
cgtcgtcgcc accatggtcc tggcctcgat cttcttcgcc ggcgttccgg cgatgacctc     780
gatgatggcc tatccgctgg cgatcggcgg ggtctgcatc ctggcctcga tcctcggcac     840
caagttcgtg aagcttggcc ccaagaacaa catcatgggg gcgctctatc gcggcttcct     900
ggtgtcggcg ggagcgtcct tcgtcgggat catcctggcc acggcgatcg tcccgggctt     960 tgcgacatc cagggcgcca acggggtgct ctattcgggc ttcgacctgt tcttgtgcgc    1020
cgtcatcggc ctgctggtca ccggtttgct gatctgggtc accgaatatt acaccggcac    1080
caatttccgc ccggtccgtt cggtcgccaa ggcctcgacc accggccacg gcaccaacgt    1140
gatccagggt ctggcgattt cgatggaggc gacggccctg ccggcgctga tcatctgcgc    1200
ggccatcatc accacctatc agctgtcggg tctgttggc atcgccatca ccgtgaccag    1260
catgctggct ttggccggga tggtcgtggc gctcgacgcc tatggtccgg tgaccgataa    1320
cgccggcggc atcgccgaaa tggccaatct gcccgaggac gtgcgcaaga ccaccgatgc    1380
gctcgacgcc gttggcaaca ccaccaaggc ggtgaccaag ggctatgcta tcggttcggc    1440
cggccttggc gccctggtgc tgttcgccgc ctataccgag atctggcct tcttcaaggc    1500 caatgtcgac gcctatccgg ccttcgccgg ggtggatgtc aacttctcgc tgtcgagccc    1560
ctatgtggtg gtcggcctgt tcatcggcgg cctgctgccc tatctgttcg gctcgatggg    1620
catgaccgcc gtcggccgcg ccgctggcag cgtcgtcgag gaggttcgcc gtcagttccg    1680
cgaaatcccg ggcatcatgg aaggcaccgc caagccggaa tacggccgct gcgtcgacat    1740
gctgaccaag gcggcgatca agagatgat catcccctcg ctgctgccgg ttctggcgcc    1800
gatcgtgctg tacttcgtta tcctcggcat cgccgataaa tcggccgcct tctcggccct    1860
gggcgccatg ctgctcggcg tgatcgtcac cggtctttc gtggcgatct cgatgaccgc    1920
cggtggcggc gcctgggaca acgccaagaa gtacatcgaa gacggccact acggtggcaa    1980
ggggtcggaa gcccataagg ccgccgtcac cggcgacacc gttggcgatc cgtacaaaga    2040
```

```
caccgccggt ccggcggtca atccgatgat caagatcacc aacatcgtcg ccctgctgct    2100
gctggcggtg ctggcccact aagagctcat cccaaatt                            2138

<210> SEQ ID NO 5
<211> LENGTH: 18
<212> TYPE: DNA
<213> ORGANISM: Artificial Sequence
<220> FEATURE:
<223> OTHER INFORMATION: Primer P1

<400> SEQUENCE: 5
tgtaaaacga cggccagt                                                  18

<210> SEQ ID NO 6
<211> LENGTH: 19
<212> TYPE: DNA
<213> ORGANISM: Artificial Sequence
<220> FEATURE:
<223> OTHER INFORMATION: Primer P2

<400> SEQUENCE: 6
aggaaacagc tatgaccat                                                 19

<210> SEQ ID NO 7
<211> LENGTH: 2265
<212> TYPE: DNA
<213> ORGANISM: Artificial Sequence
<220> FEATURE:
<223> OTHER INFORMATION: PCR product 1

<400> SEQUENCE: 7
tgtaaaacga cggccagtga attcgagctc ggtacctcgc gaatgcatct agatccaaat     60
tctgcagatg gctggcatct atcttttcgt cgtagccgcc gctctcgcgg cccttggtta    120
tggcgctctc accatcaaaa caatcatggc ggctgatgcc ggcaccgcgc gcatgcagga    180
gatttccggc gccgtgcagg aaggcgccag cgcgtttctc aatcgtcagt acaagaccat    240
cgccgtcgtc ggcgcggttg ttttcgttat tctgacggcg cttcttggca tctcggtcgg    300
cttcggcttt ctgatcggcg ccgtgtgctc gggcatcgcc ggttatgtcg gcatgtacat    360
ctcggtgcgc gccaatgtgc gcgtcgccgc cggggcccag cagggactgg cccgcggtct    420
ggaactcgcc ttccagtcgg gcgcggtgac cggcatgctg gtggccggtc tggccctgct    480
gtcggtggcc ttctattaca tcctgctcgt cggcatcggc gcgaccggcc gcgcgctgat    540
cgatccgctg gtggctctgg gctttggcgc ctcgctgatc tcgatcttcg cccgtctggg    600
tggcggcatc ttcaccaagg gcgccgacgt gggcgccgat ctggtgggca aggtcgaagc    660
ggggatcccc gaggatgacc cgcgcaatcc cgccgtcatc gccgacaacg tgggcgataa    720
cgtgggcgat tgcgccggca tggcggccga cctgttcgag acctatgccg tgaccgtcgt    780
cgccaccatg gtcctggcct cgatcttctt cgccggcgtt ccggcgatga cctcgatgat    840
ggcctatccg ctggcgatcg gcgggtctg catcctggcc tcgatcctcg gcaccaagtt    900
cgtgaagctt ggccccaaga caacatcat ggggcgctc tatcgcggct tcctggtgtc    960
ggcgggagcg tccttcgtcg ggatcatcct ggccacggcg atcgtcccgg gctttggcga   1020
catccagggc gccaacgggg tgctctattc gggcttcgac ctgttcttgt gcgccgtcat   1080
cggcctgctg gtcaccggtt tgctgatctg ggtcaccgaa tattcaccg gcaccaattt   1140 ccgcccggtc cgttcggtcg ccaaggcctc gaccaccggc cacggcacca acgtgatcca   1200
gggtctggcg atttcgatgg aggcgacggc cctgccggcg ctgatcatct gcgcggccat   1260
```

| | |
|---|---|
| catcaccacc tatcagctgt cgggtctgtt tggcatcgcc atcaccgtga ccagcatgct | 1320 |
| ggctttggcc gggatggtcg tggcgctcga cgcctatggt ccggtgaccg ataacgccgg | 1380 |
| cggcatcgcc gaaatggcca atctgcccga ggacgtgcgc aagaccaccg atgcgctcga | 1440 |
| cgccgttggc aacaccacca aggcggtgac caagggctat gctatcggtt cggccggcct | 1500 |
| tggcgccctg gtgctgttcg ccgcctatac cgaggatctg gccttcttca aggccaatgt | 1560 |
| cgacgcctat ccggccttcg ccggggtgga tgtcaacttc tcgctgtcga gccctatgt | 1620 |
| ggtggtcggc ctgttcatcg gcggcctgct gccctatctg ttcggctcga tgggcatgac | 1680 |
| cgccgtcggc cgcgccgctg gcagcgtcgt cgaggaggtt cgccgtcagt ccgcgaaat | 1740 |
| cccgggcatc atggaaggca ccgccaagcc ggaatacggc cgctgcgtcg acatgctgac | 1800 |
| caaggcggcg atcaaagaga tgatcatccc ctcgctgctg ccggttctgg cgccgatcgt | 1860 |
| gctgtacttc gttatcctcg gcatcgccga taaatcggcc gccttctcgg ccctgggcgc | 1920 |
| catgctgctc ggcgtgatcg tcaccggtct tttcgtggcg atctcgatga ccgccggtgg | 1980 |
| cggcgcctgg gacaacgcca agaagtacat cgaagacggc cactacgtg gcaagggtc | 2040 |
| ggaagcccat aaggccgccg tcaccggcga caccgttggc gatccgtaca agacaccgc | 2100 |
| cggtccggcg gtcaatccga tgatcaagat caccaacatc gtcgccctgc tgctgctggc | 2160 |
| ggtgctggcc cactaagagc tcatcccaaa ttatcggatc ccgggcccgt cgactgcaga | 2220 |
| ggcctgcatg caagcttggc gtaatcatgg tcatagctgt ttcct | 2265 |

<210> SEQ ID NO 8
<211> LENGTH: 4463
<212> TYPE: DNA
<213> ORGANISM: Artificial Sequence
<220> FEATURE:
<223> OTHER INFORMATION: Integrative vector pAH162-TetATetR-2Ter

<400> SEQUENCE: 8

| | |
|---|---|
| gacgtcctaa ttcccatgtc agccgttaag tgttcctgtg tcactgaaaa ttgctttgag | 60 |
| aggctctaag ggcttctcag tgcgttacat ccctggcttg ttgtccacaa ccgttaaacc | 120 |
| ttaaaagctt taaaagcctt atatattctt ttttttctta taaaacttaa aaccttagag | 180 |
| gctatttaag ttgctgattt atattaattt tattgttcaa acatgagagc ttagtacgtg | 240 |
| aaacatgaga gcttagtacg ttagccatga gagcttagta cgttagccat gagggtttag | 300 |
| ttcgttaaac atgagagctt agtacgttaa acatgagagc ttagtacgtg aaacatgaga | 360 |
| gcttagtacg tactatcaac aggttgaact gctgatcttc agatcctcta cgccggacgc | 420 |
| atcgtggccg atcttgcgg ccgcaaaaat taaaaatgaa gttttggagg cctcatttgg | 480 |
| tgacgaaata actaagcact tgtctcctgt ttactcccct gagcttgagg ggtcaacatg | 540 |
| aaggtcattg atagcaggat aataatacag taaaacgcta aaccaataat ccaaatccag | 600 |
| ccatcccaaa ttggtagtga atgattataa ataacagtaa acagtaatgg gccaataaca | 660 |
| ccggttgcat tggtaaggct caccaataat ccctgtaaag caccttgctc atgactcttt | 720 |
| gtttggatag acatcactcc ctgtaatgca ggtaaagcga tcccaccacc agccaataaa | 780 |
| attaaaacag ggaaatctaa ccaaccttca gatataaacg ctaaaaggc aaatgcacta | 840 |
| ctatctgcaa taaattcgag cagtactgcc gttttttcgc cccatttagt ggctattctt | 900 |
| cctgccacaa aggcttggaa tactgagtgt aaaagaccaa gacccgctaa tgaaaagcca | 960 |
| accatcatgc tattccatcc aaaacgattt tcggtaaata gcacccacac cgttgcggga | 1020 |
| atttggccta tcaattcgaa atcaaataat gattttattt tgactgatag tgacctgttc | 1080 |

-continued

```
gttgcaacaa attgataagc aatgcttttt tataatgcca acttagtata aaaaagcagg    1140
cttcagagcg atggcccccg atggtagtgt ggggtctccc catgcgagag tagggaactg    1200
ccaggcatca aataaaacga aaggctcagt cgaaagactg ggcctttcgt tttatctgtt    1260
gtttgtcggt gaacgctctc ctgagtagga caaatccgcc gggagcggat ttgaacgttg    1320
cgaagcaacg gcccggaggg tggcgggcag gacgcccgcc ataaactgcc aggcatcaaa    1380
ttaagcagaa ggccatcctg acggatggcc ttttgcgtg gccagtgcca gcttgcatg    1440 cctgcaggtc gactctagag gatccccggg taccgagctc gaattctcat gtttgacagc    1500
ttatcactga tcagtgaatt aatggcgatg acgcatcctc acgataatat ccgggtaggc    1560
gcaatcactt tcgtctctac tccgttacaa agcgaggctg ggtatttccc ggcctttctg    1620
ttatccgaaa tccactgaaa gcacagcggc tggctgagga gataaataat aaacgagggg    1680
ctgtatgcac aaagcatctt ctgttgagtt aagaacgagt atcgagatgg cacatagcct    1740
tgctcaaatt ggaatcaggt ttgtgccaat accagtagaa acagacgaag aagctagagg    1800
tgaatcacga caaagcgtat caaaaacgta tggagtaggg ctctaaactc tgtataaaaa    1860
gtttccagct agctgataac gggaaagaaa cagagaaggg cacaaatatt gtgtacttta    1920
atgtgccctt taatttattg attggtggtt gaattgtccg taacttttg atttaagtgc    1980 aaatttctaa taattagaa cactttctta aattgtcatt tggcatatta cgaacaattc    2040
cgcgtaaaaa cgttctgtta cgctaaaccc ttatccagca ggctttcaag gatgtaaacc    2100
ataacactct gcgaactagt gttacattgc gtgtagcttt gagtgggcaa ctttgtgtac    2160
acttttgtgt acccaaaaac aaaaatgtgt acccattcaa tgatcaccga cacaaagctc    2220
aggaaggcgc tcggcaagaa aagagatgat atcgagatta tttctgattc gcacgagctt    2280
tctagacgct caagttagta taaaaaagct gaacgagaaa cgtaaaatga tataaatatc    2340
aatatattaa attagatttt gcataaaaaa cagactacat aatactgtaa aacacaacat    2400
atgcagtcac tatgaatcaa ctacttagat ggtattagtg acctgtaaca gactgcgggc    2460
ccaggttatg ctgcttttaa gacccacttt cacatttaag ttgttttct aatccgcata    2520 tgatcaattc aaggccgaat aagaaggctg gctctgcacc ttggtgatca ataattcga    2580 tagcttgtcg taataatggc ggcatactat cagtagtagg tgtttccctt tcttctttag    2640
cgacttgatg ctcttgatct tccaatacgc aacctaaagt aaaatgcccc acagcgctga    2700
gtgcatataa tgcattctct agtgaaaaac cttgttggca taaaaaggct aattgatttt    2760
cgagagtttc atactgtttt tctgtaggcc gtgtacctaa atgtactttt gctccatcgc    2820
gatgacttag taaagcacat ctaaaacttt tagcgttatt acgtaaaaaa tcttgccagc    2880
tttccccttc taaagggcaa aagtgagtat ggtgcctatc taacatctca atggctaagg    2940
cgtcgagcaa agcccgctta tttttttacat gccaatacaa tgtaggctgc tctacaccta    3000
gcttctgggc gagtttacgg gttgttaaac cttcgattcc gacctcatta agcagctcta    3060
atgcgctgtt aatcacttta ctttatcta atctagacat cattaattcc taattttgt    3120 tgacactcta tcattgatag agttattta ccactcccta tcagtgatag agaaaagtga    3180
aatgaatagt tcgacaaaga tcgcattggt aattacgtta ctcgatgcca tggggattgg    3240
ccttatcatg ccagtcttgc caacgttatt acgtgaattt attgcttcgg aagatatcgc    3300
taaccacttt ggcgtattgc ttgcactta tgcgttaatg caggttatct ttgctccttg    3360
gcttggaaaa atgtctgacc gatttggtcg gcgcccagtg ctgttgttgt cattaatagg    3420
cgcatcgctg gattacttat tgctggcttt ttcaagtgcg cttttggatgc tgtatttagg    3480
```

```
ccgtttgctt tcagggatca caggagctac tggggctgtc gcggcatcgg tcattgccga    3540
taccacctca gcttctcaac gcgtgaagtg gttcggttgg ttaggggcaa gttttgggct    3600
tggtttaata gcgggcccta ttattggtgg ttttgcagga gagatttcac cgcatagtcc    3660
cttttttatc gctgcgttgc taaatattgt cactttcctt gtggttatgt tttggttccg    3720
tgaaaccaaa aatacacgtg ataatacaga taccgaagta ggggttgaga cgcaatcgaa    3780
ttcggtatac atcactttat ttaaaacgat gcccattttg ttgattattt attttttcagc   3840 gcaattgata ggccaaattc ccgcaacggt gtgggtgcta tttaccgaaa atcgttttgg    3900
atggaatagc atgatggttg gcttttcatt agcgggtctt ggtctttttac actcagtatt   3960 ccaagccttt gtggcaggaa gaatagccac taaatggggc gaaaaaacgg cagtactgct    4020
cgaatttatt gcagatagta gtgcatttgc cttttttagcg tttatatctg aaggttggtt   4080
agatttccct gttttaattt tattggctgg tggtgggatc gctttacctg cattacaggg    4140
agtgatgtct atccaaacaa agagtcatga gcaaggtgct ttacagggat tattggtgag    4200
ccttaccaat gcaaccggtg ttattggccc attactgttt actgttattt ataatcattc    4260
actaccaatt tgggatggct ggatttggat tattggttta gcgtttttact gtattattat   4320 cctgctatcg atgaccttca tgttaacccc tcaagctcag gggagtaaac aggagacaag    4380
tgcttagtta tttcgtcacc aaatgatgtt attccgcgaa atataatgac cctcttgata    4440
acccaagagg gcatttttta cga                                           4463

<210> SEQ ID NO 9
<211> LENGTH: 6545
<212> TYPE: DNA
<213> ORGANISM: Artificial Sequence
<220> FEATURE:
<223> OTHER INFORMATION: Plasmid pAH162-TetATetR-2Ter-hppA(Rru)

<400> SEQUENCE: 9
gacgtcctaa ttcccatgtc agccgttaag tgttcctgtg tcactgaaaa ttgctttgag      60
aggctctaag ggcttctcag tgcgttacat ccctggcttg ttgtccacaa ccgttaaacc     120
ttaaaagctt taaaagcctt atatattctt tttttttctta taaaacttaa aaccttagag    180
gctatttaag ttgctgattt atattaattt tattgttcaa acatgagagc ttagtacgtg    240
aaacatgaga gcttagtacg ttagccatga gagcttagta cgttagccat gagggtttag    300
ttcgttaaac atgagagctt agtacgttaa acatgagagc ttagtacgtg aaacatgaga    360
gcttagtacg tactatcaac aggttgaact gctgatcttc agatcctcta cgccggacgc    420
atcgtggccg gatcttgcgg ccgcaaaaat taaaaatgaa gttttggagg cctcatttgg    480
tgacgaaata actaagcact tgtctcctgt ttactcccct gagcttgagg ggtcaacatg    540
aaggtcattg atagcaggat aataatacag taaaacgcta accaataat ccaaatccag     600 ccatcccaaa ttggtagtga atgattataa ataacagtaa acagtaatgg gccaataaca    660
ccggttgcat tggtaaggct caccaataat ccctgtaaag caccttgctc atgactcttt    720
gtttggatag acatcactcc ctgtaatgca ggtaaagcga tcccaccacc agccaataaa    780
attaaaacag ggaaatctaa ccaaccttca gatataaacg ctaaaaggc aaatgcacta     840 ctatctgcaa taaattcgag cagtactgcc gttttttcgc cccatttagt ggctattctt    900
cctgccacaa aggcttggaa tactgagtgt aaaagaccaa gacccgctaa tgaaaagcca    960
accatcatgc tattccatcc aaaacgattt tcggtaaata gcacccacac cgttgcggga   1020
atttggccta tcaattcgaa atcaaataat gatttttattt tgactgatag tgacctgttc   1080
```

```
gttgcaacaa attgataagc aatgcttttt tataatgcca acttagtata aaaaagcagg    1140
cttcagagcg atggcccccg atggtagtgt ggggtctccc catgcgagag tagggaactg    1200
ccaggcatca aataaaacga aaggctcagt cgaaagactg ggcctttcgt tttatctgtt    1260
gtttgtcggt gaacgctctc ctgagtagga caaatccgcc gggagcggat ttgaacgttg    1320
cgaagcaacg gcccggaggg tggcgggcag gacgcccgcc ataaactgcc aggcatcaaa    1380
ttaagcagaa ggccatcctg acggatggcc ttttttgcgtg ccagtgcca agcttgcatg    1440 cctgcagatg gctggcatct atcttttcgt cgtagccgcc gctctcgcgg cccttggtta    1500
tggcgctctc accatcaaaa caatcatggc ggctgatgcc ggcaccgcgc gcatgcagga    1560
gatttccggc gccgtgcagg aaggcgccag cgcgtttctc aatcgtcagt acaagaccat    1620
cgccgtcgtc ggcgcggttg ttttcgttat tctgacggcg cttcttggca tctcggtcgg    1680
cttcggcttt ctgatcggcg ccgtgtgctc gggcatcgcc ggttatgtcg gcatgtacat    1740
ctcggtgcgc gccaatgtgc gcgtcgccgc cggggcccag cagggactgg cccgcggtct    1800
ggaactcgcc ttccagtcgg gcgcggtgac cggcatgctg gtggccggtc tggccctgct    1860
gtcggtggcc ttctattaca tcctgctcgt cggcatcggc gcgaccggcc gcgcgctgat    1920
cgatccgctg gtgctctctgg gctttggcgc ctcgctgatc tcgatcttcg cccgtctggg    1980
tggcggcatc ttccaccaagg cgccgacgt gggcgccgat ctggtgggca aggtcgaagc    2040
ggggatcccc gaggatgacc cgcgcaatcc cgccgtcatc gccgacaacg tgggcgataa    2100
cgtgggcgat tgcgccggca tggcggccga cctgttcgag acctatgccg tgaccgtcgt    2160
cgccaccatg gtcctggcct cgatcttctt cgccggcgtt ccggcgatga cctcgatgat    2220
ggcctatccg ctggcgatcg gcggggtctg catcctggcc tcgatcctcg gcaccaagtt    2280
cgtgaagctt ggccccaaga acaacatcat gggggcgctc tatcgcggct tcctggtgtc    2340
ggcgggagcg tccttcgtcg ggatcatcct ggccacggcg atcgtcccgg gctttggcga    2400
catccagggc gccaacgggg tgctctattc gggcttcgac ctgttcttgt gcgccgtcat    2460
cggcctgctg gtcaccggtt tgctgatctg ggtcaccgaa tattacaccg gcaccaattt    2520
ccgcccggtc cgttcggtcg ccaaggcctc gaccaccggc cacggcacca acgtgatcca    2580
gggtctggcg atttcgatgg aggcgacggc cctgccggcg ctgatcatct gcgcggccat    2640
catcaccacc tatcagctgt cgggtctgtt tggcatcgcc atcaccgtga ccagcatgct    2700
ggctttggcc gggatggtcg tggcgctcga cgcctatggt ccggtgaccg ataacgccgg    2760
cggcatcgcc gaaatggcca atctgcccga ggacgtgcgc aagaccaccg atgcgctcga    2820
cgccgttggc aacaccacca aggcggtgac caagggctat gctatcggtt cggccggcct    2880
tggcgccctg gtgctgttcg ccgcctatac cgaggatctg gccttcttca aggccaatgt    2940
cgacgcctat ccggccttcg ccggggtgga tgtcaacttc tcgctgtcga gccctatgt    3000 ggtggtcggc ctgttcatcg gcggcctgct gccctatctg ttcggctcga tgggcatgac    3060
cgccgtcggc cgcgccgctg gcagcgtcgt cgaggaggtt cgccgtcagt ccgcgaaat    3120 cccgggcatc atggaaggca ccgccaagcc ggaatacggc cgctgcgtcg acatgctgac    3180
caaggcggca atcaaagaga tgatcatccc ctcgctgctg ccggttctgg cgccgatcgt    3240
gctgtacttc gttatcctcg gcatcgccga taaatcggcc gccttctcgg ccctgggcgc    3300
catgctgctc ggcgtgatcg tcaccggtct tttcgtggcg atctcgatga ccgccggtgg    3360
cggcgcctgg gacaacgcca agaagtacat cgaagacgc cactacggtg gcaagggtc    3420 ggaagcccat aaggccgccg tcaccggcga caccgttggc gatccgtaca aagacaccgc    3480
```

```
cggtccggcg gtcaatccga tgatcaagat caccaacatc gtcgccctgc tgctgctggc    3540
ggtgctggcc cactaagagc tcgaattctc atgtttgaca gcttatcact gatcagtgaa    3600
ttaatggcga tgacgcatcc tcacgataat atccgggtag gcgcaatcac tttcgtctct    3660
actccgttac aaagcgaggc tgggtatttc ccggcctttc tgttatccga aatccactga    3720
aagcacagcg gctggctgag gagataaata ataaacgagg ggctgtatgc acaaagcatc    3780
ttctgttgag ttaagaacga gtatcgagat ggcacatagc cttgctcaaa ttggaatcag    3840
gtttgtgcca ataccagtag aaacagacga agaagctaga ggtgaatcac gacaaagcgt    3900
atcaaaaacg tatggagtag ggctctaaac tctgtataaa aagtttccag ctagctgata    3960
acgggaaaga aacagagaag ggcacaaata ttgtgtactt taatgtgccc tttaatttat    4020
tgattggtgg ttgaattgtc cgtaactttt tgatttaagt gcaaatttct aataaattag    4080
aacactttct taaattgtca tttggcatat tacgaacaat tccgcgtaaa aacgttctgt    4140
tacgctaaac ccttatccag caggctttca aggatgtaaa ccataacact ctgcgaacta    4200
gtgttacatt gcgtgtagct ttgagtgggc aactttgtgt acacttttgt gtacccaaaa    4260
acaaaaatgt gtacccattc aatgatcacc gacacaaagc tcaggaaggc gctcggcaag    4320
aaaagagatg atatcgagat tatttctgat tcgcacgagc tttctagacg ctcaagttag    4380
tataaaaaag ctgaacgaga aacgtaaaat gatataaata tcaatatatt aaattagatt    4440
ttgcataaaa aacagactac ataatactgt aaaacacaac atatgcagtc actatgaatc    4500
aactacttag atggtattag tgacctgtaa cagactgcgg gcccaggtta tgctgctttt    4560
aagacccact ttcacattta agttgttttt ctaatccgca tatgatcaat tcaaggccga    4620
ataagaaggc tggctctgca ccttggtgat caaataattc gatagcttgt cgtaataatg    4680
gcggcatact atcagtagta ggtgtttccc tttcttcttt agcgacttga tgctcttgat    4740
cttccaatac gcaacctaaa gtaaaatgcc ccacagcgct gagtgcatat aatgcattct    4800
ctagtgaaaa accttgttgg cataaaaagg ctaattgatt ttcgagagtt tcatactgtt    4860
tttctgtagg ccgtgtacct aaatgtactt ttgctccatc gcgatgactt agtaaagcac    4920
atctaaaact tttagcgtta ttacgtaaaa aatcttgcca gctttcccct tctaaagggc    4980
aaaagtgagt atggtgccta tctaacatct caatggctaa ggcgtcgagc aaagcccgct    5040
tattttttac atgccaatac aatgtaggct gctctacacc tagcttctgg gcgagtttac    5100
gggttgttaa accttcgatt ccgacctcat taagcagctc taatgcgctg ttaatcactt    5160 tactttatc taatctagac atcattaatt cctaattttt gttgacactc tatcattgat    5220
agagttattt taccactccc tatcagtgat agagaaaagt gaaatgaata gttcgacaaa    5280
gatcgcattg gtaattacgt tactcgatgc catgggggatt ggccttatca tgccagtctt    5340
gccaacgtta ttacgtgaat ttattgcttc ggaagatatc gctaaccact ttggcgtatt    5400
gcttgcactt tatgcgttaa tgcaggttat ctttgctcct tggcttggaa aaatgtctga    5460
ccgatttggt cggcgcccag tgctgttgtt gtcattaata ggcgcatcgc tggattactt    5520
attgctggct ttttcaagtg cgctttggat gctgtattta ggccgtttgc tttcagggat    5580
cacaggagct actgggctgt cgcggcatc ggtcattgcc gataccacct cagcttctca    5640
acgcgtgaag tggttcggtt ggttaggggc aagttttggg cttggtttaa tagcggggcc    5700
tattattggt ggttttgcag gagagattc accgcatagt ccctttttta tcgctgcgtt    5760
gctaaatatt gtcactttcc ttgtggttat gttttggttc cgtgaaacca aaaatacacg    5820
tgataataca gataccgaag tagggggttga gacgcaatcg aattcggtat acatcacttt    5880
```

```
atttaaaacg atgcccattt tgttgattat ttattttca gcgcaattga taggccaaat    5940
tcccgcaacg gtgtgggtgc tatttaccga aaatcgtttt ggatggaata gcatgatggt    6000
tggcttttca ttagcgggtc ttggtctttt acactcagta ttccaagcct ttgtggcagg    6060
aagaatagcc actaaatggg gcgaaaaaac ggcagtactg ctcgaattta ttgcagatag    6120
tagtgcattt gccttttag cgtttatatc tgaaggttgg ttagatttcc ctgttttaat    6180
tttattggct ggtggtggga tcgctttacc tgcattacag ggagtgatgt ctatccaaac    6240
aaagagtcat gagcaaggtg ctttacaggg attattggtg agccttacca atgcaaccgg    6300
tgttattggc ccattactgt ttactgttat ttataatcat tcactaccaa tttgggatgg    6360
ctggatttgg attattggtt tagcgtttta ctgtattatt atcctgctat cgatgacctt    6420
catgttaacc cctcaagctc aggggagtaa acaggagaca agtgcttagt tatttcgtca    6480
ccaaatgatg ttattccgcg aaatataatg accctcttga taacccaaga gggcattttt    6540
tacga                                                                6545
```

<210> SEQ ID NO 10
<211> LENGTH: 20
<212> TYPE: DNA
<213> ORGANISM: Artificial Sequence
<220> FEATURE:
<223> OTHER INFORMATION: Primer P3

<400> SEQUENCE: 10
ctgagtagga caaatccgcc                                                 20

<210> SEQ ID NO 11
<211> LENGTH: 19
<212> TYPE: DNA
<213> ORGANISM: Artificial Sequence
<220> FEATURE:
<223> OTHER INFORMATION: Primer P4

<400> SEQUENCE: 11
atcgaggtca tcgccggaa                                                  19

<210> SEQ ID NO 12
<211> LENGTH: 20
<212> TYPE: DNA
<213> ORGANISM: Artificial Sequence
<220> FEATURE:
<223> OTHER INFORMATION: Primer P5

<400> SEQUENCE: 12
acctgttcga gacctatgcc                                                 20

<210> SEQ ID NO 13
<211> LENGTH: 22
<212> TYPE: DNA
<213> ORGANISM: Artificial Sequence
<220> FEATURE:
<223> OTHER INFORMATION: Primer P6

<400> SEQUENCE: 13
agtagagacg aaagtgattg cg                                              22

<210> SEQ ID NO 14
<211> LENGTH: 937
<212> TYPE: DNA
<213> ORGANISM: Artificial Sequence
<220> FEATURE:
<223> OTHER INFORMATION: PCR product 2

<400> SEQUENCE: 14

```
ctgagtagga caaatccgcc gggagcggat ttgaacgttg cgaagcaacg gcccggaggg      60
tggcgggcag gacgcccgcc ataaactgcc aggcatcaaa ttaagcagaa ggccatcctg     120
acggatggcc tttttgcgtg gccagtgcca agcttgcatg cctgcagatg gctggcatct    180
atcttttcgt cgtagccgcc gctctcgcgg cccttggtta tggcgctctc accatcaaaa    240
caatcatggc ggctgatgcc ggcaccgcgc gcatgcagga gatttccggc gccgtgcagg    300
aaggcgccag cgcgtttctc aatcgtcagt acaagaccat cgccgtcgtc ggcgcggttg    360
ttttcgttat tctgacggcg cttcttggca tctcggtcgg cttcggcttt ctgatcggcg    420
ccgtgtgctc gggcatcgcc ggttatgtcg gcatgtacat ctcggtgcgc gccaatgtgc    480
gcgtcgccgc cggggcccag cagggactgg cccgcggtct ggaactcgcc ttccagtcgg    540
gcgcggtgac cggcatgctg gtggccggtc tggccctgct gtcggtggcc ttctattaca    600
tcctgctcgt cggcatcggc gcgaccggcc gcgcgctgat cgatccgctg gtggctctgg    660
gctttggcgc ctcgctgatc tcgatcttcg cccgtctggg tggcggcatc ttcaccaagg    720
gcgccgacgt gggcgccgat ctggtgggca aggtcgaagc ggggatcccc gaggatgacc    780
cgcgcaatcc cgccgtcatc gccgacaacg tgggcgataa cgtgggcgat tgcgccggca    840
tggcggccga cctgttcgag acctatgccg tgaccgtcgt cgccaccatg gtcctggcct    900
cgatcttctt cgccggcgtt ccggcgatga cctcgat                            937
```

<210> SEQ ID NO 15
<211> LENGTH: 1534
<212> TYPE: DNA
<213> ORGANISM: Artificial Sequence
<220> FEATURE:
<223> OTHER INFORMATION: PCR product 3

<400> SEQUENCE: 15

```
acctgttcga gacctatgcc gtgaccgtcg tcgccaccat ggtcctggcc tcgatcttct     60
tcgccggcgt tccggcgatg acctcgatga tggcctatcc gctggcgatc ggcggggtct    120
gcatcctggc ctcgatcctc ggcaccaagt tcgtgaagct tggccccaag aacaacatca    180
tgggggcgct ctatcgcggc ttcctggtgt cggcgggagc gtccttcgtc gggatcatcc    240
tggccacggc gatcgtcccg ggcttttggcg acatccaggg cgccaacggg gtgctctatt    300
cgggcttcga cctgttcttg tgcgccgtca tcggcctgct ggtcaccggt ttgctgatct    360
gggtcaccga atattacacc ggcaccaatt tccgcccggt ccgttcggtc gccaaggcct    420
cgaccaccgg ccacggcacc aacgtgatcc agggtctggc gatttcgatg gaggcgacgg    480
ccctgccggc gctgatcatc tgcgcggcca tcatcaccac ctatcagctg tcgggtctgt    540
ttggcatcgc catcaccgtg accagcatgc tggctttggc cgggatggtc gtggcgctcg    600
acgcctatgg tccggtgacc gataacgccg gcggcatcgc cgaaatggcc aatctgcccg    660
aggacgtgcg caagaccacc gatgcgctcg acgccgttgg caacaccacc aaggcggtga    720
ccaagggcta tgctatcggt tcggccggcc ttggcgccct ggtgctgttc gccgcctata    780
ccgaggatct ggccttcttc aaggccaatg tcgacgccta tcggccttc gccggggtgg    840
atgtcaactt ctcgctgtcg agccctatg tggtggtcg cctgttcatc ggcggcctgc    900
tgccctatct gttcggctcg atgggcgatga ccgccgtcgg ccgcgccgct ggcagcgtcg    960
tcgaggaggt tcgccgtcag ttccgcgaaa tcccgggcat catggaaggc accgccaagc   1020
cggaatacgg ccgctgcgtc gacatgctga ccaaggcggc gatcaaagag atgatcatcc   1080
```

```
cctcgctgct gccggttctg gcgccgatcg tgctgtactt cgttatcctc ggcatcgccg    1140
ataaatcggc cgccttctcg gccctgggcg ccatgctgct cggcgtgatc gtcaccggtc    1200
ttttcgtggc gatctcgatg accgccgtg gcggcgcctg ggacaacgcc aagaagtaca     1260
tcgaagacgg ccactacggt ggcaagggg cggaagccca taaggccgcc gtcaccggcg     1320
acaccgttgg cgatccgtac aaagacaccg ccggtccggc ggtcaatccg atgatcaaga    1380
tcaccaacat cgtcgccctg ctgctgctgg cggtgctggc ccactaagag ctcgaattct    1440
catgtttgac agcttatcac tgatcagtga attaatggcg atgacgcatc ctcacgataa    1500
tatccgggta ggcgcaatca ctttcgtctc tact                                1534

<210> SEQ ID NO 16
<211> LENGTH: 19
<212> TYPE: DNA
<213> ORGANISM: Artificial Sequence
<220> FEATURE:
<223> OTHER INFORMATION: Primer P7

<400> SEQUENCE: 16
atcctgctcg tcggcatcg                                                 19

<210> SEQ ID NO 17
<211> LENGTH: 20
<212> TYPE: DNA
<213> ORGANISM: Artificial Sequence
<220> FEATURE:
<223> OTHER INFORMATION: Primer P8

<400> SEQUENCE: 17
tgctgatctg ggtcaccgaa                                                20

<210> SEQ ID NO 18
<211> LENGTH: 19
<212> TYPE: DNA
<213> ORGANISM: Artificial Sequence
<220> FEATURE:
<223> OTHER INFORMATION: Primer P9

<400> SEQUENCE: 18
cagcgtcgtc gaggaggtt                                                 19

<210> SEQ ID NO 19
<211> LENGTH: 2383
<212> TYPE: DNA
<213> ORGANISM: Artificial Sequence
<220> FEATURE:
<223> OTHER INFORMATION: PCR product 4

<400> SEQUENCE: 19
ctgagtagga caaatccgcc gggagcggat ttgaacgttg cgaagcaacg gcccggaggg    60
tggcgggcag gacgcccgcc ataaactgcc aggcatcaaa ttaagcagaa ggccatcctg    120
acggatggcc ttttgcgtg gccagtgcca agcttgcatg cctgcagatg gctggcatct    180
atcttttcgt cgtagccgcc gctctcgcgg cccttggtta tggcgctctc accatcaaaa    240
caatcatggc ggctgatgcc ggcaccgcgc gcatgcagga gatttccggc gccgtgcagg    300
aaggcgccag cgcgtttctc aatcgtcagt acaagaccat cgccgtcgtc ggcgcggttg    360
ttttcgttat tctgacggcg cttcttggca tctcggtcgg cttcggcttt ctgatcggcg    420
ccgtgtgctc gggcatcgcc ggttatgtcg gcatgtacat ctcggtgcgc gccaatgtgc    480
gcgtcgccgc cggggcccag cagggactgg cccgcggtct ggaactcgcc ttccagtcgg    540
```

```
gcgcggtgac cggcatgctg gtggccggtc tggccctgct gtcggtggcc ttctattaca    600
tcctgctcgt cggcatcggc gcgaccggcc gcgcgctgat cgatccgctg gtggctctgg    660
gctttggcgc ctcgctgatc tcgatcttcg cccgtctggg tggcggcatc ttcaccaagg    720
gcgccgacgt gggcgccgat ctggtgggca aggtcgaagc ggggatcccc gaggatgacc    780
cgcgcaatcc cgccgtcatc gccgacaacg tgggcgataa cgtgggcgat tgcgccggca    840
tggcggccga cctgttcgag acctatgccg tgaccgtcgt cgccaccatg gtcctggcct    900
cgatcttctt cgccggcgtt ccggcgatga cctcgatgat ggcctatccg ctggcgatcg    960
gcggggtctg catcctggcc tcgatcctcg gcaccaagtt cgtgaagctt ggccccaaga   1020
acaacatcat gggggcgctc tatcgcggct tcctggtgtc ggcgggagcg tccttcgtcg   1080
ggatcatcct ggccacggcg atcgtcccgg gctttggcga catccagggc gccaacgggg   1140
tgctctattc gggcttcgac ctgttcttgt gcgccgtcat cggcctgctg gtcaccggtt   1200
tgctgatctg ggtcaccgaa tattacaccg gcaccaattt ccgcccggtc cgttcggtcg   1260
ccaaggcctc gaccaccggc cacggcacca acgtgatcca gggtctggcg atttcgatgg   1320
aggcgacggc cctgccggcg ctgatcatct gcgcggccat catcaccacc tatcagctgt   1380
cgggtctgtt tggcatcgcc atcaccgtga ccagcatgct ggctttggcc gggatggtcg   1440
tggcgctcga cgcctatggt ccggtgaccg ataacgccgg cggcatcgcc gaaatggcca   1500
atctgcccga ggacgtgcgc aagaccaccg atgcgctcga cgccgttggc aacaccacca   1560
aggcggtgac caagggctat gctatcggtt cggccgccct tggcgccctg gtgctgttcg   1620
ccgcctatac cgaggatctg gccttcttca aggccaatgt cgacgcctat ccggccttcg   1680
ccggggtgga tgtcaacttc tcgctgtcga gcccctatgt ggtggtcggc ctgttcatcg   1740
gcggcctgct gccctatctg ttcggctcga tgggcatgac cgccgtcggc cgcgccgctg   1800
gcagcgtcgt cgaggaggtt cgccgtcagt ccgcgaaaat cccgggcatc atggaaggca   1860
ccgccaagcc ggaatacggc cgctgcgtcg acatgctgac caaggcggcg atcaaagaga   1920
tgatcatccc ctcgctgctg ccggttctgg cgccgatcgt gctgtacttc gttatcctcg   1980
gcatcgccga taaatcggcc gccttctcgg ccctgggcgc catgctgctc ggcgtgatcg   2040
tcaccggtct tttcgtggcg atctcgatga ccgccggtgg cggcgcctgg acaacgccca   2100
agaagtacat cgaagacggc cactacggtg caagggtc ggaagcccat aaggccgccg   2160
tcaccggcga caccgttggc gatccgtaca aagacaccgc cggtccggcg tcaatccga   2220
tgatcaagat caccaacatc gtcgccctgc tgctgctggc ggtgctggcc cactaagagc   2280
tcgaattctc atgtttgaca gcttatcact gatcagtgaa ttaatggcga tgacgcatcc   2340
tcacgataat atccgggtag gcgcaatcac tttcgtctct act                     2383
```

<210> SEQ ID NO 20
<211> LENGTH: 64
<212> TYPE: DNA
<213> ORGANISM: Artificial Sequence
<220> FEATURE:
<223> OTHER INFORMATION: Primer P10

<400> SEQUENCE: 20

```
tggccagtgc caagcttgca tgcctgcagc gctcaagtta gtataaaaaa gctgaacgag    60
aaac                                                                 64
```

```
<210> SEQ ID NO 21
<211> LENGTH: 70
<212> TYPE: DNA
<213> ORGANISM: Artificial Sequence
<220> FEATURE:
<223> OTHER INFORMATION: Primer P11

<400> SEQUENCE: 21
agcggcggct acgacgaaaa gatagatgcc agccatagtt agttctcctt ccggccaatg      60
cttcgtttcg                                                            70

<210> SEQ ID NO 22
<211> LENGTH: 22
<212> TYPE: DNA
<213> ORGANISM: Artificial Sequence
<220> FEATURE:
<223> OTHER INFORMATION: Primer P12

<400> SEQUENCE: 22 cctcccttttt cgatagcgac aa                                             22

<210> SEQ ID NO 23
<211> LENGTH: 20
<212> TYPE: DNA
<213> ORGANISM: Artificial Sequence
<220> FEATURE:
<223> OTHER INFORMATION: Primer P13

<400> SEQUENCE: 23
accgttggcg atccgtacaa                                                 20

<210> SEQ ID NO 24
<211> LENGTH: 975
<212> TYPE: DNA
<213> ORGANISM: Artificial Sequence
<220> FEATURE:
<223> OTHER INFORMATION: PCR product 5

<400> SEQUENCE: 24
accgttggcg atccgtacaa agacaccgcc ggtccggcgg tcaatccgat gatcaagatc      60
accaacatcg tcgccctgct gctgctggcg gtgctggccc actaagagct cgaattctca     120
tgtttgacag cttatcactg atcagtgaat taatggcgat gacgcatcct cacgataata     180
tccgggtagg cgcaatcact ttcgtctcta ctccgttaca aagcgaggct gggtatttcc     240
cggcctttct gttatccgaa atccactgaa agcacagcgg ctggctgagg agataaataa     300
taaacgaggg gctgtatgca caaagcatct tctgttgagt taagaacgag tatcgagatg     360
gcacatagcc ttgctcaaat tggaatcagg tttgtgccaa taccagtaga aacagacgaa     420
gaagctagag gtgaatcacg acaaagcgta tcaaaaacgt atggagtagg gctctaaact     480
ctgtataaaa agtttccagc tagctgataa cgggaaagaa acagagaagg gcacaaatat     540
tgtgtacttt aatgtgccct ttaatttatt gattggtggt tgaattgtcc gtaacttttt     600
gatttaagtg caaatttcta ataaattaga acactttctt aaatggtttc actgaaacgt     660
gttcatagac tcctgccgct acgtacgggt cagcatcggc ccaggcctga gctgcttcca     720
gcgattcaaa ttcagcaata acggttgagc cagtaaatcc cgcagcccct ggatcgttac     780
tgtctaccgc tggcattgga ccagctgtca acaaacgaat caaattgttc aaatgggtgg     840
cgcggcaaac cagactacgc tcaataatgg tgtgctacag gtttatggcg cagcgaatga     900
```

| taccacgatt aaaggcgggc gcttaatcgt tgaaaaagat gggggggccg tctttgtcgc | 960 |

| tatcgaaaag ggagg | 975 |

<210> SEQ ID NO 25
<211> LENGTH: 23
<212> TYPE: DNA
<213> ORGANISM: Artificial Sequence
<220> FEATURE:
<223> OTHER INFORMATION: Primer P14

<400> SEQUENCE: 25

| tgtttcgggc ggaccaaatg ata | 23 |

<210> SEQ ID NO 26
<211> LENGTH: 20
<212> TYPE: DNA
<213> ORGANISM: Artificial Sequence
<220> FEATURE:
<223> OTHER INFORMATION: Primer P15

<400> SEQUENCE: 26

| ttgatggtga gagcgccata | 20 |

<210> SEQ ID NO 27
<211> LENGTH: 1272
<212> TYPE: DNA
<213> ORGANISM: Artificial Sequence
<220> FEATURE:
<223> OTHER INFORMATION: PCR product 6

<400> SEQUENCE: 27

| tgtttcgggc ggaccaaatg atacgtcagt gggagagatc tcactaaaaa ctggggataa | 60 |
| cgccttaaat ggcgaagaaa cggtctaaat aggctgattc aaggcattta cgggagaaaa | 120 |
| aatcggctca acatgaaga aatgaaatga ctgagtcagc cgagaagaat ttccccgctt | 180 |
| attcgcacct tccttatatt cacccatagc attggcatca actgttgagt atggtgagac | 240 |
| agttgatggt gttgtcctgg aaaaagatat ccagctggtt tatgggaccg ccaataatac | 300 |
| gaaaatcaat cctggcggag aacagcatat aaagaatttt ggtgtaagta ataatactga | 360 |
| aattaacgga gggtatcagt acattgaaat gaatggcgcc gcaggaaagg tcattttttcc | 420 |
| tgaatatgct cacatcatat aaagaaatac agataaagtt attatctgct tgtggtggtg | 480 |
| aatgcactga ccggctataa ggaaaggcca aacaagacac ggttgcaaaa accgtgccct | 540 |
| taaatattga atctctattc agaacacttt cttaaattgt catttggcat attacgaaca | 600 |
| attccgcgta aaaacgttct gttacgctaa acccttatcc agcaggcttt caaggatgta | 660 |
| aaccataaca ctctgcgaac tagtgttaca ttgcgtgtag ctttgagtgg gcaactttgt | 720 |
| gtacactttt gtgtacccaa aaacaaaaat gtgtacccat tcaatgatca ccgacacaaa | 780 |
| gctcaggaag gcgctcggca agaaaagaga tgatatcgag attatttctg attcgcacga | 840 |
| gcttttctaga cgctcaagtc gctcaagtta gtataaaaaa gcaggcttca caggcttcag | 900 |
| agcgatggcc cccgatggta gtgtggggtc tccccatgcg agagtaggga actgccaggc | 960 |
| atcaaataaa acgaaaggct cagtcgaaag actgggcctt tcgttttatc tgttgtttgt | 1020 |
| cggtgaacgc tctcctgagt aggacaaatc cgccgggagc ggatttgaac gttgcgaagc | 1080 |
| aacgccccgg agggtggcgg gcaggacgcc cgccataaac tgccaggcat caaattaagc | 1140 |
| agaaggccat cctgacggat ggcctttttg cgtggccagt gccaagcttg catgcctgca | 1200 |

```
gatggctggc atctatcttt tcgtcgtagc cgccgctctc gcggcccttg gttatggcgc    1260
tctcaccatc aa                                                        1272

<210> SEQ ID NO 28
<211> LENGTH: 2132
<212> TYPE: DNA
<213> ORGANISM: Artificial Sequence
<220> FEATURE:
<223> OTHER INFORMATION: PCR product 7

<400> SEQUENCE: 28
ctgagtagga caaatccgcc gggagcggat ttgaacgttg cgaagcaacg gcccggaggg      60
tggcgggcag gacgcccgcc ataaactgcc aggcatcaaa ttaagcagaa ggccatcctg     120
acggatggcc tttttgcgtg gccagtgcca agcttgcatg cctgcagcgc tcaagttagt     180
ataaaaaagc tgaacgagaa acgtaaaatg atataaatat caatatatta aattagattt     240
tgcataaaaa acagactaca taatactgta aaacacaaca tatgcagtca ctatgaatca     300
actacttaga tggtattagt gacctgtaac agactgcagt ggtcgaaaaa aaaagcccgc     360
actgtcaggt gcgggctttt ttctgtgtta agcttcgacg aatttctgcc attcatccgc     420
ttattatcac ttattcaggc gtagcaccag gcgtttaagg gcaccaataa ctgccttaaa     480
aaaattacgc cccgccctgc cactcatcgc agtactgttg taattcatta agcattctgc     540
cgacatggaa gccatcacag acggcatgat gaacctgaat cgccagcggc atcagcacct     600
tgtcgccttg cgtataatat ttgcccatgg tgaaacgggg gcgaagaag ttgtccatat     660 tggccacgtt taaatcaaaa ctggtgaaac tcacccaggg attggctgag acgaaaaaca     720
tattctcaat aaaccccttta gggaaatagg ccaggttttc accgtaacac gccacatctt     780
gcgaatatat gtgtagaaac tgccggaaat cgtcgtggta ttcactccag agcgatgaaa     840
acgtttcagt ttgctcatgg aaaacggtgt aacaagggtg aacactatcc catatcacca     900
gctcaccgtc tttcattgcc atacggaatt ccggatgagc attcatcagg cgggcaagaa     960
tgtgaataaa ggccggataa aacttgtgct tatttttctt tacggtcttt aaaaaggccg    1020
taatatccag ctgaacggtc tggttatagg tacattgagc aactgactga atgcctcaa     1080 aatgttcttt acgatgccat gggatatat caacggtggt atatccagtg attttttttct    1140 ccattttagc ttccttagct cctgaaaatc tcgatccga tatctagcta gagcgccgg     1200 ttgacgctgc tagtgttacc tagcgatttg tatcttactg catgttactt catgttgtca    1260
atacctgttt ttcgtgcgac ttatcaggct gtctacttat ccggagatcc acaggacggg    1320
tgtggtcgcc atgatcgcgt agtcgatagt ggctccaagt agcgaagcga gcaggactgg    1380
gcggcggcca aagcggtcgg acagtgctcc gagaacgggt gcgcatagaa attgcatcaa    1440
cgcatatagc gctagcagca cgccatagtg actggcgatg ctgtcggaat ggacgatatc    1500
ccgcaagagg cccggcagta ccggcataac caagcctatg cctacagcat ccagggtgac    1560
ggtgccgagg atgacgatga gcgcattgtt agatttcata cacggtgcct gactgcgtta    1620
gcaatttaac tgtgataaac taccgcatta agcttatcg atgataagct gtcaaacatg    1680
agaattcgaa atcaaataat gattttattt tgactgatag tgacctgttc gttgcaacaa    1740
attgataagc aatgcttttt tataatgcca acttagtata aaaaagcagg cttcaagatc    1800
ttcacctacc aaacaatgcc cccctgcaaa aataaaattc atataaaaaa catacagata    1860
accatctgcg gtgataaatt atctctggcg gtgttgacat aaataccact ggcggtgata    1920
ctgagcacat cagcaggacg cactgaccac catgaaggtg acgctcttaa aaattaagcc    1980
```

```
ctgaagaagg gcagcattca aagcagaagg ctttggggtg tgtgatacga aacgaagcat      2040
tggccggaag gagaactaac tatggctggc atctatcttt tcgtcgtagc cgccgctctc      2100
gcggcccttg gttatggcgc tctcaccatc aa                                    2132
```

```
<210> SEQ ID NO 29
<211> LENGTH: 68
<212> TYPE: DNA
<213> ORGANISM: Artificial Sequence
<220> FEATURE:
<223> OTHER INFORMATION: Primer P16

<400> SEQUENCE: 29
aaccgaagcc cggcgttcag ggttattacg ccagaagaac cgctcaagtt agtataaaaa      60
agctgaac                                                              68

<210> SEQ ID NO 30
<211> LENGTH: 68
<212> TYPE: DNA
<213> ORGANISM: Artificial Sequence
<220> FEATURE:
<223> OTHER INFORMATION: Primer P17

<400> SEQUENCE: 30
ctcggcactt gtttgccaca tattttaaa ggaaacagac tgaagcctgc ttttttatac       60
taagttgg                                                              68

<210> SEQ ID NO 31
<211> LENGTH: 1708
<212> TYPE: DNA
<213> ORGANISM: Artificial Sequence
<220> FEATURE:
<223> OTHER INFORMATION: PCR product 8

<400> SEQUENCE: 31
aaccgaagcc cggcgttcag ggttattacg ccagaagaac cgctcaagtt agtataaaaa      60
agctgaacga gaaacgtaaa atgatataaa tatcaatata ttaaattaga ttttgcataa     120
aaaacagact acataatact gtaaaacaca acatatgcag tcactatgaa tcaactactt     180
agatggtatt agtgacctgt aacagactgc agtggtcgaa aaaaaaagcc cgcactgtca     240
ggtgcgggct tttttctgtg ttaagcttcg acgaatttct gccattcatc cgcttattat     300
cacttattca ggcgtagcac caggcgttta agggcaccaa taactgcctt aaaaaaatta     360
cgccccgccc tgccactcat cgcagtactg ttgtaattca ttaagcattc tgccgacatg     420
gaagccatca cagacggcat gatgaacctg aatcgccagc ggcatcagca ccttgtcgcc     480
ttgcgtataa tatttgccca tggtgaaaac ggggcgaag aagttgtcca tattggccac     540
gtttaaatca aaactggtga aactcaccca gggattggct gagacgaaaa acatattctc     600
aataaaccct ttagggaaat aggccaggtt tcaccgtaa cacgccacat cttgcgaata     660
tatgtgtaga aactgccgga atcgtcgtg gtattcactc cagagcgatg aaaacgtttc      720
agtttgctca tggaaaacgg tgtaacaagg gtgaacacta tcccatatca ccagctcacc     780
gtctttcatt gccatacgga attccggatg agcattcatc aggcgggcaa gaatgtgaat     840
aaaggccgga taaaacttgt gcttattttt ctttacggtc tttaaaaagg ccgtaatatc     900
cagctgaacg gtctggttat aggtacattg agcaactgac tgaaatgcct caaaatgttc     960
tttacgatgc cattgggata tatcaacggt ggtatatcca gtgatttttt tctccatttt    1020
agcttcctta gctcctgaaa atctcggatc cgatatctag ctagagcgcc cggttgacgc    1080
```

-continued

| | |
|---|---|
| tgctagtgtt acctagcgat ttgtatctta ctgcatgtta cttcatgttg tcaatacctg | 1140 |
| tttttcgtgc gacttatcag gctgtctact tatccggaga tccacaggac gggtgtggtc | 1200 |
| gccatgatcg cgtagtcgat agtggctcca agtagcgaag cgagcaggac tgggcggcgg | 1260 |
| ccaaagcggt cggacagtgc tccgagaacg ggtgcgcata gaaattgcat caacgcatat | 1320 |
| agcgctagca gcacgccata gtgactggcg atgctgtcgg aatggacgat atcccgcaag | 1380 |
| aggcccggca gtaccggcat aaccaagcct atgcctacag catccagggt gacggtgccg | 1440 |
| aggatgacga tgagcgcatt gttagatttc atacacggtg cctgactgcg ttagcaattt | 1500 |
| aactgtgata aactaccgca ttaaagctta tcgatgataa gctgtcaaac atgagaattc | 1560 |
| gaaatcaaat aatgatttta ttttgactga tagtgacctg ttcgttgcaa caaattgata | 1620 |
| agcaatgctt ttttataatg ccaacttagt ataaaaagc aggcttcagt ctgtttcctt | 1680 |
| taaaaatatg tggcaaacaa gtgccgag | 1708 |

<210> SEQ ID NO 32
<211> LENGTH: 19
<212> TYPE: DNA
<213> ORGANISM: Artificial Sequence
<220> FEATURE:
<223> OTHER INFORMATION: Primer P18

<400> SEQUENCE: 32

| | |
|---|---|
| ttactaaccg aagcccggc | 19 |

<210> SEQ ID NO 33
<211> LENGTH: 20
<212> TYPE: DNA
<213> ORGANISM: Artificial Sequence
<220> FEATURE:
<223> OTHER INFORMATION: Primer P19

<400> SEQUENCE: 33

| | |
|---|---|
| cgaaaacaag cgaagacatt | 20 |

<210> SEQ ID NO 34
<211> LENGTH: 1754
<212> TYPE: DNA
<213> ORGANISM: Artificial Sequence
<220> FEATURE:
<223> OTHER INFORMATION: PCR product 9

<400> SEQUENCE: 34

| | |
|---|---|
| ttactaaccg aagcccggcg ttcagggtta ttacgccaga agaaccgctc aagttagtat | 60 |
| aaaaaagctg aacgagaaac gtaaaatgat ataaatatca atatattaaa ttagatttg | 120 |
| cataaaaaac agactacata atactgtaaa acacaacata tgcagtcact atgaatcaac | 180 |
| tacttagatg gtattagtga cctgtaacag actgcagtgg tcgaaaaaaa aagcccgcac | 240 |
| tgtcaggtgc gggctttttt ctgtgttaag cttcgacgaa tttctgccat tcatccgctt | 300 |
| attatcactt attcaggcgt agcaccaggc gtttaagggc accataaact gccttaaaaa | 360 |
| aattacgccc cgccctgcca ctcatcgcag tactgttgta attcattaag cattctgccg | 420 |
| acatggaagc catcacagac ggcatgatga acctgaatcg ccagcggcat cagcaccttg | 480 |
| tcgccttgcg tataatattt gcccatggtg aaaacggggg cgaagaagtt gtccatattg | 540 |
| gccacgttta aatcaaaact ggtgaaactc acccagggat tggctgagac gaaaaacata | 600 |
| ttctcaataa acccttatagg gaaataggcc aggttttcac cgtaacacgc cacatcttgc | 660 |
| gaatatatgt gtagaaactg ccggaaatcg tcgtggtatt cactccagag cgatgaaaac | 720 |

| | |
|---|---|
| gtttcagttt gctcatggaa aacggtgtaa caagggtgaa cactatccca tatcaccagc | 780 |
| tcaccgtctt tcattgccat acggaattcc ggatgagcat tcatcaggcg ggcaagaatg | 840 |
| tgaataaagg ccggataaaa cttgtgctta ttttctttta cggtctttaa aaaggccgta | 900 |
| atatccagct gaacggtctg gttataggta cattgagcaa ctgactgaaa tgcctcaaaa | 960 |
| tgttctttac gatgccattg ggatatatca acggtggtat atccagtgat ttttttctcc | 1020 |
| attttagctt ccttagctcc tgaaaatctc ggatccgata tctagctaga gcgcccggtt | 1080 |
| gacgctgcta gtgttaccta gcgatttgta tcttactgca tgttacttca tgttgtcaat | 1140 |
| acctgttttt cgtgcgactt atcaggctgt ctacttatcc ggagatccac aggacgggtg | 1200 |
| tggtcgccat gatcgcgtag tcgatagtgg ctccaagtag cgaagcgagc aggactgggc | 1260 |
| ggcggccaaa gcggtcggac agtgctccga aacgggtgc gcatagaaat tgcatcaacg | 1320 |
| catatagcgc tagcagcacg ccatagtgac tggcgatgct gtcggaatgg acgatatccc | 1380 |
| gcaagaggcc cggcagtacc ggcataacca agcctatgcc tacagcatcc agggtgacgg | 1440 |
| tgccgaggat gacgatgagc gcattgttag atttcataca cggtgcctga ctgcgttagc | 1500 |
| aatttaactg tgataaacta ccgcattaaa gcttatcgat gataagctgt caaacatgag | 1560 |
| aattcgaaat caataatga ttttattttg actgatagtg acctgttcgt tgcaacaaat | 1620 |
| tgataagcaa tgctttttta taatgccaac ttagtataaa aaagcaggct tcagtctgtt | 1680 |
| tcctttaaaa atatgtggca aacaagtgcc gagtattata gccaactcgc gccgaatgtc | 1740 |
| ttcgcttgtt ttcg | 1754 |

<210> SEQ ID NO 35
<211> LENGTH: 535
<212> TYPE: DNA
<213> ORGANISM: Artificial Sequence
<220> FEATURE:
<223> OTHER INFORMATION: PCR product 10

<400> SEQUENCE: 35

| | |
|---|---|
| ctgagtagga caaatccgcc gggagcggat ttgaacgttg cgaagcaacg gcccggaggg | 60 |
| tggcgggcag gacgcccgcc ataaactgcc aggcatcaaa ttaagcagaa ggccatcctg | 120 |
| acggatggcc ttttttgcgtg gccagtgcca agcttgcatg cctgcagcgc tcaagttagt | 180 |
| ataaaaagc aggcttcaag atcttcacct accaaacaat gcccccctgc aaaaaataaa | 240 |
| ttcatataaa aaacatacag ataaccatct gcggtgataa attatctctg gcggtgttga | 300 |
| cataaatacc actggcggtg atactgagca catcagcagg acgcactgac caccatgaag | 360 |
| gtgacgctct taaaaattaa gccctgaaga agggcagcat tcaaagcaga aggctttggg | 420 |
| gtgtgtgata cgaaacgaag cattggccgg aaggagaact aactatggct ggcatctatc | 480 |
| ttttcgtcgt agccgccgct ctcgcggccc ttggttatgg cgctctcacc atcaa | 535 |

<210> SEQ ID NO 36
<211> LENGTH: 46
<212> TYPE: DNA
<213> ORGANISM: Artificial Sequence
<220> FEATURE:
<223> OTHER INFORMATION: Primer P20

<400> SEQUENCE: 36

| | |
|---|---|
| aagtctagaa ggtgggaaca gaatggctgg catctatctt ttcgtc | 46 |

<210> SEQ ID NO 37
<211> LENGTH: 45
<212> TYPE: DNA
<213> ORGANISM: Artificial Sequence
<220> FEATURE:
<223> OTHER INFORMATION: Primer P21

<400> SEQUENCE: 37
gtttgtaaag aagagctttc aggattagtg ggccagcacc gccag            45

<210> SEQ ID NO 38
<211> LENGTH: 45
<212> TYPE: DNA
<213> ORGANISM: Artificial Sequence
<220> FEATURE:
<223> OTHER INFORMATION: Primer P22

<400> SEQUENCE: 38
ctggcggtgc tgcccacta atcctgaaag ctcttcttta caaac             45

<210> SEQ ID NO 39
<211> LENGTH: 34
<212> TYPE: DNA
<213> ORGANISM: Artificial Sequence
<220> FEATURE:
<223> OTHER INFORMATION: Primer P23

<400> SEQUENCE: 39
gaccaattgt atactgctgt cccatgtcat ttcc                        34

<210> SEQ ID NO 40
<211> LENGTH: 21
<212> TYPE: DNA
<213> ORGANISM: Artificial Sequence
<220> FEATURE:
<223> OTHER INFORMATION: Primer P24

<400> SEQUENCE: 40
cgcctcgccg aatttctcat c                                      21

<210> SEQ ID NO 41
<211> LENGTH: 27
<212> TYPE: DNA
<213> ORGANISM: Artificial Sequence
<220> FEATURE:
<223> OTHER INFORMATION: Primer P25

<400> SEQUENCE: 41
aagggaattc tttcggcggt gcggctc                                27

<210> SEQ ID NO 42
<211> LENGTH: 30
<212> TYPE: DNA
<213> ORGANISM: Artificial Sequence
<220> FEATURE:
<223> OTHER INFORMATION: Primer P26

<400> SEQUENCE: 42
accatgcatg ctttaatgaa ggaagagggg                             30

<210> SEQ ID NO 43
<211> LENGTH: 26
<212> TYPE: DNA
<213> ORGANISM: Artificial Sequence
<220> FEATURE:
<223> OTHER INFORMATION: Primer P27

<400> SEQUENCE: 43
gctctagacg gcagccgggt agaaac     26

<210> SEQ ID NO 44
<211> LENGTH: 33
<212> TYPE: DNA
<213> ORGANISM: Artificial Sequence
<220> FEATURE:
<223> OTHER INFORMATION: Primer P28

<400> SEQUENCE: 44
gaaacatgta tacaccacgg tatcaactct ttc     33

<210> SEQ ID NO 45
<211> LENGTH: 31
<212> TYPE: DNA
<213> ORGANISM: Artificial Sequence
<220> FEATURE:
<223> OTHER INFORMATION: Primer P29

<400> SEQUENCE: 45
attgcatgcc aaatgaaaat gatgaaaaag g     31

<210> SEQ ID NO 46
<211> LENGTH: 30
<212> TYPE: DNA
<213> ORGANISM: Artificial Sequence
<220> FEATURE:
<223> OTHER INFORMATION: Primer P30

<400> SEQUENCE: 46
tagaattcct gaaagctctt ctttacaaac     30

<210> SEQ ID NO 47
<211> LENGTH: 34
<212> TYPE: DNA
<213> ORGANISM: Artificial Sequence
<220> FEATURE:
<223> OTHER INFORMATION: Primer P31

<400> SEQUENCE: 47
ttagccgcat gctgaggctt taaggagttg acag     34

<210> SEQ ID NO 48
<211> LENGTH: 39
<212> TYPE: DNA
<213> ORGANISM: Artificial Sequence
<220> FEATURE:
<223> OTHER INFORMATION: Primer P32

<400> SEQUENCE: 48
aaatctagac tttcttacta tttttatctc tactccatc     39

<210> SEQ ID NO 49
<211> LENGTH: 45
<212> TYPE: DNA
<213> ORGANISM: Artificial Sequence
<220> FEATURE:
<223> OTHER INFORMATION: Primer P33

<400> SEQUENCE: 49
caacatggta cctctggaac gtacatgcca ccgctgagca ataac     45

```
<210> SEQ ID NO 50
<211> LENGTH: 37
<212> TYPE: DNA
<213> ORGANISM: Artificial Sequence
<220> FEATURE:
<223> OTHER INFORMATION: Primer P34

<400> SEQUENCE: 50
ctgcaggtcg accaatccgg atatagttcc tcctttc                              37

<210> SEQ ID NO 51
<211> LENGTH: 33
<212> TYPE: DNA
<213> ORGANISM: Artificial Sequence
<220> FEATURE:
<223> OTHER INFORMATION: Primer P35

<400> SEQUENCE: 51
gaatatggta ccggagctga ctgggttgaa ggc                                  33

<210> SEQ ID NO 52
<211> LENGTH: 36
<212> TYPE: DNA
<213> ORGANISM: Artificial Sequence
<220> FEATURE:
<223> OTHER INFORMATION: Primer P36

<400> SEQUENCE: 52
ctacatggta ccaatccgga tatagttcct cctttc                               36

<210> SEQ ID NO 53
<211> LENGTH: 44
<212> TYPE: DNA
<213> ORGANISM: Artificial Sequence
<220> FEATURE:
<223> OTHER INFORMATION: Primer P37

<400> SEQUENCE: 53
gaactatcta gaatcgatag gaggttaatt aacatgtcta aagg                      44

<210> SEQ ID NO 54
<211> LENGTH: 43
<212> TYPE: DNA
<213> ORGANISM: Artificial Sequence
<220> FEATURE:
<223> OTHER INFORMATION: Primer P38

<400> SEQUENCE: 54
cagttcctcg agttatttgt acaattcatc aataccatgg gta                       43

<210> SEQ ID NO 55
<211> LENGTH: 63
<212> TYPE: DNA
<213> ORGANISM: Artificial Sequence
<220> FEATURE:
<223> OTHER INFORMATION: Primer P39

<400> SEQUENCE: 55
tcttgcaaaa acagcctgcg ttttcatcag taatagcgct caagttagta taaaaaagcg     60
aac                                                                   63

<210> SEQ ID NO 56
<211> LENGTH: 66
<212> TYPE: DNA
<213> ORGANISM: Artificial Sequence
```

```
<220> FEATURE:
<223> OTHER INFORMATION: Primer P40

<400> SEQUENCE: 56
agcggcggta atgttctcaa acatgacgag gtttccttag ctgtttcctt ctagacggcc    60
aatgct                                                              66

<210> SEQ ID NO 57
<211> LENGTH: 22
<212> TYPE: DNA
<213> ORGANISM: Artificial Sequence
<220> FEATURE:
<223> OTHER INFORMATION: Primer P41

<400> SEQUENCE: 57
cgtttaccag ttctaatagc ac                                            22

<210> SEQ ID NO 58
<211> LENGTH: 21
<212> TYPE: DNA
<213> ORGANISM: Artificial Sequence
<220> FEATURE:
<223> OTHER INFORMATION: Primer P42

<400> SEQUENCE: 58
tttatagaca ccaatcccga g                                             21
```